(12) United States Patent
Brown et al.

(10) Patent No.: US 7,985,844 B2
(45) Date of Patent: Jul. 26, 2011

(54) ANTIBODY THAT SPECIFICALLY BINDS HYALURONAN SYNTHASE

(75) Inventors: Tracey J. Brown, Flemington (AU); Gary R. Brownlee, East Burwood (AU)

(73) Assignee: Alchemia Oncology Pty Limited, Eight Mile Plains (AU)

( * ) Notice: Subject to any disclaimer, the term of this patent is extended or adjusted under 35 U.S.C. 154(b) by 0 days.

(21) Appl. No.: 12/638,803

(22) Filed: Dec. 15, 2009

(65) Prior Publication Data

US 2010/0158896 A1 Jun. 24, 2010

Related U.S. Application Data

(62) Division of application No. 10/574,903, filed as application No. PCT/AU2004/001383 on Oct. 11, 2004, now Pat. No. 7,662,929.

(30) Foreign Application Priority Data

Oct. 10, 2003 (AU) ............................... 2003905551
Dec. 1, 2003 (AU) ............................... 2003906658

(51) Int. Cl.
*C07K 16/00* (2006.01)
*A61K 39/395* (2006.01)

(52) U.S. Cl. ............... 530/389.1; 530/387.1; 530/387.3; 530/388.1; 424/130.1

(58) Field of Classification Search ........................ None
See application file for complete search history.

(56) References Cited

U.S. PATENT DOCUMENTS

| | | | |
|---|---|---|---|
| 5,994,100 A | 11/1999 | Zhu et al. | |
| 6,682,904 B1 | 1/2004 | Frost | |
| 7,662,929 B2 | 2/2010 | Brown et al. | |
| 2002/0151026 A1 | 10/2002 | Briskin | |
| 2007/0286856 A1 | 12/2007 | Brown et al. | |
| 2009/0068183 A1 | 3/2009 | Brown et al. | |

FOREIGN PATENT DOCUMENTS

| | | |
|---|---|---|
| EP | 0 881 294 A2 | 12/1998 |
| JP | 2002-293740 A | 10/2002 |
| WO | WO-97/40174 A1 | 10/1997 |
| WO | WO-98/00551 A2 | 1/1998 |
| WO | WO-98/00551 A3 | 1/1998 |
| WO | WO-98/00553 A1 | 1/1998 |
| WO | WO-2004/003158 A2 | 1/2004 |
| WO | WO-2004/003158 A3 | 1/2004 |
| WO | WO-2004/082610 A2 | 9/2004 |
| WO | WO-2004/082610 A3 | 9/2004 |
| WO | WO-2005/035548 A1 | 4/2005 |
| WO | WO-2007/112475 A1 | 10/2007 |

OTHER PUBLICATIONS

Biosis Database Accession No. PREV200200186712 (Nov. 16, 2001). "Hyaluronan Synthases as Potential Oncogenes in Myeloma," Abstract only, two pages.
Itano, N. et al. (Apr. 30, 2004). "Selective Expression and Functional Characteristics of Three Mammalian Hyaluronan Synthases in Oncogenic Malignant Transformation," *The Journal of Biological Chemistry* 279(18):18679-18687.
Bullard, K.M. et al. (2003). "Hyaluronan Synthase-3 Is Regulated in Metastatic Colon Carcinoma Cells and Manipulation of Expression Alters Matrix Retention and Cellular Growth," *Int. J. Cancer* 107(5):739-746.
Chao, H. et al. (Jul. 29, 2005). "Natural Antisense mRNAs to Hyaluronan Synthase 2 Inhibit Hyaluronan Biosynthesis and Cell Proliferation," *Journal Biological Chemistry* 280(30):27513-27522.
Falkenberg, F.W. et al. (1984). *J. Clin. Chem. Clin. Biochem.* 22:867-882.
Final Office Action mailed on Feb. 23, 2009, for U.S. Appl. No. 10/574,903, filed Feb. 28, 2007, seven pages.
Hakanson, E.Y. et al. (1948). "Inhibition of Hyaluronidase by Serum in Human Cancer," Chemical Abstracts Accession No. 43:15662 & *J. Natl. Cancer Inst.* 9:129-132. (Abstract Only.).
International Search Report mailed Jan. 7, 2005, for PCT Application No. PCT/AU2004/001383, filed Oct. 11, 2004, four pages.
International Search Report mailed May 30, 2007, for PCT Application No. PCT/AU2007/000359, filed Mar. 23, 2007, three pages.
Nishida, Y. et al. (Jul. 1999). "Antisense Inhibition of Hyaluronan Synthase-2 in Human Articular Chondrocytes Inhibits Proteoglycan Retention and Matrix Assembly," *J. Biological Chem.* 274(31):21893-21899.
Non-final Office Action mailed on Aug. 19, 2008, for U.S. Appl. No. 10/574,903, filed Feb. 28, 2007, 12 pages.
Owens, R.J. et al. (1994). *Journal of Immunological Methods* 168:149-165.
Simpson, M.A. et al. (Mar. 2002). "Manipulation of Hyaluronan Synthase Expression in Prostate Adenocarcinoma Cells Alters Pericellular Matrix Retention and Adhesion to Bone Marrow Endothelial Cells," *J. Biological Chem.* 277(12):10050-10057.
Simpson, M.A. et al. (Sep. 2002). "Inhibition of Prostate Tumor Cell Hyaluronan Synthesis Impairs Subcutaneous Growth and Vascularization in Immunocompromised Mice," *Am. J. Pathol.* 161(3):849-857.
Udabage, L. et al. (2005). "The Over-Expression of *HAS2*, *Hyal-2* and *CD44* is Implicated in the Invasiveness of Breast Cancer," *Experimental Cell Research* 310:205-217.
Udabage, L. et al. (Jul. 15, 2005). "Antisense-Mediated Suppresion of Hyaluronan Synthase 2 Inhibits the Tumorigenesis and Progression of Breast Cancer," *Cancer Research* 65(14):6139-6150.
Ueki, N. et al. (2000). "Inhibition of Hyaluronan Synthesis by Vesnarinone in Cultured Human Myofibroblasts," *Biochimica et Biophysica Acta* 1495(2):160-167.
Zhang, W. et al. (2000). "Glucocorticoids Induce a Near-Total Suppression of Hyaluronan Synthase mRNA in Dermal Fibroblasts and in Osteoblasts: a Molecular Mechanism Contributing to Organ Atrophy," *Biochemical J.* 349(Part 1):91-97.

(Continued)

*Primary Examiner* — Sharon Wen
(74) *Attorney, Agent, or Firm* — Morrison & Foerster LLP

(57) ABSTRACT

Modulation of Hyaluronan (HA) synthesis and degradation is disclosed by compounds and compositions that are capable of reducing the level of hyaluronan synthase (HAS) or hyaluronidase (HYAL) or the function or activity of HAS or HYAL. The compounds and compositions can also inhibit the expression of genetic material encoding these enzymes. The compounds and compositions comprise nucleic acid molecules and interactive molecules such as antibodies, small molecule inhibitors and substrate analogs of HAS and HYAL. The compounds and compositions are useful in the prophylaxis and/or treatment of inflammatory disorders including hyperproliferative conditions, such as but not limited to, cancer and psoriasis.

7 Claims, 16 Drawing Sheets

ANTIBODY THAT SPECIFICALLY BINDS HYALURONAN SYNTHASE

This application is a divisional application of U.S. patent application Ser. No. 10/574,903 (now U.S. Pat. No. 7,662, 929), filed Feb. 28, 2007 (Int'l), which is a National Phase application under 35 U.S.C. §371 of International Application No. PCT/AU04/01383, filed Oct 11, 2004 and claims the benefit of Australian Application Nos. 2003905551, filed Oct. 10, 2003 and 2003906658, filed Dec. 1, 2003, the disclosures of which are incorporated by reference in their entirety.

BACKGROUND OF THE INVENTION

1. Field of the Invention

The present invention relates generally to the modulation of hyaluronan (HA) synthesis and degradation. More particularly, the present invention provides compositions and methods for modulating the expression of genetic material encoding HA synthase (HAS) and other enzymes or receptors primarily involved in hyaluronan metabolism; or modulating the proteins that synthesise or degrade hyaluronan including HAS function or activity. The compositions include or comprise nucleic acid molecules and interactive molecules such as antibodies and small molecule inhibitors and HAS substrate analogs. The present invention further contemplates modulation of cellular proliferation, useful in the prophylaxis and/or treatment of inflammatory disorders including hyperproliferative conditions, such as but not limited to, cancer and psoriasis 2. Description of the Prior Art Bibliographic details of the publications referred to in this specification are also collected at the end of the description.

Reference to any prior art in this specification is not, and should not be taken as, an acknowledgment or any form of suggestion that this prior art forms part of the general knowledge in any country.

Inflammatory conditions represent a major causative factor in numerous medically significant disorders. Inflammation can result from a range of stimuli from outside or within the body. However, these stimuli trigger cells and physiological processes within a host environment. Whilst a substantial amount of research has been undertaken to investigate the cellular and cytokine nature of inflammatory processes, less is known about other possible participants in inflammation.

One such class of participants is transmembrane proteins. Transmembrane proteins are involved in a range of signalling activities and many have anzymic activity.

Hyaluronan (HA) metabolism is an intricate balance between the rate of HA synthesis and degradation where depending upon the physiological role being played by the HA, the simulateneous synthesis and degradtion is carefully controlled. Hyaluronan is synthesised by a family of distinct yet related transmembrane proteins termed hyaluronan synthase (HAS) isoforms HAS1, 2 and 3, which can be distinguished from one another with respect to temporal and differential expression during mouse embryogenesis and in mature tissues, respectively and also in the molecular weight of the HA produced. The extracellular matrix polysaccharide HA or its acidic form, hyaluronic acid, is a linear, high molecular weight polymer comprised of repeating disaccharide units of (β1-3) D-glucuronate-β1-4)N-acetyl-D-glucosamine (Weissman & Meyer, *J. Am. Chem. Soc.*76: 1753, 1954). Hyaluronan is degraded by a family of enzymes known as hyaluronidases which are currently termed HYAL1, HYAL2, HYAL3 and PH-20, where like the enzymes which produce HA are also distinguished from one another with respect to temporal and differential expression during different physiological processes and disease states.

In work leading up to the present invention, it was observed that HAS and HYAL are differentially expressed under various physiological conditions. In particular, they were up-regulated during disease conditions such as an inflammatory condition or cancer. HAS, and in particular, HAS1, 2 and/or 3 and HYAL1, 2 and/or 3 represent useful drug targets.

SUMMARY OF THE INVENTION

Throughout the specification, unless the context requires otherwise, the word "comprise", or variations such as "comprises" or "comprising", will be understood to imply the inclusion of a stated element or integer or group of elements or integers but not to the exclusion of any other element or integer or group of elements or integers.

Nucleotide and amino acid sequences are referred to by a sequence identifier number (SEQ ID NO:). The SEQ ID NOs: correspond numerically to the sequence identifiers <400>1 (SEQ ID NO:1), <400>2 (SEQ ID NO:2), etc. A summary of the sequence identifier numbers is provided in Table 1. A sequence listing is provided after the claims.

The present invention is directed to compounds, such as nucleic acid and nucleic acid-like oligomer compounds or complexes comprising same, which are targeted to a nucleic acid encoding HAS and/or HYAL a nucleic acid molecule required for or which facilitates expression of HAS and/or HYAL-encoding material as well as compounds such as interactive molecules including antibodies or recombinant or chimeric or derivative forms thereof or small molecules which are specific for HAS and/or HYAL and which antahonize HAS and/or HYAL function or activity. The nucleic acid and nucleic acid-like oligomers or complexes comprising same, conveniently target to a nucleic acid encoding an isoform of HAS such as HAS1, HAS2 and/or HAS3. The nucleic acid and nucleic acid-like oligomers or complexes comprising same, conveniently target to a nucleic acid encoding an isoform of HYAL such as HYAL1, HYAL2, HYAL3 and/or PH-20. Preferred interactive molecules are antibodies such as monoclonal or polyclonal antibodies. Pharmaceutical and other compositions comprising the compounds of the subject invention are also provided. Methods of screening for modulators of HAS and HYAL gene expression in cells, tissues or animals are also contemplated. Methods of treating an animal, particularly a human, suspected of having or being prone to a disease or condition associated with HA levels or HAS gene and HYAL gene expression are also set forth herein. Such methods comprise administering a therapeutically or prophylactically effective amount of one or more of the compounds or compositions of the present invention to the subject of need of treatment or suspected of needing prophylactic treatment.

The present invention provides, therefore, in one embodiment, anti-sense, sense, siRNA, RNAi, ribozymes and DNAzymes which selectively reduce directly or indirectly, HAS and HYALgene expression. In another embodiment, the present invention provides antibodies or Fab, chimeric recombinant or derivative forms thereof.

Accordingly, one aspect of the present invention is directed to an isolated compound capable of reducing the level of hyaluronan synthase (HAS) or function or activity of HAS. Accordingly, one aspect of the present invention is directed to an isolated compound capable of reducing the level of hyaluronidases (HYAL) or function or activity of HYAL.

TABLE 1

Summary of sequence identifiers

| SEQUENCE ID NO: | DESCRIPTION |
|---|---|
| 1 | Sense primer for human HAS2 |
| 2 | Antisense primer for human HAS2 |
| 3 | Primer for PCINeo |
| 4 | Sense primer for GSP2 |
| 5 | Sense primer for GSP4 |
| 6 | Sense primer for HAS1 |
| 7 | Antisense primer for HAS1 |
| 8 | Sense primer for HAS2 |
| 9 | Sense primer for HAS2 |
| 10 | Antisense primer for HAS2 |
| 11 | Sense primer for HAS2 |
| 12 | Sense primer for HAS3 |
| 13 | Antisense primer for HAS3 |
| 14 | Sense primer for HAS3 |
| 15 | Sense primer for GAPDH |
| 16 | Antisense primer for GAPDH |
| 17 | Sense primer for GAPDH |
| 18 | Sense primer for HYAL1 |
| 19 | Antisense primer for HYAL1 |
| 20 | Sense primer HYAL2 |
| 21 | Antisense primer HYAL2 |
| 22 | Sense primer HYAL3 |
| 23 | Antisense primer HYAL3 |
| 24 | Immunising peptide HAS418 |
| 25 | Immunising peptide HAS419 |
| 26 | Immunising peptide HAS421 |
| 27 | Sense primer for HAS1 |
| 28 | Sense primer for HAS2 |
| 29 | Sense primer for HAS3 |
| 30 | Sense primer for GAPDH |
| 31 | Sense primer for HYAL1 |
| 32 | Sense primer for HYAL2 |
| 33 | Sense primer for HYAL3 |
| 34 | Antisense primer for HAS1 |
| 35 | Antisense primer for HAS2 |
| 36 | Antisense primer for HAS3 |
| 37 | Antisense primer for GAPDH |
| 38 | Antisense primer for HYAL1 |
| 39 | Antisense primer for HYAL2 |
| 40 | Antisense primer for HYAL3 |
| 41 | Hybridisation probe for HAS1 |
| 42 | Hybridisation probe for HAS2 |
| 43 | Hybridisation probe for HAS3 |
| 44 | Hybridisation probe for GAPDH |
| 45 | Sense primer for HAS2 |
| 46 | Antisense primter for HAS2 |
| 47 | Primer for pCL-neo |
| 48 | GSP2 sense primer |
| 49 | GSP4 sense primer |
| 50 | Alu sense primer |
| 51 | Alu antisense primer |

BRIEF DESCRIPTION OF THE FIGURES

(FIG. 1A, B) MDA-MB 453 cell line, (FIGS. 1C, D) MDA-MB 231, (FIGS. 1E, F) BT-549 and (FIGS. 1G, H) Hs578T. To qualitate the HA produced by the cell lines cultures were treated with 400 µg/ml dextran sulphate (●-●) and for the identification of HA degradation products the cultures did not contain dextran sulphate (○-○).

DETAILED DESCRIPTION OF THE PREFERRED EMBODIMENTS

Figure 1:
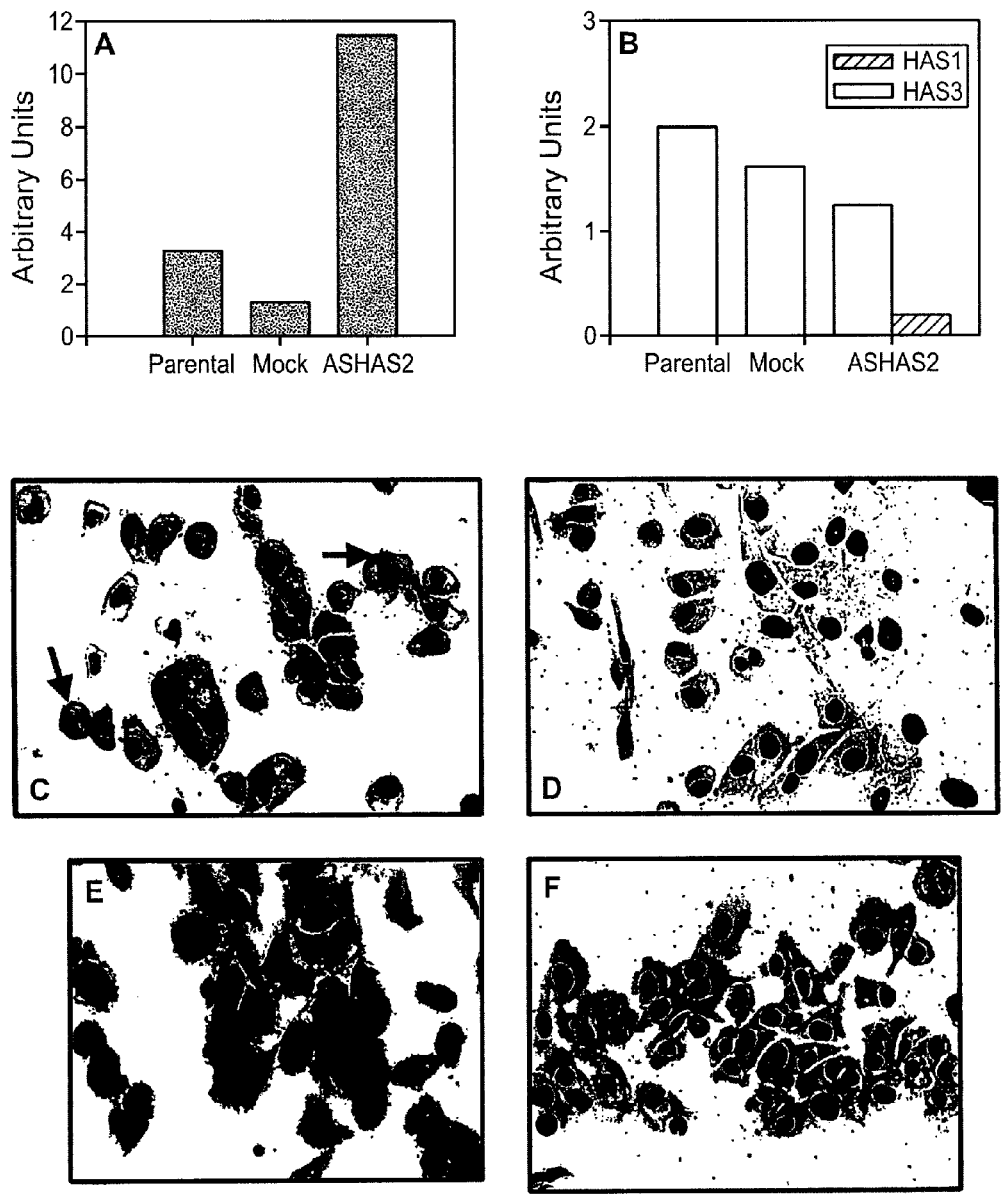
FIG. 1 is a graphical and photographical representation of Real time RT-PCR quantitation of mRNA expression of the HAS family and immunodetection of HAS2 in parental MDA-MB 231 and antisense transfectants. A: Expression and quantification of mRNA for HAS2 in parental MDA-MB 231, mock (pClneo vector only) and stable clones of MDA MB-231 expressing antisense mRNA to HAS2 (ASHAS2). B: Expression and quantification of HAS1 and HAS3 in parental, mock and ASHAS2 transfectants. C: Immunodetection of HAS2 protein on parental MDA-MB 231 and, D: on stable clones expressing antisense mRNA to HAS2. Photographs of parental and ASHAS2 transfectants at 400× magnification. In parental cells note the periphery of the cell stains positively for the HAS2 epitope (arrows) that is absent in the antisense transfected, Panel D, E and F: Immunoreactivity of parental MDA MB231 to CD44 (panel E) and antisense transfected MDA-MB 231 (Panel F). Note the complete lack of staining in the antisense transfected cells.

The present invention employs compounds, preferably nucleotides and similar species for use in modulating the function of HAS or the expression of nucleic acid molecules encoding HAS and, in a particular embodiment, HAS1, HAS2 and/or HAS3 or of a nucleic acid molecule required for or which facilitate expression of HAS genetic material (e.g. a promoter region). As used herein, reference to HAS includes any molecule with the same function. In a preferred aspect, reference to "HAS", includes reference to the isoforms HAS1, HAS2 or HAS3. In a particularly preferred embodiment, the HAS is HAS2 or HAS3. The present invention also employs compounds, preferably nucleotides and similar species for use in modulating the function of HYAL or the expression of nucleic acid molecules encoding HYAL and, in a particular embodiment, HYAL1, HYAL2, HYAL3 and/or PH-20 of a nucleic acid molecule required for or which facilitate expression of HYAL genetic material (e.g. a promoter region). As used herein, reference to HYAL includes any molecule with the same function. In a preferred aspect, reference to "HYAL", includes reference to the isoforms HYAL1, HYAL2, HYAL3 and/or PH-20. In a particularly preferred embodiment, the HYAL is HYAL1, HYAL2 or HYAL3.

Accordingly, one aspect of the present invention provides an isolated compound capable of reducing the level of hyaluronan synthase (HAS) and/or hyaluronidase or the function or activity of HAS and or HYAL.

In one embodiment, the compounds of the present invention down regulate expression of HAS and HYAL genetic material. This is accomplished by providing oligonucleotides which specifically hybridize or otherwise interact with one or more nucleic acid molecules encoding HAS and/or HYAL or a nucleic acid molecule required for or which facilitates HAS and/or HYAL gene expression. As used herein, the terms "nucleic acid" and "nucleic acid molecule encoding HAS or HYAL" have been used for convenience to encompass DNA encoding HAS, RNA (including pre-mRNA and mRNA or portions thereof) transcribed from such DNA, and also cDNA derived from such RNA. The hybridization or interaction of a compound of the present invention with a target nucleic acid may encompass antisense or sense targeting. The latter is referred to herein as sense suppression. Consequently, the present invention provides for antisense or sense inhibition. Such antisense or sense inhibition is typically based upon hydrogen bonding-based hybridization of oligonucleotide strands or segments such that at least one strand or segment is cleaved, degraded, or otherwise rendered inoperable. Alternatively, post-transcriptional gene silencing (PTGS) may be achieved using sense suppression (formally known as co-suppression). In yet another alternative, complexes comprising nucleic acid molecules and proteins (e.g. ribonucleases) such as RNAi, ribozymes and DNAzymes may be employed.

The target nucleic acid molecules include the HAS and HYAL coding sequences, a promoter region, a 3' regulatory region or a nucleotide sequence, the expression of which, facilitates or inhibits HAS or HYAL gene expression (e.g. a regulatory gene, activator gene or reporter gene).

The functions of the nucleic acid molecule to be down regulated include replication, transcription and/or translation. Where the nucleic acid molecule is RNA, the compounds may target translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA. One preferred result of such interference with target nucleic acid function is reduction in the level of expression of HAS and/or HYAL genetic material and, hence, levels of HAS and/or HYAL. Inhibition is the preferred form of modulation of expression and mRNA is the preferred target nucleic acid.

In the context of this invention, "hybridization" means the pairing of complementary strands of nucleic acids. In the present invention, the preferred mechanism of pairing involves hydrogen bonding, which may be Watson-Crick, Hoogsteen or reversed Hoogsteen hydrogen bonding, between complementary nucleoside or nucleotide bases (nucleotides) of the strands of oligomeric compounds. For example, adenine and thymine are complementary nucleotides which pair through the formation of hydrogen bonds. Hybridization can occur under varying circumstances.

An antisense or sense compound is specifically hybridizable when binding of the compound to the target nucleic acid interferes with the normal function of the target nucleic acid to cause a loss of activity, and there is a sufficient degree of complementarity to avoid non-specific binding of the antisense or sense compound to non-target nucleic acid sequences under conditions in which specific binding is desired, i.e., under physiological conditions in the case of in vivo assays or therapeutic treatment, and under conditions in which assays are performed in the case of in vitro assays.

A sense compound includes RNAi or other complex which includes PTGS.

In the present invention the phrase "stringent hybridization conditions" or "stringent conditions" refers to conditions under which a compound of the invention will hybridize to its target sequence, but to a minimal number of other sequences. Stringent conditions are sequence-dependent and will be different in different circumstances and in the context of this invention, "stringent conditions" under which oligomeric compounds hybridize to a target sequence are determined by the nature and composition of the oligomeric compounds and the assays in which they are being investigated.

"Complementary," as used herein, refers to the capacity for precise pairing between two nucleotides of an oligomeric compound. For example, if a nucleotide at a certain position of an oligonucleotide (an oligomeric compound), is capable of hydrogen bonding with a nucleotide at a certain position of a target nucleic acid, said target nucleic acid being a DNA, RNA, or oligonucleotide molecule, then the position of hydrogen bonding between the oligonucleotide and the target nucleic acid is considered to be a complementary position. The oligonucleotide and the further DNA, RNA, or oligonucleotide molecule are complementary to each other when a sufficient number of complementary positions in each molecule are occupied by nucleotides which can hydrogen bond with each other. Thus, "specifically hybridizable" and "complementary" are terms which are used to indicate a sufficient degree of precise pairing or complementarity over a sufficient number of nucleotides such that stable and specific binding occurs between the oligonucleotide and a target nucleic acid.

It is understood in the art that the sequence of an antisense or sense compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure or hairpin structure). It is preferred that the antisense or sense compounds of the present invention comprise at least 70% sequence complementarity to a target region within the target nucleic acid, such as 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100% complementarity to the nucleic acid sequence to which they are targeted. For example, an antisense or sense compound in which 18 out of 20 nucleotides of the antisense or sense compound are complementary to a target region, and would therefore specifically hybridize, would represent 90 percent complementarity. In this example, the remaining non-complementary nucleotides may be clustered or interspersed with complementary nucleotides and need not be contiguous to each other or to complementary nucleotides. As such, an antisense or sense compound which is 18 nucleotides in length having 4 (four) noncomplementary nucleotides which are flanked by two regions of complete complementarity with the target nucleic acid would have 77.8% overall complementarity with the target nucleic acid and would thus fall within the scope of the present invention. Percent complementarity of an antisense or sense compound with a region of a target nucleic acid can be determined routinely using BLAST programs (basic local alignment search tools) and PowerBLAST programs known in the art (Altschul et al., *J. Mol. Biol.* 215: 403-410, 1990; Zhang and Madden, *Genome Res.* 7: 649-656, 1997).

According to the present invention, compounds include antisense or sense nucleic acids, antisense or sense oligomeric compounds, antisense or sense oligonucleotides, ribozymes, sense oligonucleotides, full-length sense molecules, external guide sequence (EGS) oligonucleotides, alternate splicers, primers, probes, and other oligomeric compounds which hybridize to at least a portion of the target nucleic acid. As such, these compounds may be introduced in the form of single-stranded, double-stranded, circular or hairpin oligomeric compounds and may contain structural elements such as internal or terminal bulges or loops. Once introduced to a system, the compounds of the invention may elicit the action of one or more enzymes or structural proteins to effect modification of the target nucleic acid.

As used herein, an "antisense" or "sense" molecule includes an RNA molecule which, by binding to a complementary sequence in either RNA or DNA, inhibits the function and/or completion of synthesis of the latter molecule. It is involved in various regulatory systems in vivo. Artificial antisense or sense RNAs have been used to inhibit translation of specific mRNA molecules both in living cells (eukaryotic and bacterial) and in cell-free systems.

One non-limiting example of such an enzyme is RNAse H, a cellular endonuclease which cleaves the RNA strand of an RNA:DNA duplex. It is known in the art that single-stranded antisense or sense compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While the preferred form of antisense or sense compounds are single-stranded oligonucleotides, in many species the introduction of double-stranded structures, such as double-stranded RNA (dsRNA) molecules, miRNAs, short-interfering RNA molecules (siRNA) and full-length dsRNAs.

Small interfering RNAs (siRNAs) have an integral role in the phenomenon of RNA interference (RNAi). In RNAi, dsRNAs introduced into certain organisms or cells are degraded into approximately 22 nucleotide fragments. These 22 nucleotide siRNA molecules then bind to the complementary portion of their target mRNA and tag it for degradation.

A second class of regulatory small RNAs contemplated by the present invention are referred to as small temporal RNAs. Approximately 22 nucleotide lin-4 and let-7 RNAs are example of this group. These RNA molecules have a role in temporal regulation of *C. elegans* development. These are initially processed from an approximate 70 nucleotide ssRNA transcript folded into a stem loop structure. After processing, these stRNAs are thought to prevent translation of their target mRNAs by binding to the targets complementary 3' untranslated regions (UTRs). Dicer, RNAase enzyme processes both the types of RNAs (Grishok et al. *Science* 287 (562):2494-2497, 2000).

In the context of this invention, the term "oligomeric compound" refers to a polymer or oligomer comprising a plurality of monomeric units. In the context of this invention, the term "oligonucleotide" refers to an oligomer or polymer of ribonucleic acid (RNA) or deoxyribonucleic acid (DNA) or mimetics, chimeras, analogs and homologs thereof. This term includes oligonucleotides composed of naturally occurring nucleotides, sugars and covalent internucleoside (backbone) linkages as well as oligonucleotides having non-naturally occurring portions which function similarly. Such modified or substituted oligonucleotides are often preferred over native forms because of desirable properties such as, for example, enhanced cellular uptake, enhanced affinity for a target nucleic acid and increased stability in the presence of nucleases.

While oligonucleotides are a preferred form of the compounds of this invention, the present invention comprehends other families of compounds as well, including but not limited to oligonucleotide analogs and mimetics such as those herein described.

The compounds in accordance with this invention preferably comprise from about 10 to about 2000 nucleotides (i.e. from about 10 to about 2000 linked nucleosides). One of ordinary skill in the art will appreciate that the invention embodies compounds of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680,690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1080, 1090, 1100, 1110, 1120, 1130, 1140, 1150, 1160, 1170, 1180, 1190, 1200, 1210, 1220, 1230, 1240, 1250, 1260, 1270, 1280, 1290, 1300, 1310, 1320, 1330, 1340, 1350, 1360, 1370, 1380, 1390, 1400, 1410, 1420, 1430, 1440, 1450, 1460, 1470, 1480, 1490, 1500, 1510, 1520, 1530, 1540, 1550, 1560, 1570, 1580, 1590, 1600, 1610, 1620, 1630, 1640, 1650, 1660, 1670, 1680, 1690, 1700, 1710, 1720, 1730, 1740, 1750, 1760, 1770, 1780, 1790, 1800, 1810, 1820, 1830, 1840, 1850, 1860, 1870, 1880, 1890, 1900, 1910, 1920, 1930, 1940, 1950, 1960, 1970, 1980, 1990 or 2000 nucleotides in length:

Antisense or sense compounds 10-2000 nucleotides in length comprising a stretch of at least ten (10) such as 10, 11, 12, 13, 14, 15, 16, 17, 18, 19, 20, 21, 22, 23, 24, 25, 26, 27, 28, 29 or 30 consecutive nucleotides selected from within the illustrative antisense or sense compounds are considered to be suitable antisense or sense compounds as well.

Exemplary preferred antisense or sense compounds include oligonucleotide sequences that comprise at least the 10 consecutive nucleotides from the 5'-terminus of one of the illustrative preferred antisense or sense compounds (the remaining nucleotides being a consecutive stretch of the same oligonucleotide beginning immediately upstream of the 5'-terminus of the antisense or sense compound which is specifically hybridizable to the target nucleic acid and continuing until the oligonucleotide contains about 10 to about 2000 nucleotides). Similarly preferred antisense or sense compounds are represented by oligonucleotide sequences that comprise at least the 10 consecutive nucleotides from the 3'-terminus of one of the illustrative preferred antisense or sense compounds (the remaining nucleotides being a consecutive stretch of the same oligonucleotide beginning immediately downstream of the 3'-terminus of the antisense or sense compound which is specifically hybridizable to the target nucleic acid and continuing until the oligonucleotide contains about 10 to about 2000 nucleotides). One having skill in the art armed with the preferred antisense or sense compounds illustrated herein will be able, without undue experimentation, to identify further preferred antisense or sense compounds.

Candidate compounds are also referred to herein as "lead" compounds. In the present invention, the target nucleic acid encodes HAS or HYAL or is a gene required for HAS or HYAL gene expression. As indicated above, the term "HAS" includes isoforms HAS1, HAS2 and HAS3. HAS2 and HAS3 are particularly preferred. As indicated above, the term "HYAL" includes isoforms HYAL1, HYAL2, HYAL3 and PH-20. HYAL1, HYAL2 and HYAL3 are particularly preferred.

The targeting process usually also includes determination of at least one target region, segment, or site within the target nucleic acid for the antisense or sense interaction to occur such that the desired effect, e.g., to reduce expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid.

Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes). It is also known in the art that eukaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding HAS, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions which may be targeted effectively with the antisense or sense compounds of the present invention.

The open reading frame (ORF) or "coding region," which is known in the art to refer to the region between the translation initiation codon and the translation termination codon, is also a region which may be targeted effectively. Within the context of the present invention, a preferred region is the intragenic region encompassing the translation initiation or termination codon of the open reading frame (ORF) of a gene.

Other target regions include the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene), and the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of a mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. It is also preferred to target the 5' cap region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. Targeting splice sites, i.e., intron-exon junctions or exon-intron junctions, may also be particularly useful in situations where aberrant splicing is implicated in disease, or where an overproduction of a particular splice product is implicated in disease. Aberrant fusion junctions due to rearrangements or deletions are also preferred target sites. mRNA transcripts produced via the process of splicing of two (or more) mRNAs from different gene sources are known as "fusion transcripts". It is also known that introns can be effectively targeted using antisense or sense compounds targeted to, for example, DNA or pre-mRNA.

It is also known in the art that alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also preferred target nucleic acids.

The locations on the target nucleic acid to which the preferred antisense or sense compounds hybridize are hereinbelow referred to as "preferred target segments." As used herein the term "preferred target segment" is defined as at least a 10-nucleotide portion of a target region to which an active antisense or sense compound is targeted. While not wishing to be bound by theory, it is presently believed that these target segments represent portions of the target nucleic acid which are accessible for hybridization.

While the specific sequences of certain preferred target segments are set forth herein, one of skill in the art will recognize that these serve to illustrate and describe particular embodiments within the scope of the present invention. Additional preferred target segments may be identified by one having ordinary skill.

Target segments 10-2000 nucleotides in length comprising a stretch of at least ten (10) consecutive nucleotides selected from within the illustrative preferred target segments are considered to be suitable for targeting as well.

Target segments can include DNA or RNA sequences that comprise at least the 8 consecutive nucleotides from the 5'-terminus of one of the illustrative preferred target segments (the remaining nucleotides being a consecutive stretch of the same DNA or RNA beginning immediately upstream of the 5'-terminus of the target segment and continuing until the DNA or RNA contains about 10 to about 2000 nucleotides). Similarly preferred target segments are represented by DNA or RNA sequences that comprise at least the 10 consecutive nucleotides from the 3'-terminus of one of the illustrative preferred target segments (the remaining nucleotides being a consecutive stretch of the same DNA or RNA beginning immediately downstream of the 3'-terminus of the target segment and continuing until the DNA or RNA contains about 10 to about 2000 nucleotides). One having skill in the art armed with the preferred target segments illustrated herein will be able, without undue experimentation, to identify further preferred target segments.

Once one or more target regions, segments or sites have been identified, antisense or sense compounds are chosen which are sufficiently complementary to the target, i.e., hybridize sufficiently well and with sufficient specificity, to give the desired effect, i.e. to reduce HAS and/or HYAL gene expression or levels of HAS and/or HYAL.

In a further embodiment, the "preferred target segments" identified herein may be employed in a screen for additional compounds that modulate the expression of the HAS and/or HYAL gene. "Modulators" are those compounds that decrease or increase the expression of a nucleic acid molecule encoding HAS and/or HYAL andwhich comprise at least a 10-nucleotide portion which is complementary to a preferred target segment. The screening method comprises the steps of contacting a preferred target segment of a nucleic acid molecule encoding HAS and/or HYAL with one or more candidate modulators, and selecting for one or more candidate modulators which decrease or increase the expression of a nucleic acid molecule encoding HAS and/or HYAL. Once it is shown that the candidate modulator or modulators are capable of modulating (e.g. either decreasing or increasing) the expression of a nucleic acid molecule encoding HAS and/or HYAL the modulator may then be employed in further investigative studies of the function of HAS and/or HYAL, or for use as a research, diagnostic, or therapeutic agent in accordance with the present invention.

The preferred target segments of the present invention may be also be combined with their respective complementary antisense or sense compounds of the present invention to form stabilized double-stranded (duplexed) oligonucleotides.

Such double stranded oligonucleotide moieties have been shown in the art to modulate target expression and regulate translation as well as RNA processsing via an antisense or sense mechanism. Moreover, the double-stranded moieties may be subject to chemical modifications (Fire et al., *Nature* 391: 806-811, 1998; Timmons and Fire, *Nature* 395: 854, 1998; Timmons et al., *Gene* 263: 103-112, 2001; Tabara et al., *Science* 282: 430-431, 1998; Montgomery et al., 1998, supra; Tuschl et al., *Genes Dev.* 13: 3191-3197, 1999; Elbashir et al., *Nature*, 411: 494-498, 2001; Elbashir et al., *Genes Dev.* 15: 188-200, 2001). For example, such double-stranded moieties have been shown to inhibit the target by the classical hybridization of antisense or sense strand of the duplex to the target, thereby triggering enzymatic degradation of the target (Tijsterman et al., 2002, supra).

As indicated above, the present invention further contemplates interactive molecules specific for a HAS, including one or more of HAS1, 2 and/or 3 and which modifiy HAS function or activity. As indicated above, the present invention further contemplates interactive molecules specific for a HYAL, including one or more of HYAL1, HYAL2, HYAL3 and/or PH-20 and which modifiy HYAL function or activity.

The present invention provides, therefore, antagonists of HAS and/or HYAL function or activity. Such antagonists are useful in reducing the effects of HAS and/or HYAL and hence reducing or elevating levels of HA.

The term "antagonist" includes a modified HAS and/or HYAL molecule or HAS and/or HYAL substrate as well as their homologs or chemical equivalent or analogs. In a preferred embodiment, it encompasses interactive molecules such as antibodies and small molecule inhibitors.

The present invention provides, therefore, interactive molecules such as but not limited to antibodies and other immunoglobulins including fragments, derivatives, antigen binding portions, recombinant forms, chimeric forms as well as deimmunized including humanized forms thereof directed to the subject modulators and small molecule inhibitors.

Accordingly, in a preferred aspect the present invention provides antibodies that bind, interact or otherwise associate with HAS and/or HYAL and which reduce HAS and/or HYAL function or activity.

The antibodies maybe monoclonal or polyclonal antibodies, although, monoclonal antibodies are preferred. Generally, the antibodies are in isolated, homogenous or fully or partially purified form.

The antibodies may also be humanized or chimeric or are human antibodies suitable for administration to humans. These include humanized antibodies prepared, for example, from murine monoclonal antibodies, and human monoclonal antibodies which may be prepared, for example, using transgenic mice as described below, or by phage display. A "humanized" antibody includes a deimmunized antibody.

Preferably, antibodies are raised against a HAS such as HAS1, 2 or 3 or immunogenic parts thereof or immunologically homologous molecules. Preferably, antibodies are raised against a HYAL such as HYAL1, 2 or 3 or immunogenic parts thereof or immunologically homologous molecules.

Reference to an "antibody" or "antibodies" includes reference to all the various forms of antibodies, including but not limited to: full antibodies (e.g. having an intact Fc region), including, for example, monoclonal antibodies; antigen-binding antibody fragments, including, for example, Fv, Fab, Fab' and F(ab')$_2$ fragments; humanized antibodies; human antibodies (e.g., produced in transgenic animals or through phage display); and immunoglobulin-derived polypeptides produced through genetic engineering techniques. Unless otherwise specified, the terms "antibody" or "antibodies" and as used herein encompasses both full antibodies and antigen-binding fragments thereof.

Unless stated otherwise, specificity in respect of an antibody of the present invention is intended to mean that the antibody binds substantially only to its target antigen with no appreciable binding to unrelated proteins. However, it is possible that an antibody will be designed or selected to bind to two or more related proteins. A related protein includes different splice variants or fragments of the same protein or homologous proteins from different species. Such antibodies are still considered to have specificity for those proteins and are encompassed by the present invention. The term "substantially" means in this context that there is no detectable binding to a non-target antigen above basal, i.e. non-specific, levels.

The antibodies of the present invention may be prepared by well known procedures. See, for example, Monoclonal Antibodies, Hybridomas: A New Dimension in Biological Analyses, Kennet et al. (eds.), Plenum Press, New York (1980); and Antibodies: A Laboratory Manual, Harlow and Lane (eds.), Cold Spring Harbor Laboratory Press, Cold Spring Harbor, N.Y., (1988).

One method for producing an antibody of the present invention comprises immunizing a non-human animal, such as a mouse or a transgenic mouse, with HAS and/or HYAL molecule or immunogenic parts thereof whereby antibodies directed against the HAS and/or HYAL molecule or immunogenic parts are generated in said animal. Various means of increasing the antigenicity of a particular immunogen, such as administering adjuvants or conjugated antigens, comprising the antigen against which an antibody response is desired and another component, are well known to those in the art and may be utilized. Immunizations typically involve an initial immunization followed by a series of booster immunizations. Animals may be bled and the serum assayed for antibody titer. Animals may be boosted until the titer plateaus. Conjugates may be made in recombinant cell culture as protein fusions. Also, aggregating agents such as alum are suitably used to enhance the immune response.

Both polyclonal and monoclonal antibodies can be produced by this method. The methods for obtaining both types of antibodies are well known in the art. Polyclonal antibodies are less preferred but are relatively easily prepared by injection of a suitable laboratory animal with an effective amount of a modified LIF molecule, or immunogenic parts thereof, collecting serum from the animal and isolating modified LIF molecule specific antibodies by any of the known immunoadsorbent techniques. Antibodies produced by this technique are generally less favoured, because of the potential for heterogeneity of the product.

The use of monoclonal antibodies is particularly preferred because of the ability to produce them in large quantities and the homogeneity of the product. Monoclonal antibodies may be produced by conventional procedures.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature* 256:495 (1975), or may be made by recombinant DNA methods (see, e.g., U.S. Pat. No. 4,816,567). The "monoclonal antibodies" may also be isolated from phage antibody libraries using for example, the techniques described in Clackson et al., *Nature* 352:624-628, 1991 and Marks et al., *J. Mol. Biol.* 222:581-597, 1991.

The present invention contemplates a method for producing a hybridoma cell line which comprises immunizing a non-human animal, such as a mouse or a transgenic mouse, with a HAS or immunogenic parts thereof; harvesting spleen cells from the immunized animal; fusing the harvested spleen cells to a myeloma cell line to generate hybridoma cells; and identifying a hybridoma cell line that produces a monoclonal antibody that binds to a HAS or HYAL.

Such hybridoma cell lines and the HAS or HYAL monoclonal antibodies produced by them are encompassed by the present invention. Monoclonal antibodies secreted by the hybridoma cell lines are purified by conventional techniques. Hybridomas or the monoclonal antibodies produced by them may be screened further to identify monoclonal antibodies with particularly desirable properties.

The HAS and/or HYAL molecule or immunogenic part thereof that may be used to immunize animals in the initial stages of the production of the antibodies of the present invention may be from any mammalian source.

Antigen-binding fragments of antibodies of the present invention may be produced by conventional techniques. Examples of such fragments include, but are not limited to, Fab, Fab', F(ab')$_2$ and Fv fragments, including single chain Fv fragments (termed sFv or scFv). Antibody fragments and derivatives produced by genetic engineering techniques, such as disulphide stabilized Fv fragments (dsFv), single chain variable region domain (Abs) molecules, minibodies and diabodies are also contemplated for use in accordance with the present invention.

Such fragments and derivatives of monoclonal antibodies directed against HAS and/or HYAL molecules may be prepared and screened for desired properties, by known techniques, including the assays described herein. Certain of the techniques involve isolating DNA encoding a polypeptide chain (or a portion thereof) of a mAb of interest, and manipulating the DNA through recombinant DNA technology. The DNA may be fused to another DNA of interest, or altered (e.g. by mutagenesis or other conventional techniques) to add, delete, or substitute one or more amino acid residues, for example.

DNA encoding antibody polypeptides (e.g. heavy or light chain, variable region only or full length) may be isolated from B-cells of mice that have been immunized with modified LIF molecules. The DNA may be isolated using conventional procedures. Phage display is another example of a known technique whereby derivatives of antibodies may be prepared. In one approach, polypeptides that are components of an antibody of interest are expressed in any suitable recombinant expression system, and the expressed polypeptides are allowed to assemble to form antibody molecules.

Single chain antibodies may be formed by linking heavy and light chain variable region (Fv region) fragments via an amino acid bridge (short peptide linker), resulting in a single polypeptide chain. Such single-chain Fvs (scFvs) have been prepared by fusing DNA encoding a peptide linker between DNAs encoding the two variable region polypeptides (VL and VH). The resulting antibody fragments can form dimers or trimers, depending on the length of a flexible linker between the two variable domains (Korn et al., *Protein Engineering* 10: 423, 1997). Techniques developed for the production of single chain antibodies include those described in U.S. Pat. No. 4,946,778; Bird (*Science* 242: 423, 1988), Huston et at (*Proc. Natl. Acad. Sci. USA* 85: 5879, 1988) and Ward et al. (*Nature* 334: 544, 1989). Single chain antibodies derived from antibodies provided herein are encompassed by the present invention.

In one embodiment, the present invention provides antibody fragments or chimeric, recombinant or synthetic forms of the antibodies of the present invention that bind to a HAS such as HAS1, 2 and/or 3.

Techniques are known for deriving an antibody of a different subclass or isotype from an antibody of interest, i.e., subclass switching. Thus, IgG1 or IgG4 monoclonal antibodies may be derived from an IgM monoclonal antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g. DNA encoding the constant region of an antibody of the desired isotype.

The monoclonal production process described above may be used in animals, for example mice, to produce monoclonal antibodies. Conventional antibodies derived from such animals, for example murine antibodies, are known to be generally unsuitable for administration to humans as they may cause an immune response. Therefore, such antibodies may need to be modified in order to provide antibodies suitable for administration to humans. Processes for preparing chimeric and/or humanized antibodies are well known in the art and are described in further detail below.

The monoclonal antibodies herein specifically include "chimeric" antibodies in which the variable domain of the heavy and/or light chain is identical with or homologous to corresponding sequences in antibodies derived from a non-human species (e.g., murine), while the remainder of the chain(s) is identical with or homologous to corresponding sequences in antibodies derived from humans, as well as fragments of such antibodies, so long as they exhibit the desired biological activity (U.S. Pat. No. 4,816,567; and Morrison et al., *Proc. Natl. Acad. Sci. USA* 81:6851-6855, 1984).

"Humanized" forms of non-human (e.g., murine) antibodies are chimeric antibodies which contain minimal sequence derived from the non-human immunoglobulin. For the most part, humanized antibodies are human immunoglobulins (recipient antibody) in which the complementarity determining regions (CDRs) of the recipient are replaced by the corresponding CDRs from a non-human species (donor antibody) such as mouse, rat, rabbit or nonhuman primate having the desired properties, for example specificity, and affinity. In some instances, framework region residues of the human immunoglobulin are replaced by corresponding non-human residues. Furthermore, humanized antibodies may comprise residues which are not found in the recipient antibody or in the donor antibody.

These modifications are made to further refine antibody performance. In general, the humanized antibody will comprise substantially all of at least one, and typically two, variable domains, in which all or substantially all of the complementarity determining regions correspond to those of a non-human immunoglobulin and all or substantially all of the framework region residues are those of a human immunoglobulin sequence. The humanized antibody optionally also will comprise at least a portion of an immunoglobulin constant region (Fc), typically that of a human immunoglobulin. For further details, see Jones et al., *Nature* 321:522-525, 1986; Reichmann et al., *Nature* 332:323-329, 1988; Presta, *Curr. Op. Struct. Biol.* 2:593-596, 1992; Liu et al., *Proc. Natl. Acad. Sci. USA* 84: 3439, 1987; Larrick et al., *Bio/Technology* 7: 934, 1989; and Winter and Harris, *TIPS* 14: 139, 1993.

The complementarity determining regions (CDRs) of a given antibody may be readily identified, for example using the system described by Kabat et al. in Sequences of Proteins of Immunological Interest, 5th Ed., US Dept. of Health and Human Services, PHS, NIH, NIH Publication No. 91-3242, 1991).

Procedures for generating human antibodies in non-human animals have been developed and are well known to those skilled in the art. For example, transgenic mice into which genetic material encoding one or more human immunoglobulin chains has been introduced may be used to produce the antibodies of the present invention. Antibodies produced in the animals incorporate human immunoglobulin polypeptide chains encoded by the human genetic material introduced into the animal. Examples of techniques for production and use of such transgenic animals are described in U.S. Pat. Nos. 5,814,318, 5,569,825, and 5,545,806, which are incorporated by reference herein.

Another method for generating human antibodies is phage display. Phage display techniques for generating human antibodies are well known to those skilled in the art, and include the methods used by companies such as Cambridge Antibody Technology and MorphoSys and which are described in International Patent Publication Nos. WO 92/01047, WO 92/20791, WO 93/06213 and WO 93/11236.

The compounds of the present invention can also be applied in the areas of drug discovery and target validation. The present invention comprehends the use of the compounds and preferred target segments identified herein in drug discovery efforts to elucidate relationships that exist between HA, HAS or HA/HAS and HA, HYAL or HA/HYAL interaction and a disease state, phenotype, or condition. These methods include detecting or modulating HAS and/or HYAL comprising contacting a sample, tissue, cell, or organism with the compounds of the present invention, measuring the nucleic acid or protein level of HAS and/or HYAL and/or a related phenotypic or chemical endpoint at some time after treatment, and optionally comparing the measured value to a non-treated sample or sample treated with a further compound of the invention. These methods can also be performed in parallel or in combination with other experiments to determine the function of unknown genes for the process of target validation or to determine the validity of a particular gene product as a target for treatment or prevention of a particular disease, condition, or phenotype.

The present invention contemplates the use of the compounds described herein as therapeutic agents to treat subjects suffering from diseases and disorders associated with HA. Subjects treated using the compositions and compounds of the present invention include any animal who may benefit from such treatment. These include, without limitation, humans, marmosets, orangutans and gorillas, livestock animals (e.g. cows, sheep, pigs, horses, donkeys), laboratory test animals (e.g. mice, rats, guinea pigs, hamsters, rabbits), companion animals (e.g. cats, dogs) and captured wild animals (e.g. rodents, foxes, deer, kangaroos. A particularly preferred host is a human, primate or livestock animal.

The compounds of the present invention can be utilized for diagnostics, therapeutics, prophylaxis and as research reagents and kits. Furthermore, antisense or sense oligonucleotides or antibodies to HAS and/or HYAL which are able to inhibit gene expression or HAS and/or HYAL activity with exquisite specificity, are often used by those of ordinary skill to elucidate the function of particular genes or gene products or to distinguish between functions of various members of a biological pathway.

For use in kits and diagnostics, the compounds of the present invention, either alone or in combination with other compounds or therapeutics, can be used as tools in differential and/or combinatorial analyses to elucidate expression patterns of a portion or the entire complement of genes expressed within cells and tissues.

As one non-limiting example, expression patterns within cells or tissues treated with one or more antisense or sense compounds are compared to control cells or tissues not treated with antisense or sense compounds and the patterns produced are analyzed for differential levels of gene expression as they pertain, for example, to disease association, signalling pathway, cellular localization, expression level, size, structure or function of the genes examined. In another example, similar experiments are conducted with antibodies to HAS. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.* 480: 17-24, 2000; Celis et al., *FEBS Lett.* 480: 2-16, 2000), SAGE (serial analysis of gene expression) (Madden et al., *Drug Discov. Today* 5: 415-425, 2000), READS (restriction enzyme amplification of digested cDNAs) (Prashar and Weissman, *Methods Enzymol.* 303: 258-272, 1999), TOGA (total gene expression analysis) (Sutcliffe et al., *Proc. Natl. Acad. Sci. USA* 97: 1976-1981, 2000), protein arrays and proteomics (Celis et al. 2000, supra; Jungblut et al., *Electrophoresis* 20: 2100-2110, 1999), expressed sequence tag (EST) sequencing (Celis et al., 2000, supra; Larsson et al., *J. Biotechnol.*80: 143-157, 2000), subtractive RNA fingerprinting (SuRF) (Fuchs et al., *Anal. Biochem.* 286: 91-98, 2000; Larson et al., *Cytometry* 41: 203-208, 2000), subtractive cloning, differential display (DD) (Jurecic and Belmont, *Curr. Opin. Microbiol.* 3: 316-321, 2000), comparative genomic hybridization (Carulli et al., *J. Cell Biochem. Suppl.* 31: 286-296, 1998), FISH (fluorescent in situ hybridization) techniques (Going and Gusterson, *Eur. J. Cancer,* 35: 1895-1904, 1999) and mass spectrometry methods (To, *Comb. Chem. High Throughput Screen,* 3: 235-241, 2000).

The compounds of the invention are useful for research and diagnostics, because these compounds hybridize to nucleic acids encoding HAS or HYAL or bind to HAS or HYAL itself. For example, oligonucleotides that are shown to hybridize with such efficiency and under such conditions as disclosed herein as to be effective HAS or HYAL inhibitors of HAS or HYAL gene expression inhibitors will also be effective primers or probes under conditions favoring gene amplification or detection, respectively. These primers and probes are useful in methods requiring the specific detection of nucleic acid molecules encoding HAS or HYAL and in the amplification of said nucleic acid molecules for detection or for use in further studies of HAS or its gene. Hybridization of the antisense or sense oligonucleotides, particularly the primers and probes, of the invention with a nucleic acid encoding HAS or HYAL can be detected by means known in the art. Such means may include conjugation of an enzyme to the oligonucleotide, radiolabelling of the oligonucleotide or any other suitable detection means. Similarly, antibodies may be labeled with reporter molecules including enzymes and radiolabels for imaging purposes, diagnostic purposes or quantitative purposes. Kits using such detection means for detecting the level of HAS or HYAL in a sample may also be prepared.

The specificity and sensitivity of antisense or sense compounds or antibodies are also harnessed by those of skill in the art for therapeutic uses. Such compounds have been employed as therapeutic moieties in the treatment of disease states in animals, including humans.

For therapeutics, an animal, preferably a human, suspected of having a disease or disorder which can be treated by modulating the expression of the HAS and/or HYAL gene is treated by administering antisense or sense compounds in accordance with this invention. Alternatively, antibodies may be used to inhibit HAS and/or HYAL activity. For example, in one non-limiting embodiment, the methods comprise the step of administering to the animal in need of treatment, a therapeutically effective amount of a HAS and/or HYAL gene expression inhibitor. The HAS or HYAL gene expression inhibitors of the present invention effectively inhibit the activity of the HAS and/or HYAL protein or inhibit the expression of the HAS and/or HYAL gene. In one embodiment, the activity or expression of HAS or its gene in an animal is inhibited by about 10%. Preferably, the activity or expression of HAS and/or HYAL or its gene in an animal is inhibited by about 30%. More preferably, the activity or expression of HAS and/or HYAL or its gene in an animal is inhibited by 50% or more.

For example, the reduction of the expression of the HAS and/or HYAL gene may be measured in serum, adipose tissue, skin cells, liver or any other body fluid, tissue or organ of the animal. Preferably, the cells contained within said fluids, tissues or organs being analyzed contain a nucleic acid molecule encoding a HAS and/or HYAL protein.

The present invention contemplates, therefore, methods of screening for. compounds comprising, for example, contacting a candidate compound with genetic material encoding HAS and/or HYAL including mRna or HAS or HYAL itself. The screening procedure includes assaying (i) for the presence of a complex between the drug and HAS and/or HYAL or genetic material encoding same or (ii) for an alteration in the expression levels of nucleic acid molecules encoding the HAS and/or HYAL. Whole cells may also be screened for interaction between the cell and the drug.

One form of assay involves competitive binding assays. In such competitive binding assays, the candidate compound or HAS and/or HYAL is typically labeled. Free HAS and/or HYAL is separated from any putative complex and the amount of free (i.e. uncomplexed) label is a measure of the binding of the agent being tested to target molecule. One may also measure the amount of bound, rather than free, HAS and/or HYAL. It is also possible to label the compound rather than HAS or HYAL and to measure the amount of compound binding HAS or HYAL in the presence and in the absence of the compound being tested. Such compounds may inhibit HAS and/or HYAL which is useful, for example, in finding inhibitors of gene expression, or, alternatively, may potentiate HAS and/or HYAL inhibition.

Another technique for drug screening provides high throughput screening for compounds having suitable binding affinity to a target and is described in detail in Geysen (International Patent Publication No. WO 84/03564). Briefly stated, large numbers of different small peptide test compounds are synthesized on a solid substrate, such as plastic pins or some other surface. The peptide test compounds are reacted with HAS and/or HYAL and washed. Bound HAS and/or HYAL molecules are then detected by methods well known in the art. This method may be adapted for screening for non-peptide, chemical entities. This aspect, therefore, extends to combinatorial approaches to screening for HAS and/or HYAL antagonists or agonists.

Purified HAS and/or HYAL can be coated directly onto plates for use in the aforementioned drug screening techniques. However, non-neutralizing antibodies to the target may also be used to immobilize the target on the solid phase.

Another useful group of compounds is a mimetic. A mimetic in this context refers to a substance which has some chemical similarity to the substrate of HAS and/or HYAL but which antagonises HAS and/or HYAL activity. A mimetic may be a carbohydrate or peptide or chemical molecule that mimics elements of secondary structure (Johnson et al., "Peptide Turn Mimetics" in *Biotechnology and Pharmacy*, Pezzuto et al., Eds., Chapman and Hall, New York, 1993). The underlying rationale behind the use of mimetics is that the backbone of the substrate of HAS and/or HYAL exists chiefly to orient the substrate in such a way as to facilitate molecular interactions with HAS and HYAL. A mimetic is designed to permit molecular interactions similar to the natural molecule. Peptide or non-peptide mimetics may be useful, for example, to inhibit the activity of HAS and/or HYAL.

The designing of mimetics to a pharmaceutically active compound is a known approach to the development of pharmaceuticals based on a "lead" compound. This might be desirable where the active compound is difficult or expensive to synthesize or where it is unsuitable for a particular method of administration. Mimetic design, synthesis and testing are generally used to avoid randomly screening large numbers of molecules for a desired property.

There are several steps commonly taken in the design of a mimetic from a compound having a given desired property. First, the particular parts of the compound that are critical and/or important in determining the desired property are determined. In the case of a peptide, this can be done by systematically varying the amino acid residues in the peptide, e.g. by substituting each residue in turn. Alanine scans of peptides are commonly used to refine such peptide motifs. These parts or residues constituting the active region of the compound are known as its "pharmacophore".

Once the pharmacophore has been found, its structure is modeled according to its physical properties, e.g. stereochemistry, bonding, size and/or charge, using data from a range of sources, e.g. spectroscopic techniques, x-ray diffraction data and NMR. Computational analysis, similarity mapping (which models the charge and/or volume of a pharmacophore, rather than the bonding between atoms) and other techniques can be used in this modeling process.

In a variant of this approach, the three-dimensional structure of the ligand and its binding partner are modeled. This can be especially useful where the ligand and/or binding partner change conformation on binding, allowing the model to take account of this in the design of the mimetic. Modeling can be used to generate inhibitors which interact with the linear sequence or a three-dimensional configuration.

A template molecule is then selected onto which chemical groups which mimic the pharmacophore can be grafted. The template molecule and the chemical groups grafted onto it can conveniently be selected so that the mimetic is easy to synthesize, is likely to be pharmacologically acceptable, and does not degrade in vivo, while retaining the biological activity of the lead compound. Alternatively, where the mimetic is peptide-based, further stability can be achieved by cyclizing the peptide, increasing its rigidity. The mimetic or mimetics found by this approach can then be screened to see whether they have the target property, or to what extent they exhibit it. Further optimization or modification can then be carried out to arrive at one or more final mimetics for in vivo or clinical testing.

The goal of rational drug design is to produce structural analogs of biologically active polypeptides of interest or of small molecules with which they interact (e.g. agonists, antagonists, inhibitors or enhancers) in order to fashion drugs which are, for example, more active or stable forms of the polypeptide, or which, e.g. enhance or interfere with the function of a polypeptide in vivo. See, e.g. Hodgson (*Bio/Technology* 9: 19-21, 1991). In one approach, the three-dimensional structure of HAS and/or HYAL interest is determined by x-ray crystallography, by computer modeling or most typically, by a combination of approaches. Useful information regarding the structure of a polypeptide may also be gained by modeling based on the structure of homologous proteins. An example of rational drug design is the development of HIV protease inhibitors (Erickson et al., *Science* 249: 527-533, 1990). In addition, target molecules may be analyzed by an alanine scan (Wells, *Methods Enzymol.* 202: 2699-2705, 1991). In this technique, an amino acid residue is replaced by Ala and its effect on the peptide's activity is determined. Each of the amino acid residues of the peptide is analyzed in this manner to determine the important regions of the peptide.

It is also possible to isolate a HAS and/or HYAL -specific antibody, selected by a functional assay and then to solve its crystal structure. In principle, this approach yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced banks of peptides. Selected peptides would then act as the pharmacore.

Two-hybrid screening is also useful in identifying other members of a biochemical or genetic pathway associated with a target. Two-hybrid screening conveniently uses *Saccharomyces cerevisiae* and *Saccharomyces pombe*. Target interactions and screens for inhibitors can be carried out using the yeast two-hybrid system, which takes advantage of transcriptional factors that are composed of two physically separable, functional domains. The most commonly used is the yeast GAL4 transcriptional activator consisting of a DNA binding domain and a transcriptional activation domain. Two different cloning vectors are used to generate separate fusions of the GAL4 domains to genes encoding potential binding proteins. The fusion proteins are co-expressed, targeted to the nucleus and if interactions occur, activation of a reporter gene (e.g. lacZ) produces a detectable phenotype. In the present case, for example, *S. cerevisiae* is co-transformed with a library or vector expressing a cDNA GAL4 activation domain fusion, and a vector expressing a target gene such as, for example, HAS or HYAL gene fused to GAL4. If lacZ is used as the reporter gene, co-expression of the fusion proteins will produce a blue color. Small molecules or other candidate compounds which interact with a target will result in loss of color of the cells. Reference may be made to the yeast two-hybrid systems as disclosed by Munder et al. (*Appl. Microbiol. Biotechnol.* 52(3): 311-320, 1999) and Young et al., *Nat. Biotechnol.* 16(10): 946-950, 1998). Molecules thus identified by this system are then re-tested in animal cells.

As indicated above, the present invention also extends to small molecule inhibitors identified as described above and which bind and inhibit the activity of HAS and/or HYAL.

It is to be understood that unless otherwise indicated, the subject invention is not limited to specific formulations of components, manufacturing methods, dosage regiments, treatment protocols or the like, as such may vary. It is also to be understood that the terminology used herein is for the purpose of describing particular embodiments only and is not intended to be limiting.

It must be noted that, as used in the subject specification, the singular forms "a", "an" and "the" include plural aspects unless the context clearly dictates otherwise. Thus, for example, reference to "a compound" includes a single compound, as well as two or more compounds; reference to "an antibody" includes a single antibody, as well as two or more antibodies; and so forth.

The terms "compound", "active agent", "pharmacologically active agent", "medicament", "active" and "drug" are used interchangeably herein to refer to an antagonist of HAS and/or HYAL function or activity or of expression of genetic material encoding same which induces a desired pharmacological and/or physiological effect such as but not limited to controlling inflammation and reducing cancer growth. The terms also encompass pharmaceutically acceptable and pharmacologically active ingredients of those active agents specifically mentioned herein including but not limited to salts, esters, amides, prodrugs, active metabolites, analogs and the like. When the terms "compound", "active agent", "pharmacologically active agent", "medicament", "active" and "drug" are used, then it is to be understood that this includes the active agent per se as well as pharmaceutically acceptable, pharmacologically active salts, esters, amides, prodrugs, metabolites, analogs, etc. The term "compound" is not to be construed as a chemical compound only but extends to RNA and DNA encoding a modified LIF molecule.

The terms "effective amount" and "therapeutically effective amount" of the compound as used herein mean a sufficient amount of the agent to provide the desired therapeutic or physiological effect such as inhibiting inflammation or reducing the growth or spread of cancer cells. Undesirable effects, e.g. side effects, are sometimes manifested along with the desired therapeutic effect; hence, a practitioner balances the potential benefits against the potential risks in determining what is an appropriate "effective amount". The exact amount required will vary from subject to subject, depending on the species, age and general condition of the subject, mode of administration and the like. Thus, it may not be possible to specify an exact "effective amount". However, an appropriate "effective amount" in any individual case may be determined by one of ordinary skill in the art using only routine experimentation. The present invention extends to a method of treatment or prophylaxis.

By "pharmaceutically acceptable" carrier, excipient or diluent is meant a pharmaceutical vehicle comprised of a material that is not biologically or otherwise undesirable, i.e. the material may be administered to a subject along with the selected active agent without causing any or a substantial adverse reaction. Carriers may include excipients and other additives such as diluents, detergents, coloring agents, wetting or emulsifying agents, pH buffering agents, preservatives, and the like.

Similarly, a "pharmacologically acceptable" salt, ester, amide, prodrug or derivative of a compound as provided herein is a salt, ester, amide, prodrug or derivative that this not biologically or otherwise undesirable.

The terms "treating" and "treatment" as used herein refer to reduction in severity and/or frequency of symptoms of diseases or disorders or physiological conditions elimination of symptoms and/or underlying cause, prevention of the occurrence of symptoms of disease and/or their underlying cause and improvement or remediation of conditions associated with cytokine activity.

"Treating" a patient may involve prevention of the disorder or disease condition or physiological event in a susceptible individual as well as treatment of a clinically symptomatic individual by inhibiting a disease or disorder.

Accordingly, another aspect of the present invention is directed towards therapeutic or prophylactic composition comprising a compound capable of reducing the levels or activity of HAS and/or HYAL and hence reducing levels of HA.

The compositions and compounds of the present invention can be used in the treatment or prevention of diseases associated with HA. The present invention contemplates treatment of diseases and disorders such as A-Beta-Lipoproteinemia, A-V, A Beta-2-Microglobulin Amyloidosis, A-T, A1AD, A1AT, Aagenaes, Aarskog syndrome, Aarskog-Scott Syndrome, Aase-smith syndrome, Aase Syndrome, AAT, Abderhalden-Kaufmann-Lignac Syndrome, Abdominal Muscle Deficiency Syndrome, Abdominal Wall Defect, Abdominal Epilepsy, Abdominal Migraine, Abductor Spasmodic Dysphonia, Abductor Spastic Dysphonia, Abercrombie Syndrome, blepharon-Macrostomia Syndrome, ABS, Absence of HPRT, Absence of Corpus Callosum Schinzel Typ, Absence Defect of Limbs Scalp and Skull, Absence of Menstruation Primar, Absence of HGPRT, Absorptive Hyperoxaluriaor Enteric, Abt-Letterer-Siwe Disease, ACADL, ACADM Deficiency, ACADM, ACADS, Acanthocytosis-Neurologic Disorder, Acanthocytosis, Acantholysis Bullosa, Acanthosis Nigricans, Acanthosis Bullosa, Acanthosis Nigricans With Insulin Resistance Type A, Acanthosis Nigricans With Insulin Resistance Type B, Acanthotic Nevus, Acatalasemia, Acatalasia, ACC, Accessory Atrioventricular Pathways, Accessory Atrioventricular Pathways, Acephaly, ACF with Cardiac Defects, Achalasia, Achard-Thiers Syndrome, ACHARD (Marfan variant), Achard's syndrome, Acholuric Jaundice, Achondrogenesis, Achondrogenesis Type IV, Achondrogenesis Type III, Achondroplasia, Achondroplasia Tarda, Achondroplastic Dwarfism, Achoo Syndrome, Achromat, Achromatope, Achromatopic, Achromatopsia, Achromic Nevi, Acid Ceramidase Deficiency, Acid Maltase Deficiency, Acid Maltase Deficiency, Acid Beta-glucosidase Deficiency, Acidemia Methylmalonic, Acidemia Propionic, Acidemia with Episodic Ataxia and Weakness, Acidosis, Aclasis Tarsoepiphyseal, ACM, Acoustic Neurilemoma, Acoustic Neuroma, ACPS with Leg Hypoplasia, ACPS II, ACPS IV, ACPS III, Acquired Aphasia with Convulsive Disorder, Acquired Brown Syndrome, Acquired Epileptic Aphasia, Acquired Factor XIII Deficiency, Acquired Form of ACC (caused by infection while still in womb), Acquired Hyperoxaluria, Acquired Hypogammaglobulinemia, Acquired Immunodeficiency Syndrome (AIDS), Acquired Iron Overload, Acquired Lipodystrophy, Acquired Partial Lipodystrophy, Acquired Wandering Spleen, ACR, Acral Dysostosis with Facial and Genital Abnormalities, Acro Renal, Acrocallosal Syndrome Schinzel Type, Acrocephalosyndactyly, Acrocephalosyndactyly Type I, Acrocephalosyndactyly Type I Subtype I, Acrocephalopolysyndactyly Type II, Acrocephalopolysyndactyly Type III, Acrocephalopolysyndactyly Type IV, Acrocephalosyndactyly V (ACS5 or ACS V) Subtype I, Acrocephaly Skull Asymmetry and Mild Syndactyly, Acrocephaly, Acrochondrohyperplasia, Acrodermatitis Enteropathica, Acrodysostosis, Acrodystrophic Neuropathy, Acrodystrophic Neuropathy, Acrofacial Dysostosis Nager Type, Acrofacial Dysostosis Nager Type, Acrofacial Dysostosis Postaxial Type, Acrofacial Dysostosis Type Genee-Wiedep, Acrogeria Familial, Acromegaly, Acromelalgia Hereditary, Acromesomelic Dysplasia, Acromesomelic Dwarfism, Acromicric Skeletal Dysplasia, Acromicric Dysplasia, Acroosteolysis with Osteoporosis and Changes in Skull and Mandible, Acroosteolysis, Acroparesthesia, ACS I, ACS Type II, ACS Type III, ACS, ACS3, ACTH Deficiency, Action Myoclonus, Acute Brachial Neuritis Syndrome, Acute Brachial Radiculitis Syndrome, Acute Cerebral Gaucher Disease, Acute Cholangitis, Acute Disseminated Encephalomyeloradiculopathy, Acute Disseminated Histiocytosis-X, Acute Hemorrhagic Polioencephalitis, Acute Idiopathic Polyneuritis, Acute Immune-Mediation Polyneuritis, Acute Infantile Pelizaeus-Merzbacher Brain Sclerosis, Acute Intermittant Porphyria, Acute Porphyrias, Acute Sarcoidosis, Acute Shoulder Neuritis, Acute Toxic Epidermolysis, Acyl-CoA Dehydrogenase Deficiency Long-Chain, Acyl-CoA Dehydrogenase Deficiency Short-Chain, Acyl-CoA Dihydroxyacetone Acyltransferase, Acyl-coenzyme A Oxidase Deficiency, ADA, ADA Deficiency, Adam Complex, Adamantiades-Behcet's Syndrome, Adamantinoma, Adams Oliver Syndrome, Adaptive Colitis, ADD combined type, ADD, Addison Disease with Cerebral Sclerosis, Addison's Anemia, Addison's Anemia, Addison's Disease, Addison's Disease, Addison's Disease, Addison-Biermer Anemia, Addison-Biermer Anemia, Addison-Schilder Disease, Addisonian Pernicious Anemia, Addisonian Pernicious Anemia, Adducted Thumbs-Mental Retardation, Adductor Spasmodic Dysphonia, Adductor Spastic Dysphonia, Adenoma Associated Virilism of Older Women, Adenomatosis of the Colon and Rectum, Adenomatous polyposis of the Colon, Adenomatous Polyposis Familial, Adenosine Deaminase Deficiency, Adenosine Deaminase Deficiency, Adenylosuccinase deficiency, ADHD predominantly hyperactive-impulsive type, ADHD predominantly inattentive type, ADHD, Adhesive Arachnoiditis, Adie Syndrome, Adie's Syndrome, Adie's Tonic Pupil, Adie's Pupil, Adipogenital Retinitis Pigmentosa Polydactyly, Adipogenital-Retinitis Pigmentosa Syndrome, Adiposa Dolorosa, Adiposis Dolorosa, Adiposogenital Dystrophy, Adolescent Cystinosis, ADPKD, Adrenal Cortex Adenoma, Adrenal Disease, Adrenal Hyperfunction resulting from Pituitary ACTH Excess, Adrenal Hypoplasia, Adrenal Insufficiency, Adrenal Neoplasm, Adrenal Virilism, Adrenal Virilism, Adreno-Retinitis Pigmentosa-Polydactyly Syndrome, Adrenocortical Insufficiency, Adrenocortical Hypofunction, Adrenocorticotropic Hormone Deficiency Isolated, Adrenogenital Syndrome, Adrenogenital Syndrome, Adrenoleukodystrophy, Adrenomyeloneuropathy, Adreno-Retinitis Pigmentosa-Polydactyly Syndrome, Adult Cystinosis, Adult Dermatomyositis, Adult Hypophosphatasia, Adult Macula Lutea Retinae Degeneration, Adult Onset ALD, Adult-Onset Ceroidosis, Adult Onset Medullary Cystic Disease, Adult Onset Pernicious Anemia, Adult Onset Pernicious Anemia, Adult Onset Schindler Disease, Adult-Onset Subacute Necrotizing Encephalomyelopathy, Adult Onset Pernicious Anemia, Adult Polycystic Kidney Disease, Adult Onset Medullary Cystic Disease, Adynlosuccinate Lyase Deficiency, AE, AEC Syndrome, AFD, AFD, Afibrinogenemia, African Siderosis, AGA, Aganglionic Megacolon, Age Related Macular Degeneration, Agenesis of Commissura Magna Cerebri, Agenesis of Corpus Callosum, Agenesis of Corpus Callosum-Infantile Spasms-Ocular Anomalies, Agenesis of Corpus Callosum and Chorioretinal Abnormality, Agenesis of Corpus Callosum-Chorioretinitis Abnormality, Aggressive mastocytosis, Agnosis Primary, AGR Triad, AGU, Agyria, Agyria-pachygria-band spectrum, AHC, AHD, AHDS, AHF Deficiency, AHG Deficiency, AHO, Ahumada Del Castillo, Aicardi Syndrome, Aicardi Syndrome, AIED, AIMP, AIP, AIS, AIS, Akinetic Seizure, ALA-D Porphyria, Alactasia, Alactasia, Alagille Syndrome, Aland Island Eye Disease (X-Linked), Alaninuria, Albers-Schonberg Disease, Albinism, Albinism, Albinismus, Albinoidism, Albright Hereditary Osteodystrophy, Alcaptonuria, Alcaptonuria, Alcohol-Related Birth Defects, Alcoholic Embryopathy, Ald, ALD, ALD, Aldosterone, Aldosteronism With Normal Blood Pressure, Aldrich Syndrome, Alexander's Disease, Alexanders Disease, Algodystrophy, Algoneurodystrophy, Alkaptonuria, Alkaptonuric Ochronosis, Alkyl DHAP synthase deficiency, Allan-Herndon-Dudley Syndrome, Allan-Herndon Syndrome, Allan-Herndon-Dudley Mental Retardation, Allergic Granulomatous Antitis, Allergic Granulomatous Angiitis of Cronkhite-Canada, Alobar Holoprosencephaly, Alopecia Areata, Alopecia Areata, Alopecia Celsi, Alopecia Cicatrisata, Alopecia Circumscripta, Alopecia-Poliosis-Uveitis-Vitiligo-Deafness-Cutaneous-Uveo-O, Alopecia Seminuniversalis, Alopecia Totalis, Alopecia Universalis, Alpers Disease, Alpers Disease, Alpers Diffuse Degeneration of Cerebral Gray Matter with Hepatic Cirrhosis, Alpers Progressive Infantile Poliodystrophy, Alpha-1-Antitrypsin Deficiency, Alpha-1 4 Glucosidase Deficiency, Alpha-1 4 Glucosidase Deficiency, Alpha-Galactosidase A Deficiency, Alpha-Galactosidase B Deficiency, Alpha-1 4 Glucosidase Deficiency, Alpha High-Density Lipoprotein Deficieny, Alpha-L-Fucosidase Deficiency Fucosidosis Type 3, Alpha-GalNAc Deficiency Schindler Type, Alpha-1 4 Glucosidase Deficiency, Alpha-L-Fucosidase Deficiency Fucosidosis Type 3, Alphalipoproteinemia, Alpha Mannosidosis, Alpha-N-Acetylgalactosaminidase Deficiency Schindler Type, Alpha-NAGA Deficiency Schindler Type, Alpha-Neuraminidase Deficiency, Alpha-Thalassemialmental retardation syndorme non-deletion type, Alphalipoproteinemia, Alport Syndrome, ALS, Alstroem's Syndrome, Alstroem, Alstrom Syndrome, Alternating Hemiplegia Syndrome, Alternating Hemiplegia of Childhood, Alzheimer's Disease, Amaurotic Familial Idiocy, Amaurotic Familial Idiocy, Amaurotic Familial Idiocy Adult, Amaurotic Familial Infantile Idiocy, Amaurotic Familial Infantile Idiocy, Ambiguous Genitalia, AMC, AMD, Ameloblastoma, Amelogenesis Imperfecta, Amenorrhea-Galactorrhea Nonpuerperal, Amenorrhea-Galactorrhea-FSH Decrease Syndrome, Amenorrhea, Amino Acid Disorders, Aminoaciduria-Osteomalacia-Hyperphosphaturia Syndrome, AMN, AMN, Amniocentesis, Amniocentesis, Amniotic Bands, Amniotic Band Syndrome, Amniotic Band Disruption Complex, Amniotic Band Sequence, Amniotic Rupture Sequence, Amputation Congenital, AMS, Amsterdam Dwarf Syndrome de Lange, Amylo-1 6-Glucosidase Deficiency, Amyloid Arthropathy of Chronic Hemodialysis, Amyloid Corneal Dystrophy, Amyloid Polyneuropathy, Amyloidosis, Amyloidosis of Familial Mediterranean Fever, Amylopectinosis, Amyoplasia Congenita, Amyotrophic Lateral Sclerosis, Amyotrophic Lateral Sclerosis, Amyotrophic Lateral Sclerosis-Polyglucosan Bodies, AN, AN 1, AN 2, Anal Atresia, Anal Membrane, Anal Rectal Malformations, Anal Rectal Malformations, Anal Stenosis, Analine 60 Amyloidosis, Analphalipoproteinemia, Analrectal, Analrectal, Analrectal, Anaplastic Astrocytoma, Andersen Disease, Anderson-Fabry Disease, Andersen Glycogenosis, Anderson-Warburg Syndrome, Andre Syndrome, Andre Syndrome Type II, Androgen Insensitivity, Androgen Insensitivity Syndrome Partial, Androgen Insensitivity Syndrome, Androgen Insensitivity Syndrome Partial, Androgenic Steroids, Anemia Autoimmune Hemolytic, Anemia Blackfan Diamond, Anemia, Congenital, Triphalangeal Thumb Syndrome, Anemia Hemolytic Cold Antibody, Anemia Hemolytic Cold Antibody, Anemia Hemolytic with PGK Deficiency, Anemia Pernicious, Anencephaly, Angelman Syndrome, Angio-Osteohypertrophy Syndrome, Angiofollicular Lymph Node Hyperplasia, Angiohemophilia, Angiokeratoma Corporis, Angiokeratoma Corporis Diffusum, Angiokeratoma Diffuse, Angiomatosis Retina, Angiomatous Lymphoid, Angioneurotic Edema Hereditary, Anhidrotic Ectodermal Dysplasia, Anhidrotic X-Linked Ectodermal Dysplasias, Aniridia, Aniridia-Ambiguous Genitalia-Mental Retardation, Aniridia Associated with Mental Retardation, Aniridia-Cerebellar Ataxia-Mental Deficiency, Aniridia Partial-Cerebellar Ataxia-Mental Retardation, Aniridia Partial-Cerebellar Ataxia-Oligophrenia, Aniridia Type I, Aniridia Type II, Aniridia-Wilms' Tumor Association, Aniridia-Wilms' Tumor-Gonadoblastoma, Ankyloblepharon-Ectodermal Defects-Cleft Lip/Palate, Ankylosing Spondylitis, Ankylosing Spondylitis, Annular groves, Anodontia, Anodontia, Anodontia Vera, Anomalous Trichromasy, Anomalous Dysplasia of Dentin, Coronal Dentin Dysplasia, Anomic Aphasia, Anophthalmia, Anorectal, Anorectal Malformations, Anosmia, Anterior Bowing of the Legs with Dwarfism, Anterior Membrane Corneal Dystrophy, Anti-Convulsant Syndrome, Anti-Epstein-Barr Virus Nuclear Antigen (EBNA) Antibody Deficiency, Antibody Deficiency, Antibody Deficiency with near normal Immunoglobulins, Antihemophilic Factor Deficiency, Antihemophilic Globulin Deficiency, Antiphospholipid Syndrome, Antiphospholipid Syndrome, Antiphospholipid Antibody Syndrome, Antithrombin III Deficiency, Antithrombin III Deficiency Classical (Type I), Antitrypsin Deficiency, Antley-Bixler Syndrome, Antoni's Palsy, Anxietas Tibialis, Aorta Arch Syndrome, Aortic and Mitral Atresia with Hypoplasic Left Heart Syndrome, Aortic Stenosis, Aortic Stenosis, Aparoschisis, APC, APECED Syndrome, Apert Syndrome, Aperts, Aphasia, Aplasia Axialis Extracorticales Congenital, Aplasia Cutis Congenita, Aplasia Cutis Congenita with Terminal Transverse Limb Defects, Aplastic Anemia, Aplastic Anemia with Congenital Anomalies, APLS, Apnea, Appalachian Type Amyloidosis, Apple Peel Syndrome, Apraxia, Apraxia, Apraxia Buccofacial, Apraxia Constructional, Apraxia Ideational, Apraxia Ideokinetic, Apraxia Ideomotor, Apraxia Motor, Apraxia Oculomotor, APS, Arachnitis, Arachnodactyly Contractural Beals Type, Arachnodactyly, Arachnoid Cysts, Arachnoiditis Ossificans, Arachnoiditis, Aran-Duchenne, Aran-Duchenne Muscular Atrophy, Aregenerative Anemia, Arginase Deficiency, Argininemia, Arginino Succinase Deficiency, Argininosuccinase Deficiency, Argininosuccinate Lyase Deficiency, Argininosuccinic Acid Lyase-ASL, Argininosuccinic Acid Synthetase Deficiency, Argininosuccinic Aciduria, Argonz-Del Castillo Syndrome, Arhinencephaly, Armenian Syndrome, Arnold-Chiari Malformation, Arnold-Chiari Syndrome, ARPKD, Arrhythmic Myoclonus, Arrhythmogenic Right Ventricular Dysplasia, Arteriohepatic Dysplasia, Arteriovenous Malformation, Arteriovenous Malformation, Arteriovenous Malformation of the Brain, Arteritis Giant Cell, Arthritis, Arthritis Urethritica, Arthro-Dento-Osteodysplasia, Arthro-Ophthalmopathy, Arthrochalasis Multiplex Congenita, Arthrogryposis Multiplex Congenita, Arthrogryposis Multiplex Congenita, Distal, Type IIA, ARVD, Arylsulfatase-B Deficiency, AS, AS, AS, AS, ASA Deficiency, Ascending Paralysis, ASD, Atrioseptal Defects, ASH, Ashermans Syndrome, Ashkenazi Type Amyloidosis, ASL Deficiency, Aspartylglucosaminuria, Aspartylglycosaminuria, Asperger's Syndrome, Asperger's Type Autism, Asphyxiating Thoracic Dysplasia, Asplenia Syndrome, ASS Deficiency, Asthma, Astrocytoma Grade I (Benign), Astrocytoma Grade II (Benign), Asymmetric Crying Facies with Cardiac Defects, Asymmetrical septal hypertrophy, Asymptomatic Callosal Agenesis, AT, AT III Deficiency, AT III Variant IA, AT III Variant Ib, AT 3, Ataxia, Ataxia Telangiectasia, Ataxia Telangiectasia, Ataxia with Lactic Acidosis Type II, Ataxia Cerebral Palsy, Ataxiadynamia, Ataxiophemia, ATD, Athetoid Cerebral Palsy, Atopic Eczema, Atresia of Esophagus with or without Tracheoesophageal Fistula, Atrial Septal Defects, Atrial Septal Defect Primum, Atrial and Septal and Small Ventricular Septal Defect, Atrial Flutter, Atrial Fibrillation, Atriodigital Dysplasia, Atrioseptal Defects, Atrioventricular Block, Atrioventricular Canal Defect, Atrioventricular Septal Defect, Atrioventricular Septal Defect, Atrophia Bulborum Hereditaria, Atrophic Beriberi, Atrophy Olivopontocerebellar, Attention Deficit Disorder, Attention Deficit Hyperactivity Disorder, Attenuated Adenomatous Polyposis Coli, Atypical Amyloidosis, Atypical Hyperphenylalaninemia, Atypical Hyperphenylalaninemia, Auditory Canal Atresia, Auriculotemporal Syndrome, Autism, Autism Asperger's Type, Autism Dementia Ataxia and Loss of Purposeful Hand Use, Autism Infantile Autism, Autoimmune Addison's Disease, Autoimmune Hemolytic Anemia, Autoimmune Hemolytic Anemia, Autoimmune Hemolytic Anemia, Autoimmune Hemolytic Anemia, Autoimmune Hepatitis, Autoimmune-Polyendocrinopathy-Candidias, Autoimmune Polyglandular Disease Type I, Autosomal Dominant Albinism, Autosomal Dominant Compelling Helioophthalmic Outburst Syndrome, Autosomal Dominant Desmin Distal myopathy with Late Onset, Autosomal Dominant EDS, Autosomal Dominant Emery-Dreifuss Muscular Dystrophy, Autosomal Dominant Keratoconus, Autosomal Dominant Pelizaeus-Merzbacher Brain Sclerosis, Autosomal Dominant Polycystic Kidney Disease, Autosomal Dominant Spinocerebellar Degeneration, Autosomal Recessive Agammaglobulinemia, Autosomal Recessive Centronuclear myopathy, Autosom al Recessive Conradi-Hunermann Syndrome, Autosomal Recessive EDS, Autosomal Recessive Emery-Dreifuss Muscular Dystrophy, Autosomal Recessive Forms of Ocular Albinism, Autosomal Recessive Inheritance Agenesis of Corpus Callosum, Autosomal Recessive Keratoconus, Autosomal Recessive Polycystic Kidney Disease, Autosomal Recessive Severe Combined Immunodeficiency, AV, AV, AVM, AVSD, AWTA, Axilla Abscess, Axonal Neuropathy Giant, Azorean Neurologic Disease, B-K Mole Syndrome, Babinski-Froelich Syndrome, BADS, Baillarger's Syndrome, Balkan Disease, Baller-Gerold Syndrome, Ballooning Mitral Valve, Balo Disease Concentric Sclerosis, Baltic Myoclonus Epilepsy, Bannayan-Zonana syndrome (BZS), Bannayan-Riley-Ruvalcaba syndrome, Banti's Disease, Bardet-Biedl Syndrome, Bare Lymphocyte Syndrome, Barlow's syndrome, Barraquer-Simons Disease, Barrett Esophagus, Barrett Ulcer, Barth Syndrome, Barth syndrome, Bartter's Syndrome, Basal Cell Nevus Syndrome, Basedow Disease, Bassen-Kornzweig Syndrome, Batten Disease, Batten-Mayou Syndrome, Batten-Spielmeyer-Vogt's Disease, Batten. Turner Syndrome, Batten Turner Type Congenital myopathy, Batten-Vogt Syndrome, BBB Syndrome, BBB Syndrome (Opitz), BBB Syndrome, BBBG Syndrome, BCKD Deficiency, BD, BDLS, BE, Beals Syndrome, Beals Syndrome, Beals-Hecht Syndrome, Bean Syndrome, BEB, BEB, Bechterew Syndrome, Becker Disease, Becker Muscular Dystrophy, Becker Muscular Dystrophy, Becker Nevus, Beckwith Wiedemann Syndrome, Beckwith-Syndrome, Begnez-Cesar's Syndrome, Behcet's syndrome, Behcet's Disease, Behcet's Disease, Behr 1, Behr 2, Bell's Palsy, Benign Acanthosis Nigricans, Benign Astrocytoma, Benign Cranial Nerve Tumors, Benign Cystinosis, Benign Essential Blepharospasm, Benign Essential Tremor, Benign Familial Hematuria, Benign Focal Amyotrophy, Benign Focal Amyotrophy of ALS, Benign Hydrocephalus, Benign Hypermobility Syndrome, Benign Keratosis Nigricans, Benign Paroxysmal Peritonitis, Benign Recurrent Hematuria, Benign Recurrent Intrahepatic Cholestasis, Benign Spinal Muscular Atrophy with Hypertrophy of the Calves, Benign Symmetrical Lipomatosis, Benign Tumors of the Central Nervous System, Berardinelli-Seip Syndrome, Berger's Disease, Beriberi, Berman Syndrome, Bernard-Horner Syndrome, Bernard-Soulier Syndrome, Besnier Prurigo, Best Disease, Beta-Alanine-Pyruvate Aminotransferase, Beta-Galactosidase Deficiency Morquio Syndrome, Beta-Glucuronidase Deficiency, Beta Oxidation Defects, Beta-oxidation Defects, Beta Thalassemia Major, Beta Thalassemia Minor, Betalipoprotein Deficiency, Bethlem myopathy, Beuren Syndrome, BH4 Deficiency, BH4 Deficiency, Biber-Haab-Dimmer Corneal Dystrophy, Bicuspid Aortic Valve, Bicuspid Aortic Valve, Biedl-Bardet, Bifid Cranium, Bifunctional Enzyme Deficiency, Bilateral Acoustic Neurofibromatosis, Bilateral Acoustic Neuroma, Bilateral Right-Sidedness Sequence, Bilateral Renal Agenesis, Bilateral Temporal Lobe Disorder, Bilious Attacks, Bilirubin Glucuronosyltransferase Deficiency Type I, Binder Syndrome, Binswanger's Disease, Binswanger's Encephalopathy, Biotinidase deficiency, Bird-Headed Dwarfism Seckel Type, Birth Defects, Birthmark, Bitemporal Forceps Marks Syndrome, Biventricular Fibrosis, Bjornstad Syndrome, B-K Mole Syndrome, Black Locks-Albinism-Deafness of Sensoneural Type (BADS), Blackfan-Diamond Anemia, Blennorrheal Idiopathic Arthritis, Blepharophimosis, Ptosis, Epicanthus Inversus Syndrome, Blepharospasm, Blepharospasm, Blepharospasm Benign Essential, Blepharospasm Oromandibular Dystonia, Blessig Cysts, BLFS, Blindness, Bloch-Siemens Incontinentia Pigmenti Melanoblastosis Cutis Linearis, Bloch-Siemens-Sulzberger Syndrome, Bloch-Sulzberger Syndrome, Blood types, Blood type A, Blood type B, Blood type AB, Blood type O, Bloom Syndrome, Bloom-Torre-Mackacek Syndrome, Blue Rubber Bleb Nevus, Blue Baby, Blue Diaper Syndrome, BMD, BOD, BOFS, Bone Tumor-Epidermoid Cyst-Polyposis, Bonnet-Dechaume-Blanc Syndrome, Bonnevie-Ulrich Syndrome, Book Syndrome, BOR Syndrome, BORJ, Borjeson Syndrome, Borjeson-Forssman-Lehmann Syndrome, Bowen Syndrome, Bowen-Conradi Syndrome, Bowen-Conradi Hutterite, Bowen-Conradi Type Hutterite Syndrome, Bowman's Layer, BPEI, BPES, Brachial Neuritis, Brachial Neuritis Syndrome, Brachial Plexus Neuritis, Brachial-Plexus-Neuropathy, Brachiocephalic Ischemia, Brachmann-de Lange Syndrome, Brachycephaly, Brachycephaly, Brachymorphic Type Congenital, Bradycardia, Brain Tumors, Brain Tumors Benign, Brain Tumors Malignant, Branched Chain Alpha-Ketoacid Dehydrogenase Deficiency, Branched Chain Ketonuria I, Brancher Deficiency, Branchio-Oculo-Facial Syndrome, Branchio-Oto-Renal Dysplasia, Branchio-Oto-Renal Syndrome, Branchiooculofacial Syndrome, Branchiootic Syndrome, Brandt Syndrome, Brandywine Type Dentinogenesis Imperfecta, Brandywine type Dentinogenesis Imperfecta, Breast Cancer, BRIC Syndrome, Brittle Bone Disease, Broad Beta Disease, Broad Thumb Syndrome, Broad Thumbs and Great Toes Characteristic Facies and Mental Retardation, Broad Thumb-Hallux, Broca's Aphasia, Brocq-Duhring Disease, Bronze Diabetes, Bronze Schilder's Disease, Brown Albinism, Brown Enamel Hereditary, Brown-Sequard Syndrome, Brown Syndrome, BRRS, Brueghel Syndrome, Bruton's Agammaglobulinemia Common, BS, BSS, Buchanan's Syndrome, Budd's Syndrome, Budd-Chiari Syndrome, Buerger-Gruetz Syndrome, Bulbospinal Muscular Atrophy-X-linked, Bulldog Syndrome, Bullosa Hereditaria, Bullous CIE, Bullous CIE, Bullous Congenital Ichthyosiform Erythroderma, Bullous Ichthyosis, Bullous Pemphigoid, Burkitt's Lymphoma, Burkitt's Lymphoma African type, Burkitt's Lymphoma Non-african type, BWS, Byler's Disease, C Syndrome, C1 Esterase Inhibitor Dysfunction Type II Angioedema, C1-INH, C1 Esterase Inhibitor Deficiency Type I Angioedema, C1NH, Cacchi-Ricci Disease, CAD, CADASIL, CAH, CAH, Calcaneal Valgus, Calcaneovalgus, Calcium Pyrophosphate Dihydrate Deposits, Callosal Agenesis and Ocular Abnormalities, Calves-Hypertrophy of Spinal Muscular Atrophy, Campomelic Dysplasia, Campomelic Dwarfism, Campomelic Syndrome, Camptodactyly-Cleft Palate-Clubfoot, Camptodactyly-Limited Jaw Excursion, Camptomelic Dwarfism, Camptomelic Syndrome, Camptomelic Syndrome Long-Limb Type, Camurati-Engelmann Disease, Camurati-Engelmann Disease, Canada-Cronkhite Disease, Canavan disease, Canavan's Disease Included, Canavan's Leukodystrophy, Cancer, Cancer Family Syndrome Lynch Type, Cantrell Syndrome, Cantrell-Haller-Ravich Syndrome, Cantrell Pentalogy, Carbamyl Phosphate Synthetase Deficiency, Carbohydrate Deficient Glycoprotein Syndrome, Carbohydrate-Deficient Glycoprotein Syndrome Type Ia, Carbohydrate-Induced Hyperlipemia, Carbohydrate Intolerance of Glucose Galactose, Carbon Dioxide Acidosis, Carboxylase Deficiency Multiple, Cardiac-Limb Syndrome, Cardio-auditory Syndrome, Cardioauditory Syndrome of Jervell and Lange-Nielsen, Cardiocutaneous Syndrome, Cardio-facial-cutaneous syndrome, Cardiofacial Syndrome Cayler Type, Cardiomegalia Glycogenica Diffusa, Cardiomegalia Glycogenica Diffusa, Cardiomyopathic Lentiginosis, Cardio myopathy, Cardio myopathy, Cardio myopathy Associated with Desmin Storage myopathy, Cardio myopathy Due to Desmin Defect, Cardio myopathy-Neutropenia Syndrome, Cardio myopathy-Neutropenia Syndrome, Cardio myopathy-Neutropenia Syndrome Lethal Infantile Cardio myopathy, Cardiopathic Amyloidosis, Cardiospasm, Cardocardiac Syndrome, Carnitine-Acylcarnitine Translocase Deficiency, Carnitine Deficiency and Disorders, Carnitine Deficiency Primary, Carnitine Deficiency Secondary, Carnitine Deficiency Secondary to MCAD Deficiency, Carnitine Deficiency Syndrome, Carnitine Palmitoyl Transferase I & II (CPT I & II), Carnitine Palmitoyltransferase Deficiency, Carnitine Palmitoyltransferase Deficiency Type 1, Carnitine Palmitoyltransferase Deficiency Type 2 benign classical muscular form included severe infantile form included, Carnitine Transport Defect (Primary Carnitine Deficiency), Carnosinase Deficiency, Carnosinemia, Caroli Disease, Carpenter syndrome, Carpenter's, Cartilage-Hair Hypoplasia, Cartilage-Hair Hypoplasia, Castleman's Disease, Castleman's Disease Hyaline Vascular Type, Castleman's Disease Plasma Cell Type, Castleman Tumor, Cat Eye Syndrome, Cat's Cry Syndrome, Catalayse deficiency, Cataract-Dental Syndrome, Cataract X-Linked with Hutchinsonian Teeth, Catecholamine hormones, Catel-Manzke Syndrome, Catel-Manzke Type Palatodigital Syndrome, Caudal Dysplasia, Caudal Dysplasia Sequence, Caudal Regression Syndrome, Causalgia Syndrome Major, Cavemomas, Cavernous Angioma, Cavernous Hemangioma, Cavernous Lymphangioma, Cavernous Malformations, Cayler Syndrome, Cazenave's Vitiligo, CBGD, CBGD, CBPS, CBPS, CCA, CCD, CCD, CCHS, CCM Syndrome, CCMS, CCO, CD, CDG1 a, CDG1A, CDGS Type Ia, CDGS Type Ia, CDGS, CDI, CdLS, Celiac Disease, Celiac sprue, Celiac Sprue-Dermatitis, Cellelar Immunodeficiency with Purine Nucleoside Phosphorylase Deficiency, Celsus' Vitiligo, Central Apnea, Central Core Disease, Central Core Disease, Central Diabetes Insipidus, Central Form Neurofibromatosis, Central Hypoventilation, Central Sleep Apnea, Centrifugal Lipodystrophy, Centronuclear myopathy, CEP, Cephalocele, Cephalothoracic Lipodystrophy, Ceramide Trihexosidase Deficiency, Cerebellar Agenesis, Cerebellar Aplasia, Cerebellar Hemiagenesis, Cerebellar Hypoplasia, Cerebellar Vermis Aplasia, Cerebellar Vermis Agenesis-Hypernea-Episodic Eye Moves-Ataxia-Retardation, Cerebellar Syndrome, Cerebellarparenchymal Disorder IV, Cerebellomedullary Malformation Syndrome, Cerebellomedullary Malformation Syndrome, Cerebello-Oculocutaneous Telangiectasia, Cerebelloparenchymal Disorder IV Familial, Cerebellopontine Angle Tumor, Cerebral Arachnoiditis, Cerebral Autosomal Dominant Arteriopathy with Subcortical Infarcts and Leukodystrophy, Cerebral Beriberi, Cerebral Diplegia, Cerebral Gigantism, Cerebral Malformations Vascular, Cerebral Palsy, Cerebro-Oculorenal Dystrophy, Cerebro-Oculo-Facio-Skeletal Syndrome, Cerebrocostomandibular syndrome, Cerebrohepatorenal Syndrome, Cerebromacular Degeneration, Cerebromacular Degeneration, Cerebromuscular Dystrophy Fukuyama Type, Cerebroocular Dysgenesis, Cerebroocular Dysplasia-Muscular Dystrophy Syndrome, Cerebrooculofacioskeletal Syndrome, Cerebroretinal Arteriovenous Aneurysm, Cerebroside Lipidosis, Cerebrosidosis, Cerebrotendinous Xanthomatosis, Cerebrovascular Ferrocalcinosis, Ceroid-Lipofuscinosis Adult form, Cervical Dystonia, Cervical Dystonia, Cervico-Oculo-Acoustic Syndrome, Cervical Spinal Stenosis, Cervical Vertebral Fusion, CES, CF, CFC syndrome, CFIDS, CFND, CGD, CGF, CGF, Chalasodermia Generalized, Chanarin Dorfman Disease, Chanarin Dorfman Syndrome, Chanarin Dorfman Ichthyosis Syndrome, Chandler's Syndrome, Charcot's Disease, Charcot-Marie-Tooth, Charcot-Marie-Tooth Disease, Charcot-Marie-Tooth Disease Variant, Charcot-Marie-Tooth-Roussy-Levy Disease, CHARGE Association, Charge Syndrome, CHARGE Syndrome, Chaund's Ectodermal Dysplasias, Chediak-Higashi Syndrome, Chediak-Higashi Syndrome, Chediak-Steinbrinck-Higashi Syndrome, Cheilitis Granulomatosa, Cheiloschisis, Chemke Syndrome, Cheney Syndrome, Cherry Red Spot and Myoclonus Syndrome, CHF, CHH, CHH, Chiari's Disease, Chiari Malformation I, Chiari Malformation, Chiari Type I (Chiari Malformation I), Chiari Type II (Chiari Malformation II), Chiari I Syndrome, Chiari-Budd Syndrome, Chiari-Frommel Syndrome, Chiari Malformation II, CHILD Syndrome, CHILD Ichthyosis Syndrome, CHILD Syndrome Ichthyosis, Childhood Adrenoleukodystrophy, Childhood Dermatomyositis, Childhood-onset Dystonia, Childhood Cyclic Vomiting, Childhood Giant Axonal Neuropathy, Childhood Hypophasphatasia, Childhood Muscular Dystrophy, CHN, Cholestasis, Cholestasis Hereditary Norwegian Type, Cholestasis Intrahepatic, Cholestasis Neonatal, Cholestasis of Oral Contraceptive Users, Cholestasis with Peripheral Pulmonary Stenosis, Cholestasis of Pregnancy, Cholesterol Desmolase Deficiency, Cholesterol Desmolase Deficiency, Chondrodysplasia Punctata, Chondrodystrophia Calcificans Congenita, Chondrodystrophia Fetalis, Chondrodystrophic Myotonia, Chondrodystrophy, Chondrodystrophy with Clubfeet, Chondrodystrophy Epiphyseal, Chondrodystrophy Hyperplastic Form, Chondroectodermal Dysplasias, Chondrogenesis Imperfecta, Chondrohystrophia, Chondroosteodystrophy, Choreoacanthocytosis, Chorionic Villi Sampling, Chorioretinal Anomalies, Chorioretinal Anomalies with ACC, Chorireninal Coloboma-Joubert Syndrome, Choroidal Sclerosis, Choroideremia, Chotzen Syndrome, Chotzen Syndrome, Christ-Siemens-Touraine Syndrome, Christ-Siemans-Touraine Syndrome, Christmas Disease, Christmas Tree Syndrome, Chromosome 3 Deletion of Distal 3p, Chromosome 3 Distal 3p Monosomy, Chromosome 3-Distal 3q2 Duplication, Chromosome 3-Distal 3q2 Trisomy, Chromosome 3 Monosomy 3p2, Chromosome 3q Partial Duplication Syndrome, Chromosome 3q, Partial Trisomy Syndrome, Chromosome 3-Trisomy 3q2, Chromosome 4 Deletion 4q31-qter Syndrome, Chromosome 4 Deletion 4q32-qter Syndrome, Chromosome 4 Deletion 4q33-qter Syndrome, Chromosome 4 Long Arm Deletion, Chromosome 4 Long Arm Deletion, Chromosome 4 Monosomy 4q, Chromosome 4-Monosomy 4q, Chromosome 4 Monosomy Distal 4q, Chromosome 4 Partial Deletion 4p, Chromosome 4, Partial Deletion of the Short Arm, Chromosome 4 Partial Monosomy of Distal 4q, Chromosome 4 Partial Monosomy 4p, Chromosome 4 Partial Trisomy 4 (q25-qter), Chromosome 4 Partial Trisomy 4 (q26 or q27-qter), Chromosome 4 Partial Trisomy 4 (q31 or 32-qter), Chromosome 4 Partial Trisomy 4p, Chromosome 4 Partial Trisomies 4q2 and 4q3, Chromosome 4 Partial Trisomy Distal 4, Chromosome 4 Ring, Chromosome 4 4q Terminal Deletion Syndrome, Chromosome 4q-Syndrome, Chromosome 4q-Syndrome, Chromosome 4 Trisomy 4, Chromosome 4 Trisomy 4p, Chromosome 4 XY/47 XXY (Mosiac), Chromosome 5 Monosomy 5p, Chromosome 5, Partial Deletion of the Short Arm Syndrome, Chromosome 5 Trisomy 5p, Chromosome 5 Trisomy 5p Complete (5p11-pter), Chromosome 5 Trisomy 5p Partial (5p13 or 14-pter), Chromosome 5p-Syndrome, Chromosome 6 Partial Trisomy 6q, Chromosome 6 Ring, Chromosome 6 Trisomy 6q2, Chromosome 7 Monosomy 7p2, Chromosome 7 Partial Deletion of Short Arm (7p2-), Chromosome 7 Terminal 7p Deletion [del (7) (p21-p22)], Chromosome 8 Monosomy 8p2, Chromosome 8 Monosomy 8p21-pter, Chromosome 8 Partial Deletion (short arm), Chromosome 8 Partial Monosomy 8p2, Chromosome 9 Complete Trisomy 9P, Chromosome 9 Partial Deletion of Short Arm, Chromosome 9 Partial Monosomy 9p, Chromosome 9 Partial Monosomy 9p22, Chromosome 9 Partial Monosomy 9p22-pter, Chromosome 9 Partial Trisomy 9P Included, Chromosome 9 Ring, Chromosome 9 Tetrasomy 9p, Chromosome 9 Tetrasomy 9p Mosaicism, Chromosome 9 Trisomy 9p (Multiple Variants), Chromosome 9 Trisomy 9 (pter-p21 to q32) Included, Chromosome 9 Trisomy Mosaic, Chromosome 9 Trisomy Mosaic, Chromosome 10 Distal Trisomy 10q, Chromosome 10 Monosomy, Chromosome 10 Monosomy 10p, Chromosome 10, Partial Deletion (short arm), Choromsome 10, 10p-Partial, Chromosome 10 Partial Trisomy 10q24-qter, Chromosome 10 Trisomy 10q2, Partial Monosomy of Long Arm of Chromosome 11, Chromosome 11 Partial Monosomy 11q, Chromosome 11 Partial Trisomy, Chromosome 11 Partial Trisomy 11q13-qter, Chromosome 11 Partial Trisomy 11q21-qter, Chromosome 11 Partial Trisomy 1 1q23-qter, Chromosome 11q,Partial Trisomy, Chromosome 12 Isochromosome 12p Mosaic, Chromosome 13 Partial Monosomy 13q, Chromosome 13, Partial Monosomy of the Long Arm, Chromosome 14 Ring, Chromosome 14 Trisomy, Chromosome 15 Distal Trisomy 15q, Chromosome r15, Chromosome 15 Ring, Chromosome 15 Trisomy 15q2, Chromosome 15q, Partial Duplication Syndrome, Chromosome 17 Interstitial Deletion 17p, Chromosome 18 Long Arm Deletion Syndrome, Chromosome 18 Monosomy 18p, Chromosome 18 Monosomy 18Q, Chromosome 18 Ring, Chromosome 18 Tetrasomy 18p, Chromosome 18q-. Syndrome, Chromosome 21 Mosaic 21 Syndrome, Chromosome 21 Ring, Chromosome 21 Translocation 21 Syndrome, Chromosome 22 Inverted Duplication (22pter-22q 11), Chromosome 22 Partial Trisomy (22pter-22q 11), Chromosome 22 Ring, Chromosome 22 Trisomy Mosaic, Chromosome 48 XXYY, Chromosome 48 XXXY, Chromosome r15, Chromosomal Triplication, Chromosome Triplication, Chromosome Triploidy Syndrome, Chromosome X, Chromosome XXY, Chronic Acholuric Jaundice, Chronic Adhesive Arachnoiditis, Chronic Adrenocortical Insufficiency, Chronic Cavernositis, Chronic Congenital Aregenerative Anemia, Chronic Dysphagocytosis, Chronic Familial Granulomatosis, Chronic Familial Icterus, Chronic Fatigue Immune Dysfunction Syndrome (CFIDS), Chronic Granulomatous Disease, Chronic Guillain-Barre Syndrome, Chronic Idiopathic Jaundice, Chronic Idiopathic Polyneuritis (CIP), Chronic Inflammatory Demyelinating Polyneuropathy, Chronic Inflammatory Demyelinating Polyradiculoneuropathy, Chronic Motor Tic, Chronic Mucocutaneous Candidiasis, Chronic Multiple Tics, Chronic Non-Specific Ulcerative Colitis, Chronic Non-Specific Ulcerative Colitis, Chronic Obliterative Cholangitis, Chronic Peptic Ulcer and Esophagitis Syndrome, Chronic Progressive Chorea, Chronic Progressive External Ophthalmoplegia Syndrome, Chronic Progressive External Ophthalmoplegia and myopathy, Chronic Progressive External Ophthalmoplegia with Ragged Red Fibers, Chronic Relapsing Polyneuropathy, Chronic Sarcoidosis, Chronic Spasmodic Dysphonia, Chronic Vomiting in Childhood, CHS, Churg-Strauss Syndrome, Cicatricial Pemphigoid, CIP, Cirrhosis Congenital Pigmentary, Cirrhosis, Cistinuria, Citrullinemia, CJD, Classic Schindler Disease, Classic Type Pfeiffer Syndrome, Classical Maple Syrup Urine Disease, Classical Hemophilia, Classical Form Cockayne Syndrome Type I (Type A), Classical Leigh's Disease, Classical Phenylketonuria, Classical X-Linked Pelizaeus-Merzbacher Brain Sclerosis, CLE, Cleft Lip/Palate Mucous Cysts Lower Lip PP Digital and Genital Anomalies, Cleft Lip-Palate Blepharophimosis Lagophthalmos and Hypertelorism, Cleft Lip/Palate with Abnormal Thumbs and Microcephaly, Cleft palate-joint contractures-dandy walker. malformations, Cleft Palate and Cleft Lip, Cleidocranial Dysplasia w/Micrognathia, Absent Thumbs, & Distal Aphalangia, Cleidocranial Dysostosis, Cleidocranial Dysplasia, Click murmur syndrome, CLN1, Clonic Spasmodic, Cloustons Syndrome, Clubfoot, CMDI, CMM, CMT, CMTC, CMTX, COA Syndrome, Coarctation of the aorta, Coarctation of the aorta, Coats' Disease, Cobblestone dysplasia, Cochin Jewish Disorder, Cockayne Syndrome, COD-MD Syndrome, COD, Coffin Lowry Syndrome, Coffin Syndrome, Coffin Siris Syndrome, COFS Syndrome, Cogan Corneal Dystrophy, Cogan Reese Syndrome, Cohen Syndrome, Cold Agglutinin Disease, Cold Antibody Disease, Cold Antibody Disease, Cold Antibody Hemolytic Anemia, Cold Agglutinin Disease, Cold Agglutinin Disease, Colitis Ulcerative, Colitis Gravis, Colitis Gravis, Colitis Ulcerative Chronic Non-Specific Ulcerative Colitis, Collodion Baby, Coloboma Heart Defects Atresia of the Choanae Retardation of Growth and Development Genital and Urinary Anomalies and Ear Anomalies, Coloboma, Coloboma, Colonic Neurosis, Color blindness, Color blindness, Colour blindness, Colour blindness, Colpocephaly, Columnar-Like Esophagus, Combined Cone-Rod Degeneration, Combined Immunodeficiency with Immunoglobulins, Combined Mesoectodermal Dysplasia, Common Variable Hypogammaglobulinemia, Common Variable Immunodeficiency, Common Ventricle, Communicating Hydrocephalus, Complete Absense of Hypoxanthine-Guanine Phosphoribosyltranferase, Complete Atrioventricular Septal Defect, Complement Component 1 Inhibitor Deficiciency, Complement Component C1 Regulatory Component Deficiency, Complete Heart Block, Complex Carbohydrate Intolerance, Complex Regional Pain Syndrome, Complex V ATP Synthase Deficiency, Complex I, Complex I NADH dehydrogenase deficiency, Complex II, Complex II Succinate dehydrogenase deficiency, Complex III, Complex III Ubiquinone-cytochrome c oxidoreductase deficiency, Complex IV, Complex IV Cytochrome c oxidase deficiency, Complex IV Deficiency, Complex V, Cone-Rod Degeneration, Cone-Rod Degeneration Progressive, Cone Dystrophy, Cone-Rod Dystrophy, Confluent Reticular Papillomatosis, Congenital with low PK Kinetics, Congenital Absence of Abdominal Muscles, Congenital Absence of the Thymus and Parathyroids, Congenital Achromia, Congenital Addison's Disease, Congenital Adrenal Hyperplasia, Congenital Adreneal Hyperplasia, Congenital Afibrinogenemia, Congenital Alveolar Hypoventilation, Congenital Anemia of Newborn, Congenital Bilateral Persylvian Syndrome, Congenital Brown Syndrome, Congenital Cardiovascular Defects, Congenital Central Hypoventilation Syndrome, Congenital Cerebral Palsy, Congenital Cervical Synostosis, Congenital Clasped Thumb with Mental Retardation, Congenital Contractural Arachnodactyly, Congenital Contractures Multiple with Arachnodactyly, Congenital Cyanosis, Congenital Defect of the Skull and Scalp, Congenital Dilatation of Intrahepatic Bile Duct, Congenital Dysmyelinating Neuropathy, Congenital Dysphagocytosis, Congenital Dysplastic Angiectasia, Congenital Erythropoietic Porphyria, Congenital Erythropoietic Porphyria, Congenital Factor XIII Deficiency, Congenital Failure of Autonomic Control of Respiration, Congenital Familial Nonhemolytic Jaundice Type I, Congenital Familial Protracted Diarrhea, Congenital Form Cockayne Syndrome Type H (Type B), Congenital Generalized Fibromatosis, Congenital German Measles, Congenital Giant Axonal Neuropathy, Congenital Heart Block, Congenital Heart Defects, Congenital Hemidysplasia with Ichthyosis Erythroderma and Limb Defects, Congenital Hemolytic Jaundice, Congenital Hemolytic Anemia, Congenital Hepatic Fibrosis, Congenital Hereditary Corneal Dystrophy, Congenital Hereditary Lymphedema, Congenital Hyperchondroplasia, Congenital Hypermyelinating Polyneuropathy, Congenital Hypomyelination Neuropathy, Congenital Hypomyelination, Congenital Hypomyelination Neuropathy, Congenital Hypomyelination (Onion Bulb) Polyneuropathy, Congenital Ichthyosiform Erythroderma, Congenital Keratoconus, Congenital Lactic Acidosis, Congenital Lactose Intolerance, Congenital Lipodystrophy, Congenital Liver Cirrhosis, Congenital Lobar Emphysema, Congenital Localized Emphysema, Congenital Macroglossia, Congenital Medullary Stenosis, Congenital Megacolon, Congenital Melanocytic Nevus, Congenital Mesodermal Dysmorphodystrophy, Congenital Mesodermal Dystrophy, Congenital Microvillus Atrophy, Congenital Multiple Arthrogryposis, Congenital Myotonic Dystrophy, Congenital Neuropathy caused by Hypomyelination, Congenital Pancytopenia, Congenital Pernicious Anemia, Congenital Pernicious Anemia due to Defect of Intrinsic Factor, Congenital Pernicious Anemia due to Defect of Intrinsic Factor, Congenital Pigmentary Cirrhosis, Congenital Porphyria, Congenital Proximal myopathy Associated with Desmin Storage myopathy, Congenital Pulmonary Emphysema, Congenital Pure Red Cell Anemia, Congenital Pure Red Cell Aplasia, Congenital Retinal Blindness, Congenital Retinal Cyst, Congenital Retinitis Pigmentosa, Congenital Retinoschisis, Congenital Rod Disease, Congenital Rubella Syndrome, Congenital Scalp Defects with Distal Limb Reduction Anomalies, Congenital Sensory Neuropathy, Congenital SMA with arthrogryposis, Congenital Spherocytic Anemia, Congenital Spondyloepiphyseal Dysplasia, Congenital Tethered Cervical Spinal Cord Syndrome, Congenital Tyrosinosis, Congenital Varicella Syndrome, Congenital Vascular Cavernous Malformations, Congenital Vascular Veils in the Retina, Congenital Word Blindness, Congenital Wandering Spleen (Pediatric), Congestive Cardio myopathy, Conical Cornea, Conjugated Hyperbilirubinemia, Conjunctivitis, Conjunctivitis Ligneous, Conjunctivo-Urethro-Synovial Syndrome, Conn's Syndrome, Connective Tissue Disease, Conradi Disease, Conradi Hunermann Syndrome, Constitutional Aplastic Anemia, Constitutional Erythroid Hypoplasia, Constitutional Eczema, Constitutional Liver Dysfunction, Constitutional Thrombopathy, Constricting Bands Congenital, Constrictive Pericarditis with Dwarfism, Continuous Muscle Fiber Activity Syndrome, Contractural Arachnodactyly, Contractural Arachnodactyly, Contractures of Feet Muscle Atrophy and Oculomotor Apraxia, Convulsions, Cooley's anemia, Copper Transport Disease, Coproporphyria Porphyria Hepatica, Cor Triatriatum, Cor Triatriatum Sinistrum, Cor Triloculare Biatriatum, Cor Biloculare, Cori Disease, Cornea Dystrophy, Corneal Amyloidosis, Corneal Clouding-Cutis Laxa-Mental Retardation, Corneal Dystrophy, Cornelia de Lange Syndrome, Coronal Dentine Dysplasia, Coronary Artery Disease, Coronary Heart Disease, Corpus Callosum Agenesis, Cortical-Basal Ganglionic Degeneration, Corticalis Deformaris, Cortico-Basal Ganglionic Degeneration (CBGD), Corticobasal Degeneration, Corticosterone Methloxidase Deficiency Type I, Corticosterone Methyloxidase Deficiency Type II, Cortisol, Costello Syndrome, Cot Death, COVESDEM Syndrome, COX, COX Deficiency, COX Deficiency French-Canadian Type, COX Deficiency Infantile Mitochondrial myopathy de Toni-Fanconi-Debre included, COX Deficiency Type Benign Infantile Mitochondrial Mypoathy, CP, CPEO, CPEO with myopathy, CPEO with Ragged-Red Fibers, CPPD Familial Form, CPT Deficiency, CPTD, Cranial Arteritis, Cranial Meingoencephalocele, Cranio-Oro-Digital Syndrome, Craniocarpotarsal dystrophy, Craniocele, Craniodigital Syndrome-Mental Retardation Scott Type, Craniofacial Dysostosis, Craniofacial Dysostosis-PD Arteriosus-Hypertrichosis-Hypoplasia of Labia, Craniofrontonasal Dysplasia, Craniometaphyseal Dysplasia, Cranioorodigital Syndrome, Cranioorodigital Syndrome Type II, Craniostenosis Crouzon Type, Craniostenosis, Craniostenosis, Craniosynostosis-Choanal Atresia-Radial Humeral Synostosis, Craniosynostosis-Hypertrichosis-Facial and Other Anomalies, Craniosynostosis Midfacial Hypoplasia and Foot Abnormalities, Craniosynostosis Primary, Craniosynostosis-Radial Aplasia Syndrome, Craniosynostosis with Radial Defects, Cranium Bifidum, CREST Syndrome, CREST Syndrome, Creutzfeldt Jakob Disease, Cridu Chat Syndrome, Crib Death, Crigler Najjar Syndrome Type I, Crohn's Diseas, Crohn's Disease, Cronkhite-Canada Syndrome, Cross Syndrome, Cross' Syndrome, Cross-McKusick-Breen Syndrome, Crouzon, Crouzon Syndrome, Crouzon Craniofacial Dysostosis, Cryoglobulinemia Essential Mixed, Cryptophthalmos-Syndactyly Syndrome, Cryptorchidism-Dwarfism-Subnormal Mentality, Crystalline Corneal Dystrophy of Schnyder, CS, CSD, CSID, CSO, CST Syndrome, Curly Hair-Ankyloblephanon-Nail Dysplasia, Curschmann-Batten-Steinert Syndrome, Curth Macklin Type Ichthyosis Hystric, Curth-Macklin Type, Cushing's, Cushing Syndrome, Cushing's III, Cutaneous Malignant Melanoma Hereditary, Cutaneous Porphyrias, Cutis Laxa, Cutis Laxa, Cutis Laxa-Growth Deficiency Syndrome, Cutis Marmorata Telangiectatica Congenita, CVI, CVID, CVS, CVS, Cyclic vomiting syndrome, Cystic Disease of the Renal Medulla, Cystic Disease of the Renal Medulla, Cystic Hygroma, Cystic Fibrosis, Cystic Lymphangioma, Cystine-Lysine-Arginine-Ornithinuria, Cystine Storage Disease, Cystinosis, Cystinuria, Cystinuria with Dibasic Aminoaciduria, Cystinuria Type I, Cystinuria Type II, Cystinuria Type III, Cysts of the Renal Medulla Congenital, Cysts of the Renal Medulla Congenital, Cytochrome C Oxidase Deficiency, D.C., Dacryosialoadenopathy, Dacryosialoadenopathia, Dalpro, Dalton, Daltonism, Danbolt-Cross Syndrome, Dancing Eyes-Dancing Feet Syndrome, Dandy-Walker Syndrome, Dandy-Walker Cyst, Dandy-Walker Deformity, Dandy Walker Malformation, Danish Cardiac Type Amyloidosis (Type III), Darier Disease, Davidson's Disease, Davies' Disease, DBA, DBS, DC, DD, De Barsy Syndrome, De Barsy-Moens-Diercks Syndrome, de Lange Syndrome, De Morsier Syndrome, De Santis Cacchione Syndrome, de Toni-Fanconi Syndrome, Deafness Congenital and Functional Heart Disease, Deafness-Dwarfism-Retinal Atrophy, Deafness-Functional Heart Disease, Deafness Onychodystrophy Osteodystrophyand Mental Retardation, Deafness and Pili Torti Bjornstad Type, Deafness Sensorineural with Imperforate Anus and Hypoplastic Thumbs, Debrancher Deficiency, Deciduous Skin, Defect of Enterocyte Intrinsic Factor Receptor, Defect of Enterocyte Intrinsic Factor Receptor, Defect in Natural Killer Lymphocytes, Defect of Renal Reabsorption of Carnitine, Deficiency of Glycoprotein Neuraminidase, Deficiency of Mitochondrial Respiratory Chain Complex IV, Deficiency of Platelet Glycoprotein Ib, Deficiency of Von Willebrand Factor Receptor, Deficiency of Short-Chain Acyl-CoA Dehydrogenase (ACADS, Deformity with Mesomelic Dwarfism, Degenerative Chorea, Degenerative Lumbar Spinal Stenosis, Degos Disease, Degos-Kohlmeier Disease, Degos Syndrome, DEH, Dejerine-Roussy Syndrome, Dejerine Sottas Disease, Deletion 9p Syndrome Partial, Deletion 11q Syndrome Partial, Deletion 13q Syndrome Partial, Delleman-Oorthuys Syndrome, Delleman Syndrome, Dementia with Lobar Atrophy and Neuronal Cytoplasmic Inclusions, Demyelinating Disease, DeMyer Syndrome, Dentin Dysplasia Coronal, Dentin Dysplasia Radicular, Dentin Dysplasia Type I, Dentin Dysplasia Type II, Dentinogenesis Imperfecta Brandywine type, Dentinogenesis Imperfecta Shields Type, Dentinogenesis Imperfecta Shields Type, Dentinogenesis Imperfecta Type III, Dentinogenesis Imperfecta Type III, Dento-Oculo-Osseous Dysplasia, Dento-Oculo-Osseous Dysplasia, Dentooculocutaneous Syndrome, Denys-Drash Syndrome, Depakene, Depakene™ exposure, Depakote, Depakote Sprinkle, Depigmentation-Gingival Fibromatosis-Microphthalmia, Dercum Disease, Dercum Disease, Dermatitis Atopic, Dermatitis Exfoliativa, Dermatitis Herpetiformis, Dermatitis Multiformis, Dermatochalasia Generalized, Dermatolysis Generalized, Dermatomegaly, Dermatomyositis sine myositis, Dermatomyositis, Dermatosparaxis, Dermatostomatitis Stevens Johnson Type, Desbuquois Syndrome, Desmin Storage myopathy, Desquamation of Newborn, Deuteranomaly, Deuteranomaly, Developmental Reading Disorder, Developmental Gerstmann Syndrome, Devergie Disease, Devic Disease, Devic Syndrome, Dextrocardia-Bronchiectasis and Sinusitis, Dextrocardia with Situs Inversus, DGS, DGSX Golabi-Rosen Syndrome Included, DH, DHAP alkyl transferase deficiency, DHBS Deficiency, DHBS Deficiency, DHOF, DHPR Deficiency, DHPR Deficiency, Diabetes Insipidus, Diabetes Insipidus Diabetes Mellitus Optic Atrophy and Deafness, Diabetes Insipidus Neurohypophyseal, Diabetes Insulin Dependent, Diabetes Mellitus, Diabetes Mellitus Addison's Disease Myxedema, Diabetic Acidosis, Diabetic Bearded Woman Syndrome, Diamond-Blackfan Anemia, Diaphragmatic Apnea, Diaphyseal Aclasis, Diastrophic Dwarfism, Diastrophic Dysplasia, Diastrophic Nanism Syndrome, Dicarboxylic Aminoaciduria, Dicarboxylicaciduria Caused by Defect in Beta-Oxidation of Fatty Acids, Dicarboxylicaciduria due to Defect in Beta-Oxidation of Fatty Acids, Dicarboxylicaciduria due to MCADH Deficiency, Dichromasy, Dicker-Opitz, DID-MOAD, Diencephalic Syndrome, Diencephalic Syndrome of Childhood, Diencephalic Syndrome of Emaciation, Dienoyl-CoA Reductase Deficiency, Diffuse Cerebral Degeneration in Infancy, Diffuse Degenerative Cerebral Disease, Diffuse Idiopathic Skeletal Hyperostosis, Diffusum-Glycopeptiduria, DiGeorge Syndrome, DiGeorge Syndrome, Digital-Oro-Cranio Syndrome, Digito-Oto-Palatal Syndrome, Digito-Oto-Palatal Syndrome Type I, Digito-Oto-Palatal Syndrome Type II, Dihydrobiopterin Synthetase Deficiency, Dihydrobiopterin Synthetase Deficiency, Dihydropteridine Reductase Deficiency, Dihydropteridine Reductase Deficiency, Dihydroxyacetonephosphate synthase, Dilated (Congestive) Cardio myopathy, Dimitri Disease, Diplegia of Cerebral Palsy, Diplo-Y Syndrome, Disaccharidase Deficiency, Disaccharide Intolerance I, Discoid Lupus, Discoid Lupus Erythematosus, DISH, Disorder of Cornification, Disorder of Cornification Type I, Disorder of Cornification 4, Disorder of Cornification 6, Disorder of Cornification 8, Disorder of Cornification 9 Netherton's Type, Disorder of Cornification 11 Phytanic Acid Type, Disorder of Cornification 12 (Neutral Lipid Storage Type), Disorder of Conification 13, Disorder of Cornification 14, Disorder of Cornification 14 Trichothiodystrophy Type, Disorder of Cornification 15 (Keratitis Deafness Type), Disorder of Cornification 16, Disorder of Cornification 18 Erythrokeratodermia Variabilis Type, Disorder of Cornification 19, Disorder of Cornification 20, Disorder of Cornification 24, Displaced Spleen, Disseminated Lupus Erythematosus, Disseminated Neurodermatitis, Disseminated Sclerosis, Distal 11q Monosomy, Distal 11q-Syndrome, Distal Arthrogryposis Multiplex Congenita Type IIA, Distal Arthrogryposis Multiplex Congenita Type IIA, Distal Arthrogryposis Type IIA, Distal Arthrogryposis Type 2A, Distal Duplication 6q, Distal Duplication 10q, Dup(10q) Syndrome, Distal Duplication 15q, Distal Monosomy 9p, Distal Trisomy 6q, Distal Trisomy 10q Syndrome, Distal Trisomy 11q, Divalproex, DJS, DKC, DLE, DLPIII, DM, DMC Syndrome, DMC Disease, DMD, DNS Hereditary, DOC I, DOC 2, DOC 4, DOC 6 (Harlequin Type), DOC 8 Curth-Macklin Type, DOC 11 Phytanic Acid Type, DOC 12 (Neutral Lipid Storage Type), DOC 13, DOC 14, DOC 14 Trichiodystrophy Type, DOC 15 (Keratitis Deafness Type), DOC 16, DOC 16 Unilateral Hemidysplasia Type, DOC 18, DOC 19, DOC 20, DOC 24, Dohle's Bodies-Myelopathy, Dolichospondylic Dysplasia, Dolichostenomelia, Dolichostenomelia Syndrome, Dominant Type Kenny-Caffe Syndrome, Dominant Type Myotonia Congenita, Donahue Syndrome, Donath-Landsteiner Hemolytic Anemia, Donath-Landsteiner Syndrome, DOOR Syndrome, DOORS Syndrome, Dopa-responsive Dystonia (DRD), Dorfman Chanarin Syndrome, Dowling-Meara Syndrome, Down Syndrome, DR Syndrome, Drash Syndrome, DRD, Dreifuss-Emery Type Muscular Dystrophy with Contractures, Dressler Syndrome, Drifting Spleen, Drug-induced Acanthosis Nigricans, Drug-induced Lupus Erythematosus, Drug-related Adrenal Insufficiency, Drummond's Syndrome, Dry Beriberi, Dry Eye, DTD, Duane's Retraction Syndrome, Duane Syndrome, Duane Syndrome Type IA 1B and 1C, Duane Syndrome Type 2A 2B and 2C, Duane Syndrome Type 3A 3B and 3C, Dubin Johnson Syndrome, Dubowitz Syndrome, Duchenne, Duchenne Muscular Dystrophy, Duchenne's Paralysis, Duhring's Disease, Duncan Disease, Duncan's Disease, Duodenal Atresia, Duodenal Stenosis, Duodenitis, Duplication 4p Syndrome, Duplication 6q Partial, Dupuy's Syndrome, Dupuytren's Contracture, Dutch-Kennedy Syndrome, Dwarfism, Dwarfism Campomelic, Dwarfism Cortical Thickening of the Tubular Bones & Transient Hypocalcemia, Dwarfism Levi's Type, Dwarfism Metatropic, Dwarfism-Onychodysplasia, Dwarfism-Pericarditis, Dwarfism with Renal Atrophy and Deafness, Dwarfism with Rickets, DWM, Dyggve Melchior Clausen Syndrome, Dysautonomia Familial, Dysbetalipoproteinemia Familial, Dyschondrodysplasia with Hemangiomas, Dyschondrosteosis, Dyschromatosis Universalis Hereditaria, Dysencephalia Splanchnocystica, Dyskeratosis Congenita, Dyskeratosis Congenita Autosomal Recessive, Dyskeratosis Congenita Scoggins Type, Dyskeratosis Congenita Syndrome, Dyskeratosis Follicularis Vegetans, Dyslexia, Dysmyelogenic Leukodystrophy, Dysmyelogenic Leukodystrophy-Megalobare, Dysphonia Spastica, Dysplasia Epiphysialis Punctata, Dysplasia Epiphyseal Hemimelica, Dysplasia of Nails With Hypodontia, Dysplasia Cleidocranial, Dysplasia Fibrous, Dysplasia Gigantism SyndromeX-Linked, Dysplasia Osteodental, Dysplastic Nevus Syndrome, Dysplastic Nevus Syndrome, Dysplastic Nevus Type, Dyssynergia Cerebellaris Myoclonica, Dyssynergia Esophagus, Dystonia, Dystonia, Dystopia Canthorum, Dystopia Canthorum, Dystrophia Adiposogenitalis, Dystrophia Endothelialis Cornea, Dystrophia Mesodermalis, Dystrophic Epidermolysis Bullosa, Dystrophic Epidermolysis Bullosa, Dystrophy, Asphyxiating Thoracic, Dystrophy Myotonic, E-D Syndrome, Eagle-Barrett Syndrome, Eales Retinopathy, Eales Disease, Ear Anomalies-Contractures-Dysplasia of Bone with Kyphoscoliosis, Ear Patella Short Stature Syndrome, Early Constraint Defects, Early Hypercalcemia Syndrome with Elfin Facie, Early-onset Dystonia, Eaton Lambert Syndrome, EB, Ebstein's anomaly, EBV Susceptibility (EBVS), EBVS, ECD, ECPSG, Ectodermal Dysplasias, Ectodermal Dysplasia Anhidrotic with Cleft Lip and Cleft Palate, Ectodermal Dysplasia-Exocrine Pancreatic Insufficiency, Ectodermal Dysplasia Rapp-Hodgkin type, Ectodermal and Mesodermal Dysplasia Congenital, Ectodermal and Mesodermal Dysplasia with Osseous Involvement, Ectodermosis Erosiva Pluriorificialis, Ectopia Lentis, Ectopia Vesicae, Ectopic ACTH Syndrome, Ectopic Adrenocorticotropic Hormone Syndrome, Ectopic Anus, Ectrodactilia of the Hand, Ectrodactyly, Ectrodactyly-Ectodermal Dysplasia-Clefting Syndrome, Ectrodactyly Ectodermal Dysplasias Clefting Syndrome, Ectrodactyly Ectodermal Dysplasia Cleft Lip/Cleft Palate, Eczema, Eczema-Thrombocytopenia-Immunodeficiency Syndrome, EDA, EDMD, EDS, EDS Arterial-Ecchymotic Type, EDS Arthrochalasia, EDS Classic Severe Form, EDS Dysfibronectinemic, EDS Gravis Type, EDS Hypermobility, EDS Kyphoscoliotic, EDS Kyphoscoliosis, EDS Mitis Type, EDS Ocular-Scoliotic, EDS Progeroid, EDS Periodontosis, EDS Vascular, EEC Syndrome, EFE, EHBA, EHK, Ehlers Danlos Syndrome, Ehlers-Danlos syndrome, Ehlers Danlos IX, Eisenmenger Complex, Eisenmenger's complex, Eisenmenger Disease, Eisenmenger Reaction, Eisenmenger Syndrome, Eisenmenger Syndrome, Ekbom Syndrome, Ekman-Lobstein Disease, Ektrodactyly of the Hand, Ektrodactyly of the Hand, EKV, Elastin fiber disorders, Elastorrhexis Generalized, Elastosis Dystrophica Syndrome, Elective Mutism (obsolete), Elective Mutism, Electrocardiogram (ECG or EKG), Electron Transfer Flavoprotein (ETF) Dehydrogenase Deficiency: (GAII & MADD), Electrophysiologic study (EPS), Elephant Nails From Birth, Elephantiasis Congenita Angiomatosa,Hemangiectatic Hypertrophy, Elfin Facies with Hypercalcemia, Ellis-van Creveld Syndrome, Ellis Van Creveld Syndrome, Embryoma Kidney, Embryonal Adenomyosarcoma Kidney, Embryonal Carcinosarcoma Kidney, Embryonal Mixed Tumor Kidney, EMC, Emery Dreyfus Muscular Dystrophy, Emery-Dreifuss Muscular Dystrophy, Emery-Dreifuss Syndrome, EMF, EMG Syndrome, Empty Sella Syndrome, Encephalitis Periaxialis Diffusa, Encephalitis Periaxialis Concentrica, Encephalocele, Encephalofacial Angiomatosis, Encephalopathy, Encephalotrigeminal Angiomatosis, Enchondromatosis with Multiple Cavernous Hemangiomas, Endemic Polyneuritis, Endocardial Cushion Defect, Endocardial Cushion Defect, Endocardial Cushion Defects, Endocardial Dysplasia, Endocardial Fibroelastosis (EFE), Endogenous Hypertriglyceridemia, Endolymphatic Hydrops, Endometrial Growths, Endometriosis, Endomyocardial Fibrosis, Endothelial Corneal Dystrophy Congenital, Endothelial Epithelial Corneal Dystrophy, Endothelium, Engelmann Disease, Enlarged Tongue, Enterocolitis, Enterocyte Cobalamin Malabsorption, Eosinophia Syndrome, Eosinophilic Cellulitis, Eosinophilic Fasciitis, Eosinophilic Granuloma, Eosinophilic Syndrome, Epidermal Nevus Syndrome, Epidermolysis bullosa, Epidermolysis Bullosa, Epidermolysis Bullosa Acquisita, Epidermolysis Bullosa Hereditaria, Epidermolysis Bullosa Letalias, Epidermolysis Hereditaria Tarda, Epidermolytic Hyperkeratosis, Epidermolytic Hyperkeratosis (Bullous CIE), Epilepsia Procursiva, Epilepsy, Epinephrine, Epiphyseal Changes and High Myopia, Epiphyseal Osteochondroma Benign, Epiphysealis Hemimelica Dysplasia, Episodic-Abnormal Eye Movement, Epithelial Basement Membrane Corneal Dystrophy, Epithelial Corneal Dystrophy of Meesmann Juvenile, Epitheliomatosis Multiplex with Nevus, Epithelium, Epival, EPS, Epstein-Barr Virus-Induced Lymphoproliferative Disease in Males, Erb-Goldflam syndrome, Erdheim Chester Disease, Erythema Multiforme Exudativum, Erythema Polymorphe Stevens Johnson Type, Erythroblastophthisis, Erythroblastosis Fetalis, Erythroblastosis Neonatorum, Erythroblastotic Anemia of Childhood, Erythrocyte Phosphoglycerate Kinase Deficiency, Erythrogenesis Imperfecta, Erythrokeratodermia Progressiva Symmetrica, Erythrokeratodermia Progressiva Symmetrica Ichthyosis, Erythrokeratodermia Variabilis, Erythrokeratodermia Variabilis, Erythrokeratodermia Variabilis Type, Erythrokeratolysis Hiemalis, Erythrokeratolysis Hiemalis, Erythrokeratolysis Hiemalis, Erythropoietic Porphyrias, Erythropoietic Porphyria, Escobar Syndrome, Esophageal Atresia, Esophageal Aperistalsis, Esophagitis-Peptic Ulcer, Esophagus Atresia and/or Tracheoesophageal Fistula, Essential Familial Hyperlipemia, Essential Fructosuria, Essential Hematuria, Essential Hemorrhagic Thrombocythemia, Essential Hemorrhagic Thrombocythemia, Essential Mixed Cryoglobulinemia, Essential Moschowitz Disease, Essential Thrombocythemia, Essential Thrombocythemia, Essential Thrombocythemia, Essential Thrombocytopenia, Essential Thrombocytosis, Essential Thrombocytosis, Essential Tremor, Esterase Inhibitor Deficiency, Estren-Dameshek variant of Fanconi Anemia, Estrogen-related Cholestasis, ET, ET, ETF, Ethylmalonic Adipicaciduria, Eulenburg Disease, pc, EVCS, Exaggerated Startle Reaction, Exencephaly, Exogenous Hypertriglyceridemia, Exomphalos-Macroglossia-Gigantism Syndrom, Exophthalmic Goiter, Expanded Rubella Syndrome, Exstrophy of the Bladder, EXT, External Chondromatosis Syndrome, Extrahepatic Biliary Atresia, Extramedullary Plasmacytoma, Exudative Retinitis, Eye Retraction Syndrome, FA1, FAA, Fabry Disease, FAC, FACB, FACD, FACE, FACF, FACG, FACH, Facial Nerve Palsy, Facial Paralysis, Facial Ectodermal Dysplasias, Facial Ectodermal Dysplasia, Facio-Scapulo-Humeral Dystrophy, Facio-Auriculo-Vertebral Spectrum, Facio-cardio-cutaneous syndrome, Facio-Fronto-Nasal Dysplasia, Faciocutaneoskeletal Syndrome, Faciodigitogenital syndrome, Faciogenital dysplasia, Faciogenitopopliteal Syndrome, Faciopalatoosseous Syndrome, Faciopalatoosseous Syndrome Type II, Facioscapulohumeral muscular dystrophy, Factitious Hypoglycemia, Factor VIII Deficiency, Factor IX Deficiency, Factor IX Deficiency, Factor XI Deficiency, Factor XII deficiency, Factor XIII Deficiency, Fahr Disease, Fahr's Disease, Failure of Secretion Gastric Intrinsic Factor, Fairbank Disease, Fallot's Tetralogy, Familial Acrogeria, Familial Acrogeria, Familial Acromicria, Familial Acromicria, Familial Adenomatous Colon Polyposis, Familial Adenomatous Polyposis with Extraintestinal Manifestations, Familial Alobar Holoprosencephaly, Familial Alpha-Lipoprotein Deficiency, Familial Amyotrophic Chorea with Acanthocytosis, Familial Arrhythmic Myoclonus, Familial Articular Chondrocalcinosis, Familial Atypical Mole-Malignant Melanoma Syndrome, Familial Broad Beta Disease, Familial Calcium Gout, Familial Calcium Pyrophosphate Arthropathy, Familial Chronic Obstructive Lung Disease, Familial Continuous Skin Peeling, Familial Cutaneous Amyloidosis, Familial Dysproteinemia, Familial Emphysema, Familial Enteropathy Microvillus, Familial Foveal Retinoschisis, Familial Hibernation Syndrome, Familial High Cholesterol, Familial Hemochromatosis, Familial High Blood Cholesterol, Familial High-Density Lipoprotein Deficiency, Familial High Serum Cholesterol, Familial Hyperlipidema, Familial Hypoproteinemia with Lymphangietatic Enteropathy, Familial Jaundice, Familial Juvenile Nephronophtisis-Associated Ocular Anomaly, Familial Lichen Amyloidosis (Type IX), Familial Lumbar Stenosis, Familial Lymphedema Praecox, Familial Mediterranean Fever, Familial Multiple Polyposis, Familial Nuchal Bleb, Familial Paroxysmal Polyserositis, Familial Polyposis Coli, Familial Primary Pulmonary Hypertension, Familial Renal Glycosuria, Familial Splenic Anemia, Familial Startle Disease, Familial Visceral Amyloidosis (Type VIII), FAMMM, FANCA, FANCB, FANCC, FANCD, FANCE, Fanconi Panmyelopathy, Fanconi Pancytopenia, Fanconi II, Fanconi's Anemia, Fanconi's Anemia Type I, Fanconi's Anemia Complementation Group, Fanconi's Anemia Complementation Group A, Fanconi's Anemia Complementation Group B, Fanconi's Anemia Complementation Group C, Fanconi's Anemia Complementation Group D, Fanconi's Anemia Complementation Group E, Fanconi's Anemia Complementation Group G, Fanconi's Anemia Complementation Group H, Fanconi's Anemia Estren-Dameshek Variant, FANF, FANG, FANH, FAP, FAPG, Farber's Disease, Farber's Lipogranulomatosis, FAS, Fasting Hypoglycemia, Fat-Induced Hyperlipemia, Fatal Granulomatous Disease of Childhood, Fatty Oxidation Disorders, Fatty Liver with Encephalopathy, FAV, FCH, FCMD, FCS Syndrome, FD, FDH, Febrile Mucocutaneous Syndrome Stevens Johnson Type, Febrile Neutrophilic Dermatosis Acute, Febrile Seizures, Feinberg's syndrome, Feissinger-Leroy-Reiter Syndrome, Female Pseudo-Turner Syndrome, Femoral Dysgenesis Bilateral-Robin Anomaly, Femoral Dysgenesis Bilateral, Femoral Facial Syndrome, Femoral Hypoplasia-Unusual Facies Syndrome, Fetal Alcohol Syndrome, Fetal Anti-Convulsant Syndrome, Fetal Cystic Hygroma, Fetal Effects of Alcohol, Fetal Effects of Chickenpox, Fetal Effects of Thalidomide, Fetal Effects of Varicella Zoster Virus, Fetal Endomyocardial Fibrosis, Fetal Face Syndrome, Fetal Iritis Syndrome, Fetal Transfusion Syndrome, Fetal Valproate Syndrome, Fetal Valproic Acid Exposure Syndrome, Fetal Varicella Infection, Fetal Varicella Zoster Syndrome, FFDD Type II, FG Syndrome, FGDY, FHS, Fibrin Stabilizing Factor Deficiency, Fibrinase Deficiency, Fibrinoid Degeneration of Astrocytes, Fibrinoid Leukodystrophy, Fibrinoligase Deficiency, Fibroblastoma Perineural, Fibrocystic Disease of Pancreas, Fibrodysplasia Ossificans Progressiva, Fibroelastic Endocarditis, Fibromyalgia, Fibromyalgia-Fibromyositis, Fibromyositis, Fibrosing Cholangitis, Fibrositis, Fibrous Ankylosis of Multiple Joints, Fibrous Cavemositis, Fibrous Dysplasia, Fibrous Plaques of the Penis, Fibrous Sclerosis of the Penis, Fickler-Winkler Type, Fiedler Disease, Fifth Digit Syndrome, Filippi Syndrome, Finnish Type Amyloidosis (Type V), First Degree Congenital Heart Block, First and Second Branchial Arch Syndrome, Fischer's Syndrome, Fish Odor Syndrome, Fissured Tongue, Flat Adenoma Syndrome, Flatau-Schilder Disease, Flavin Containing Monooxygenase 2, Floating Beta Disease, Floating-Harbor Syndrome, Floating Spleen, Floppy Infant Syndrome, Floppy Valve Syndrome, Fluent aphasia, FMD, FMF, FMO Adult Liver Form, FMO2, FND, Focal Dermal Dysplasia Syndrome, Focal Dermal Hypoplasia, Focal Dermato-Phalangeal Dysplasia, Focal Dystonia, Focal Epilepsy, Focal Facial Dermal Dysplasia Type II, Focal Neuromycitonia, FODH, Folling Syndrome, Fong Disease, FOP, Forbes Disease, Forbes-Albright Syndrome, Forestier's Disease, Forsius-Eriksson Syndrome (X-Linked), Fothergill Disease, Fountain Syndrome, Foveal Dystrophy Progressive, FPO Syndrome Type II, FPO, Fraccaro Type Achondrogenesis (Type IB), Fragile X syndrome, Franceschetti-Zwalen-Klein Syndrome, Francois Dyscephaly Syndrome, Francois-Neetens Speckled Dystrophy, Flecked Corneal Dystrophy, Fraser Syndrome, FRAXA, FRDA, Fredrickson Type I Hyperlipoproteinemia, Freeman-Sheldon Syndrome, Freire-Maia Syndrome, Frey's Syndrome, Friedreich's Ataxia, Friedreich's Ataxia, Friedreich's Disease, Friedreich's Tabes, FRNS, Froelich's Syndrome, Frommel-Chiari Syndrome, Frommel-Chiari Syndrome Lactation-Uterus Atrophy, Frontodigital Syndrome, Frontofacionasal Dysostosis, Frontofacionasal Dysplasia, Frontonasal Dysplasia, Frontonasal Dysplasia with Coronal Craniosynostosis, Fructose-1-Phosphate Aldolase Deficiency, Fructosemia, Fructosuria, Fryns Syndrome, FSH, FSHD, FSS, Fuchs Dystrophy, Fucosidosis Type 1, Fucosidosis Type 2, Fucosidosis Type 3, Fukuhara Syndrome, Fukuyama Disease, Fukuyama Type Muscular Dystrophy, Fukuyama Type Muscular Dystrophy, Fumarylacetoacetase deficiency, Furrowed Tongue, G Syndrome, G6PD Deficiency, G6PD, GA I, GA IIB, GA IIA, GA II, GAII & MADD, Galactorrhea-Amenorrhea Syndrome Nonpuerperal, Galactorrhea-Amenorrhea without Pregnancy, Galactosamine-6-Sulfatase Deficiency, Galactose-I-Phosphate Uridyl Transferase Deficiency, Galactosemia, GALB Deficiency, Galloway-Mowat Syndrome, Galloway Syndrome, GALT Deficiency, Gammaglobulin Deficiency, GAN, Ganglioside Neuraminidase Deficiency, Ganglioside Sialidase Deficiency, Gangliosidosis GM1 Type 1, Gangliosidosis GM2 Type 2, Gangliosidosis Beta Hexosaminidase 13 Deficiency, Gardner Syndrome, Gardner Syndrome, Gargoylism, Garies-Mason Syndrome, Gasser Syndrome, Gastric Intrinsic Factor Failure of Secretion, Enterocyte Cobalamin, Gastrinoma, Gastritis, Gastroesophageal Laceration-Hemorrhage, Gastroschisis, Gaucher Disease, Gaucher-Schlagenhaufer, Gayet-Wernicke Syndrome, GBS, GCA, GCM Syndrome, GCPS, Gee-Herter Disease, Gee-Thaysen Disease, Gehrig's Disease, Gelineau's Syndrome, Genee-Wiedemann Syndrome, Generalized Dystonia, Generalized Familial Neuromyotonia, Generalized Fibromatosis, Generalized Flexion Epilepsy, Generalized Glycogenosis, Generalized Glycogenosis, Generalized Hyperhidrosis, Generalized Lipofuscinosis, Generalized Myasthenia Gravis, Generalized Myotonia, Generalized Sporadic Neuromyotonia, Genetic Disorders, Genital Defects, Genital and Urinary Tract Defects, Genital and Urinary Tract Defects, Gerstmann Syndrome, Gerstmann Tetrad, GHBP, GHD, GHR, Giant Axonal Disease, Giant Axonal Neuropathy, Giant Benign Lymphoma, Giant Cell Glioblastoma Astrocytoma, Giant Cell Arteritis, Giant Cell Disease of the Liver, Giant Cell Hepatitis, Giant Cell of Newborns Cirrhosis, Giant Cyst of the Retina, Giant Lymph Node Hyperplasia, Giant Platelet Syndrome Hereditary, Giant Tongue, gic Macular Dystrophy, Gilbert's Disease, Gilbert Syndrome, Gilbert-Dreyfus Syndrome, Gilbert-Dreyfus Syndrome, Gilbert-Lereboullet Syndrome, Gilford Syndrome, Gilles de la Tourette's syndrome, Gillespie Syndrome, Gingival Fibromatosis-Abnormal Fingers Nails Nose Ear Splenomegaly, GLA Deficiency, GLA, GLB1, Glioma Retina, Global aphasia, Globoid Leukodystrophy, Glossoptosis Micrognathia and Cleft Palate, Glucocerebrosidase deficiency, Glucocerebrosidosis, Glucose-6-Phosphate Dehydrogenase Deficiency, Glucose-6-Phosphate Tranport Defect, Glucose-6-Phospate Translocase Deficiency, Glucose-G-Phosphatase Deficiency, Glucose-Galactose Malabsorption, Glucose-Galactose Malabsorption, Glucosyl Ceramide Lipidosis, Glutaric Aciduria I, Glutaric Acidemia I, Glutaric Acidemia II, Glutaric Aciduria II, Glutaric Aciduria Type II, Glutaric Aciduria Type III, Glutaricacidemia I, Glutaricacidemia II, Glutaricaciduria I, Glutaricaciduria II, Glutaricaciduria Type IIA, Glutaricaciduria Type IIB, Glutaryl-CoA Dehydrogenase Deficiency, Glutaurate-Aspartate Transport Defect, Gluten-Sensitive Enteropathy, Glycogen Disease of Muscle Type VII, Glycogen Storage Disease I, Glycogen Storage Disease III, Glycogen Storage Disease IV, Glycogen Storage Disease Type V, Glycogen Storage Disease VI, Glycogen Storage Disease VII, Glycogen Storage Disease VIII, Glycogen Storage Disease Type II, Glycogen Storage Disease-Type II, Glycogenosis, Glycogenosis Type I, Glycogenosis Type IA, Glycogenosis Type IB, Glycogenosis Type II, Glycogenosis Type II, Glycogenosis Type III, Glycogenosis Type IV, Glycogenosis Type V, Glycogenosis Type VI, Glycogenosis Type VII, Glycogenosis Type VIII, Glycolic Aciduria, Glycolic Aciduria, Glycolipid Lipidosis, GM2 Gangliosidosis Type 1, GM2 Gangliosidosis Type 1, GNPTA, Goitrous Autoimmune Thyroiditis, Goldenhar Syndrome, Goldenhar-Gorlin Syndrome, Goldscheider's Disease, Goltz Syndrome, Goltz-Gorlin Syndrome, Gonadal Dysgenesis 45 X, Gonadal Dysgenesis XO, Goniodysgenesis-Hypodontia, Goodman Syndrome, Goodman, Goodpasture Syndrome, Gordon Syndrome, Gorlin's Syndrome, Gorlin-Chaudhry-Moss Syndrome, Gottron Erythrokeratodermia Congenitalis Progressiva Symmetrica, Gottron's Syndrome, Gougerot-Carteaud Syndrome, Grand Mal Epilepsy, Granular Type Corneal Dystrophy, Granulomatous Arteritis, Granulomatous Colitis, Granulomatous Dermatitis with V Eosinophilia, Granulomatous Ileitis, Graves Disease, Graves' Hyperthyroidism, Graves' Disease, Greig Cephalopolysyndactyly Syndrome, Groenouw Type I Corneal Dystrophy, Groenouw Type II Comeal Dystrophy, Gronblad-Strandberg Syndrome, Grotton Syndrome, Growth Hormone Receptor Deficiency, Growth Hormone Binding Protein Deficiency, Growth Hormone Deficiency, Growth-Mental Deficiency Syndrome of Myhre, Growth Retardation-Rieger Anomaly, GRS, Gruber Syndrome, GS, GSD6, GSD8, GTS, Guanosine Triphosphate-Cyclohydrolase Deficiency, Guanosine Triphosphate-Cyclohydrolase Deficiency, Guenther Porphyria, Guerin-Stern Syndrome, Guillain-Barré, Guillain-Barre Syndrome, Gunther Disease, H Disease, H. Gottron's Syndrome, H. Gottron's Syndrome, Habit Spasms, HAE, Hageman Factor Deficiency, Hageman factor, Haim-Munk Syndrome, Hajdu-Cheney Syndrome, Hajdu Cheney, HAL Deficiency, Hall-Pallister Syndrome, Hallermann-Streiff-Francois syndrome, Hallermann-Streiff Syndrome, Hallervorden-Spatz Disease, Hallervorden-Spatz Syndrome, Hallopeau-Siemens Disease, Hallux Duplication Postaxial Polydactyly and Absence of Corpus Callosum, Halushi-Behcet's Syndrome, Hamartoma of the Lymphatics, Hand-Schueller-Christian Syndrome, HANE, Hanhart Syndrome, Happy Puppet Syndrome, Harada Syndrome, HARD +/−E Syndrome, HARD Syndrome, Hare Lip, Harlequin Fetus, Harlequin Type DOC 6, Harlequin Type Ichthyosis, Harlequin Type Ichthyosis, Harley Syndrome, Harrington Syndrome, Hart Syndrome, Hartnup Disease, Hartnup Disorder, Hartnup Syndrome, Hashimoto's Disease, Hashimoto-Pritzker Syndrome, Hashimoto's Syndrome, Hashimoto's Thyroiditis, Hashimoto's Thyroiditis, Hashimoto-Pritzker Syndrome, Hay Well's Syndrome, Hay-Wells Syndrome of Ectodermal Dysplasia, HCMM, HCP, HCTD, HD, Heart-Hand Syndrome (Holt-Oram Type), Heart Disease, Hecht Syndrome, HED, Heerferdt-Waldenstrom and Lofgren's Syndromes, Hegglin's Disease, Heinrichsbauer Syndrome, Hemangiomas, Hemangioma Familial, Hemangioma-Thrombocytopenia Syndrome, Hemangiomatosis Chondrodystrophica, Hemangiomatous Branchial Clefts-Lip Pseudocleft Syndrome, Hemifacial Microsomia, Hemimegalencephaly, Hemiparesis of Cerebral Palsy, Hemiplegia of Cerebral Palsy, Hemisection of the Spinal Cord, Hemochromatosis, Hemochromatosis Syndrome, Hemodialysis-Related Amyloidosis, Hemoglobin Lepore Syndromes, Hemolytic Anemia of Newborn, Hemolytic Cold Antibody Anemia, Hemolytic Disease of Newborn, Hemolytic-Uremic Syndrome, Hemolytic-Uremic Syndrome, Hemophilia, Hemophilia A, Hemophilia B, Hemophilia B Factor IX, Hemophilia C, Hemorrhagic Dystrophic Thrombocytopenia, Hemorrhagica Aleukia, Hemosiderosis, Hepatic Fructokinase Deficiency, Hepatic Phosphorylase Kinase Deficiency, Hepatic Porphyria, Hepatic Porphyrias, Hepatic Porphyrias, Hepatic Veno-Occlusive Diseas, Hepato-Renal Syndrome, Hepatolenticular Degeneration, Hepatophosphorylase Deficiency, Hepatorenal Glycogenosis, Hepatorenal Syndrome, Hepatorenal Tyrosinemia, Hereditary Acromelalgia, Hereditary Alkaptonuria, Hereditary Amyloidosis, Hereditary Angioedema, Hereditary Areflexic Dystasia, Heredopathia Atactica Polyneuritiformis, Hereditary Ataxia, Hereditary Ataxia, Hereditary Ataxia Friedrich's Type, Hereditary Benign Acanthosis Nigricans, Hereditary Cerebellar Ataxia, Hereditary Chorea, Hereditary Chronic Progressive Chorea, Hereditary Connective Tissue Disorders, Hereditary Coproporphyria, Hereditary Coproporphyria Porphyria, Hereditary Cutaneous Malignant Melanoma, Hereditary Deafness-Retinitis Pigmentosa, Heritable Disorder of Zinc Deficiency, Hereditary DNS, Hereditary Dystopic Lipidosis, Hereditary Emphysema, Hereditary Fructose Intolerance, Hereditary Hemorrhagic Telangiectasia, Hereditary Hemorrhagic Telangiectasia Type I, Hereditary Hemorrhagic Telangiectasia Type II, Hereditary Hemorrhagic Telangiectasia Type III, Hereditary Hyperuricemia and Choreoathetosis Syndrome, Hereditary Leptocytosis Major, Hereditary Leptocytosis Minor, Hereditary Lymphedema, Hereditary Lymphedema Tarda, Hereditary Lymphedema Type I, Hereditary Lymphedema Type II, Hereditary Motor Sensory Neuropathy, Hereditary Motor Sensory Neuropathy I, Hereditary Motor Sensory Neuropathy Type III, Hereditary Nephritis, Hereditary Nephritis and Nerve Deafness, Hereditary Nephropathic Amyloidosis, Hereditary Nephropathy and Deafness, Hereditary Nonpolyposis Colorectal Cancer, Hereditary Nonpolyposis Colorectal Carcinoma, Hereditary Nonspherocytic Hemolytic Anemia, Hereditary Onychoosteodysplasia, Hereditary Optic Neuroretinopathy, Hereditary Polyposis Coli, Hereditary Sensory and Autonomic Neuropathy Type I, Hereditary Sensory and Autonomic Neuropathy Type II, Hereditary Sensory and Autonomic Neuropathy Type III, Hereditary Sensory Motor Neuropathy, Hereditary Sensory Neuropathy type I, Hereditary Sensory Neuropathy Type I, Hereditary Sensory Neuropathy Type II, Hereditary Sensory Neuropathy Type III, Hereditary Sensory Radicular Neuropathy Type I, Hereditary Sensory Radicular Neuropathy Type I, Hereditary Sensory Radicular Neuropathy Type II, Hereditary Site Specific Cancer, Hereditary Spherocytic Hemolytic Anemia, Hereditary Spherocytosis, Hereditary Tyrosinemia Type 1, Heritable Connective Tissue Disorders, Herlitz Syndrome, Hermans-Herzberg Phakomatosis, Hermansky-Pudlak Syndrome, Hermansky-Pudlak Syndrome, Hermaphroditism, Herpes Zoster, Herpes Iris Stevens-Johnson Type, Hers Disease, Heterozygous Beta Thalassemia, Hexoaminidase Alpha-Subunit Deficiency (Variant B), Hexoaminidase Alpha-Subunit Deficiency (Variant B), HFA, HFM, HGPS, HH, HRHO, HHRH, HHT, Hiatal Hernia-Microcephaly-Nephrosis Galloway Type, Hidradenitis Suppurativa, Hidrosadenitis Axillaris, Hidrosadenitis Suppurativa, Hidrotic Ectodermal Dysplasias, HIE Syndrome, High Imperforate Anus, High Potassium, High Scapula, HIM, Hirschsprung's Disease, Hirschsprung's Disease Acquired, Hirschsprung Disease Polydactyly of Ulnar & Big Toe and VSD, Hirschsprung Disease with Type D Brachydactyly, Hirsutism, HIS Deficiency, Histidine Ammonia-Lyase (HAL) Deficiency, Histidase Deficiency, Histidinemia, Histidinemia, Histiocytosis, Histiocytosis X, HLHS, HLP Type II, HMG, HMI, HMSN I, HNHA, HOCM, Hodgkin Disease, Hodgkin's Disease, Hodgkin's Lymphoma, Hollaender-Simons Disease, Holmes-Adie Syndrome, Holocarboxylase Synthetase Deficiency, Holoprosencephaly, Holoprosencephaly Malformation Complex, Holoprosencephaly Sequence, Holt-Oram Syndrome, Holt-Oram Type Heart-Hand Syndrome, Homocystinemia, Homocystinuria, Homocystinuria, Homogentisic Acid Oxidase Deficiency, Homogentisic Acidura, Homozygous Alpha-I-Antitrypsin Deficiency, HOOD, Homer Syndrome, Horton's disease, HOS, HOS1, Houston-Harris Type Achrondrogenesis (Type IA), HPS, HRS, HS, HS, HS, HS, HS, HSAN Type I, HSAN Type II, HSAN-III, HSMN, HSMN Type III, HSN I, HSN-III, Huebner-Herter Disease, Hunner's Patch, Hunner's Ulcer, Hunter Syndrome, Hunter Syndrome, Hunter-Thompson Type Acromesomelic Dysplasia, Huntington's Chorea, Huntington's Disease, Hurler Disease, Hurler Disease, Hurler Syndrome, Hurler-Scheie Syndrome, HUS, HUS, Hutchinson-Gilford Progeria Syndrome, Hutchinson-Gilford Syndrome, Hutchinson-Weber-Peutz Syndrome, Hutchinson-Weber-Peutz Syndrome, Hutterite Syndrome Bowen-Conradi Type, Hyaline Panneuropathy, Hydranencephaly, Hydrocephalus, Hydrocephalus Agyria and Retinal Dysplasia, Hydrocephalus Internal Dandy-Walker Type, Hydrocephalus Noncommunicating Dandy-Walker Type, Hydrocephaly, Hydronephrosis With Peculiar Facial Expression, Hydroxylase Deficiency, Hygroma Colli, Hyper-IgE Syndrome, Hyper-IgM Syndrome, Hyper IgM Syndrome, Hyperaldosteronism, Hyperaldosteronism With Hypokalemic Alkatosis, Hyperaldosteronism Without Hypertension, Hyperammonemia, Hyperammonemia Due to Carbamylphosphate Synthetase Deficiency, Hyperammonemia Due to Ornithine Transcarbamylase Deficiency, Hyperammonemia Type II, Hyper-Beta Camosinemia, Hyperbilirubinemia I, Hyperbilirubinemia II, Hypercalcemia Familial with Nephrocalcinosis and Indicanuria, Hypercalcemia-Supravalvar Aortic Stenosis, Hypercalciuric Rickets, Hypercapnic acidosis, Hypercatabolic Protein-Losing Enteropathy, Hyperchloremic acidosis, Hypercholesterolemia, Hypercholesterolemia Type IV, Hyperchylomicronemia, Hypercystinuria, Hyperekplexia, Hyperextensible joints, Hyperglobulinemic Purpura, Hyperglycinemia with Ketoacidosis and Lactic Acidosis Propionic Type, Hyperglycinemia Nonketotic, Hypergonadotropic Hypogonadism, Hyperimmunoglobulin E Syndrome, Hyperimmunoglobulin E-Recurrent Infection Syndrome, Hyperimmunoglobulinemia E-*Staphylococcal*, Hyperkalemia, Hyperkinetic Syndrome, Hyperlipemic Retinitis, Hyperlipidemia I, Hyperlipidemia IV, Hyperlipoproteinemia Type I, Hyperlipoproteinemia Type III, Hyperlipoproteinemia Type IV, Hyperoxaluria, Hyperphalangy-Clinodactyly of Index Finger with Pierre Robin Syndrome, Hyperphenylalanemia, Hyperplastic Epidermolysis Bullosa, Hyperpnea, Hyperpotassemia, Hyperprebeta-Lipoproteinemia, Hyperprolinemia Type I, Hyperprolinemia Type II, Hypersplenism, Hypertelorism with Esophageal Abnormalities and Hypospadias, Hypertelorism-Hypospadias Syndrome, Hypertrophic Cardio myopathy, Hypertrophic Interstitial Neuropathy, Hypertrophic Interstitial Neuritis, Hypertrophic Interstitial Radiculoneuropathy, Hypertrophic Neuropathy of Refsum, Hypertrophic Obstructive Cardio myopathy, Hyperuricemia Choreoathetosis Self-multilation Syndrome, Hyperuricemia-Oligophrenia, Hypervalinemia, Hypocalcified (Hypomineralized) Type, Hypochondrogenesis, Hypochrondroplasia, Hypogammaglobulinemia, Hypogammaglobulinemia Transient of Infancy, Hypogenital Dystrophy with Diabetic Tendency, Hypoglossia-Hypodactylia Syndrome, Hypoglycemia, Hypoglycemia, Exogenous Hypoglycemia, Hypoglycemia with Macroglossia, Hypoglycosylation Syndrome Type Ia, Hypoglycosylation Syndrome Type Ia, Hypogonadism with Anosmia, Hypogonadotropic Hypogonadism and Anosmia, Hypohidrotic Ectodermal Dysplasia, Hypohidrotic Ectodermal Dysplasia Autosomal Dominant type, Hypohidrotic Ectodermal Dysplasias Autorecessive, Hypokalemia, Hypokalemic Alkalosis with Hypercalciuria, Hypokalemic Syndrome, Hypolactasia, Hypomaturation Type (Snow-Capped Teeth), Hypomelanosis of Ito, Hypomelia-Hypotrichosis-Facial Hemangioma Syndrome, Hypomyelination Neuropathy, Hypoparathyroidism, Hypophosphatasia, Hypophosphatemic Rickets with Hypercalcemia, Hypopigmentation, Hypopigmentation, Hypopigmented macular lesion, Hypoplasia of the Depressor Anguli Oris Muscle with Cardiac Defects, Hypoplastic Anemia, Hypoplastic Congenital Anemia, Hypoplastic Chondrodystrophy, Hypoplastic Enamel-Onycholysis-Hypohidrosis, Hypoplastic (Hypoplastic-Explastic) Type, Hypoplastic Left Heart Syndrome, Hypoplastic Left Heart Syndrome, Hypoplastic-Triphalangeal Thumbs, Hypopotassemia Syndrome, Hypospadias-Dysphagia Syndrome, Hyposmia, Hypothalamic Hamartoblastoma Hypopituitarism Imperforate Anus Polydactyly, Hypothalamic Infantilism-Obesity, Hypothyroidism, Hypotonia-Hypomentia-Hypogonadism-Obesity Syndrome, Hypoxanthine-Guanine Phosphoribosyltranferase Defect (Complete Absense of), I-Cell Disease, Iatrogenic Hypoglycemia, IBGC, IBIDS Syndrome, IBM, IBS, IC, I-Cell Disease, ICD, ICE Syndrome Cogan-Reese Type, Icelandic Type Amyloidosis (Type VI), I-Cell Disease, Ichthyosiform Erythroderma Corneal Involvement and Deafness, Ichthyosiform Erythroderma Hair Abnormality Growth and Men, Ichthyosiform Erythroderma with Leukocyte Vacuolation, Ichthyosis, Ichthyosis Congenita, Ichthyosis Congenital with Trichothiodystrophy, Ichthyosis Hystrix, Ichthyosis Hystrix Gravior, Ichthyosis Linearis Circumflexa, Ichthyosis Simplex, Ichthyosis Tay Syndrome, Ichthyosis Vulgaris, Ichthyosis Vulgaris, Ichthyotic Neutral Lipid Storage Disease, Icteric Leptospirosis, Icterohemorrhagic Leptospirosis, Icterus (Chronic Familial), Icterus Gravis Neonatorum, Icterus Intermittens Juvenalis, Idiopathic Alveolar Hypoventilation, Idiopathic Amyloidosis, Idiopathic Arteritis of Takayasu, Idiopathic Basal Ganglia Calcification (IBGC), Idiopathic Brachial Plexus Neuropathy, Idiopathic Cervical Dystonia, Idiopathic Dilatation of the Pulmonary Artery, Idiopathic Dilatation of the Pulmonary Artery, Idiopathic Facial Palsy, Idiopathic Familial Hyperlipemia, Idiopathic Hypertrophic Subaortic Stenosis, Idiopathic Hypoproteinemia, Idiopathic Immunoglobulin Deficiency, Idiopathic Neonatal Hepatitis, Idiopathic Non-Specific Ulcerative Colitis, Idiopathic Non-Specific Ulcerative Colitis, Idiopathic Peripheral Periphlebitis, Idiopathic Pulmonary Fibrosis, Idiopathic Refractory Sideroblastic Anemia, Idiopathic Refractory Sideroblastic Anemia, Idiopathic Renal Hematuria, Idiopathic Steatorrhea, Idiopathic Thrombocythemia, Idiopathic Thrombocythemia, Idiopathic Thrombocytopenic Purpura, Idiopathic Thrombocytopenia Purpura (ITP), IDPA, IDPA, IgA Nephropathy, IgA Nephropathy, IHSS, Ileitis, Ileocolitis, Illinois Type Amyloidosis, ILS, IM, IMD2, IMD5, IMD5, Immune Defect due to Absence of Thymus, Immune Hemolytic Anemia Paroxysmal Cold, Immunodeficiency with Ataxia Telangiectasia, Immunodeficiency Cellular with Abnormal Immunoglobulin Synthesis, Immunodeficiency Common Variable Unclassifiable, Immunodeficiency with Hyper-IgM, Immunodeficiency with Leukopenia, Immunodeficiency-2, Immunodeficiency-5 (IMD5), Immunoglobulin Deficiency, Imperforate Anus, Imperforate Anus with Hand Foot and Ear Anomalies, Imperforate Nasolacrimal Duct and Premature Aging Syndrome, Impotent Neutrophil Syndrome, Inability To Open Mouth Completely And Short Finger-Flexor, INAD, INAD, Inborn Error of Urea Synthesis Arginase Type, Inborn Error of Urea Synthesis Arginino Succinic Type, Inborn Errors of Urea Synthesis Carbamyl Phosphate Type, Inborn Error of Urea Synthesis Citrullinemia Type, Inborn Errors of Urea Synthesis Glutamate Synthetase Type, INCL, Inclusion body myositis, Incomplete Atrioventricular Septal Defect, Incomplete Testicular Feminization, Incomplete Testicular Feminization, Incontinentia Pigmenti, Incontinentia Pigmenti, Incontinenti Pigmenti Achromians, Index Finger Anomaly with Pierre Robin Syndrome, Indiana Type Amyloidosis (Type II), Indolent systemic mastocytosis, Infantile Acquired Aphasia, Infantile Autosomal Recessive Polycystic Kidney Disease, Infantile Beriberi, Infantile Cerebral Ganglioside, Infantile Cerebral Ganglioside, Infantile Cerebral Paralysis, Infantile Cystinosis, Infantile Epileptic, Infantile Fanconi Syndrome with Cystinosis, Infantile Finnish Type Neuronal Ceroid Lipofuscinosis, Infantile Gaucher Disease, Infantile Hypoglycemia, Infantile Hypophasphatasia, Infantile Lobar Emphysema, Infantile Myoclonic Encephalopathy, Infantile Myoclonic Encephalopathy and Polymyoclonia, Infantile Myofibromatosis, Infantile Necrotizing Encephalopathy, Infantile Neuronal Ceroid Lipofuscinosis, Infantile Neuroaxonal Dystrophy, Infantile Onset Schindler Disease, Infantile Phytanic Acid Storage Disease, Infantile Refsum Disease (IRD), Infantile Sipoidosis GM-2 Gangliosideosis (Type S), Infantile Sipoidosis GM-2 Gangliosideosis (Type S, Infantile Sleep Apnea, Infantile Spasms, Infantile Spinal Muscular Atrophy (all types), Infantile Spinal Muscular Atrophy ALS, Infantile Spinal Muscular Atrophy Type I, Infantile Type Neuronal Ceroid Lipofuscinosis, Infectious Jaundice, Inflammatory Breast Cancer, Inflammatory Linear Nevus Sebaceous Syndrome, Iniencephaly, Insulin Resistant Acanthosis Nigricans, Insulin Lipodystrophy, Insulin dependent Diabetes, Intention Myoclonus, Intermediate Cystinosis, Intermediate Maple Syrup Urine Disease, Intermittent Ataxia with Pyruvate Dehydrogenase Deficiency, Intermittent Ataxia with Pyruvate Dehydrogenase Deficiency, Intermittent Maple Syrup Urine Disease, Internal Hydrocephalus, Interstitial Cystitis, Interstitial Deletion of 4q Included, Interstitial Deletion of 4q-Included, Intestinal Lipodystrophy, Intestinal Lipophagic Granulomatosis, Intestinal Lymphangiectasia, Intestinal Polyposis I, Intestinal Polyposis II, Intestinal Polyposis II, Intestinal Polyposis III, Intestinal Polyposis-Cutaneous Pigmentation Syndrome, Intestinal Polyposis-Cutaneous Pigmentation Syndrome, Intestinal Pseudoobstruction with External Ophthalmoplegia, Intracranial Neoplasm, Intracranial Tumors, Intracranial Vascular Malformations, Intrauterine Dwarfism, Intrauterine Synechiae, Inverted Smile And Occult Neuropathic Bladder, Iowa Type Amyloidosis (Type IV), IP, IPA, Iridocorneal Endothelial Syndrome, Iridocorneal Endothelial (ICE) Syndrome Cogan-Resse Type, Iridogoniodysgenesis With Somatic Anomalies, Iris Atrophy with Corneal Edema and Glaucoma, Iris Nevus Syndrome, Iron Overload Anemia, Iron Overload Anemia, Iron Overload Disease, Irritable Bowel Syndrome, Irritable Colon Syndrome, Isaacs Syndrome, Isaacs-Merten Syndrome, Ischemic Cardio myopathy, Isolated Lissencephaly Sequence, Isoleucine 33 Amyloidosis, Isovaleric Acid CoA Dehydrogenase Deficiency, Isovaleric Acidaemia, Isovalericacidemia, Isovaleryl CoA Carboxylase Deficiency, ITO Hypomelanosis, ITO, ITP, ITP, IVA, Ivemark Syndrome, Iwanoff Cysts, Jackknife Convulsion, Jackson-Weiss Craniosynostosis, Jackson-Weiss Syndrome, Jacksonian Epilepsy, Jacobsen Syndrome, Jadassohn-Lewandowsky Syndrome, Jaffe-Lichenstein Disease, Jakob's Disease, Jakob-Creutzfeldt Disease, Janeway I, Janeway Dysgammaglobulinemia, Jansen Metaphyseal Dysostosis, Jansen Type Metaphyseal Chondrodysplasia, Jarcho-Levin Syndrome, Jaw-Winking, JBS, JBS, JDMS, Jegher's Syndrome, Jegher's Syndrome, Jejunal Atresia, Jejunitis, Jejunoileitis, Jervell and Lange-Nielsen Syndrome, Jeune Syndrome, JMS, Job Syndrome, Job-Buckley Syndrome, Johanson-Blizzard Syndrome, John Dalton, Johnson-Stevens Disease, Jonston's Alopecia, Joseph's Disease, Joseph's Disease Type I, Joseph's Disease Type II, Joseph's Disease Type III, Joubert Syndrome, Joubert-Bolthauser Syndrome, JRA, JRA, Juberg Hayward Syndrome, Juberg-Marsidi Syndrome, Juberg-Marsidi Mental Retardation Syndrome, Jumping Frenchmen, Jumping Frenchmen of Maine, Juvenile Arthritis, Juvenile Arthritis, Juvenile Autosomal Recessive Polycystic Kidney Disease, Juvenile Cystinosis, Juvenile (Childhood) Dermatomyositis (JDMS), Juvenile Diabetes, Juvenile Gaucher Disease, Juvenile Gout Choreoathetosis and Mental Retardation Syndrome, Juvenile Intestinal Malabsorption of Vit B12, Juvenile Intestinal Malabsorption of Vitamin B12, Juvenile Macular Degeneration, Juvenile Pernicious Anemia, Juvenile Retinoschisis, Juvenile Rheumatoid Arthritis, Juvenile Rheumatoid Arthritis, Juvenile Spinal Muscular Atrophy Included, Juvenile Spinal Muscular Atrophy ALS Included, Juvenile Spinal Muscular Atrophy Type III, Juxta-Articular Adiposis Dolorosa, Juxta-Articular Adiposis Dolorosa, Juxtaglomerular Hyperplasia, Kabuki Make-Up Syndrome, Kahler Disease, Kallmann Syndrome, Kanner Syndrome, Kanzaki Disease, Kaposi Disease (not Kaposi Sarcoma), Kappa Light Chain Deficiency, Karsch-Neugebauer Syndrome, Karsch-Neugebauer Syndrome, Kartagener Syndrome-Chronic Sinobronchial Disease and Dextrocardia, Kartagener Triad, Kasabach-Merritt Syndrome, Kast Syndrome, Kawasaki Disease, Kawasaki Syndrome, KBG Syndrome, KD, Kearns-Sayre Disease, Kearns-Sayre Syndrome, Kearns-Sayre Syndrome, Kennedy Disease, Kennedy Syndrome, Kennedy Type Spinal and Bulbar Muscular Atrophy, Kennedy-Stefanis Disease, Kenny Disease, Kenny Syndrome, Kenny Type Tubular Stenosis, Kenny-Caffe Syndrome, Kera. Palmoplant. Con. Pes Planus Ony. Periodon. Arach., Keratitis Ichthyosis Deafness Syndrome, Keratoconus, Keratoconus, Keratoconus Posticus Circumscriptus, Keratolysis, Keratolysis Exfoliativa Congenita, Keratolytic Winter Erythema, Keratomalacia, Keratosis Follicularis, Keratosis Follicularis Spinulosa Decalvans, Keratosis Follicularis Spinulosa Decalvans Ichthyosis, Keratosis Nigricans, Keratosis Palmoplantaris with Periodontopathia and Onychogryposis, Keratosis Palmoplantaris Congenital Pes Planus Onychogryposis Periodontosis Arachnodactyly, Keratosis Palmoplantaris Congenital, Pes Planus, Onychogryphosis, Periodontosis, Arachnodactyly, Acroosteolysis, Keratosis Rubra Figurata, Keratosis Seborrheica, Ketoacid Decarboxylase Deficiency, Ketoaciduria, Ketotic Glycinemia, Ketotic Glycinemia, KFS, KID Syndrome, Kidney Agenesis, Kidneys Cystic-Retinal Aplasia Joubert Syndrome, Killian Syndrome, Killian/Teschler-Nicola Syndrome, Kiloh-Nevin syndrome III, Kinky Hair Disease, Kinsbourne Syndrome, Kleeblattschadel Deformity, Kleine-Levin Syndrome, Kleine-Levin Hibernation Syndrome, Klinefelter, Klippel-Feil Syndrome, Klippel-Feil Syndrome Type I, Klippel-Feil Syndrome Type II, Klippel-Feil Syndrome Type III, Klippel Trenaunay Syndrome, Klippel-Trenaunay-Weber Syndrome, Kluver-Bucy Syndrome, KMS, Kniest Dysplasia, Kniest Syndrome, Kobner's Disease, Koebberling-Dunnigan Syndrome, Kohlmeier-Degos Disease, Kok Disease, Korsakoff Psychosis, Korsakoff's Syndrome, Krabbe's Disease Included, Krabbe's Leukodystrophy, Kramer Syndrome, KSS, KSS, KTS, KTW Syndrome, Kufs Disease, Kugelberg-Welander Disease, Kugelberg-Welander Disease, Kugelberg-Welander Syndrome, Kugelberg-Welander, Kugelberg-Welander Syndrome, Kussmaul-Landry Paralysis, KWS, L-3-Hydroxy-Acyl-CoA Dehydrogenase (LCHAD) Deficiency, Laband Syndrome, Labhart-Willi Syndrome, Labyrinthine Syndrome, Labyrinthine Hydrops, Lacrimo-Auriculo-Dento-Digital Syndrome, Lactase Isolated Intolerance, Lactase Deficiency, Lactation-Uterus Atrophy, Lactic Acidosis Leber Hereditary Optic Neuropathy, Lactic and Pyruvate Acidemia with Carbohydrate Sensitivity, Lactic and Pyruvate Acidemia with Episodic Ataxia and Weakness, Lactic and Pyruvate Acidemia with Carbohydrate Sensitivity,Lactic and Pyruvate, Lactic acidosis, Lactose Intolerance of Adulthood, Lactose Intolerance, Lactose Intolerance of Childhood, Lactose Intolerance, LADD Syndrome, LADD, Lafora Disease Included, Lafora Body Disease, Laki-Lorand Factor Deficiency, LAM, Lambert Type Ichthyosis, Lambert-Eaton Syndrome, Lambert-Eaton Myasthenic Syndrome, Lamellar Recessive Ichthyosis, Lamellar Recessive Ichthyosis, Lamellar Ichthyosis; Lamellar Recessive Ichthyosis, Lancereaux-Mathieu-Weil Spirochetosis, Landau-Kleffner Syndrome, Landouzy Dejerine Muscular Dystrophy, Landry Ascending Paralysis, Langer-Salidino Type Achondrogensis (Type II), Langer Giedion Syndrome, Langerhans-Cell Granulomatosis, Langerhans-Cell Histiocytosis (LCH), Large Atrial and Ventricular Defect, Laron Dwarfism, Laron Type Pituitary Dwarfism, Larsen Syndrome, Laryngeal Dystonia, Latah (Observed in Malaysia), Late Infantile Neuroaxonal Dystrophy, Late Infantile Neuroaxonal Dystrophy, Late Onset Cockayne Syndrome Type III (Type C), Late-Onset Dystonia, Late-Onset Immunoglobulin Deficiency, Late-Onset Immunoglobulin Deficiency, Late Onset Pelizaeus-Merzbacher Brain Sclerosis, Lattice Corneal Dystrophy, Lattice Dystrophy, Launois-Bensaude, Launois-Cleret Syndrome, Laurence Syndrome, Laurence-Moon Syndrome, Laurence-Moon/Bardet-Biedl, Lawrence-Seip Syndrome, LCA, LCAD Deficiency, LCAD, LCAD, LCAD, LCADH Deficiency, LCH, LCHAD, LCHAD, LCPD, Le Jeune Syndrome, Leband Syndrome, Leber's Amaurosis, Leber's Congenital Amaurosis,Congenital Absence of the Rods and Cones, Leber's Congenital Tapetoretinal Degeneration, Leber's Congenital Tapetoretinal Dysplasia, Leber's Disease, Leber's Optic Atrophy, Leber's Optic Neuropathy, Left Ventricular Fibrosis, Leg Ulcer, Legg-Calve-Perthes Disease, Leigh's Disease, Leigh's Disease, Leigh's Syndrome, Leigh's Syndrome (Subacute Necrotizing Encephalomyelopathy), Leigh Necrotizing Encephalopathy, Lennox-Gastaut Syndrome, Lentigo-Polypose-Digestive Syndrome, Lentigo-Polypose-Digestive Syndrome, Lenz Dysmorphogenetic Syndrome, Lenz Dysplasia, Lenz Microphthalmia Syndrome, Lenz Syndrome, LEOPARD Syndrome, Leprechaunism, Leprechaunism, Leptomeningeal Angiomatosis, Leptospiral Jaundice, Leri-Weill Disease, Leri-Weil Dyschondrosteosis, Leri-Weil Syndrome, Lermoyez Syndrome, Leroy Disease, Lesch Nyhan Syndrome, Lethal Infantile Cardio myopathy, Lethal Neonatal Dwarfism, Lethal Osteochondrodysplasia, Letterer-Siwe Disease, Leukocytic Anomaly Albinism, Leukocytic Inclusions with Platelet Abnormality, Leukodystrophy, Leukodystrophy with Rosenthal Fibers, Leukoencephalitis Periaxialis Concentric, Levine-Critchley Syndrome, Levulosuria, Levy-Hollister Syndrome, LGMD, LGS, LHON, LHON, LIC, Lichen Ruber Acuminatus, Lichen Acuminatus, Lichen Amyloidosis, Lichen Planus, Lichen Psoriasis, Lignac-Debre-Fanconi Syndrome, Lignac-Fanconi Syndrome, Ligneous Conjunctivitis, Limb-Girdle Muscular Dystrophy, Limb Girdle Muscular Dystrophy, Limb Malformations-Dento-Digital Syndrome, Limit Dextrinosis, Linear Nevoid Hypermelanosis, Linear Nevus Sebacous Syndrome, Linear Scleroderma, Linear Sebaceous Nevus Sequence, Linear Sebaceous Nevus Syndrome, Lingua Fissurata, Lingua Plicata, Lingua Scrotalis, Linguofacial Dyskinesia, Lip Pseudocleft-hemangiomatous Branchial Cyst Syndrome, Lipid Granulomatosis, Lipid Histiocytosis, Lipid Kerasin Type, Lipid Storage Disease, Lipid-Storage myopathy Associated with SCAD Deficiency, Lipidosis Ganglioside Infantile, Lipidosis Ganglioside Infantile, Lipoatrophic Diabetes Mellitus, Lipodystrophy, Lipoid Corneal Dystrophy, Lipoid Hyperplasia-Male Pseudohermaphroditism, Lipoid Hyperplasia-Male Pseudohermaphroditism, Lipomatosis of Pancreas Congenital, Lipomucopolysaccharidosis Type I, Lipomyelomeningocele, Lipoprotein Lipase Deficiency Familial, LIS, LIS1, Lissencephaly 1, Lissencephaly Type I, Lissencephaly variants with agenesis of the corpus callosum cerebellar hypoplasia or other anomalies, Little Disease, Liver Phosphorylase Deficiency, LKS, LM Syndrome, Lobar Atrophy, Lobar Atrophy of the Brain, Lobar Holoprosencephaly, Lobar Tension Emphysema in Infancy, Lobstein Disease (Type I), Lobster Claw Deformity, Lobster Claw Deformity, Localized Epidermolysis Bullosa, Localized Lipodystrophy, Localized Neuritis of the Shoulder Girdle, Loeffler's Disease, Loeffler Endomyocardial Fibrosis with Eosinophilia, Loeffler Fibroplastic Parietal Endocarditis, Loken Syndrome, Loken-Senior Syndrome, Long-Chain 3-hydroxyacyl-CoA Dehydrogenase (LCHAD), Long Chain Acyl CoA Dehydrogenase Deficiency, Long-Chain Acyl-CoA Dehydrogenase (ACADL), Long-Chain Acyl-CoA Dehydrogenase Deficiency, Long QT Syndrome without Deafness, Lou Gehrig's Disease, Lou Gehrig's Disease Included, Louis-Bar Syndrome, Low Blood Sugar, Low-Density Beta Lipoprotein Deficiency, Low Imperforate Anus, Low Potassium Syndrome, Lowe syndrome, Lowe's Syndrome, Lowe-Bickel Syndrome, Lowe-Terry-MacLachlan Syndrome, LS, LS, LTD, Lubs Syndrome, Lubs Syndrome, Luft Disease, Lumbar Canal Stenosis, Lumbar Spinal Stenosis, Lumbosacral Spinal Stenosis, Lundborg-Unverricht Disease, Lundborg-Unverricht Disease Included, Lupus, Lupus, Lupus Erythematosus, Luschka-Magendie Foramina Atresia, Lyell Syndrome, Lyelles Syndrome, Lymphadenoid Goiter, Lymphangiectati c Protein-Losing Enteropathy, Lymphangioleiomatosis, Lymphangioleimyomatosis, Lymphangiomas, Lymphatic Malformations, Lynch Syndromes, Lynch Syndrome I, Lynch Syndrome II, Lysosomal Alpha-N-Acetylgalactosaminidase Deficiency Schindler Type, Lysosomal Glycoaminoacid Storage Disease-Angiokeratoma Corporis Diffusum, Lysosomal Glucosidase Deficiency, Lysosomal Glucosidase Deficiency, MAA, Machado Disease, Machado-Joseph Disease, Macrencephaly, Macrocephaly, Macrocephaly Hemihypertrophy, Macrocephaly with Multiple Lipomas and Hemangiomata, Macrocephaly with Pseudopapilledema and Multiple Hemangiomata, Macroglobulinemia, Macroglossia, Macroglossia-Omphalocele-Visceromegaly Syndrome, Macrostomia Ablepheron Syndrome, Macrothrombocytopenia Familial Bemard-Soulier Type, Macula Lutea degeneration, Macular Amyloidosis, Macular Degeneration, Macular Degeneration Disciform, Macular Degeneration Senile, Macular Dystrophy, Macular Type Corneal Dystrophy, MAD, MAD, Madelung's Disease, Maffucci Syndrome, Major Epilepsy, Malabsorption, Malabsorption-Ectodermal Dysplasia-Nasal Alar Hypoplasia, Maladie de Roger, Maladie de Tics, Male Malformation of Limbs and Kidneys, Male Turner Syndrome, Malignant Acanthosis, Malignant Acanth6sis Nigricans, Malignant Astrocytoma, Malignant Atrophic Papulosis, Malignant Fever, Malignant Hyperphenylalaninemia, Malignant Hyperphenylalaninemia, Malignant Hyperpyrexia, Malignant Hyperthermia, Malignant Melanoma, Malignant Tumors of the Central Nervous System, Mallory-Weiss Laceration, Mallory-Weiss Tear, Mallory-Weiss Syndrome, Mammary Paget's Disease, Mandibular Ameloblastoma, Mandibulofacial Dysostosis, Mannosidosis, Map-Dot-Fingerprint Type Corneal Dystrophy, Maple Syrup Urine Disease, Maple Syrup Urine Disease, Marble Bones, Marchiafava-Micheli Syndrome, Marcus Gunn Jaw-Winking Syndrome, Marcus Gunn Phenomenon, Marcus Gunn Ptosis with jaw-winking, Marcus Gunn Syndrome, Marcus Gunn (Jaw-Winking) Syndrome, Marcus Gunn Ptosis (with jaw-winking), Marden-Walker Syndrome, Marden-Walker Type Connective Tissue Disorder, Marfan's Abiotrophy, Marfan-Achard syndrome, Marfan Syndrome, Marfan Syndrome, Marfan's Syndrome I, Marfan's Variant, Marfan-Achard syndrome, Marfanoid Hypermobility Syndrome, Marginal Corneal Dystrophy, Marie's Ataxia, Marie's Ataxia, Marie Disease, Marie-Sainton Disease, Marie Strumpell Disease, Marie-Strumpell Spondylitis, Marinesco-Sjogren Syndrome, Marinesco-Sjogren-Gorland Syndrome, Marker X Syndrome, Maroteaux Lamy Syndrome, Maroteaux Type Acromesomelic Dysplasia, Marshall's Ectodermal Dysplasias With Ocular and Hearing Defects, Marshall-Smith Syndrome, Marshall Syndrome, Marshall Type Deafness-Myopia-Cataract-Saddle Nose, Martin-Albright Syndrome, Martin-Bell Syndrome, Martorell Syndrome, MASA Syndrome, Massive Myoclonia, Mast Cell Leukemia, Mastocytosis, Mastocytosis With an Associated Hematologic Disorder, Maumenee Corneal Dystrophy, Maxillary Ameloblastoma, Maxillofacial Dysostosis, Maxillonasal Dysplasia, Maxillonasal Dysplasia Binder Type, Maxillopalpebral Synkinesis, May-Hegglin Anomaly, MCAD Deficiency, MCAD, MCAD, MCAD, McArdle Disease, McCune-Albright, MCD, McKusick Type Metaphyseal Chondrodysplasia, McKusick Type Metaphyseal Chondrodysplasia, MCR, MCTD, Meckel Syndrome, Meckel-Gruber Syndrome, Median Cleft Face Syndrome, Mediterranean Anemia, Medium-Chain Acyl-CoA dehydrogenase (ACADM), Medium Chain Acyl-CoA Dehydrogenase (MCAD) Deficiency, Medium-Chain Acyl-CoA Dehydrogenase Deficiency, Medium Chain Acyl CoA Dehydrogenase Deficiency, Medullary Cystic Disease, Medullary Cystic Disease, Medullary Sponge Kidney, MEF, Megaesophagus, Megalencephaly, Megalencephaly with Hyaline Inclusion, Megalencephaly with Hyaline Panneuropathy, Megaloblastic Anemia, Megaloblastic Anemia of Pregnancy, Megalocornea-Mental Retardation Syndrome, Meier-Gorlin Syndrome, Meige's Lymphedema, Meige's Syndrome, Melanodermic Leukodystrophy, Melanoplakia-Intestinal Polyposis, Melanoplakia-Intestinal Polyposis, MELAS Syndrome, MELAS, Melkersson Syndrome, Melnick-Fraser Syndrome, Melnick-Needles Osteodysplasty, Melnick-Needles Syndrome, Membranous Lipodystrophy, Mendes Da Costa Syndrome, Meniere Disease, Meniere's Disease, Meningeal Capillary Angiomatosis, Menkes Disease, Menke's Syndrome I, Mental Retardation Aphasia Shuffling Gait Adducted Thumbs (MASA), Mental Retardation-Deafness-Skeletal Abnormalities-Coarse Face with Full Lips, Mental Retardation with Hypoplastic 5th Fingernails and Toenails, Mental Retardation with Osteocartilaginous Abnormalities, Mental Retradation-X-linked with Growth Delay-Deafness-Microgenitalism, Menzel Type OPCA, Mermaid Syndrome, MERRF, MERRF Syndrome, MERRF, Merten-Singleton Syndrome, MES, Mesangial IGA Nephropathy, Mesenteric Lipodystrophy, Mesiodens-Cataract Syndrome, Mesodermal Dysmorphodystrophy, Mesomelic Dwarfism-Madelung Deformity, Metabolic Acidosis, Metachromatic Leukodystrophy, Metatarsus Varus, Metatropic Dwarfism Syndrome, Metatropic Dysplasia, Metatropic Dysplasia I, Metatropic Dysplasia II, Methylmalonic Acidemia, Methylmalonic Aciduria, Meulengracht's Disease, MFD1, MG, MH, MHA, Micrencephaly, Microcephalic Primordial Dwarfism I, Microcephaly, Microcephaly-Hiatal Hernia-Nephrosis Galloway Type, Microcephaly-Hiatal Hernia-Nephrotic Syndrome, Microcystic Corneal Dystrophy, Microcythemia, Microlissencephaly, Microphthalmia, Microphthalmia, Microphthalmia or Anophthalmos with Associated Anomalies, Micropolygyria With Muscular Dystrophy, Microtia Absent Patellae Micrognathia Syndrome, Microvillus Inclusion Disease, MID, Midsystolic-click-late systolic murmur syndrome, Miescher's Type I Syndrome, Mikulicz Syndrome, Mikulicz-Radecki Syndrome, Mikulicz-Sjogren Syndrome, Mild Autosomal Recessive, Mild Intermediate Maple Syrup Urine Disease, Mild Maple Syrup Urine Disease, Miller Syndrome, Miller-Dieker Syndrome, Miller-Fisher Syndrome, Milroy Disease, Minkowski-Chauffard Syndrome, Minor Epilepsy, Minot-Von Willebrand Disease, Mirror-Image Dextrocardia, Mitochondrial Beta-Oxidation Disorders, Mitochondrial and Cytosolic, Mitochondrial Cytopathy, Mitochondrial Cytopathy, Kearn-Sayre Type, Mitochondrial Encephalopathy, Mitochondrial Encephalo myopathy Lactic Acidosis and Strokelike Episodes, Mitochondrial myopathy, Mitochondrial myopathy Encephalopathy Lactic Acidosis Stroke-Like Episode, Mitochondrial PEPCK Deficiency, Mitral-valve prolapse, Mixed Apnea, Mixed Connective Tissue Disease, Mixed Connective Tissue Disease, Mixed Hepatic Porphyria, Mixed Non-Fluent Aphasia, Mixed Sleep Apnea, Mixed Tonic and Clonic Torticollis, MJD, MKS, ML I, ML II, ML II, ML III, ML IV, ML Disorder Type I, ML Disorder Type II, ML Disorder Type III, ML Disorder Type IV, MLNS, MMR Syndrome, MND, MNGIE, MNS, Mobitz I, Mobitz II, Mobius Syndrome, Moebius Syndrome, Moersch-Woltmann Syndrome, Mohr Syndrome, Monilethrix, Monomodal Visual Amnesia, Mononeuritis Multiplex, Mononeuritis Peripheral, Mononeuropathym Peripheral, Monosomy 3p2, Monosomy 9p Partial, Monosomy 11q Partial, Monosomy 13q Partial, Monosomy 18q Syndrome, Monosomy X, Monostotic Fibrous Dysplasia, Morgagni-Turner-Albright Syndrome, Morphea, Morquio Disease, Morquio Syndrome, Morquio Syndrome A, Morquio Syndrome B, Morquio-Brailsford Syndrome, Morvan Disease, Mosaic Tetrasomy 9p, Motor Neuron Disease, Motor Neuron Disease, Motor Neuron Syndrome, Motor Neurone Disease, Motoneuron Disease, Motoneurone Disease, Motor System Disease (Focal and Slow), Moya-moya Disease, Moyamoya Disease, MPS, MPS I, MPS I H, MPS 1 H/S Hurler/Scheie Syndrome, MPS I S Scheie Syndrome, MPS II, MPS IIA, MPS IIB, MPS II-AR Autosomal Recessive Hunter Syndrome, MPS II-XR, MPS II-XR Severe Autosomal Recessive, MPS III, MPS III A B C and D Sanfiloppo A, MPS IV, MPS IV A and B Morquio A, MPS V, MPS VI, MPS VI Severe Intermediate Mild Maroteaux-Lamy, MPS VII, MPS VII Sly Syndrome, MPS VIII, MPS Disorder, MPS Disorder I, MPS Disorder II, MPS Disorder III, MPS Disorder VI, MPS Disorder Type VII, MRS, MS, MSA, MSD, MSL, MSS, MSUD, MSUD, MSUD Type Ib, MSUD Type II, Mucocutaneous Lymph Node Syndrome, Mucolipidosis I, Mucolipidosis II, Mucolipidosis II, Mucolipidosis III, Mucolipidosis IV, Mucopolysaccharidosis, Mucopolysaccharidosis I-H, Mucopolysaccharidosis I-S, Mucopolysaccharidosis II, Mucopolysaccharidosis III, Mucopolysaccharidosis IV, Mucopolysaccharidosis VI, Mucopolysaccharidosis VII, Mucopolysaccharidosis Type I, Mucopolysaccharidosis Type II, Mucopolysaccharidosis Type III, Mucopolysaccharidosis Type VII, Mucosis, Mucosulfatidosis, Mucous Colitis, Mucoviscidosis, Mulibrey Dwarfism, Mulibrey Nanism Syndrome, Mullerian Duct Aplasia-Renal Aplasia-Cervicothoracic Somite Dysplasia, Mullerian Duct-Renal-Cervicothoracic-Upper Limb Defects, Mullerian Duct and Renal Agenesis with Upper Limb and Rib Anomalies, Mullerian-Renal-Cervicothoracic Somite Abnormalities, Multi-Infarct Dementia Binswanger's Type, Multicentric Castleman's Disease, Multifocal Eosinophilic Granuloma, Multiple Acyl-CoA Dehydrogenase Deficiency, Multiple Acyl-CoA Dehydrogenase Deficiency, Multiple Acyl-CoA Dehydrogenase Deficiency/Glutaric Aciduria Type II, Multiple Angiomas and Endochondromas, Multiple Carboxylase Deficiency, Multiple Cartilaginous Enchondroses, Multiple Cartilaginous Exostoses, Multiple Enchondromatosis, Multiple Endocrine Deficiency Syndrome Type II, Multiple Epiphyseal Dysplasia, Multiple Exostoses, Multiple Exostoses Syndrome, Multiple Familial Polyposis, Multiple Lentigines Syndrome, Multiple Myeloma, Multiple Neuritis of the Shoulder Girdle, Multiple Osteochondromatosis, Multiple Peripheral Neuritis, Multiple Polyposis of the Colon, Multiple Pterygium Syndrome, Multiple Sclerosis, Multiple Sclerosis, Multiple Sulfatase Deficiency, Multiple Symmetric Lipomatosis, Multiple System Atrophy, Multisynostotic Osteodysgenesis, Multisynostotic Osteodysgenesis with Long Bone Fractures, Mulvihill-Smith Syndrome, MURCS Association, Murk Jansen Type Metaphyseal Chondrodysplasia, Muscle Carnitine Deficiency, Muscle Core Disease, Muscle Phosphofructokinase Deficiency, Muscular Central Core Disease, Muscular Dystrophy, Muscular Dystrophy Classic X-linked Recessive, Muscular Dystrophy Congenital With Central Nervous System Involvement, Muscular Dystrophy Congenital Progressive with Mental Retardation, Muscular Dystrophy Facioscapulohumeral, Muscular Rheumatism, Muscular Rigidity—Progressive Spasm, Musculoskeletal Pain Syndrome, Mutilating Acropathy, Mutilating Acropathy, Mutism, mvp, MVP, MWS, Myasthenia Gravis, Myasthenia Gravis, Myasthenia Gravis Pseudoparalytica, Myasthenic Syndrome of Lambert-Eaton, Myelinoclastic Diffuse Sclerosis, Myelomatosis, Myhre Syndrome, Myoclonic Astatic Petit Mal Epilepsy, Myoclonic Dystonia, Myoclonic Encephalopathy of Infants, Myoclonic Epilepsy, Myoclonic Epilepsy Hartung Type, Myoclonus Epilepsy Associated with Ragged Red Fibers, Myoclonic Epilepsy and Ragged-Red Fiber Disease, Myoclonic Progressive Familial Epilepsy, Myoclonic Progressice Familial Epilepsy, Myoclonic Seizure, Myoclonus, Myoclonus Epilepsy, Myoencephalopathy Ragged-Red Fiber Disease, Myofibromatosis, Myofibromatosis Congenital, Myogenic Facio-Scapulo-Peroneal Syndrome, Myoneurogastointestinal Disorder and Encephalopathy, Myopathic Arthrogryposis Multiplex Congenita, Myopathic Carnitine Deficiency, myopathy Central Fibrillar, myopathy Congenital Nonprogressive, myopathy Congenital Nonprogressive with Central Axis, myopathy with Deficiency of Carnitine Palmitoyltransferase, myopathy-Marinesco-Sjogren Syndrome, myopathy-Metabolic Carnitine Palmitoyltransderase Deficiency, myopathy Mitochondrial-Encephalopathy-Lactic Acidosis-Stroke, myopathy with Sarcoplasmic Bodies and Intermediate Filaments, Myophosphorylase Deficiency, Myositis Ossificans Progressiv, Myotonia Atrophica, Myotonia Congenita, Myotonia Congenita Intermittens, Myotonic Dystrophy, Myotonic myopathy Dwarfism Chondrodystrophy Ocular and Facial Anomalies, Myotubular myopathy, Myotubular myopathy X-linked, Myproic Acid, Myriachit (Observed in Siberia), Myxedema, N-Acetylglucosamine-1-Phosphotransferase Deficiency, N-Acetyl Glutamate Synthetase Deficiency, NADH-CoQ reductasedeficiency, Naegeli Ectodermal Dysplasias, Nager Syndrome, Nager Acrofacial Dysostosis Syndrome, Nager Acrofacial Dysostosis Syndrome, Nager Syndrome, NAGS Deficiency, Nail Dystrophy-Deafness Syndrome, Nail Dysgenesis and Hypodontia, Nail-Patella Syndrome, Nance-Horan Syndrome, Nanocephalic Dwarfism, Nanocephaly, Nanophthalmia, Narcolepsy, Narcoleptic syndrome, NARP, Nasal-fronto-faciodysplasia, Nasal Alar Hypoplasia Hypothyroidism Pancreatic Achylia Congenital Deafness, Nasomaxillary Hypoplasia, Nasu Lipodystrophy, NBIAI, ND, NDI, NDP, Necrotizing Encephalomyelopathy of Leigh's, Necrotizing Respiratory Granulomatosis, Neill-Dingwall Syndrome, Nelson Syndrome, Nemaline myopathy, Neonatal Adrenoleukodystrophy, Neonatal Adrenoleukodystrophy (NALD), Neonatal Adrenoleukodystrophy (ALD), Neonatal Autosomal Recessive Polycystic Kidney Disease, Neonatal Dwarfism, Neonatal Hepatitis, Neonatal Hypoglycemia, Neonatal Lactose Intolerance, Neonatal Lymphedema due to Exudative Enteropathy, Neonatal Progeroid Syndrome, Neonatal Pseudo-Hydrocephalic Progeroid Syndrome of Wiedemann-Rautenstrauch, Neoplastic Arachnoiditis, Nephroblastom, Nephrogenic Diabetes Insipidus, Nephronophthesis Familial Juvenile, Nephronophthesis Familial Juvenile, Nephropathic Cystinosis, Nephropathy-Pseudohermaphroditism-Wilms Tumor, Nephrosis-Microcephaly Syndrome, Nephrosis-Neuronal Dysmigration Syndrome, Nephrotic-Glycosuric-Dwarfism-Rickets-Hypophosphatemic Syndrome, Netherton Disease, Netherton Syndrome, Netherton Syndrome Ichthyosis, Nettleship Falls Syndrome (X-Linked), Neu-Laxova Syndrome, Neuhauser Syndrome, Neural-tube defects, Neuralgic Amyotrophy, Neuralgic Amyotrophy, Neuraminidase Deficiency, Neuraocutaneous melanosis, Neurinoma of the Acoustic Nerve, Neurinoma, Neuroacanthocytosis, Neuroaxonal Dystrophy Schindler Type, Neurodegeneration with brain iron accumulation type 1 (NBIA1), Neurofibroma of the Acoustic Nerve, Neurogenic Arthrogryposis Multiplex Congenita, Neuromyelitis Optica, Neuromyotonia, Neuromyotonia, Focal, Neuromyotonia, Generalized, Familial, Neuromytonia, Generalized,Sporadic, Neuronal Axonal Dystrophy Schindler Type, Neuronal Ceroid Lipofuscinosis Adult Type, Neuronal Ceroid Lipofuscinosis Juvenile Type, Neuronal Ceroid Lipofuscinosis Type I, Neuronopathic Acute Gaucher Disease, Neuropathic Amyloidosis, Neuropathic Beriberi, Neuropathy Ataxia and Retinitis Pigmentosa, Neuropathy of Brachialpelxus Syndrome, Neuropathy Hereditary Sensory Type I, Neuropathy Hereditary Sensory Type II, Neutral Lipid Storage Disease, Nevii, Nevoid Basal Cell Carcinoma Syndrome, Nevus, Nevus Cavernosus, Nevus Comedonicus, Nevus Depigmentosus, Nevus Sebaceous of Jadassohn, Nezelof's Syndrome, Nezelof's Thymic Aplasia, Nezelof Type Severe Combined Immunodeficiency, NF, NF1, NF2, NF-1, NF-2, NHS, Niemann Pick Disease, Nieman Pick disease Type A (acute neuronopathic form), Nieman Pick disease Type B, Nieman Pick Disease Type C (chronic neuronopathic form), Nieman Pick disease Type D (Nova Scotia variant), Nieman Pick disease Type E, Nieman Pick disease Type F (sea-blue histiocyte disease), Night Blindness, Nigrospinodentatal Degeneration, Niikawakuroki Syndrome, NLS, NM, Noack Syndrome Type I, Nocturnal Myoclonus Hereditary Essential Myoclonus, Nodular Cornea Degeneration, Non-Bullous CIE, Non-Bullous Congenital Ichthyosiform Erythroderma, Non-Communicating Hydrocephalus, Non-Deletion Type Alpha-Thalassemia/Mental Retardation syndrome, Non-Ketonic Hyperglycinemia Type I (NKHI), Non-Ketotic Hyperglycinemia, Non-Lipid Reticuloendotheliosis, Non-Neuronopathic Chronic Adult Gaucher Disease, Non-Scarring Epidermolysis Bullosa, Nonarteriosclerotic Cerebral Calcifications, Nonarticular Rheumatism, Noncerebral,Juvenile Gaucher Disease, Nondiabetic Glycosuria, Nonischemic Cardio myopathy, Nonketotic Hypoglycemia and Carnitine Deficiency due to MCAD Deficiency, Nonketotic Hypoglycemia Caused by Deficiency of Acyl-CoA Dehydrogenase, Nonketotic Glycinemia, Nonne's Syndrome, Nonne-Milroy-Meige Syndrome, Nonopalescent Opalescent Dentine, Nonpuerperal Galactorrhea-Amenorrhea, Nonsecretory Myeloma, Nonspherocytic Hemolytic Anemia, Nontropical Sprue, Noonan Syndrome, Norepinephrine, Normal Pressure Hydrocephalus, Norman-Roberts Syndrome, Norrbottnian Gaucher Disease, Norrie Disease, Norwegian Type Hereditary Cholestasis, NPD, NPS, NS, NSA, Nuchal Dystonia Dementia Syndrome, Nutritional Neuropathy, Nyhan Syndrome, OAV Spectrum, Obstructive Apnea, Obstructive Hydrocephalus, Obstructive Sleep Apnea, OCC Syndrome, Occlusive Thromboaortopathy, OCCS, Occult Intracranial Vascular Malformations, Occult Spinal Dysraphism Sequence, Ochoa Syndrome, Ochronosis, Ochronotic Arthritis, OCR, OCRL, Octocephaly, Ocular Albinism, Ocular Herpes, Ocular Myasthenia Gravis, Oculo-Auriculo-Vertebral Dysplasia, Oculo-Auriculo-Vertebral Spectrum, Oculo-Bucco-GenitalSyndrome, Oculocerebral Syndrome with Hypopigmentation, Oculocerebrocutaneous Syndrome, Oculo-Cerebro-Renal, Oculocerebrorenal Dystrophy, Oculocerebrorenal Syndrome, Oculocraniosomatic Syndrome (obsolete), Oculocutaneous Albinism, Oculocutaneous Albinism Chediak-Higashi Type, Oculo-Dento-Digital Dysplasia, Oculo-Dento-Digital Dysplasia, Oculodentodigital Syndrome, Oculo-Dento-Osseous Dysplasia, Oculo-Dento-Osseous Dysplasia, Oculo Gastrointestinal Muscular Dystrophy, Oculo Gastrointestinal Muscular Dystrophy, Oculogastrointestinal Muscular Dystrophy, Oculomandibulodyscephaly with hypotrichosis, Oculomandibulofacial Syndrome, Oculomotor with Congenital Contractures and Muscle Atrophy, Oculosympathetic Palsy, ODD Syndrome, ODD Syndrome, ODOD, Odontogenic Tumor, Odontotrichomelic Syndrome, OFD, OFD Syndrome, Ohio Type Amyloidosis (Type VII), OI, OI Congenita, OI Tarda, Oldfield Syndrome, Oligohydramnios Sequence, Oligophrenia Microphthalmos, Oligophrenic Polydystrophy, Olivopontocerebellar Atrophy, Olivopontocerebellar Atrophy, Olivopontocerebellar Atrophy with Dementia and Extrapyramidal Signs, Olivopontocerebellar Atrophy with Retinal Degeneration, Olivopontocerebellar Atrophy I, Olivopontocerebellar Atrophy II, Olivopontocerebellar Atrophy III, Olivopontocerebellar Atrophy IV, Olivopontocerebellar Atrophy V, Oilier Disease, Oilier Osteochondromatosis, Omphalocele-Visceromegaly-Macroglossia Syndrome, Ondine's Curse, Onion-Bulb Neuropathy, Onion Bulb Polyneuropathy, Onychoosteodysplasia, Onychotrichodysplasia with Neutropenia, OPCA, OPCA I, OPCA II, OPCA III, OPCA IV, OPCA V, OPD Syndrome, OPD Syndrome Type I, OPD Syndrome Type II, OPD I Syndrome, OPD II Syndrome, Ophthalmoarthropathy, Ophthalmoplegia-Intestinal Pseudoobstruction, Ophthalmoplegia, Pigmentary Degeneration of the Retina and Cadio myopathy, Ophthalmoplegia Plus Syndrome, Ophthalmoplegia Syndrome, Opitz BBB Syndrome, Opitz BBB/G Compound Syndrome, Opitz BBBG Syndrome, Opitz-Frias Syndrome, Opitz G Syndrome, Opitz G/BBB Syndrome, Opitz Hypertelorism-Hypospadias Syndrome, Opitz-Kaveggia Syndrome, Opitz Oculogenitolaryngeal Syndrome, Opitz Trigonocephaly Syndrome, Opitz Syndrome, Opsoclonus, Opsoclonus-Myoclonus, Opthalmoneuromyelitis, Optic Atrophy Polyneuropathy and Deafness, Optic Neuroencephalomyelopathy, Optic Neuromyelitis, Opticomyelitis, Optochiasmatic Arachnoiditis, Oral-Facial Clefts, Oral-facial Dyskinesia, Oral Facial Dystonia, Oral-Facial-Digital Syndrome, Oral-Facial-Digital Syndrome Type I, Oral-Facial-Digital Syndrome I, Oral-Facial-Digital Syndrome II, Oral-Facial-Digital Syndrome III, Oral-Facial-Digital Syndrome IV, Orbital Cyst with Cerebral and Focal Dermal Malformations, Ornithine Carbamyl Transferase Deficiency, Ornithine Transcarbamylase Deficiency, Orocraniodigital Syndrome, Orofaciodigital Syndrome, Oromandibular Dystonia, Orthostatic Hypotension, Osler-Weber-Rendu disease, Osseous-Oculo-Dento Dysplasia, Osseous-Oculo-Dento Dysplasia, Osteitis deformans, Osteochondrodystrophy Deformans, Osteochondroplasia, Osteodysplasty of Melnick and Needles, Osteogenesis Imperfect, Osteogenesis Imperfecta, Osteogenesis Imperfecta Congenita, Osteogenesis Imperfecta Tarda, Osteohypertrophic Nevus Flammeus, Osteopathia Hyperostotica Scleroticans Multiplex Infantalis, Osteopathia Hyperostotica Scleroticans Multiplex Infantalis, Osteopathyrosis, Osteopetrosis, Osteopetrosis Autosomal Dominant Adult Type, Osteopetrosis Autosomal Recessive Malignant Infantile Type, Osteopetrosis Mild Autosomal Recessive Intermediate Typ, Osteosclerosis Fragilis Generalisata, Osteosclerotic Myeloma, Ostium Primum Defect (endocardial cushion defects included), Ostium Secundum Defect, OTC Deficiency, Oto Palato Digital Syndrome, Oto-Palato-Digital Syndrome Type I, Oto-Palatal-Digital Syndrome Type II, Otodental Dysplasia, Otopalatodigital Syndrome, Otopalataldigital Syndrome Type II, Oudtshoorn Skin, Ovarian Dwarfism Turner Type, Ovary Aplasia Turner Type, OWR, Oxalosis, Oxidase deficiency, Oxycephaly, Oxycephaly, Oxycephaly-Acrocephaly, P-V, PA, PAC, Pachyonychia Ichtyosiforme, Pachyonychia Congenita with Natal Teeth, Pachyonychia Congenita, Pachyonychia Congenita Keratosis Disseminata Circumscripta (follicularis), Pachyonychia Congenita Jadassohn-Lewandowsky Type, PAF with MSA, Paget's Disease, Paget's Disease of Bone, Paget's Disease of the Breast, Paget's Disease of the Nipple, Paget's Disease of the Nipple and Areola, Pagon Syndrome, Painful Ophthalmoplegia, PAIS, Palatal Myoclonus, Palato-Oto-Digital Syndrome, Palatal-Oto-Digital Syndrome Type I, Palatal-Oto-Digital SyndromeType II, Pallister Syndrome, Pallister-Hall Syndrome, Pallister-Killian Mosaic Syndrome, Pallister Mosaic Aneuploidy, Pallister Mosaic Syndrome, Pallister Mosaic Syndrome Tetrasomy 12p, Pallister-W Syndrome, Palmoplantar Hyperkeratosis and Alopecia, Palsy, Pancreatic Fibrosis, Pancreatic Insufficiency and Bone Marrow Dysfunction, Pancreatic Ulcerogenic Tumor Syndrome, Panmyelophthisis, Panmyelopathy, Pantothenate kinase associated neurodegeneration (PKAN), Papillon-Lefevre Syndrome, Papillotonic Psuedotabes, Paralysis Periodica Paramyotonica, Paralytic Beriberi, Paralytic Brachial Neuritis, Paramedian Lower Lip Pits-Popliteal Pyerygium Syndrome, Paramedian Diencephalic Syndrome, Paramyeloidosis, Paramyoclonus Multiple, Paramyotonia Congenita, Paramyotonia Congenita of Von Eulenburg, Parkinson's disease, Paroxysmal Atrial Tachycardia, Paroxysmal Cold Hemoglobinuria, Paroxysmal Dystonia, Paroxysmal Dystonia Choreathetosis, Paroxysmal Kinesigenic Dystonia, Paroxysmal Nocturnal Hemoglobinuria, Paroxysmal Normal Hemoglobinuria, Paroxysmal Sleep, Parrot Syndrome, Parry Disease, Parry-Romberg Syndrome, Parsonage-Turner Syndrome, Partial Androgen Insensitivity Syndrome, Partial Deletion of the Short Arm of Chromosome 4, Partial Deletion of the Short Arm of Chromosome 5, Partial Deletion of Short Arm of Chromosome 9, Partial Duplication 3q Syndrome, Partial Duplication 15q Syndrome, Partial Facial Palsy With Urinary Abnormalities, Partial Gigantism of Hands and Feet-Nevi-Hemihypertrophy-Macrocephaly, Partial Lipodystrophy, Partial Monosomy of Long Arm of Chromosome 11, Partial Monosomy of the Long Arm of Chromosome 13, Partial Spinal Sensory Syndrome, Partial Trisomy 11q, Partington Syndrome, PAT, Patent Ductus Arteriosus, Pathological Myoclonus, Pauciarticular-Onset Juvenile Arthritis, Pauciarticular-Onset Juvenile Arthritis, Paulitis, PBC, PBS, PC Deficiency, PC Deficiency Group A, PC Deficiency Group B, PC, Eulenburg Disease, PCC Deficiency, PCH, PCLD, PCT, PD, PDA, PDH Deficiency, PDH Deficiency, Pearson Syndrome Pyruvate Carboxylase Deficiency, Pediatric Obstructive Sleep Apnea, Peeling Skin Syndrome, Pelizaeus-Merzbacher Disease, Pelizaeus-Merzbacher Brain Sclerosis, Pelizaeus-Merzbacher Brain Sclerosis, Pellagra-Cerebellar Ataxia-Renal Aminoaciduria Syndrome, Pelvic Pain Syndrome, Pemphigus Vulgaris, Pena Shokeir II Syndrome, Pena Shokeir Syndrome Type II, Penile Fibromatosis, Penile Fibrosis, Penile Induration, Penta X Syndrome, Pentalogy of Cantrell, Pentalogy Syndrome, Pentasomy X, PEPCK Deficiency, Pepper Syndrome, Perheentupa Syndrome, Periarticular Fibrositis, Pericardial Constriction with Growth Failure, Pericollagen Amyloidosis, Perinatal Polycystic Kidney Diseases, Perineal Anus, Periodic Amyloid Syndrome, Periodic Peritonitis Syndrome, Periodic Somnolence and Morbid Hunger, Periodic Syndrome, Peripheral Cystoid Degeneration of the Retina, Peripheral Dysostosis-Nasal Hypoplasia-Mental Retardation, Peripheral Neuritis, Peripheral Neuropathy, Peritoneopericardial Diaphragmatic Hernia, Pernicious Anemia, Pernicious Anemia, Pernicious Anemia, Peromelia with Micrognathia, Peroneal Muscular Atrophy, Peroneal Nerve Palsy, Peroutka Sneeze, Peroxisomal Acyl-CoA Oxidase, Peroxisomal Beta-Oxidation Disorders, Peroxisomal Bifunctional Enzyme, Peroxisomal Thiolase, Peroxisomal Thiolase Deficiency, Persistent Truncus Arteriosus, Perthes Disease, Petit Mal Epilepsy, Petit Mal Variant, Peutz-Jeghers Syndrome, Peutz-Jeghers Syndrome, Peutz-Touraine Syndrome, Peutz-Touraine Syndrome, Peyronie Disease, Pfeiffer, Pfeiffer Syndrome Type I, PGA I, PGA II, PGA II, PGA HI, PGK, PH Type I, PH Type I, Pharyngeal Pouch Syndrome, PHD Short-Chain Acyl-CoA Dehydrogenase Deficiency, Phenylalanine Hydroxylase Deficiency, Phenylalaninemia, Phenylketonuria, Phenylketonuria, Phenylpyruvic Oligophrenia, Phocomelia, Phocomelia Syndrome, Phosphoenolpyruvate Carboxykinase Deficiency, Phosphofructokinase Deficiency, Phosphoglycerate Kinase Deficiency, Phosphoglycerokinase, Phosphorylase 6 Kinase Deficiency, Phosphorylase Deficiency Glycogen Storage Disease, Phosphorylase Kinase Deficiency of Liver, Photic Sneeze Reflex, Photic Sneezing, Phototherapeutic keratectomy, PHS, Physicist John Dalton, Phytanic Acid Storage Disease, Pi Phenotype ZZ, PI, Pick Disease of the Brain, Pick's Disease, Pick's Disease, Pickwickian Syndrome, Pierre Robin Anomalad, Pierre Robin Complex, Pierre Robin Sequence, Pierre Robin Syndrome, Pierre Robin Syndrome with Hyperphalangy and Clinodactyly, Pierre-Marie's Disease, Pigmentary Degeneration of Globus Pallidus Substantia Nigra Red Nucleus, Pili Torti and Nerve Deafness, Pili Torti-Sensorineural Hearing Loss, Pituitary Dwarfism II, Pituitary Tumor after Adrenalectomy, Pityriasis Pilaris, Pityriasis Rubra Pilaris, PJS, PJS, PKAN, PKD, PKD, PKD1, PKD2, PKD3, PKU, PKU, PKUI, Plagiocephaly, Plagiocephaly, Plagiocephaly, Plasma Cell Myeloma, Plasma Cell Leukemia, Plasma Thromboplastin Component Deficiency, Plasma Transglutaminase Deficiency, Plastic Induration Corpora Cavernosa, Plastic Induration of the Penis, PLD, Plicated Tongue, PLS, PMD, Pneumorenal Syndrome, PNH, PNM, PNP Deficiency, POD, POH, Poikiloderma Atrophicans and Cataract, Poikiloderma Congenitale, Poland Anomaly, Poland Sequence, Poland Syndactyly, Poland Syndrome, Poliodystrophia Cerebri Progressiva, Polyarthritis Enterica, Polyarteritis Nodosa, Polyarticular-Onset Juvenile Arthritis Type I, Polyarticular-Onset Juvenile Arthritis Type II, Polyarticular-Onset Juvenile Arthritis Types I and II, Polychondritis, Polycystic Kidney Disease, Polycystic Kidney Disease Medullary Type, Polycystic Kidney Disease Medullary Type, Polycystic Liver Disease, Polycystic Ovary Disease, Polycystic Renal Diseases, Polydactyly-Joubert Syndrome, Polydysplastic Epidermolysis Bullosa, Polydystrophia Oligophrenia, Polydystrophic Dwarfism, Polyglandular Autoimmune Syndrome Type III, Polyglandular Autoimmune Syndrome Type II, Polyglandular Autoimmune Syndrome Type I, Polyglandular Autoimmune Syndrome Type II, Polyglandular Deficiency Syndrome Type II, Polyglandular Syndromes, Polymorphic Macula Lutea Degeneration, Polymorphic Macular Degeneration, Polymorphism of Platelet Glycoprotien Ib, Polymorphous Corneal Dystrophy Hereditary, Polymyalgia Rheumatica, Polymyalgia Rheumatica, Polymyositis and Dermatomyositis,Primary Agammag-lobulinemi, Polyneuritis Peripheral, Polyneuropathy-Deafness-Optic Atrophy, Polyneuropathy Peripheral, Polyneuropathy and Polyradiculoneuropathy, Polyostotic Fibrous Dysplasia, Polyostotic Sclerosing Histiocytosis, Polyposis Familial, Polyposis Gardner Type, Polyposis Hamartomatous Intestinal, Polyposis Hamartomatous Intestinal, Polyposis-Osteomatosis-Epidermoid Cyst Syndrome, Polyposis Skin Pigmentation Alopecia and Fingernail Changes, Polyps and Spots Syndrome, Polyps and Spots Syndrome, Polyserositis Recurrent, Polysomy Y, Polysyndactyly with Peculiar Skull Shape, Polysyndactyly-Dysmorphic Craniofacies Greig Type, Pompe Disease, Pompe Disease, Popliteal Pterygium Syndrome, Porcupine Man, Porencephaly, Porencephaly, Porphobilinogen deaminase (PBG-D), Porphyria, Porphyria Acute Intermittant, Porphyria Acute Intermittent, Porphyria ALA-D, Porphyria Cutanea Tarda, Porphyria Cutanea Tarda, Porphyria Cutanea Tarda Hereditaria, Porphyria Cutanea Tarda Symptomatica, Porphyria Hepatica Variegate, Porphyria Swedish Type, Porphyria Variegate, Porphyriam Acute Intermittent, Porphyrins, Porrigo Decalvans, Port Wine Stains, Portuguese Type Amyloidosis, Post-Infective Polyneuritis, Postanoxic Intention Myoclonus, Postaxial Acrofacial Dysostosis, Postaxial Polydactyly, Postencephalitic Intention Myoclonus, Posterior Corneal Dystrophy Hereditary, Posterior Thalamic Syndrome, Postmyelographic Arachnoiditis, Postnatal Cerebral Palsy, Postoperative Cholestasis, Postpartum Galactorrhea-Amenorrhea Syndrome, Postpartum Hypopituitarism, Postpartum Panhypopituitary Syndrome, Postpartum Panhypopituitarism, Postpartum Pituitary Necrosis, Postural Hypotension, Potassium-Losing Nephritis, Potassium Loss Syndrome, Potter Type I Infantile Polycystic Kidney Diseases, Potter Type III Polycystic Kidney Disease, PPH, PPS, Prader-Willi Syndrome, Prader-Labhart-Willi Fancone Syndrome, Prealbumin Tyr-77 Amyloidosis, Preexcitation Syndrome, Preexcitation Syndrome, Pregnenolone Deficiency, Premature Atrial Contractions, Premature Senility Syndrome, Premature Supraventricular Contractions, Premature Ventricular Complexes, Prenatal or Connatal Neuroaxonal Dystrophy, Presenile Dementia, Presenile Macula Lutea Retinae Degeneration, Primary Adrenal Insufficiency, Primary Agammaglobulinemias, Primary Aldosteronism, Primary Alveolar Hypoventilation, Primary Amyloidosis, Primary Anemia, Primary Anemia, Primary Beriberi, Primary Biliary, Primary Biliary Cirrhosis, Primary Brown Syndrome, Primary Carnitine Deficiency, Primary Central Hypoventilation Syndrome, Primary-Ciliary Dyskinesia Kartagener Type, Primary Cutaneous Amyloidosis, Primary Dystonia, Primary Failure Adrenocortical Insufficiency, Primary Familial Hypoplasia of the Maxilla, Primary Hemochromatosis, Primary Hyperhidrosis, Primary Hyperoxaluria [Type I], Primary Hyperoxaluria Type 1 (PH1), Primary Hyperoxaluria Type I, Primary Hyperoxaluria Type II, Primary Hyperoxaluria Type III, Primary Hypogonadism, Primary Intestinal Lymphangiectasia, Primary Lateral Sclerosis, Primary Nonhereditary Amyloidosis, Primary Obliterative Pulmonary Vascular Disease, Primary Progressive Multiple Sclerosis, Primary Pulmonary Hypertension, Primary Reading Disability, Primary Renal Glycosuria, Primary Sclerosing Cholangitis, Primary Thrombocythemia, Primary Thrombocythemia, Primary Tumors of Central Nervous System, Primary Visual Agnosia, Proctocolitis Idiopathic, Proctocolitis Idiopathic, Progeria of Adulthood, Progeria of Childhood, Progeroid Nanism, Progeriod Short Stature with Pigmented Nevi, Progeroid Syndrome of De Barsy, Progressive Autonomic Failure with Multiple System Atrophy, Progressive Bulbar Palsy, Progressive Bulbar Palsy Included, Progressive Cardiomyopathic Lentiginosis, Progressive Cerebellar Ataxia Familial, Progressive Cerebral Poliodystrophy, Progressive Choroidal Atrophy, Progressive Diaphyseal Dysplasia, Progressive Diaphyseal Dysplasia, Progressive Facial Hemiatrophy, Progressive Familial Myoclonic Epilepsy, Progressive Hemifacial Atrophy, Progressive Hypoerythemia, Progressive Infantile Poliodystrophy, Progressive Lenticular Degeneration, Progressive Lipodystrophy, Progressive Muscular Dystrophy of Childhood, Progressive Myoclonic Epilepsy, Progressive Osseous Heteroplasia, Progressive Pallid Degeneration Syndrome, Progressive Pallid Degeneration Syndrome, Progressive Spinobulbar Muscular Atrophy, Progressive Supranuclear Palsy, Progressive Systemic Sclerosis, Progressive Tapetochoroidal Dystrophy, Proline Oxidase Deficiency, Propionic Acidemia, Propionic Acidemia, Propionic Acidemia Type I (PCCA Deficiency), Propionic Acidemia Type II (PCCB Deficiency), Propionyl CoA Carboxylase Deficiency, Propionyl CoA Carboxylase Deficiency, Protanomaly, Protanopia, Protein-Losing Enteropathy Secondary to Congestive Heart Failure, Proteus Syndrome, Proximal Deletion of 4q Included, Proximal Deletion of 4q-Included, PRP, PRS, Prune Belly Syndrome, PS, Pseudo-Hurler Polydystrophy, Pseudo-Polydystrophy, Pseudoacanthosis Nigricans, Pseudoachondroplasia, Pseudochol inesterase Deficiency, Pseudogout Familial, Pseudohemophilia, Pseudohermaphroditism, Pseudohermaphroditism, Pseudohermaphroditism-Nephron Disorder-Wilm's Tumor, Pseudohypertrophic Muscular Dystrophy, Pseudohypoparathyroidism, Pseudohypoparathyroidism, Pseudohypophosphatasia, Pseudopolydystrophy, Pseudothalidomide Syndrome, Pseudoxanthoma Elasticum, Pseudoxanthoma Elasticum, Psoriasis, Psorospermosis Follicularis, PSP, PSS, Psychomotor Convulsion, Psychomotor Epilepsy, Psychomotor Equivalent Epilepsy, PTC Deficiency, Pterygium, Pterygium Colli Syndrome, Pterygium Universale, Pterygolymphangiectasia, Pulmonary Atresia, Pulmonary Lymphangiomyomatosis, Pulmonary Stenosis, Pulmonic Stenosis-Ventricular Septal Defect, Pulp Stones, Pulpal Dysplasia, Pulseless Disease, Pure Alymphocytosis, Pure Cutaneous Histiocytosis, Purine Nucleoside Phosphorylase Deficiency, Purpura Hemorrhagica, Purtilo Syndrome, PXE, PXE Dominant Type, PXE Recessive Type, Pycnodysostosis, Pyknodysostosis, Pyknoepilepsy, Pyroglutamic Aciduria, Pyroglutamicaciduria, Pyrroline Carboxylate Dehydrogenase Deficiency, Pyruvate Carboxylase Deficiency, Pyruvate Carboxylase Deficiency Group A, Pyruvate Carboxylase Deficiency Group B, Pyruvate Dehydrogenase Deficiency, Pyruvate Dehydrogenase Deficiency, Pyruvate Dehydrogenase Deficiency, Pyruvate Kinase Deficiency, q25-qter, q26 or q27-qter, q31 or 32-qter, QT Prolongation with Extracellular Hypohypocalcinemia, QT Prolongation without Congenital Deafness, QT Prolonged with Congenital Deafness, Quadriparesis of Cerebral Palsy, Quadriplegia of Cerebral Palsy, Quantal Squander, Quantal Squander, r4, r6, r14, r 18, r21, r22, Rachischisis Posterior, Radial Aplasia-Amegakaryocytic Thrombocytopenia, Radial Aplasia-Thrombocytopenia Syndrome, Radial Nerve Palsy, Radicular Neuropathy Sensory, Radicular Neuropathy Sensory, Radicular Neuropathy Sensory Recessive, Radicular Dentin Dysplasia, Rapid-onset Dystonia-parkinsonism, Rapp-Hodgkin Syndrome, Rapp-Hodgkin (hypohidrotic) Ectodermal Dysplasia syndrome, Rapp-Hodgkin Hypohidrotic Ectodermal Dysplasias, Rare hereditary ataxia with polyneuritic changes and deafness caused by a defect in the enzyme phytanic acid hydroxylase, Rautenstrauch-Wiedemann Syndrome, Rautenstrauch-Wiedemann Type Neonatal Progeria, Raynaud's Phenomenon, RDP, Reactive Functional Hypoglycemia, Reactive Hypoglycemia Secondary to Mild Diabetes, Recessive Type Kenny-Caffe Syndrome, Recklin Recessive Type Myotonia Congenita, Recklinghausen Disease, Rectoperineal Fistula, Recurrent Vomiting, Reflex Neurovascular Dystrophy, Reflex Sympathetic Dystrophy Syndrome, Refractive Errors, Refractory Anemia, Refrigeration Palsy, Refsum Disease, Refsum's Disease, Regional Enteritis, Reid-Barlow's syndrome, Reifenstein Syndrome, Reifenstein Syndrome, Reiger Anomaly- Growth Retardation, Reiger Syndrome, Reimann Periodic Disease, Reimann's Syndrome, Reis-Bucklers Corneal Dystrophy, Reiter's Syndrome, Reiter's Syndrome, Relapsing Guillain-Barre Syndrome, Relapsing-Remitting Multiple Sclerosis, Renal Agenesis, Renal Dysplasia-Blindness Hereditary, Renal Dysplasia-Retinal Aplasia Loken-Senior Type, Renal Glycosuria, Renal Glycosuria Type A, Renal Glycosuria Type 13, Renal Glycosuria Type O, Renal-Oculocerebrodystrophy, Renal-Retinal Dysplasia with Medullary Cystic Disease, Renal-Retinal Dysplasia with Medullary Cystic Disease, Renal-Retinal Dystrophy Familial, Renal-Retinal Syndrome, Rendu-Osler-Weber Syndrome, Respiratory Acidosis, Respiratory Chain Disorders, Respiratory Myoclonus, Restless Legs Syndrome, Restrictive Cardio myopathy; Retention Hyperlipemia, Rethore Syndrome (obsolete), Reticular Dysgenesis, Retinal Aplastic-Cystic Kidneys-Joubert Syndrome, Retinal Cone Degeneration, Retinal Cone Dystrophy, Retinal Cone-Rod Dystrophy, Retinitis Pigmentosa, Retinitis Pigmentosa and Congenital Deafness, Retinoblastoma, Retinol Deficiency, Retinoschisis, Retinoschisis Juvenile, Retraction Syndrome, Retrobulbar Neuropathy, Retrolenticular Syndrome, Rett Syndrome, Reverse Coarction, Reye Syndrome, Reye's Syndrome, RGS, Rh Blood Factors, Rh Disease, Rh Factor Incompatibility, Rh Incompatibility, Rhesus Incompatibility, Rheumatic Fever, Rheumatoid Arthritis, Rheumatoid Myositis, Rhinosinusogenic Cerebral Arachnoiditis, Rhizomelic Chondrodysplasia Punctata (RCDP),Acatalasemia,Classical Refsum disease, RHS, Rhythmical Myoclonus, Rib Gap Defects with Micrognathia, Ribbing Disease (obsolete), Ribbing Disease, Richner-Hanhart Syndrome, Rieger Syndrome, Rieter's Syndrome, Right Ventricular Fibrosis, Riley-Day Syndrome, Riley-Smith syndrome, Ring Chromosome 14, Ring Chromosome 18, Ring 4, Ring 4 Chromosome, Ring 6, Ring 6 Chromosome, Ring 9, Ring 9 Chromosome R9, Ring 14, Ring 15, Ring 15 Chromosome (mosaic pattern), Ring 18, Ring Chromosome 18, Ring 21, Ring 21 Chromosome, Ring 22, Ring 22 Chromosome, Ritter Disease, Ritter-Lyell Syndrome, RLS, RMSS, Roberts SC-Phocomelia Syndrome, Roberts Syndrome, Roberts Tetraphocomelia Syndrome, Robertson's Ectodermal Dysplasias, Robin Anomalad, Robin Sequence, Robin Syndrome, Robinow Dwarfism, Robinow Syndrome, Robinow Syndrome Dominant Form, Robinow Syndrome Recessive Form, Rod myopathy, Roger Disease, Rokitansky's Disease, Romano-Ward Syndrome, Romberg Syndrome, Rootless Teeth, Rosenberg-Chutorian Syndrome, Rosewater Syndrome, Rosewater Syndrome, Rosselli-Gulienatti Syndrome, Rothmund-Thomson Syndrome, Roussy-Levy Syndrome, RP, RS X-Linked, RS, RS, RSDS, RSH Syndrome, RSS, RSTS, RTS, RTS, RTS, Rubella Congenital, Rubinstein Syndrome, Rubinstein-Taybi Syndrome, Rubinstein Taybi Broad Thumb-Hallux syndrome, Rufous Albinism, Ruhr's Syndrome, Russell's Diencephalic Cachexia, Russell's Syndrome, Russell Syndrome, Russell-Silver Dwarfism, Russell-Silver Syndrome, Russell-Silver Syndrome X-linked, Ruvalcaba-Myhre-Smith syndrome (RMSS), Ruvalcaba Syndrome, Ruvalcaba Type Osseous Dysplasia with Mental Retardation, Sacral Regression, Sacral Agenesis Congenital, SAE, Saethre-Chotzen Syndrome, Sakati, Sakati Syndrome, Sakati-Nyhan Syndrome, Salaam Spasms, Salivosudoriparous Syndrome, Salzman Nodular Corneal Dystrophy, Sandhoff Disease, Sanfilippo Syndrome, Sanfilippo Type A, Sanfilippo Type B, Santavuori Disease, Santavuori-Haltia Disease, Sarcoid of Boeck, Sarcoidosis, Sarcoidosis, Sathre-chotzen, Saturday Night Palsy, SBMA, SC Phocomelia Syndrome, SC Syndrome, SCA 3, SCAD Deficiency, SCAD Deficiency Adult-Onset Localized, SCAD Deficiency Congenital Generalized, SCAD, SCAD, SCAD, SCADH Deficiency, Scalded Skin Syndrome, Scalp Defect Congenital, Scaphocephaly, Scaphocephaly, Scaphocephaly, Scapula Elevata, Scapuloperoneal myopathy, Scapuloperoneal Muscular Dystrophy, Scapuloperoneal Syndrome Myopathic Type, Scarring Bullosa, Scarring Bullosa, SCHAD, Schaumann's Disease, Scheie Syndrome, Schereshevkii-Tumer Syndrome, Schilder Disease, Schilder Encephalitis, Schilder's Disease, Schindler Disease Type I (Infantile Onset), Schindler Disease Infantile Onset, Schindler Disease, Schindler Disease Type II (Adult Onset), Schinzel Syndrome, Schinzel-Giedion Syndrome, Schinzel Acrocallosal Syndrome, Schinzel-Giedion Midface-Retraction Syndrome, Schizencephaly, Schmid Type Metaphyseal Chondrodysplasia, Schmid Metaphyseal Dysostosis, Schmid-Fraccaro Syndrome, Schmidt Syndrome, Schopf-Schultz-Passarge Syndrome, Schueller-Christian Disease, Schut-Haymaker Type, Schwartz-Jampel-Aberfeld Syndrome, Schwartz-Jampel Syndrome Types 1A and 1B, Schwartz-Jampel Syndrome, Schwartz-Jampel Syndrome Type 2, SCI, D SCID, Scleroderma, Scleroderma, Sclerosis Familial Progressive Systemic, Sclerosis Diffuse Familial Brain, Scott Craniodigital Syndrome With Mental Retardation, Scrotal Tongue, SCS, SCS, SD, SDS, SDYS, Seasonal Conjunctivitis, Sebaceous Nevus Syndrome, Sebaceous nevus, Seborrheic Keratosis, Seborrheic Warts, Seckel Syndrome, Seckel Type Dwarfism, Second Degree Congenital Heart Block, Secondary Amyloidosis, Secondary Blepharospasm, Secondary Non-tropical Sprue, Secondary Brown Syndrome, Secondary Beriberi, Secondary Generalized Amyloidosis, Secondary Dystonia, Secretory Component Deficiency, Secretory IgA Deficiency, SED Tarda, SED Congenital, SEDC, Segmental linear achromic nevus, Segmental Dystonia, Segmental Myoclonus, Seip Syndrome, Seitelberger Disease, Seitelberger Disease, Seizures, Selective Deficiency of IgG Subclasses, Selective Mutism, Selective Deficiency of IgG Subclass, Selective IgM Deficiency, Selective Mutism, Selective IgA Deficiency, Self-Healing Histiocytosis, Semilobar Holoprosencephaly, Seminiferous Tubule Dysgenesis, Senile Retinoschisis, Senile Warts, Senior-Loken Syndrome, Sensory Neuropathy Hereditary Type I, Sensory Neuropathy Hereditary Type II, Sensory Neuropathy Hereditary Type I, Sensory Radicular Neuropathy, Sensory Radicular Neuropathy, Sensory Radicular Neuropathy Recessive, Septic Progressive Granulomatosis, Septo-Optic Dysplasia, Serous Circumscribed Meningitis, Serum Protease Inhibitor Deficiency, Serum Carnosinase Deficiency, Setleis Syndrome, Severe Combined Immunodeficiency, Severe Combined Immunodeficiency with Adenosine Deaminase Deficiency, Severe Combined Immunodeficiency (SCID), Sex Reversal, Sexual Infantilism, SGB Syndrome, Sheehan Syndrome, Shields Type Dentinogenesis Imperfecta, Shingles,varicella-zoster virus, Ship Beriberi, SHORT Syndrome, Short Arm 18 Deletion Syndrome, Short Chain Acyl CoA Dehydrogenase Deficiency, Short Chain Acyl-CoA Dehydrogenase (SCAD) Deficiency, Short Stature and Facial Telangiectasis, Short Stature Facial/Skeletal Anomalies-Retardation-Macrodontia, Short Stature-Hyperextensibility-Rieger Anomaly-Teething Delay, Short Stature-Onychodysplasia, Short Stature Telangiectatic Erythema of the Face, SHORT Syndrome, Shoshin Beriberi, Shoulder girdle syndrome, Shprintzen-Goldberg Syndrome, Shulman Syndrome, Shwachman-Bodian Syndrome, Shwachman-Diamond Syndrome, Shwachman Syndrome, Shwachman-Diamond-Oski Syndrome, Shwachmann Syndrome, Shy Drager Syndrome, Shy-Magee Syndrome, SI Deficiency, Sialidase Deficiency, Sialidosis Type I Juvenile, Sialidosis Type II Infantile, Sialidosis, Sialolipidosis, Sick Sinus Syndrome, Sickle Cell Anemia, Sickle Cell Disease, Sickle Cell-Hemoglobin C Disease, Sickle Cell-Hemoglobin D Disease, Sickle Cell-Thalassemia Disease, Sickle Cell Trait, Sideroblastic Anemias, Sideroblastic Anemia, Sideroblastosis, Sideroblastosis, SIDS, Siegel-Cattan-Mamou Syndrome, Siemens-Bloch type Pigmented Dermatosis, Siemens Syndrome, Siewerling-Creutzfeldt Disease, Siewert Syndrome, Silver Syndrome, Silver-Russell Dwarfism, Silver-Russell Syndrome, Simmond's Disease, Simons Syndrome, Simplex Epidermolysis Bullosa, Simpson Dysmorphia Syndrome, Simpson-Golabi-Behmel Syndrome, Sinding-Larsen-Johansson Disease, Singleton-Merten Syndrome, Sinus Arrhythmia, Sinus Venosus, Sinus tachycardia, Sirenomelia Sequence, Sirenomelus, Situs Inversus Bronchiectasis and Sinusitis, SJA Syndrome, Sjogren Larsson Syndrome Ichthyosis, Sjogren Syndrome, Sjogren Larsson Syndrome Ichthyosis, Sjögren's Syndrome, SJS, Skeletal dysplasia, Skeletal Dysplasia Weismann Netter Stuhl Type, Skin Peeling Syndrome, Skin Neoplasms, Skull Asymmetry and Mild Retardation, Skull Asymmetry and Mild Syndactyly, SLE, Sleep Epilepsy, Sleep Apnea, SLO, Sly Syndrome, SMA, SMA Infantile Acute Form, SMA I, SMA III, SMA type I, SMA type II, SMA type III, SMA3, SMAX1, SMCR, Smith Lemli Opitz Syndrome, Smith Magenis Syndrome, Smith-Magenis Chromosome Region, Smith-McCort Dwarfism, Smith-Opitz-Inborn Syndrome, Smith Disease, Smoldering Myeloma, SMS, SMS, SNE, Sneezing From Light Exposure, Sodium valproate, Solitary Plasmacytoma of Bone, Sorsby Disease, Sotos Syndrome, Souques-Charcot Syndrome, South African Genetic Porphyria, Spasmodic Dysphonia, Spasmodic Torticollis, Spasmodic Torticollis, Spasmodic Wryneck, Spastic Cerebral Palsy, Spastic Colon, Spastic Dysphonia, Spastic Paraplegia, SPD Calcinosis, Specific Antibody Deficiency with Normal Immunoglobulins, Specific Reading Disability, SPH2, Spherocytic Anemia, Spherocytosis, Spherophakia-Brachymorphia Syndrome, Sphingomyelin Lipidosis, Sphingomyelinase Deficiency, Spider fingers, Spielmeyer-Vogt Disease, Spielmeyer-Vogt-Batten Syndrome, Spina Bifida, Spina Bifida, Spina Bifida Aperta, Spinal Arachnoiditis, Spinal Arteriovenous Malformation, Spinal Ataxia Hereditofamilial, Spinal and Bulbar Muscular Atrophy, Spinal Diffuse Idiopathic Skeletal Hyperostosis, Spinal DISH, Spinal Muscular Atrophy, Spinal Muscular Atrophy, Spinal Muscular Atrophy All Types, Spinal Muscular Atrophy Type ALS, Spinal Muscular Atrophy-Hypertrophy of the Calves, Spinal Muscular Atrophy Type I, Spinal Muscular Atrophy Type III, Spinal Muscular Atrophy type 3, Spinal Muscular Atrophy-Hypertrophy of the Calves, Spinal Ossifying Arachnoiditis, Spinal Stenosis, Spino Cerebellar Ataxia, Spinocerebellar Atrophy Type I, Spinocerebellar Ataxia Type I (SCA1), Spinocerebellar Ataxia Type II (SCAII), Spinocerebellar Ataxia Type III (SCAIII), Spinocerebellar Ataxia Type III (SCA 3), Spinocerebellar Ataxia Type IV (SCAIV), Spinocerebellar Ataxia Type V (SCAV), Spinocerebellar Ataxia Type VI (SCAVI), Spinocerebellar Ataxia Type VII (SCAVII), Spirochetal Jaundice, Splenic Agenesis Syndrome, Splenic Ptosis, Splenoptosis, Split Hand Deformity-Mandibulofacial Dysostosis, Split Hand Deformity-Mandibulofacial Dysostosis, Split Hand Deformity, Split-Hand Deformity, Spondyloarthritis, Spondylocostal Dysplasia—Type I, Spondyloepiphyseal Dysplasia Tarda, Spondylothoracic Dysplasia, Spondylotic Caudal Radiculopathy, Sponge Kidney, Spongioblastoma Multiforme, Spontaneous Hypoglycemia, Sprengel Deformity, Spring Ophthalmia, SRS, ST, Stale Fish Syndrome, Staphylococcal Scalded Skin Syndrome, Stargardt's Disease, Startle Disease, Status Epilepticus, Steele-Richardson-Olszewski Syndrome, Steely Hair Disease, Stein-Leventhal Syndrome, Steinert Disease, Stengel's Syndrome, Stengel-Batten-Mayou-Spielmeyer-Vogt-Stock Disease, Stenosing Cholangitis, Stenosis of the Lumbar Vertebral Canal, Stenosis, Steroid Sulfatase Deficiency, Stevanovic's Ectodermal Dysplasias, Stevens Johnson Syndrome, Stevens-Johnson Syndrome, STGD, Stickler Syndrome, Stickler Syndrome, Stiff-Man Syndrome, Stiff Man Syndrome, Stiff Person Syndrome, Still's Disease, Stilling-Turk-Duane Syndrome, Stillis Disease, Stimulus-Sensitive Myoclonus, Stone Man Syndrome, Stone Man, Streeter Anomaly, Striatonigral Degeneration Autosomal Dominant Type, Striopallidodentate Calcinosis, Stroma, Descemet's Membrane, Stromal Corneal Dystrophy, Struma Lymphomatosa, Sturge-Kalischer-Weber. Syndrome, Sturge Weber Syndrome, Sturge-Weber Phakomatosis, Subacute Necrotizing Encephalomyelopathy, Subacute Necrotizing Encephalomyelopathy, Subacute Spongiform Encephalopathy, Subacute Necrotizing Encephalopathy, Subacute Sarcoidosis, Subacute Neuronopathic, Subaortic Stenosis, Subcortical Arteriosclerotic Encephalopathy, Subendocardial Sclerosis, Succinylcholine Sensitivity, Sucrase-Isomaltase Deficiency Congenital, Sucrose-Isomaltose Malabsorption Congenital, Sucrose Intolerance Congenital, Sudanophilic Leukodystrophy ADL, Sudanophilic Leukodystrophy Pelizaeus-Merzbacher Type, Sudanophilic Leukodystrophy Included, Sudden Infant Death Syndrome, Sudeck's Atrophy, Sugio-Kajii Syndrome, Summerskill Syndrome, Summit Acrocephalosyndactyly, Summitt's Acrocephalosyndactyly, Summitt Syndrome, Superior Oblique Tendon Sheath Syndrome, Suprarenal glands, Supravalvular Aortic Stenosis, Supraventricular tachycardia, Surdicardiac Syndrome, Surdocardiac Syndrome, SVT, Sweat Gland Abscess, Sweating Gustatory Syndrome, Sweet Syndrome, Swiss Cheese Cartilage Syndrome, Syndactylic Oxycephaly, Syndactyly Type I with Microcephaly and Mental Retardation, Syndromatic Hepatic Ductular Hypoplasia, Syringomyelia, Systemic Aleukemic Reticuloendotheliosis, Systemic Amyloidosis, Systemic Carnitine Deficiency, Systemic Elastorrhexis, Systemic Lupus Erythematosus, Systemic Mast Cell Disease, Systemic Mastocytosis, Systemic-Onset Juvenile Arthritis, Systemic-Onset Juvenile Arthritis, Systemic Sclerosis, Systopic Spleen, T-Lymphocyte Deficiency, Tachyalimentation Hypoglycemia, Tachycardia, Takahara syndrome, Takayasu Disease, Takayasu Arteritis, Takayasu Arteritis, Talipes Calcaneus, Talipes Equinovarus, Talipes Equinus, Talipes Varus, Talipes Valgus, Tandem Spinal Stenosis, Tangier Disease, Tapetoretinal Degeneration, TAR Syndrome, Tardive Dystonia, Tardive Muscular Dystrophy, Tardive Dyskinesia, Tardive Oral Dyskinesia, Tardive Dyskinesia, Tardive Dystonia, Tardy Ulnar Palsy, Target Cell Anemia, Tarsomegaly, Tarui Disease, TAS Midline Defects Included, TAS Midline Defect, Tay Sachs Disease, Tay Sachs Sphingolipidosis, Tay Sachs Disease, Tay Syndrome Ichthyosis, Tay Sachs Sphingolipidosis, Tay Syndrome Ichthyosis, Taybi Syndrome Type I, Taybi Syndrome, TCD, TCOF1, TCS, TD, TDO Syndrome, TDO-I, TDO-II, TDO-III, Telangiectasis, Telecanthus with Associated Abnormalities, Telecanthus With Associated Abnormalities, Telecanthus-Hypospadias Syndrome, Temporal Lobe Epilepsy, Temporal Arteritis/Giant Cell Arteritis, Temporal Arteritis, TEN, Tendon Sheath Adherence Superior Obliqu, Tension Myalgia, Terminal Deletion of 4q Included, Terminal Deletion of 4q-Included, Terrian Comeal Dystrophy, Teschler-Nicola/Killian Syndrome, Tethered Spinal Cord Syndrome, Tethered Cord Malformation Sequence, Tethered Cord Syndrome, Tethered Cervical Spinal Cord Syndrome, Tetrahydrobiopterin Deficiencies, Tetrahydrobiopterin Deficiencies, Tetralogy of Fallot, Tetralogy of Fallot, Tetraphocomelia-Thrombocytopenia Syndrome, Tetrasomy Short Arm of Chromosome 9, Tetrasomy 9p, Tetrasomy Short Arm of Chromosome 18, Thalamic Syndrome, Thalamic Pain Syndrome, Thalamic Hyperesthetic Anesthesia, Thalassemia Intermedia, Thalassemia Minor, Thalassemia Major, Thiamine Deficiency, Thiamine-Responsive Maple Syrup Urine Disease, Thin-Basement-Membrane Nephropathy, Thiolase deficiency, RCDP, Acyl-CoA dihydroxyacetonephosphate acyltransferase, Third and Fourth Pharyngeal Pouch Syndrome, Third Degree Congenital (Complete) Heart Block, Thomsen Disease, Thoracic-Pelvic-Phalangeal Dystrophy, Thoracic Spinal Canal, Thoracoabdominal Syndrome, Thoracoabdominal Ectopia Cordis Syndrome, Three M Syndrome, Three-M Slender-Boned Nanism, Thrombasthenia of Glanzmann and Naegeli, Thrombocythemia Essential, Thrombocytopenia-Absent Radius Syndrome, Thrombocytopenia-Hemangioma Syndrome, Thrombocytopenia-Absent Radii Syndrome, Thrombophilia Hereditary Due to AT III, Thrombotic Thrombocytopenic Purpura, Thromboulcerative Colitis, Thromboulcerative Colitis, Thymic Dysplasia with Normal Immunoglobulins, Thymic Agenesis, Thymic Aplasia DiGeorge Type, Thymic Hypoplasia Agammaglobulinemias Primary Included, Thymic Hypoplasia DiGeorge Type, Thymus Congenital Aplasia, Tic Douloureux, Tics, Tinel's syndrome, Tolosa Hunt Syndrome, Tonic Spasmodic Torticollis, Tonic Pupil Syndrome, Tooth and Nail Syndrome, Tooth and Nail Syndrome, Torch Infection, TORCH Syndrome, Torsion Dystonia, Torticollis, Torticollis, Total Lipodystrophy, Total anomalous pulmonary venous connection, Touraine's Aphthosis, Tourette Syndrome, Tourette's disorder, Townes-Brocks Syndrome, Townes Syndrome, Toxic Paralytic Anemia, Toxic Epidermal Necrolysis, Toxopachyosteose Diaphysaire Tibio-Peroniere, Toxopachyosteose, Toxoplasmosis Other Agents Rubella Cytomegalovirus Herpes Simplex, Tracheoesophageal Fistula with or without Esophageal Atresia, Tracheoesophageal Fistula, Transient neonatal myasthenia gravis, Transitional Atrioventricular Septal Defect, Transposition of the great arteries, Transtelephonic Monitoring, Transthyretin Methionine-30 Amyloidosis (Type I), Trapezoidocephaly-Multiple Synostosis Syndrome, Treacher Collins Syndrome, Treacher Collins-Franceschetti Syndrome 1, Trevor Disease, Triatrial Heart, Tricho-Dento-Osseous Syndrome, Trichodento Osseous Syndrome, Trichopoliodystrophy, Trichorhinophalangeal Syndrome, Trichorhinophalangeal Syndrome, Tricuspid atresia, Trifunctional Protein Deficiency, Trigeminal Neuralgia, Triglyceride Storage Disease Impaired Long—CH ain Fatty Acid Oxidation, Trigonitis, Trigonocephaly, Trigonocephaly, Trigonocephaly, Trigonocephaly Syndrome, Trigonocephaly "C" Syndrome, Trimethylaminuria, Triphalangeal Thumbs-Hypoplastic Distal Phalanges-Onychodystrophy, Triphalangeal Thumb Syndrome, Triple Symptom Complex of Behcet, Triple X Syndrome, Triplo X Syndrome, Triploid Syndrome, Triploidy, Triploidy Syndrome, Trismus-Pseudocamptodactyly Syndrome, Trisomy, Trisomy G Syndrome, Trisomy X, Trisomy 6q Partial, Trisomy 6q Syndrome Partial, Trisomy 9 Mosaic, Trisomy 9P Syndrome (Partial) Included, Trisomy 1 lq Partial, Trisomy 14 Mosaic, Trisomy 14 Mosaicism Syndrome, Trisomy 21 Syndrome, Trisomy 22 Mosaic, Trisomy 22 Mosaicism Syndrome, TRPS, TRPS1, TRPS2, TRPS3, True Hermaphroditism, True Hermaphroditism, Truncus arteriosus, Tryptophan Malabsorption, Tryptophan Pyrrolase Deficiency, TS, TTP, TTTS, Tuberous Sclerosis, Tubular Ectasia, Turcot Syndrome, Turner Syndrome, Turner-Kieser Syndrome, Turner Phenotype with Normal Chromosomes (Karyotype), Turner-Varny Syndrome, Turricephaly, Twin-Twin Transfusion Syndrome, Twin-to-Twin Transfusion Syndrome, Type A, Type B, Type AB, Type O, Type I Diabetes, Type I Familial Incomplete Male, Type I Familial Incomplete Male Pseudohermaphroditism, Type I Gaucher Disease, Type I (PCCA Deficiency), Type I Tyrosinemia, Type II Gaucher Disease, Type II Histiocytosis, Type II (PCCB Deficiency), Type II Tyrosinnemia, Type IIA Distal Arthrogryposis Multiplex Congenita, Type HI Gaucher Disease, Type III Tyrosinemia, Type III Dentinogenesis Imperfecta, Typical Retinoschisis, Tyrosinase Negative Albinism (Type I), Tyrosinase Positive Albinism (Type II), Tyrosinemia type 1 acute form, Tyrosinemia type 1 chronic form, Tyrosinosis, UCE, Ulcerative Colitis, Ulcerative Colitis Chronic Non-Specific, Ulnar-Mammary Syndrome, Ulnar-Mammary Syndrome of Pallister, Ulnar Nerve Palsy, UMS, Unclassified FODs, Unconjugated Benign Bilirubinemiav, Underactivity of Parathyroid, Unilateral Ichthyosiform Erythroderma with Ipsilateral Malformations Limb, Unilateral Chondromatosis, Unilateral Defect of Pectoralis Muscle and Syndactyly of the Hand, Unilateral Hemidysplasia Type, Unilateral Megalencephaly, Unilateral Partial Lipodystrophy, Unilateral Renal Agenesis, Unstable Colon, Unverricht Disease, Unverricht-Lundborg Disease, Unverricht-Lundborg-Laf Disease, Unverricht Syndrome, Upper Limb—Cardiovascular. Syndrome (Holt-Oram), Upper Motor Neuron Disease, Upper Airway Apnea, Upper Airway Apnea, Urea Cycle Defects or Disorders, Urea Cycle Disorder Arginase Type, Urea Cycle Disorder Arginino Succinase Type, Urea Cycle Disorders Carbamyl Phosphate Synthetase Type, Urea Cycle Disorder Citrullinemia Type, Urea Cycle Disorders N-Acrtyl Glutamate Synthetase Typ, Urea Cycle Disorder OTC Type, Urethral Syndrome, Urethro-Oculo-Articular Syndrome, Uridine Diphosphate Glucuronosyltransferase Severe Def. Type I, Urinary Tract Defects, Urofacial Syndrome, Uroporphyrinogen III cosynthase, Urticaria pigmentosa, Usher Syndrome, Usher Type I, Usher Type II, Usher Type III, Usher Type IV, Uterine Synechiae, Uoporphyrinogen I-synthase, Uveitis, Uveomeningitis Syndrome, V-CJD, VACTEL Association, VACTERL Association, VACTERL Syndrome, Valgus Calcaneus, Valine Transaminase Deficiency, Valinemia, Valproic Acid, Valproate acid exposure, Valproic acid exposure, Valproic acid, Van Buren's Disease, Van der Hoeve-Habertsma-Waardenburg-Gauldi Syndrome, Variable Onset Immunoglobulin Deficiency Dysgammaglobulinemia, Variant Creutzfeldt-Jakob Disease (V-CJD), Varicella Embryopathy, Variegate Porphyria, Variegate Porphyria, Variegate Porphyria, Vascular Birthmarks, Vascular Dementia Binswanger's Type, Vascular Erectile Tumor, Vascular Hemophilia, Vascular Malformations, Vascular Malformations of the Brain, Vasculitis, Vasomotor Ataxia, Vasopressin-Resistant Diabetes Insipidus, Vasopressin-Sensitive Diabetes Insipidus, VATER Association, Vcf syndrome, Vcfs, Velocardiofacial Syndrome, VeloCardioFacial Syndrome, Venereal Arthritis, Venous Malformations, Ventricular Fibrillation, Ventricular Septal Defects, Congenital Ventricular Defects, Ventricular Septal Defect, Ventricular Tachycardia, Venual Malformations, VEOHD, Vermis Aplasia, Vermis Cerebellar Agenesis, Vernal Keratoconjunctivitis, Verruca, Vertebral Anal Tracheoesophageal Esophageal Radial, Vertebral Ankylosing Hyperostosis, Very Early Onset Huntington's Disease, Very Long Chain Acyl-CoA Dehydrogenase (VLCAD) Deficiency, Vestibular Schwannoma, Vestibular Schwannoma Neurofibromatosis, Vestibulocerebellar, Virchow's Oxycephaly, Visceral Xanthogranulomatosis, Visceral Xantho-Granulomatosis, Visceral myopathy-External Ophthalmoplegia, Visceromegaly-Umbilical Hernia-Macroglossia Syndrome, Visual Amnesia, Vitamin A Deficiency, Vitamin B-1 Deficiency, Vitelline Macular Dystrophy, Vitiligo, Vitiligo, Vitiligo Capitis, Vitreoretinal Dystrophy, VKC, VKH Syndrome, VLCAD, VLCAD, Vogt Syndrome, Vogt Cephalosyndactyly, Vogt Koyanagi Harada Syndrome, Vogt Koyanagi Harada Syndrome, Vogt Koyanagi Harada Syndrome, Von Bechterew-Strumpell Syndrome, Von Eulenburg Paramyotonia Congenita, Von Frey's Syndrome, Von Gierke Disease, Von Hippel-Lindau Syndrome, Von Mikulicz Syndrome, Von Recklinghausen Disease, Von Willebrandt Disease, VP, Vrolik Disease (Type II), VSD, VSD, Vulgaris Type Disorder of Cornification, Vulgaris Type Ichthyosis, W Syndrome, Waardenburg Syndrome, Waardenburg-Klein Syndrome, Waardenburg Syndrome Type I (WS1), Waardenburg Syndrome Type II (WS2), Waardenburg Syndrome Type IIA (WS2A), Waardenburg Syndrome Type IIB (WS2B), Waardenburg Syndrome Type III (WS3), Waardenburg Syndrome Type IV (WS4), Waelsch's Syndrome, WAGR Complex, WAGR Syndrome, WAGR Syndrome, Waldenstroem's Macroglobulinemia, Waldenstrom's Purpura, Waldenstrom's Syndrome, Waldmann Disease, Walker-Warburg Syndrome, Wandering Spleen, Warburg Syndrome, Warm Antibody Hemolytic Anemia, Warm Reacting Antibody Disease, Wartenberg Syndrome, WAS, Water on the Brain, Watson Syndrome, Watson-Alagille Syndrome, Waterhouse-Friderichsen syndrome, Waxy Disease, WBS, Weaver Syndrome, Weaver-Smith Syndrome, Weber-Cockayne Disease, Wegener's Granulomatosis, Wegener's Granulomatosis, Well Disease, Weil Syndrome, Weill-Marchesani, Weill-Marchesani Syndrome, Weill-Reyes Syndrome, Weismann-Netter-Stuhl Syndrome, Weissenbacher-Zweymuller Syndrome, Wells Syndrome, Wenckebach, Werdnig-Hoffman Disease, Werdnig-Hoffmann Disease, Werdnig-Hoffman disease, Werdnig-Hoffman Disease, Werdnig-Hoffman Paralysis, Werlhof's Disease, Werner Syndrome, Wernicke's (C) I Syndrome, Wernicke's aphasia, Wemicke-Korsakoff Syndrome, West Syndrome, Wet Beriberi, WHCR, Whipple's Disease, Whipple Disease, Whistling face syndrome, Whistling Face-Windmill Vane Hand Syndrome, White-Darier Disease, Whitnall-Norman Syndrome, Whorled nevoid hypermelanosis, WHS, Wieacker Syndrome, Wieacher Syndrome, Wieacker-Wolff Syndrome, Wiedmann-Beckwith Syndrome, Wiedemann-Rautenstrauch Syndrome, Wildervanck Syndrome, Willebrand-Juergens Disease, Willi-Prader Syndrome, Williams Syndrome, Williams Syndrome, Williams-Beuren Syndrome, Wilms' Tumor, Wilms' Tumor-Aniridia-Gonadoblastoma-Mental Retardation Syndrome, Wilms Tumor Aniridia Gonadoblastoma Mental Retardation, Wilms' Tumor-Aniridia-Genitourinary Anomalies-Mental Retardation Syndrome, Wilms Tumor-Pseudohermaphroditism-Nephropathy, Wilms Tumor and Pseudohermaphroditism, Wilms Tumor-Pseuodohermaphroditism-Glomerulopathy, Wilson's Disease, Winchester Syndrome, Winchester-Grossman Syndrome, Wiskott-Aldrich Syndrome, Wiskott-Aldrich Type Immunodeficiency, Witkop Ectodermal Dysplasias, Witkop Tooth-Nail Syndrome, Wittmaack-Ekbom Syndrome, WM Syndrome, WMS, WMS, WNS, Wohlfart-Disease, Wohlfart-Kugelberg-Welander Disease, Wolf Syndrome, Wolf-Hirschhorn Chromosome Region (WHCR), Wolf-Hirschhorn Syndrome, Wolff-Parkinson-White Syndrome, Wolff-Parkinson-White syndrome, Wolff Parkinson White Syndrome, Wolfram Syndrome, Wolman Disease (Lysomal Acid Lypase Deficiency), Woody Guthrie's Disease, WPW Syndrome, WPW Syndrome, Writer's Cramp, WS, WS, WS, WSS, WWS, Wyburn-Mason Syndrome, Wyburn-Mason Syndrome, X-Linked Addison's Disease, X-linked Adrenoleukodystrophy (X-ALD), X-linked Adult Onset Spinobulbar Muscular Atrophy, X-linked Adult Spinal Muscular Atrophy, X-Linked Agammaglobulinemia with Growth Hormone Deficiency, X-Linked Agammaglobulinemia, Lymphoproliferate X-Linked Syndrome, X-linked Cardio myopathy and Neutropenia, X-Linked Centronuclear myopathy, X-linked Copper Deficiency, X-linked Copper Malabsorption, X-Linked Dominant Conradi-Hunermann Syndrome, X-Linked Dominant Inheritance Agenesis of Corpus Callosum, X-Linked Dystonia-parkinsonism, X-Linked Ichthyosis, X Linked. Ichthyosis, X-Linked Infantile Agammaglobulinemia, X-Linked Infantile Nectrotizing Encephalopathy, X-linked Juvenile Retinoschisis, X-linked Lissencephaly, X-linked Lymphoproliferative Syndrome, X-linked Mental Retardation-Clasped Thumb Syndrome, X-Linked Mental Retardation with Hypotonia, X-linked Mental Retardation and Macroorchidism, X-Linked Progressive Combined Variable Immunodeficiency, X-Linked Recessive Conradi-Hunermann Syndrome, X-Linked Recessive Severe Combined Immunodeficiency, X-Linked Recessive Severe Combined Immunodeficiency, X-Linked Retinoschisis, X-linked Spondyloepiphyseal Dysplasia, Xanthine Oxidase Deficiency (Xanthinuria Deficiency, Hereditary), Xanthinuria Deficiency, Hereditary (Xanthine Oxidase Deficiency), Xanthogranulomatosis Generalized, Xanthoma Tuberosum, Xeroderma Pigmentosum, Xeroderma Pigmentosum Dominant Type, Xeroderma Pigmentosum Type A I XPA Classical Form, Xeroderma Pigmentosum Type B II XPB, Xeroderma Pigmentosum Type E V XPE, Xeroderma Pigmentosum Type C III XPC, Xeroderma Pigmentosum Type D IV XPD, Xeroderma Pigmentosum Type F VI XPF, Xeroderma Pigmentosum Type G VII XPG, Xeroderma Pigmentosum Variant Type XP-V, Xeroderma-Talipes-and Enamel Defect, Xerodermic Idiocy, Xerophthalmia, Xerotic Keratitis, XLP, XO Syndrome, XP, XX Male Syndrome, Sex Reversal, XXXXX Syndrome, XXY Syndrome, XYY Syndrome, XYY Chromosome Pattern, Yellow Mutant Albinism, Yellow Nail Syndrome, YKL, Young Female Arteritis, Yunis-Varon Syndrome, YY Syndrome, Z-E Syndrome, Z- and -Protease Inhibitor Deficiency, Zellweger Syndrome, Zellweger syndrome, Zellweger cerebro-hepato-renal syndrome, ZES, Ziehen-Oppenheim Disease (Torsion Dystonia), Zimmermann-Laband Syndrome, Zinc Deficiency Congenital, Zinsser-Cole-Engman Syndrome, ZLS, Zollinger-Ellison Syndrome.

As used herein a "cancer" refers to a group of diseases and disorders that are characterized by uncontrolled cellular growth (e.g. formation of tumor) without any differentiation of those cells into specialized and different cells. Cancers which can be treated using the methods of the present invention include, without being limited to, ABL1 protooncogene, AIDS Related Cancers, Acoustic Neuroma, Acute Lymphocytic Leukaemia, Acute Myeloid Leukaemia, Adenocystic carcinoma, Adrenocortical Cancer, Agnogenic myeloid metaplasia, Alopecia, Alveolar soft-part sarcoma, Anal cancer, Angiosarcoma, Aplastic Anaemia, Astrocytoma, Ataxia-telangiectasia, Basal Cell Carcinoma (Skin), Bladder Cancer, Bone Cancers, Bowel cancer, Brain Stem Glioma, Brain and CNS Tumors, Breast Cancer, CNS tumors, Carcinoid Tumors, Cervical Cancer, Childhood Brain Tumors, Childhood Cancer, Childhood Leukaemia, Childhood Soft Tissue Sarcoma, Chondrosarcoma, Choriocarcinoma, Chronic Lymphocytic Leukaemia, Chronic Myeloid Leukaemia, Colorectal Cancers, Cutaneous T-Cell Lymphoma, Dermatofibrosarcoma-protuberans, Desmoplastic-Small-Round-Cell-Tumor, Ductal Carcinoma, Endocrine Cancers, Endometrial Cancer, Ependymoma, Esophageal Cancer, Ewing's Sarcoma, Extra-Hepatic Bile Duct Cancer, Eye Cancer, Eye:

Melanoma, Retinoblastoma, Fallopian Tube cancer, Fanconi Anaemia, Fibrosarcoma, Gall Bladder Cancer, Gastric Cancer, Gastrointestinal Cancers, Gastrointestinal-Carcinoid-Tumor, Genitourinary Cancers, Germ Cell Tumors, Gestational-Trophoblastic-Disease, Glioma, Gynaecological Cancers, Haematological Malignancies, Hairy Cell Leukaemia, Head and Neck Cancer, Hepatocellular Cancer, Hereditary Breast Cancer, Histiocytosis, Hodgkin's Disease, Human Papillomavirus, Hydatidiform mole, Hypercalcemia, Hypopharynx Cancer, IntraOcular Melanoma, Islet cell cancer, Kaposi's sarcoma, Kidney Cancer, Langerhan's-Cell-Histiocytosis, Laryngeal Cancer, Leiomyosarcoma, Leukaemia, Li-Fraumeni Syndrome, Lip Cancer, Liposarcoma, Liver Cancer, Lung Cancer, Lymphedema, Lymphoma, Hodgkin's Lymphoma, Non-Hodgkin's Lymphoma, Male Breast Cancer, Malignant-Rhabdoid-Tumor-of-Kidney, Medulloblastoma, Melanoma, Merkel Cell Cancer, Mesothelioma, Metastatic Cancer, Mouth Cancer, Multiple Endocrine Neoplasia, Mycosis Fungoides, Myelodysplastic Syndromes, Myeloma, Myeloproliferative Disorders, Nasal Cancer, Nasopharyngeal Cancer, Nephroblastoma, Neuroblastoma, Neurofibromatosis, Nijmegen Breakage Syndrome, Non-Melanoma Skin Cancer, Non-Small-Cell-Lung-Cancer-(NSCLC), Ocular Cancers, Oesophageal Cancer, Oral cavity Cancer, Oropharynx Cancer, Osteosarcoma, Ostomy Ovarian Cancer, Pancreas Cancer, Paranasal Cancer, Parathyroid Cancer, Parotid Gland Cancer, Penile Cancer, Peripheral-Neuroectodermal-Tumors, Pituitary Cancer, Polycythemia vera, Prostate Cancer, Rare-cancers-and-associated-disorders, Renal Cell Carcinoma, Retinoblastoma, Rhabdomyosarcoma, Rothmund-Thomson Syndrome, Salivary Gland Cancer, Sarcoma, Schwannoma, Sezary syndrome, Skin Cancer, Small Cell Lung Cancer (SCLC), Small Intestine Cancer, Soft Tissue Sarcoma, Spinal Cord Tumors, Squamous-Cell-Carcinoma-(skin), Stomach Cancer, Synovial sarcoma, Testicular Cancer, Thymus Cancer, Thyroid Cancer, Transitional-Cell-Cancer-(bladder), Transitional-Cell-Cancer-(renal-pelvis–/–ureter), Trophoblastic Cancer, Urethral Cancer, Urinary System Cancer, Uroplakins, Uterine sarcoma, Uterus Cancer, Vaginal Cancer, Vulva Cancer, Waldenstrom's-Macroglobulinemia; Wilms' Tumor.

The compounds of the invention can be utilized in pharmaceutical compositions by adding an effective amount of a compound to a suitable pharmaceutically acceptable diluent or carrier. Use of the compounds and methods of the invention may also be useful prophylactically.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally preferred. In addition, linear compounds may have internal nucleotide complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Specific examples of preferred antisense or sense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleotide is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,72.1,218; 5,672,697 and 5,625,050.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439.

In other preferred oligonucleotide mimetics, both the sugar and the internucleoside linkage (i.e. the backbone), of the nucleotide units are replaced with novel groups. The nucleotide units are maintained for hybridization with an appropriate target nucleic acid. One such compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleotides are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262. Further teaching of PNA compounds can be found in Nielsen et al., *Science* 254: 1497-1500, 1991.

Preferred embodiments of the present invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[$(CH_2)_nO]_mCH_3$, O$(CH_2)_nOCH_3$, O$(CH_2)_nNH_2$, O$(CH_2)_nCH_3$, O$(CH_2)_nONH_2$, and O$(CH_2)_nON[(CH_2)_nCH_3]_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'—O—$CH_2CH_2OCH_3$, also known as 2'-O-(2-methoxyethyl) or 2'-MOE) (Martin et al., *Helv. Chim. Acta*, 78: 486-504, 1995) i.e., an alkoxyalkoxy group. A further preferred modification includes 2'-dimethylaminooxyethoxy, i.e., a O$(CH_2)_2ON(CH_3)_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—N($CH_3$)$_2$, also described in examples hereinbelow.

Other preferred modifications include 2'-methoxy (2'-O—$CH_3$), 2'-aminopropoxy (2'-O$CH_2CH_2CH_2NH_2$), 2'-allyl (2'-$CH_2$—CH=$CH_2$), 2'-O—allyl (2'-O—$CH_2$—CH=$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920.

A further preferred modification of the sugar includes Locked Nucleic Acids (LNAs) in which the 2'-hydroxyl group is linked to the 3' or 4' carbon atom of the sugar ring, thereby forming a bicyclic sugar moiety. The linkage is preferably a methylene (—$CH_2$—)$_n$ group bridging the 2' oxygen atom and the 4' carbon atom wherein n is 1 or 2. LNAs and preparation thereof are described in WO 98/39352 and WO 99/14226.

Oligonucleotides may also include nucleotide (often referred to in the art simply as "base") modifications or substitutions. As used herein, "unmodified" or "natural" nucleotides include the purine bases adenine (A) and guanine (G), and the pyrimidine bases thymine (T), cytosine (C) and uracil (U). Modified nucleotides include other synthetic and natural nucleotides such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleotides include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido [5,4-b][1,4]benzoxazin-2(3H)-one), carbazole cytidine (2H-pyrimido[4,5-b]indol-2-one), pyridoindole cytidine (H-pyrilo[3',2':4,5]pyrrolo[2,3-d]pyrimidin-2-one). Modified nucleotides may also include those in which the purine or pyrimidine base is replaced with other heterocycles, for example 7-deaza-adenine, 7-deazaguanosine, 2-aminopyridine and 2-pyridone. Further nucleotides include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie, International Edition*, 30: 613, 1991, and those disclosed by Sanghvi, Y. S., Chapter 15, *Antisense Research and Applications*, pages 289-302, Crooke, S. T. and Lebleu, B., ed., CRC Press, 1993. Certain of these nucleotides are particularly useful for increasing the binding affinity of the compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are presently preferred base substitutions, even more particularly when combined with 2'-O-methoxyethyl sugar modifications.

Representative United States patents that teach the preparation of certain of the above noted modified nucleotides as well as other modified nucleotides include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; and 5,681,941.

Another modification of the oligonucleotides of the invention involves chemically linking to the oligonucleotide one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application PCT/US92/09196, filed Oct. 23, 1992, and U.S. Pat. No. 6,287,860, the entire disclosure of which are incorporated herein by reference. Conjugate moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

It is not necessary for all positions in a given compound to be uniformly modified, and in fact more than one of the aforementioned modifications may be incorporated in a single compound or even at a single nucleoside within an oligonucleotide.

The present invention also includes antisense or sense compounds which are chimeric compounds. "Chimeric" antisense compounds or "chimeras", in the context of this invention, are antisense or sense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, increased stability and/or increased binding affinity for the target nucleic acid. An additional region of the oligonucleotide may serve as a substrate for enzymes capable of cleaving RNA:DNA or RNA:RNA hybrids. By way of example, RNAse H is a cellular endonuclease which cleaves the RNA strand of an RNA:DNA duplex. Activation of RNase H, therefore, results in cleavage of the RNA target, thereby greatly enhancing the efficiency of oligonucleotide-mediated inhibition of gene expression. The cleavage of RNA:RNA hybrids can, in like fashion, be accomplished through the actions of endoribonucleases, such as RNAseL which cleaves both cellular and viral RNA. Cleavage of the RNA target can be routinely detected by gel electrophoresis and, if necessary, associated nucleic acid hybridization techniques known in the art.

Chimeric antisense or sense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922.

The compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense or sense compounds of the invention encompass any pharmaceutically acceptable salts, esters, or salts of such esters, or any other compound which, upon administration to an animal, including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94/26764 and U.S. Pat. No. 5,770,713 to Imbach el al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. For oligonucleotides, preferred examples of pharmaceutically acceptable salts and their uses are further described in U.S. Pat. No. 6,287,860.

The present invention also includes pharmaceutical compositions and formulations which include the antisense or sense compounds or interactive compounds of the present invention. The pharmaceutical compositions of the present invention may be administered in any number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. The compounds may be modified for oral administration. For example, oligonucleotides with at least one 2'-O-methoxyethyl modification are useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

Emulsions are typically heterogenous systems of one liquid dispersed in another in the form of droplets usually exceeding 0.1 μm in diameter. Emulsions may contain additional components in addition to the dispersed phases, and the active drug which may be present as a solution in either the aqueous phase, oily phase or itself as a separate phase.

Microemulsions are included as an embodiment of the present invention. Emulsions and their uses are well known in the art and are further described in U.S. Pat. No. 6,287,860, which is incorporated herein in its entirety.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes which are believed to interact with negatively charged DNA molecules to form a stable complex. Liposomes that are pH-sensitive or negatively—CH arged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860, which is incorporated herein in its entirety.

The pharmaceutical formulations and compositions of the present invention may also include surfactants. The use of surfactants in drug products, formulations and in emulsions is well known in the art. Surfactants and their uses are further described in U.S. Pat. No. 6,287,860.

In one embodiment, the present invention employs various penetration enhancers to effect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non—CH elating non-surfactants. Penetration enhancers and their uses are further described in U.S. Pat. No. 6,287,860.

One of skill in the art will recognize that formulations are routinely designed according to their intended use, i.e. route of administration.

Preferred formulations for topical administration include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

For topical or other administration, oligonucleotides of the invention may be encapsulated within liposomes or may form complexes thereto, in particular to cationic liposomes. Alternatively, oligonucleotides or interactive molecules (e.g. antibodies) may be complexed to lipids, in particular to cationic lipids. Preferred fatty acids and esters, pharmaceutically acceptable salts thereof, and their uses are further described in U.S. Pat. No. 6,287,860.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof.

Preferred bile acids/salts and fatty acids and their uses are further described in U.S. Pat. No. 6,287,860, which is incorporated herein in its entirety. Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides or antibodies or other interactive molecules of the invention may be delivered orally, in granular form including sprayed dried particles, or complexed to form micro or nanoparticles. Oligonucleotide complexing agents and their uses are further described in U.S. Pat. No. 6,287,860.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Certain embodiments of the present invention provide pharmaceutical compositions containing one or more oligomeric compounds and one or more other chemotherapeutic agents. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bis—CH loroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Combinations of antisense or sense compounds and other non-antisense drugs are also within the scope of this invention. Two or more combined compounds may be used together or sequentially.

In another related embodiment, compositions of the invention may contain one or more antisense or sense compounds, or one or more interactive molecules such as antibodies targeted to a first nucleic acid target or protein and one or more additional compounds targeted to a second nucleic acid target or protein. Alternatively, compositions of the subject invention may contain two or more antisense or sense compounds or tow or more interactive compounds targeted to different regions of the same nucleic acid target or protein.

The formulation of therapeutic compositions and their subsequent administration (dosing) is within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual compounds, and can generally be estimated based on $EC_{50}s$ found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the compound is administered in maintenance doses, ranging from 0.01 µg to 100 g per kg of body weight, once or more daily, to once every 20 years. Examples of effective amounts include 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and 100 g/kg body weight.

The present invention is further described by the following non-limiting Examples.

EXAMPLE 1

Cell Line

The MDA-MB 231 human breast cancer cell line was obtained from American tissue culture collection (Rockville, USA) and cultivated at 37° C. in 100% (v/v) air, and maintained in Leibovitz L-15 Medium (Sigma, St Louis, Mo., USA), supplemented with 10% foetal calf serum (CSL, Melbourne, Australia) and antibiotic/antimycotic reagents (Sigma, St Louis, Mo., USA).

EXAMPLE 2

Isolation of the cDNA for Human HAS2 and Construction of an Antisense Expression Vector The cDNA for human HAS2 was generated by designing gene specific primers from the published sequence of Watanabe and Yamaguchi (1996; Genbank accession no. U54804) and consisted of the following primers: sense 5'>GAGCTGAACAAGATGCATTGTGAGAGC (SEQ ID NO: 1) and antisense 5'GACATGGTGCTT-GATGTAT-GATCTTCCAT (SEQ ID NO: 2). Total RNA harvested from exponentially dividing human dermal fibroblasts was used as the template for RT-PCR to generate a 1.7 kb cDNA fragment of HAS2, which was cloned directly into pGEM®-T vector (Promega Corporation, Madisom, USA). The cDNA for HAS2 was subsequently subcloned into the pCI-Neo expression vector (Promega Corporation, Madisom, USA) and isolated clones containing the insert in the antisense orientation were identified by restriction endonuclease mapping and automated sequencing.

EXAMPLE 3

Transfection of Human ASHAS2 and Mock into MDA-MB 231 Human Breast Caner Cells

The ASHAS2-pCl-Neo construct and pCl-neo vector were transfected into human MDA-MB 231 breast cells using Lipofectamine™ plus reagent (Gibco life technologies, USA) according to the manufacture's instructions. Prior to commencing studies transfected cells were selected for at least one month in the presence of 500 pg/mL G418 antibiotic.

EXAMPLE 4

Detecting the Incorporation of the Stable Transfection into the Genome

PCR on purified genomic DNA isolated from ASHAS2-pCINeo transfectants was performed to confirm the incorporation of the antisense construct into the genome. In brief, a gene specific primer for pCINeo: 5'-GCACAGATGCG-TAAGGAG-3' (SEQ ID NO:3) was used in combination with two specific HAS2 primers of the following sequence: GSP2 sense 5'-GCTGTGTACATGACCTCGCGCTTGCCGCC-3' (SEQ ID NO:4) and GSP4 sense, 5'-GGCGGGAAG-TAAACTCGAC-3' (SEQ ID NO:5). When used in the following combination; pCIneo/GSP2 and pClneo/GSP4 expected size products of 1443 and 2223 bp were amplified respectively.

EXAMPLE 5

Quantification of mRNA for HAS1, 2 and 3

Real time PCR was used to quantitate the relative mRNA levels of HAS1, HAS2, and HAS3 in parental, mock and ASHAS2 transfected cells using gene specific primers and an internal oligonucleotide probe. In brief, total RNA was purified from experimental cells using Rneasy® (Qaigen, Melbourne, Australia) which was then used to generate single stranded cDNA by incubating 2 µg RNA with 0.5 µg/uL random primers and superscript reverse tranlcriptase. For quantitative real time PCR gene specific primers for each HAS isoform and an internal oligonucleotide probe were used. In brief, the primers consisted of the following: HASI, sense, 5'CCTGCATCAGCGGTCCTCTA 3' (SEQ ID NO: 6); HAS1 antisense, 5'GCCGGTCA-TCCCCAAAAG 3' (SEQ ID NO: 7); HAS1 probe, 5' AACCTCTTGCAGCAGTTTCT-TGAGGCC 3' (SEQ ID NO: 8); HAS2 sense, 5' CAGTC-CTGGCTTCGAGCAG 3' (SEQ ID NO: 9); HAS2 antisense, 5' TTGGGAGAAAAGTCTTTGGCT 3' (SEQ ID NO: 10); HAS2 probe, 5' CCATTGAACCAG-AGACTTGAAA-CAGCCC 3' (SEQ ID NO: 11); HAS3 sense, 5' TTGCACT-GTGGTCGTCAACTT 3' (SEQ ID NO: 12); HAS3 antisense, 5' GTCGAGGTCAAACGTTGTGAG 3' (SEQ ID NO: 13); HAS3 probe, 5' TCAAATCAAAAACAGGCAGGTA-CAGGTAGTGG 3' (SEQ ID NO: 14); GAPDH sense, 5'AAGGTGAAGGTCGGAGTCAAC 3' (SEQ ID NO: 15); GAPDH antisense, 5' GAGTTAAAA-GCAGCCCTGGTG 3' (SEQ ID NO: 16); GAPDH probe, 5' TTTGGTCGTAT-TGGGCGCCTGG3' (SEQ ID NO: 17). For HAS internal probes the reporter dye 6-carboxylfluorescein (6-FAM™) and quencher 6-carboxytetramethyl rhodamine (TAMRA™) were labelled at the 5' and 3' respectively. For GAPDH internal probes the reporter 6-FAM™ was substituted with VIC™ (Applied Biosystems California, USA). The PCR reaction was performed in a final volume of 30 pL and consisted of 1× Taqman reaction mix, 6 µM of HAS forward and reverse primer, 1.5 pM of probe, 1 pM of each GAPDH primer and 500 nM of GAPDH probe. PCR amplification was by denaturation for 10 minutes at 95° C. followed by annealing for 2 minutes at 50° C. followed by 40 cycles of 15 seconds at 95° C. and 1 minute at 60° C. Thermocycling and fluorescence measurement were performed in a ABI Prism 7700® sequence detection system (Applied Biosystems, California, USA). To allow comparison between samples the relative hyaluronan synthase signals were normalised with internal GAPDH control measurements.

EXAMPLE 6

Characterization of Hyaluronidase Gene Expression

To determine the state of hyaluronidase gene expression for HYAL1,2 and 3, RT-PCR was performed on total RNA extracted from experimental cells harvested at 80 and 100% confluency. The gene specific primer sets were designed from sequences retrieved from GenBank and consisted of;: HYAL1 (GenBank accession no. NM007312) sense, 5'-GCACAGGGAAGTCACAGATGTATGTGC-3' (SEQ ID NO:18); HYAL1 antisense, 5'-CCACTGGTCACGTTCAG-GATGAAG-3 (SEQ ID NO:19)'; HYAL2 (GenBank accession no. NM003773) sense 5'-GATGTGTATCGCC-GGT-TATCACGCC-3' (SEQ ID NO:20); HYAL2 antisense 5'-CGTAGACTGGGAG-TGCATGGTTGGC-3' (SEQ ID NO:21); HYAL3 (GenBank accession no. NM003549) sense, 5'-GCACTGATGGAGGATACGCTGCG-3' (SEQ ID NO:22); HYAL3 antisense, 5'-GCTGGTGACTG-CAGGC-CATCGCTGC-3' (SEQ ID NO:23). Amplified sequences were visualised by agarose gel electrophoresis containing ethidium bromide and identity confirmed by automated DNA sequencing.

EXAMPLE 7

Cell Proliferation Assay

Parental, mock and ASHAS2 transfectants were harvested at approximately 80% confluency and seeded in to 24-well plates at differing cell densities, ranging from $5 \times 10^3$ cells to $9 \times 10^4$ cells/well. The rate of cell growth was then followed for 24, 48, 72, and 96 hours after plating. All cell counts were determined using an automated Coulter counter.

EXAMPLE 8

Immunohistochemistry

To allow immunodetection and comparison between parental, mock and ASHAS2-pCNeo transfected MDA-MB-231 cells specific antibodies to HAS2 and Hyal2 were kindly gifted from Dr Paraskevi Heldin and Dr Robert Stern respectively. Anti-human CD44 Clone DF1485 was purchased from DAKO (Denmark) and used according to manufacturers instructions. Cells were seeded into 8-well chamber slides at a density of $2 \times 10^4$ cells/well and grown for a further 24 hours at 37° C. The cells were fixed in Histochoice® for 15 minutes before blocking heterophile proteins by incubation in PBS containing 10% FCS. The primary antibodies were diluted to (cite concentration NOT dilution) in antibody diluent (PBS containing 1% human serum and 1% FCS) then incubated on slides for 60 min at room temperature. Endogenous peroxidase activity was blocked by immersion of slides in 0.3% $H_2O_2$ in methanol for 20 min prior to incubation with a peroxidase-conjugated rabbit anti-sheep secondary antiserum for 60 min at RT. The immunocomplexes were visualised by applying 3,3'-Diaminobenzidene substrate (Sigma Fast DAB) for 5-10 minutes, then counterstained with haematoxylin, dehydrated and mounted.

EXAMPLE 9

Cell Cycle Analysis by Flow Cytometry

The transfected and control cells were seeded at $2 \times 10^5$ cells/25 cm² flask in the presence of 2 mM thymidine and grown until 50% confluent. Cells were washed then returned to normal culture medium and harvested, by trypsinisation, at the following time points; Oh, 4 h, 8 h, 12 h, 16 h, 20 h, 24 h, 28 h, 32 h, and 36 h then fixed in 95% ethanol for 2 h at 4° C. Cells were pretreated with 100 µg/mL RNAase (Sigma) and 50 µg/ml propidium iodide (, Sigma) for 30 minutes at 37° C. before determining the cell cycle stage in a FACS-Calibur™ analytical instrument (Becton Dickinson, San Jose, Calif.).

EXAMPLE 10

Migration Assay

The Boyden chamber chemoinvasion assay was performed as described previously (Thompson et al., 1992). Matrigel® (50 µg) was dried onto polycarbonate filters (12 µm pore, PVP free, Nucleopore, Pleasanton, Calif.) and then reconstituted at 37° C. Normal growth media (L-15 medium) containing 0.1% bovine serum albumin (Miles Biochemicals, Kankakee, Ill.) was used as the chemoattractant. Cells were harvested in the logarithmic growth phaseby trypsinisation, washed twice with serum-free L-15 medium containing 0.1% bovine serum albumin then seeded at 300,000 cells/1 ml chamber and 70,000 cells/0.2 ml chamber. Each experiment was performed in triplicate. Chambers were incubated in a humidified incubator at 37° C. for 6 hours. To determine the population of cells which had traversed the Matrigel®, the filters were stained with Diff-Quik® (American Scientific Products, McGaw PK., Ill.) then counted.

EXAMPLE 11

Particle Exclusion Assay and Cell Morphology

The HA-dependent pericellular matrix was visualised around breast cancer cells from control and transfected cultures by the exclusion of fixed human erythrocytes described by Clarris & Fraser (1968). Morphological differences as well as the particle exclusion assay in the control and transfected MDA-MB 231 cells were photographed on a Nikon Optiflot inverted phase contrast microscope (Nikon Company, Japan) 24 h and 60 h after plating.

EXAMPLE 12

Effect of the HA Production

Cells were seeded at $2.5 \times 10^5$/cells in 25 cm² culture flasks and incubated at 37° C. for 24 h, 48 h, 72 h, 96 h, 120 h and 144 h. At each time points cells were trypsinized and counted using an automated coulter counter. HA concentration in the harvested culture medium was determined using a hyaluronic acid binding protein (HABP) assay, with the standards and reaction buffer provided Corgenix Inc (Colorado, USA).

EXAMPLE 13

Size Exclusion Chromatography to Determine MW of HA Synthesized

Cells were seeded at $7.5 \times 10^5$ cells in 75 cm² culture flasks and grown for 24 h in complete medium supplemented with 5 µCi of D[6-³H]-Glucosamine hydrochloride. a. To determine the MW of ³H-HA in the medium, samples were subjected to size exclusion chromatography on a Sephacryl S-1000 SF. In brief, gel column (1.6 m×90 m) were packed according to manufactures instructions, equilibrated and eluted with phosphate buffer containing 0.2% (v/v) TX-100. The molecular weight of HA in the culture medium was calculated using linear regression of $K_{av}$ versus HA of known molecular weights ranging from $>1.67 \times 10^7$, $K_{av}$=0 to $4.4 \times 10^3$, $K_{av}$=1. Fraction range of column S-1000 $7 \times 10^4$-$1.7 \times 10^7$ Da.

EXAMPLE 14

Mammary Fat Pad Inoculation of MDA-MB 231 Cells

Parental, mock and ASHAS2 transfected cells were harvested in the logarithmic growth phase by scraping. Cells were resuspended to a final density of $2 \times 10^6$ cells in L-15 medium supplemented with 0.1% glucose +/− Matrigel® (v/v WHAT IS THE PERCENTAGE?) then immediately injected into the mammary fat pad of 5 weeks old female CBA nude mice (n=11 does each treatment group consist of 11). Tumor growth was recorded twice weekly by measuring three perpendicular diameters (d1, d2, d3). Tumor volume was then calculated using the formula: (⅙)π(d1d2d3). On the day 84 mice were humanely killed and liver, kidneys, brain and lungs removed at autopsy and stored at −20° C. For histological examination half of the primary tumor was fixed in 4% formaldehyde and embedded in paraffin, then 5 µm sections from this tissue was examined by H&E staining. The remaining portion of the tumor was frozen at −20° C. until further analysis.

EXAMPLE 15

DNA Extraction from Soft Organs and Quantification of Metastasis of MDA-MD 231

Quantitative Alu PCR was used to detect metastasis of MDA-MD 231 from the primary tumor to other organs collected at autopsy. In brief, DNA was extracted by griding samples under liquid nitrogen and resuspending in a DNA lysis buffer. DNA was then purified using standard phenol-chloroform methodology followed by ethanol precipitation and reconstition in TE buffer. The purified DNA was adjusted to a final concentration of 10 ng/pL in TE buffer pH7.2, aliquoted and stored at −20° C. until analysis. To remove exogenous human DNA contamination the reaction mix was treated with 17 U/ml nuclease S7 (Roche) in the presence of 1 mM $CaCl_2$ at 37° C. for 24 hours prior to PCR. Quantitative Alu PCR was then performed on purified gemomic DNA samples (10 ng) in a GeneAmp 5700® Sequence Detection System (Applied Biosystems, Australia). In brief, each sample was tested in duplicate in a final reaction volume of 25 μL consisting of 0.625 U Taq DNA polymerase (Roche; Mannheim, Germany), 10 mM Tris-HCl pH 8.3, 1.5 mM $MgCl_2$, 50 mM KCl, 200 μM dNTPs, 8% DMSO, 1 pg/ml 6-carboxy-X-rhodamine (Molecular Probes; Eugene, Oregon USA), 1 in 40000 dilution of SYBR Green I (Molecular Probes) and 100 nM of each Alu primer. Following an initial denaturation incubation at 95° C. for 2 minutes, amplification occurred over 40 cycles, which consisted of denaturation at 95° C. for 5 seconds, annealing at 65° C. for 60 seconds, and extension at 75° C. for 15 seconds during which the intensity of fluorescence was measured. A dissociation curve was then generated from 60° C. to 95° C. On each 96-well reaction plate, a standard curve was prepared by serially diluting human DNA into mouse DNA which permitted the quantification of the tissue burden of human tumor cells in the mouse organs removed at autopsy.

EXAMPLE 16

Transfection of Antisense HAS2 in MDA-MB 231 Transfected Cells

Incorporation of the antisense HAS2-pCINeo construct into the genome of MDA-MB 231 was confirmed by PCR analysis on highly purified DNA extracted from the transfected cells. When used in the following combination; pCIneo/GSP2 and pCIneo/GSP4 expected size products of 1443 and 2223 bp were reproducibly amplified from stable clones harbouring the antisense HAS2 construct. Genomic DNA isolated from parental and mock transfected tested negative.

EXAMPLE 17

Transfection with Antisense HAS2 Alters Expression Profiles of HAS and Hyaluronidase Genes in MDA-MB 231

Endogenous levels of mRNA for HAS2 in parental cells were quantitated using real time PCR and compared with the values obtained from mock and antisense HAS2 transfected cells. Concomitant to these experiments, HAS1 and HAS3 mRNA levels were also quantitated using real time PCR with HYAL1, 2 and 3 expression characterised by standard RT-PCR methodology. To allow comparison of real time HAS expression between transfected and parental cells the level of each mRNA quantitated was normalised with respective internal GAPDH controls. The endogenous level of HAS2 mRNA expression in parental cells is shown in FIG. 1a, which was slightly decreased in the mock transfectants. In contrast, mRNA expression in ASHAS2 transfected cells was increased 3- to 4-fold and 8- to 9-fold when compared with parental and mock transfectants cells respectively (FIG. 1a). Moderate HAS3 expression was also detected and was comparable in parental mock and antisense transfected cells FIG. 1b. Consistant throughout this study was the expression of HAS1 in antisense transfectants which could not be detected in both parental cells and mock transfectants (FIG. 1b).

Both parental and mock transfected control cultures stained positive for the HA receptor CD44 and Hyal-2. The staining for CD44 in both controls was most evident in the plasma membrane with areas of intense focal membrane staining (FIG. 1 panel E). No CD44 epitope reactivity could be detected in ASHAS2 transfectants (FIG. 1 panel F). Similar observation were recorded for the reactivity with Hyal-2 antibody where control cultures stained positively, which localised to the plasma membrane and also appeared as cytoplasmic vesicles whereas no reactivity could be detected in ASHAS2 transfectants. These results indicate that perturbation of functional CD44 and Hyal2, as observed in ASHAS2 transfectants, alter the catabolism of HA culminating in a significant increase in the amount HA in the culture medium.

EXAMPLE 18

Characteristics of MDA MB 231 Breast Cancer Cell in a Tumor Xenograft Model

Figure 2:
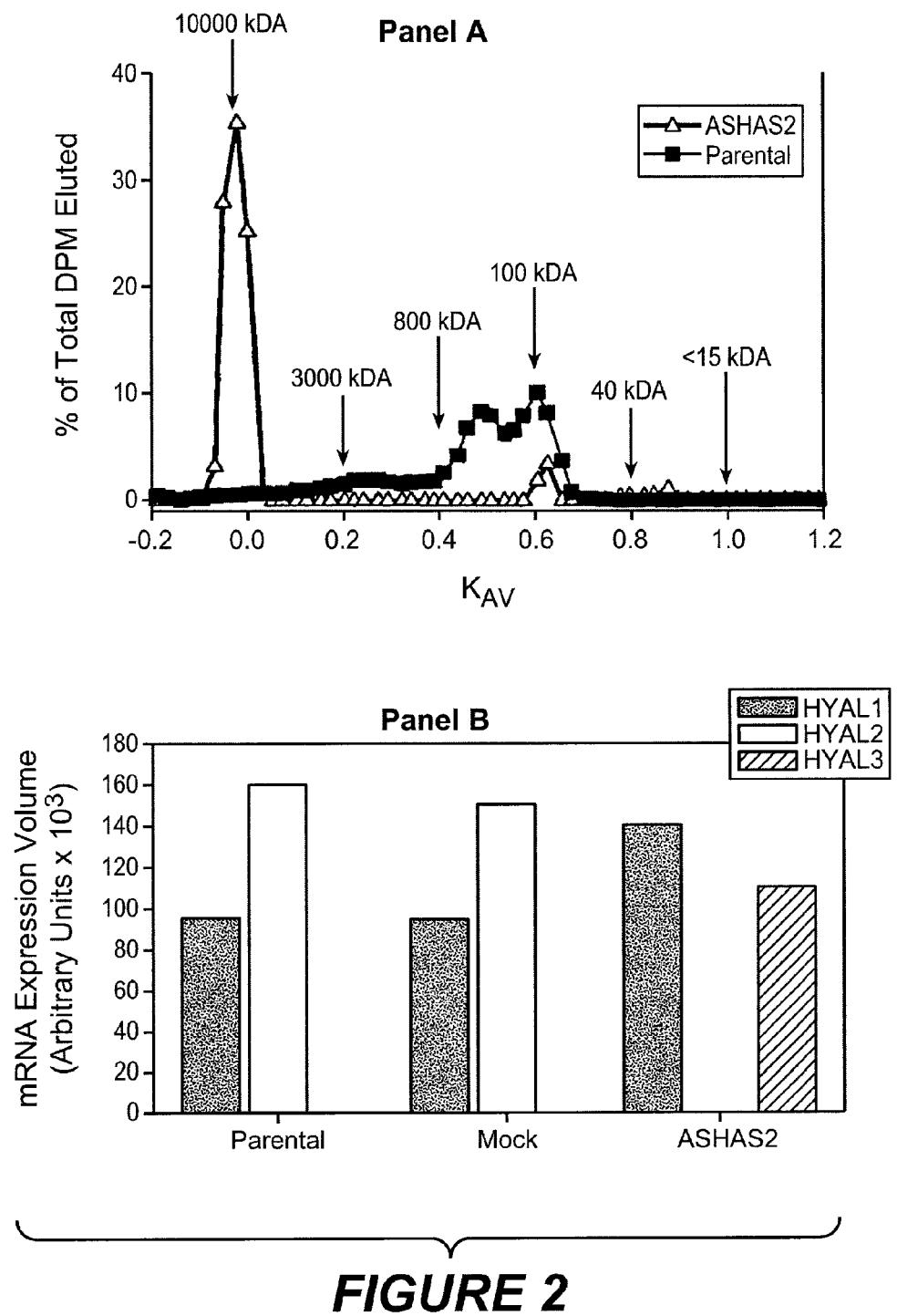
FIG. 2 is a graphical representation of the characterization of the molecular weigh of HA synthesised and differential expression of the hyaluronidase genes by parental, mock and HAS2 antisense transfected MDA-MB 231. A: Cells were seeded at $7.5 \times 10^5$ cells in 75 cm$^2$ culture flasks and grown for 24 h in complete medium supplemented with 5 µCi of D-[6-$^3$H]-glucosamine hydrochloride. To determine the MW of $^3$H-HA in the medium, samples were subjected to size exclusion chromatography on a Sephacryl® S-1000 SF eluted in 0.15 M NaCl/phosphate pH 7.25 at 13.6 ml/h. This figure demonstrates the differences in molecular weight synthesized by parental MDA-MD 231 and their transfected counterparts harbouring antisense mRNA to HAS2. B: Total RNA extracted from parental, mock and ASHAS2 transfected MDA-MD 231 was analysed by RT-PCR to detect the levels of the hyaluronidase genes, notable HYAL-1, 2 and 3. PCR products were resolved by agarose gel electrophoresis containing ethidium bromide. Stained gels were then subjected to densitometric analysis to allow comparison of levels for each HYAL gene between parental, mock and ASHAS2 transfected cells. Note, both parental and mock-transfected MDA-MD 231 cells express comparable levels of both HYAL-1 and 2 but do not express HYAL-2. In contrast ASHAS2 transfected cells, HYAL-2 is not expressed whereas HYAL-3 was detected and HYAL-1 was moderately increased in expression.

Interestingly, antisense inhibition of HAS2 profoundly altered the expression of Hyal-1, 2 and 3 in MDA-MD 231. Hyal-3 could not be detected in both parental or mock transfectants, which both expressed comparable levels of mRNA for Hyal-1 and to a much greater extent Hyal-2, which was also comparable between these two controls (FIG. 2).

In contrast, inhibition of HAS2 expression resulted in the down regulation of Hyal-2 mRNA to the point where it was not detectable even after 35 cycles of PCR. Hyal-1 expression in antisense transfectants was moderately increased when compared with both parental and mock controls and Hyal-3 was also detected in the antisense transfectants. Thus by preventing the production of a functional HAS2 protein in the MDA-MD 231 cell line, Hyal-2 gene expression has been down regulated concomitant to the upregulation of HAS1 and Hya13, genes that are not normally expressed in this cell line.

Immunohistochemistry with a specific HAS2 antibody was used to determine the extent of cell surface reactivity. Whereas both parental and mock transfected cells stained positively for HAS2 protein (FIG. 1, panel B), which localised mostly to the plasma membrane, efficient blockage of translation in the antisense HAS2 transfectants was evidenced by the lack of immunoreactivity with the HAS2 antibody (FIG. 1 panel C).

The molecular mass of HA synthesised by parental, mock and antisense transfected cells was determined by Sephacyl® S-1000 size exclusion chromatography. The parental cell line synthesised three distinct molecular weights of HA estimated to be 3000 kDa, 40,000 and 100,000 Da respectively which reflects the products of the HAS isoforms expressed in the parental cell line, notably HAS2 and 3. Antisense HAS2 transfectants synthesised HA which was eluted in the void volume that corresponds to a molecular weight $>1.67 \times 10^7$. Another fraction corresponding to a Mw of 100,000 Da was also detected in the medium from antisense transfectants but the percentage of radioactive precursor incorporation was much less than that observed in the parental cell line (FIG. 2). These elution profiles were shown to be 100% susceptible to digestion with *Streptomyces* hyaluronidase.

Figure 3:
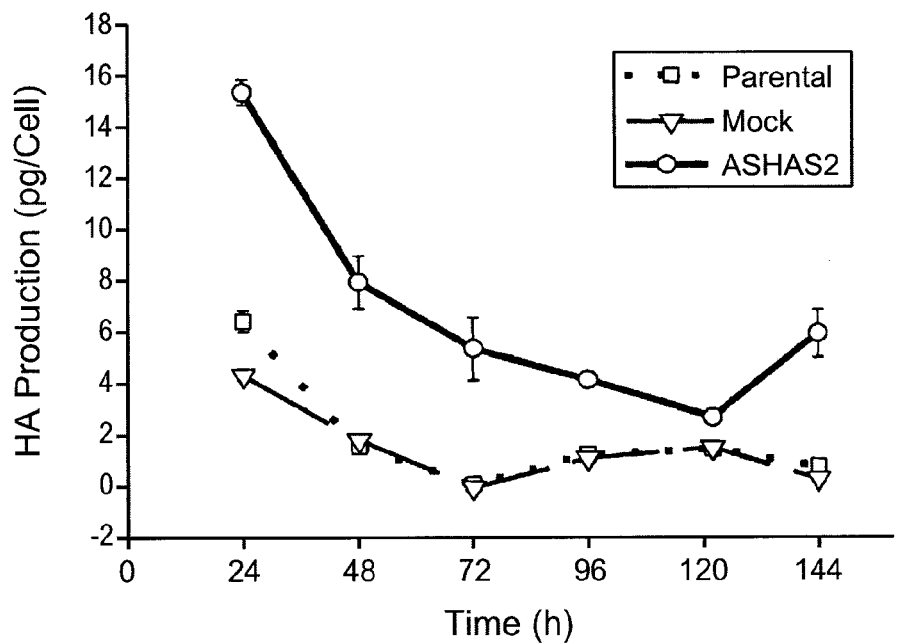
FIG. 3 is a graphical representation of the quantification and comparison HAS in parental, mock and ASHAS2 transfected MDA-MB 231. Cells were seeded at $2.5 \times 10^5$/cells in 25 cm$^2$ culture flasks and incubated at 37° C. for 24 h, 48 h, 72 h, 96 h, 120 h and 144 h At each time points cells were trypsinized and counted using an automated coulter counter. HA concentration in the harvested culture medium was determined using a hyaluronic acid binding protein (HABP) assay, with the standards and reaction buffer provided Corgenix Inc (Colorado, USA). HA synthesis by parental and mock transfected MDA-MB 231 was comparable over the duration of the experiment. In contrast, HA synthesis was significantly increased in ASHAS2 transfectants, where approximately 2- to 7-fold more HA was liberated into the culture medium.

Antisense inhibition of HAS2 results in altered hyaluronan metabolism. Due to the altered HAS and HYAL gene expression in ASHAS2 MDA-MB 231 transfectants the amount of hyaluronan in cell contact culture medium was quantitated using an enzyme linked protein assay specific for HA. HA production was quantitated from samples collected in triplicate at the same time points established in the proliferation assay. The data collected was graphed as HA synthesised (picogram per cell: pg/cell/day). Cell contact medium from antisense HAS2-MDA-MB 231 transfectants contained a significantly greater amount of hyaluronan when compared with either parental cells of mock transfectants (FIG. 3). On average ASHAS2 cultures synthesised 6.79 pg of HA/cell/day over the duration of the experiment with one noticeable exception at 48 hours where synthesis was increased to 12 pg/cell/day. In contrast parental and mock transfectants synthesised approximately 1.1 and 1.4 pgHA/cell/day respectively over the duration of the experiment. The exclusion of fixed erythrocytes was used to indirectly visualise the HA pericellular matrix in the ASHAS2 transfectants which was then compared with that observed in the parental or mock transfectants. In these experiments there was no evidence to suggest any gross difference in the thickness of the pericellular matrix, which was comparable to that observed in control cultures (FIG. 3b).

Throughout the experiments the morphology of the antisense transfected cells were compared with control cells. The ASHAS2 transfectants were readily distinguishable by their morphology which was akin to cells undergoing mitosis and/or migration, that is, small rounded cells that were loosely adhered to the growth surface. Consistent throughout these observations was the decrease in cell number in ASHAS2 transfectants when compared with control cultures.

EXAMPLE 19

Figure 4:
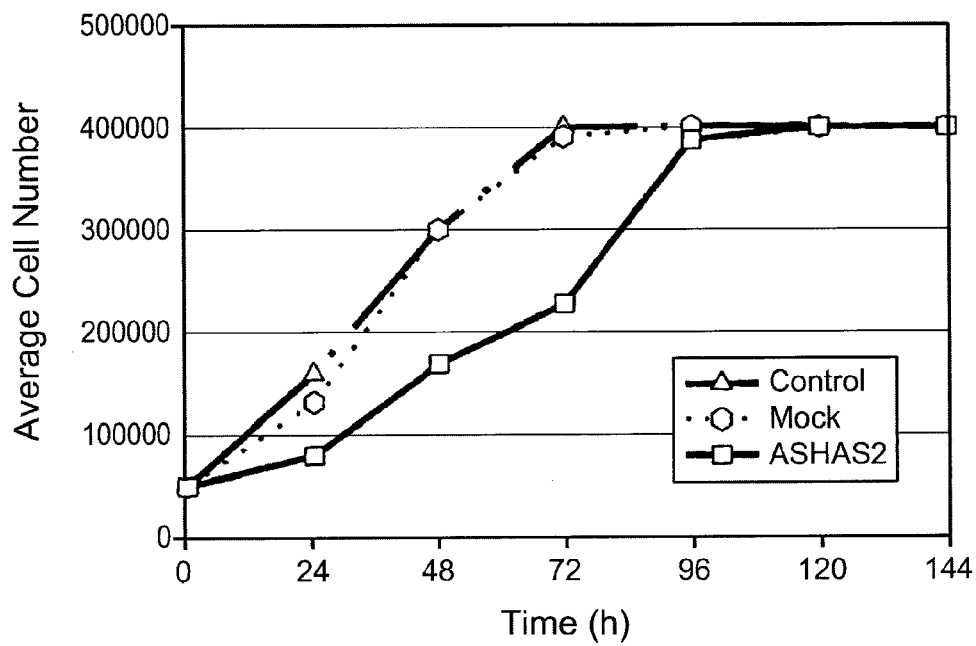
FIG. 4 is a graphical representation showing characterisation of cell proliferation in parental, mock and ASHAS2 transfected MDA MB 231. Parental, mock and ASHAS2 transfectants were harvested at approximately 80% confluency and seeded in to 24-well plates at a cell-density of $5 \times 10^3$ cells/well. The rate of cell growth was then followed for 24, 48, 72, and 96hours after plating. All cell counts were determined using an automated Coulter counter. Whereas both parental and mock transfected MDA-MB 231 displayed expontential cell growth until 72 hours where cells became confluent, the ASHAS2 transfected cells grew at a much slower rate with an approximate 'lag' period in cell doubling of 24 hours.

HAS2 Inhibition Decreases Breast Cancer Cell Proliferation and Migration in vitro To compare the effect of antisense inhibition of HAS2 during active cell growth, parental, mock and ASHAS2 transfected cells were seeded at identical sub-confluent densities and at defined times were harvested and the total cell count estimated using a Coulter counter. In both control cultures a doubling of cell number every 24 hours was observed until the 72 hour sample point where cultures reached confluency (FIG. 4). In contrast stable transfectants harbouring ASHAS2 cell growth was profoundly affected by the lack of a functional HAS2 protein. Specifically, ASHAS2 transfectants displayed a lag period of approximately 24 hours to reach similar densities to that observed in control cultures at all subsequent time points where cell number was enumerated (FIG. 4). Confluency in ASHAS2 cultures occurred at approximately 96- to 120 hours of cell growth after seeding compared with 72 hours in both control cultures. These observations therefore highlight the importance of the co-ordinated expression of a functional HAS2 in cell proliferation.

Figure 5:
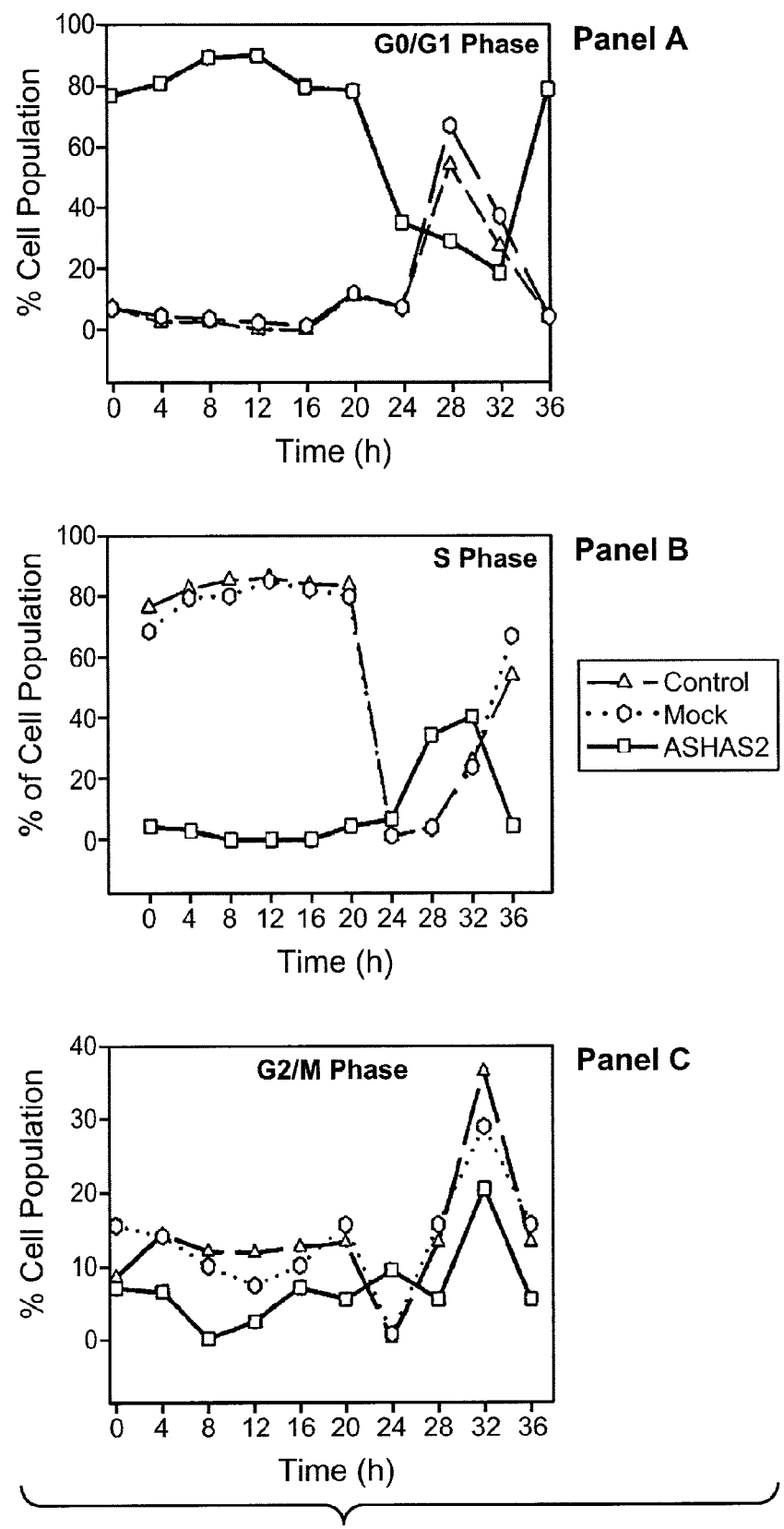
FIG. 5 is a graphical representation of the effect of antisense inhibition of HAS2 on cell cycle. The transfected and control cells were seeded at $2 \times 10^5$ cells/25 cm$^2$ flask in the presence of 2 mM thymidine and grown until 50% confluent. Cells were washed then returned to normal culture medium and harvested, by trypsinisation, at the following time points; 0 h, 4 h, 8 h, 12 h, 16 h, 20 h, 24 h, 28 h, 32 h, and 36 h then fixed in 95% w/v ethanol for 2 h at 4° C. Cells were pretreated with 100 µg/mL RNAase (Sigma) and 50 µg/ml propidium iodide (Sigma) for 30 minutes at 37° C. before determining the cell cycle stage in a FACS-Calibur™ analytical instrument (Becton Dickinson, San Jose, Calif.). Panel A: population of cells in $G_0/G1$; Panel B: in S phase, and PANEL C: in G2/M phase. Note the delay of 24 hours of entry into S PHASE in the ASHAS2 MDA MB 231 transfectants.

Concomitant to these observations flow cytometric analysis was also performed on parental, mock and ASHAS2 transfectants to determine relative DNA content at defined time points after plating at sub-confluent densities (FIG. 5). The percentage of the ASHAS2 transfected cells in the cell cycle phases $G_0/G_1$, S and $G_2/M$ 28 hours after plating were 80%, 0% and 9% respectively (FIG. 5). In contrast the corresponding figures in the parental cells for cell cycle phases $G_0/G_1$, S and $G_2/M$ were 4%, 75% and 15% respectively (FIG. 5). These results are consistent with the observation in the 'lag' period of 24 hours in the proliferation assay where antisense inhibition induced a transient delay of entry into S-phase by approximately 24 hours (FIG. 5) thereby reinforcing the importance of HAS2 expression during cellular proliferation in cultures of MBA-MD-231.

Figure 6:
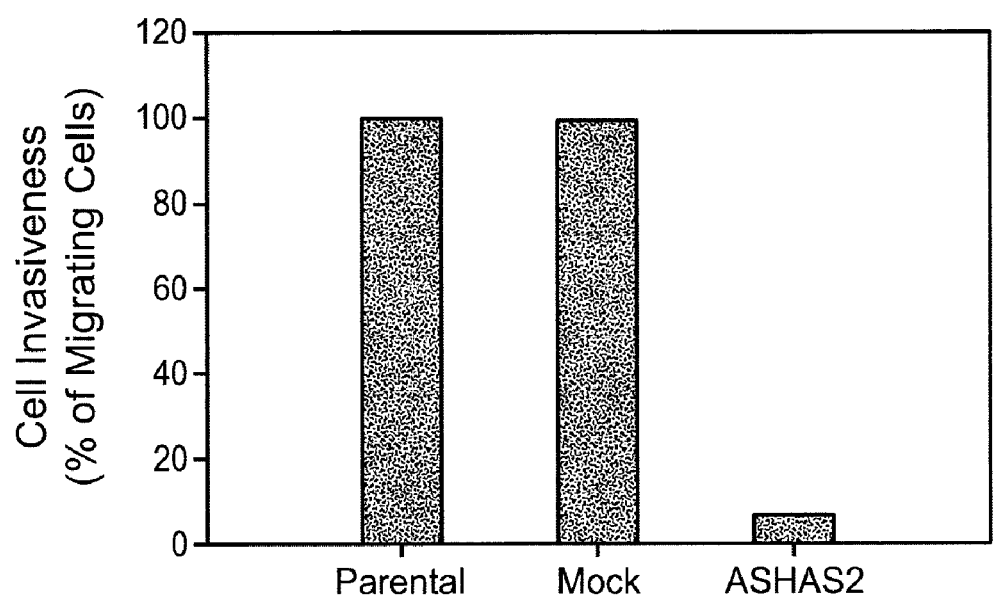
FIG. 6 is the graphical representation of the effect of HAS2 inhibition on the migratory behaviour of the highly metastatic MDA MD 231 cell line. The migration rate of parental, mock and antisense transfected cells, was examined using the Boyden chamber chemoinvasion assay as described in materials and methods. Whereas parental and mock transfectants displayed 100% migration, cells harbouring antisense to HAS2 were inhibited in migration by 93%.

The ability for cancer cells to migrate is a fundamental characteristic in highly metastatic cancer cells. To characterise the highly invasive characteristics of MDA MB-231 the chemoinvasion assay using the Boyden chamber was used. Migratory rates were then compared between parental, mock and ASHAS2 transfected MDA MB-231. Both parental and mock transfectants displayed typical migratory behaviour with 100% of cell population invading the matrigel onto the underlying filter (FIG. 6). In contrast, stable transfectants harbouring antisense HAS2 resulted in 93% inhibition of migration when compared with either controls tested (FIG. 6).

EXAMPLE 20

Figure 7:
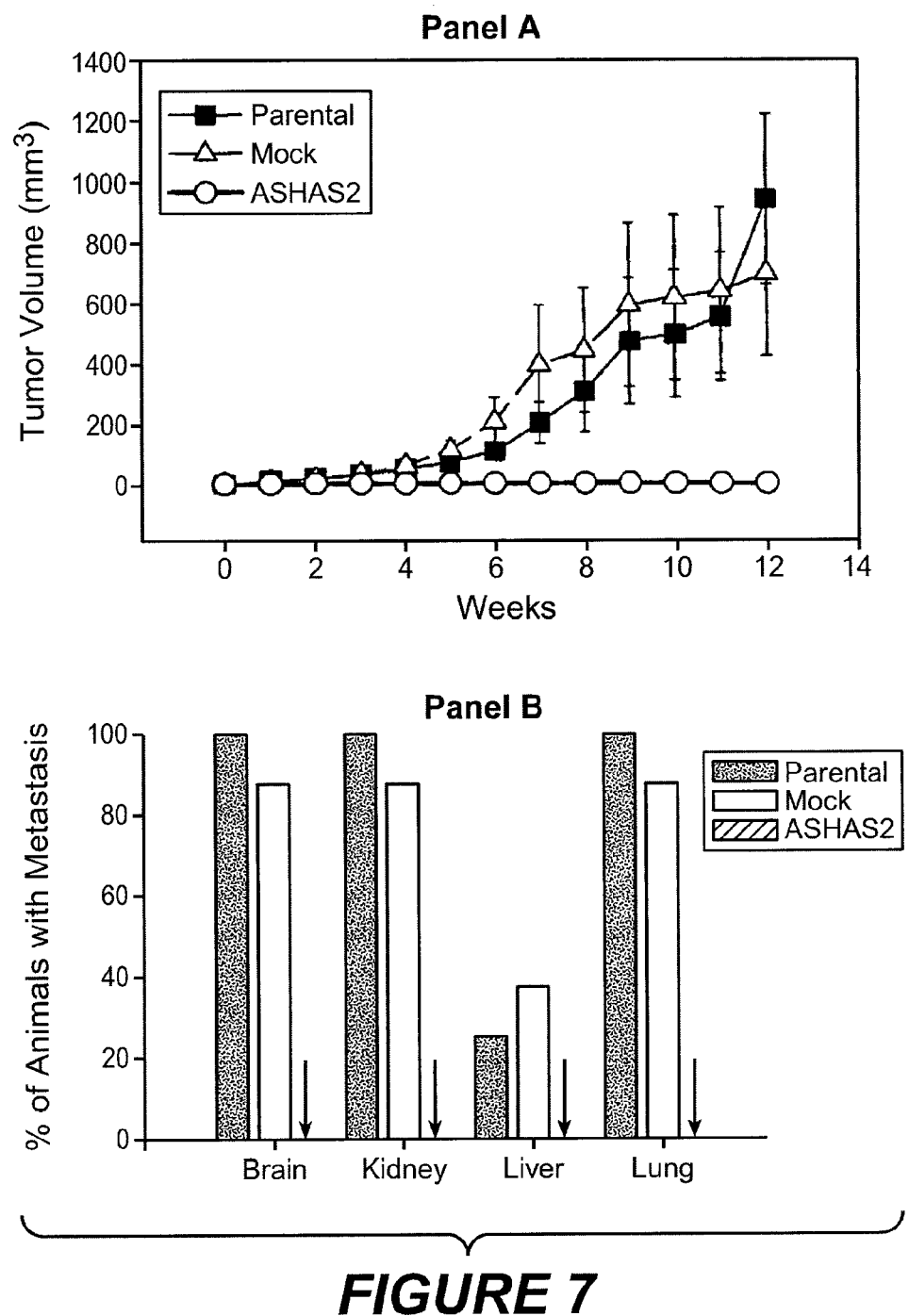
FIG. 7 is the graphical representation of the effect of antisense HAS2 inhibition on the tumorgenicity and metastasis of MDA MB 231. A: Parental, mock and ASHAS2 transfectants were inoculated into the mammary fat pad of nude mice. Primary tumor growth was followed over a 12 week period following implantation after which the extent of metastasis to other organs detected using Alu PCR. Mice inoculated with parental or mock transfected MDA MB 231 readily established primary tumors which were comparable in growth over the duration of the 12 week experiment. Mice inoculated with parental or mock transfected MDA MB 231 readily established primary tumors which were comparable in growth over the duration of the 12 week experiment. In contrast, however, mice inoculated with ASHAS2 transfectants did not establish primary tumors. B: Soft organ metastasis in mice inoculated with parental, mock and antisense transfected MDA MD 231. As assessed by Alu PCR, metastasis was most prevalent in brain, and lung but was also detected in kidneys and the liver in samples prepared from mice injected with either parental or mock transfectant MDA-MD 231 cells. No metastasis could be found in the aforementioned organs in mice that were injected with ASHAS2 transfectants.

HAS2 Inhibition Totally Inhibits the Growth and Progression of Primary and Secondary Breast Cancer To examine the effects of antisense inhibition of HAS2 on tumor growth, parental, mock and ASHAS2 transfectants inoculated into the mammary fat pad of nude mice. Primary tumor growth was followed over a 12 week period following implantation after which the extent of metastasis to other organs detected using Alu PCR. Mice inoculated with parental or mock transfected MDA MB 231 readily established primary tumors which were comparable in growth over the duration of the 12week experiment (FIG. 7). In contrast, however, mice inoculated with ASHAS2 transfectants did not establish primary tumors (FIG. 7). In other experiments Matrigel was also included in the inoculation medium used to ensure viability of injected ASHAS2 transfectants. Again, no primary tumor could be detected over the duration of the 12 week experiment (data not shown). As assessed by Alu PCR, metastasis was most prevalent in brain, and lung but was also detected in kidneys and the liver in samples prepared from mice injected with either parental or mock transfectant MDA-MD 231 cells (FIG. 7b). Despite the reported sensitivity of this assay, which is able to detect 1 human cell/$1 \times 10^6$ mouse cells, no metastasis could be found in the aforementioned organs in mice that were injected with ASHAS2 transfectants (FIG. 7) were determined to find any metastasis to soft organs, however, there were no detectable metastases with the HAS2 antisense and significantly high levels of metastasis were found in the brain and lung compared to the kidney and liver in the parental mice groups (FIG. 7b).

EXAMPLE 21

Over-Expression of HAS2, HYAL2 and CD44 Correlates with the Invasiveness of Breast Cancer Culture of Human Breast Cancer Cells Aneuploid human breast adenocarcinoma cell lines, MDA-MB-231, MDA-MB-435, MDA-MB-468, MDA-MB-453, MDA-MB-361, T47D, MCF-7A, BT-549, ZR-75-1 and Hs578T were obtained from the American Tissue Culture Collection, Rockville, USA. All cell culture propagation reagents were obtained from Sigma, St Louis, Mo., USA. Cell lines, MDA-MB-231, MDA-MB-435, MDA-MB-468, MDA-MB-453 and MDA-MB-361 were routinely grown and subcultured as a monolayer in 175 cm2 culture flasks in Leibovitz L-15 Medium supplemented with 10% fetal calf serum (FCS) at 37° C. in 100% (v/v) air. The ZR-75-1. cell line was grown in RPMI Medium supplemented with 10% FCS, 2 mM L-glutamine, 1.5 g/L sodium bicarb, 4.5 g/L glucose, 10 mM HEPES, 1 mM sodium pyruvate at 37° C. in humidity controlled incubator in 5% (v/v) $CO_2$. The T47D cell line was maintained in a humidified incubator at 37° C. in 5% $CO_2$ in RPMI supplemented with 10% FCS, 4.5 g/L of glucose, 10 mM HEPES, 1 mM sodium pyruvate, 7.1 µg/ml of insulin. BT-549 cell line was maintained in a humidified incubator at 37° C. in 5% $CO_2$ in RPMI supplemented with 10% FCS and 0.8 µg/ml of insulin. Hs578T cell line was cultivated in a humidified incubator at 37° C. in 5% $CO_2$ in DMEM supplemented with 10% FCS and 10 µg/ml of insulin. MCF-7 cell line was cultivated in a humidified incubator at 37° C. in 5% $CO_2$ in MEM supplemented with 10% FCS, 1 mM sodium pyruvate and 10 µg/ml of insulin. All cell cultures were routinely maintained in media containing antibiotic/antimycotic reagents.

Quantification of mRNA for HAS1, 2 and 3

Real time and comparative reverse transcriptase PCR were used respectively to quantitate the relative mRNA levels of the HA synthases (HAS1-3) in the ten human breast cancer cell lines by using gene specific primers and an internal oligonucleotide probe (Table 2). RNA was extracted from triplicate cultures of cells grown to both exponential and plateau phase using RNeasy® Mini Kits (QIAGEN, Basel, Switzerland). In brief, total RNA was purified from exponentially growing cells using TRI-reagent® (Sigma) which was used to generate single stranded cDNA by incubating 2 µg RNA with 0.5 µg/µl random primers and Superscript™ reverse trancriptase (Invitrogen, Carlsbad, Calif., USA). For quantitative real time PCR gene specific primers for each HAS isoform and an internal oligonucleotide probe were used. For HAS internal probes the reporter dye 6-carboxylfluorescein (6-FAM™) and quencher 6-carboxytetramethyl rhodamine (TAMRA™) was labelled at the 5' and 3'respectively. For GAPDH internal probes the reporter 6-FAM™ was substituted with VIC™ (Applied Biosystems, Foster City, Calif., USA). The PCR reaction was performed in a final volume of 30 µl and consisted of 1× Taqman reaction mix, 6 µM of HAS forward and reverse primer, 1.5 µM of probe, 1 µM of each GAPDH primer and 500 nM of GAPDH probe. PCR amplification was performed by denaturation for 10 min at 95° C. followed by annealing for 2 min at 50° C. followed by 40 cycles of 15 seconds at 95° C. and 1 min at 60° C. Thermocycling and fluorescence measurement were performed in an ABI Prism 7700® sequence detection system (Applied Biosystems). Relative quantitation was performed by normalizing threshold cycle (Ct) values of each sample gene with Ct values of the GAPDH. ΔCt corresponds to the difference between the Ct of the HAS genes of interest and the Ct of the GAPDH. Data are presented as fold-change difference relative to parental (arbitrarily set to 100) calculated according to the formula describing relative PCR quantitation $2^{-(\Delta CtHAS-\Delta CtGAPDH)}$.

Characterisation of Hyaluronidase Gene Expression

To determine the hyaluronidase gene expression for HYAL-1, 2 and 3, RT-PCR was performed on total RNA extracted from cells in both the exponential and growth arrested phases. The gene specific primer sets were designed from sequences retrieved from GenBank® (refer Table 2). Amplified sequences were visualised by agarose gel electrophoresis containing ethidium bromide and their identity confirmed by automated DNA sequencing. To quantitate the relative abundance of each PCR product, ethidium bromide stained agarose gels containing amplified fragments were subjected to densitometric analysis using ProXpress™ Imager (Perkin Elmer, Boston, Mass., USA) and the data analysed using Phoretix™ 1 D software (Phoretic International, Newcastle, UK).

Quantitation of the Synthesis and Catabolism of Liberated and Cell-Associated Hyaluronan Triplicate cultures of the human breast cancer cell lines were seeded at $7.5 \times 10^5$ cells/75 $cm^2$ culture flask and were grown with 400 µg/ml of dextran sulphate (500 kDa $M_r$ and 17% sulphur-substituted; Pharmacia Fine Chemicals, Uppsala, Sweden) as a means of inhibiting endogenous hyaluronidase activity and enabling the characterisation of hyaluronidase digestion products (Udabage et al, 2004). Cultures were grown for 24 h during which time cell cultures reached 85% confluence and then for a further 24 h until growth arrest was observed. At the conclusion of the incubation period, cells were harvested by trypsinization and counted using a Coulter counter. Media was used for quantitation of the liberated HA. Cell-associated extracellular HA was obtained by centrifugation of the celUtrypsin fraction at 400 $g_{av}$ in a Beckman TJ-6 centrifuge where the supernatant was quantitated for HA. Intracellular HA concentration was determined by treating the cell pellet as follows: the cell pellet was lysed under hypotonic conditions by resuspending in 10 mM HEPES pH 7.2 followed by disruption in a Dounce homogeniser using 20 strokes every 15 min. Cell lysis was confirmed by Giemsa stain and examination by light microscopy. To dissociate the HA from binding proteins, the cell lysate was heated to 37° C. with 0.5% v/v Triton X-114 in 10 mM HEPES buffer pH 7.2 (Prehm, 1990). The HA/detergent micelles were centrifuged at 1500 $g_{av}$ for 5 min and the upper aqueous phase was analysed for HA. The individual analyses of the intra and extracellular HA fractions were not within the detection limits of the HA ELISA (>50 ng/ml), therefore the extracellular and intracellular fractions were pooled and characterised for HA concentrations.

Hyaluronan production was quantitated using an enzymelinked HA binding protein assay (Corgenix Inc, Colorado, USA). The assay was performed as directed by manufacturer's instructions. In brief, duplicate 100 µl of samples and the HA standards (0 ng/ml, 50 ng/ml, 100 ng/ml, 200 ng/ml, 500 ng/ml and 800 ng/ml) were aliquoted into a 96 well plate coated with HA binding protein (HABP), incubated for 60 minutes at room temperature (RT) followed by four washes with PBS. One hundred µl of HABP conjugated to horseradish peroxidase was added and incubated at for 30 minutes at RT. After further PBS washes the reaction was visualised with 100 µl of 3,3',5,5'-tetramethylbenzidine (TMB) after a 30 min, RT incubation. The reaction was sopped with 100 µl of 0.36N sulfuric acid and read at 450 nm (650 nm reference) in a BioRad 350 microplate reader. Growth media that had not been exposed to cells was used to determine the endogenous HA background, this figure was subtracted from all results.

Visualisation of the Hyaluronan Gylcocalyx

The HA-dependent pericellular matrix was visualised around the breast cancer cells by the addition of fixed human erythrocytes as described by Clarris & Fraser (1968). In brief, human erythrocytes were fixed overnight in 1.5% v/v formaldehyde in PBS at RT and were then washed exhaustively in PBS. In the last wash sodium azide was added to a final concentration of 0.1% v/v and the cells stored at 4° C. Breast cancer monolayers were washed twice in PBS, 37° C. and then incubated with 5 ml PBS to which 50 µl of fixed erythrocytes (~$10^8$ cells/ml) was added. The particles were allowed to settle for 15-30 min after which the HA-dependent pericellular matrix was recorded by photography on a Nikon Optiflot inverted phase contrast microscope. The specificity of this method was demonstrated by incubation of the breast cancer cultures with Streptomyces hyaluronidse, where cells were covered with 10 units/ml of hyaluronidase followed by incubation at 37° C. for 15-30 min. Monolayers were washed twice in PBS, 37° C. and covered with a 5 ml suspension of fixed erythrocytes as previously described. The particles were allowed to settle for 15-30 min, observed and photographed as described above.

Characterisation of the Molecular Weight of Hyaluronan Produced by Human Breast Cancer Cells Cells were seeded at $7.5 \times 10^5$ cells/75 $cm^2$ culture flask and were grown for 24 h in growth media containing 400 µg/ml DS and 250 pCi D-[6-$^3$H] glucosamine hydrochloride (Perkin Elmer, Boston, Mass., USA). At the conclusion of the 24 h incubation period, the media was removed and exhaustively dialysed (Mr exclusion of 6 kDa) against 10 mM Tris-HCl/ 0.15 M sodium chloride/0.02% sodium azide pH 7.4 at 4° C. The dialysate and dialysis fluid were chromatographically analysed for the identification of [$^3$H] HA and its degradation products. [$^3$H]HA of >5 kD was subjected to size exclusion chromatography in a Sephacryl® S-1000 gel eluted in 0.15 M NaCl/phosphate pH 7.25 which contained 19 mM NaH$_2$PO$_4$, 38 mM Na$_2$HPO$_4$ and 94 mM NaCl at 13.6 ml/h. The dialysis fluid (molecules <5 kD) was subjected to size exclusion chromatography in a Superose® 12 gel eluted in the above-mentioned buffer at an elution rate of 20 ml/h. Molecular weight estimations were calculated using calibration data for HA in Sephacryl® S-1000 and Superose® 12 data generated from commercially purchased HA fractions of high monodispersity ranging from 10 k to 5000 kDa (CPN, Czech Republic and Pharmacia). To determine the percentage incorporation D-[6-$^3$H] glucosamine hydrochloride into Ha macromolecules, the non-dialysable (molecules >5 kDa) dpm was subjected to digestion by 10 TRU of *Streptomyces* hyaluronidase at pH 6, 37° C. for 24 h. Digested material was subjected to chromatography in both Sephacryl® S-1000 and Superose® 12 where profiles were compared to equivalent undigested sample. Any [$^3$H] material not digested by hyaluronidase was excluded from the chromatography profiles. For the calculation of column recoveries, counts in each fraction were taken as significant when >3 S.D. above the mean background dpm, with the background determined taking an equal number of sample points before and after $V_o$ and $V_t$, where the average number taken was 20.

Evaluation of Breast Cancer Cell Line Invasiveness: Boyden Chamber Migration Assay Invasion assays were performed using modified Boyden chambers with polycarbonate Nucleopore membrane (Corning, Corning, N.Y., USA). Pre-coated filters (6.5 mm in diameter, 12 μm pore-size, Matrigel 100 μg/cm$^2$) were rehydrated with 100 μl of Leibovitz L-15 media supplemented with 0.1% w/v BSA (Sigma). Exponentially growing cells were harvested with trypsin/EDTA (Sigma), washed twice with serum-free growth medium containing 0.1% w/v BSA then added to the top chamber (3×10$^5$ cells/1ml chamber). Normal growth media containing 10% v/v FCS was used as the chemo attractant. After incubation for 6 h at 37° C., non-invaded cells on the upper surface of the filter were wiped with a cotton swab, and migrated cells on the lower surface of the filter were fixed and stained with Diff-Quick kit. Invasiveness was determined by counting cells in five microscopic fields per well, and the extent of invasion was expressed as an average number of cells per microscopic field. Each experiment was performed in triplicate on two separate days where data is represented as % of migrating cells compared to the parental cell line.

Quantitation of Hyaluronan Receptors, RHAMM and CD44

Cell extracts were obtained by hypotonic lysis of exponentially growing cells in 10 mM HEPES pH 7.2 followed by disruption in a Dounce homogeniser using 20 strokes every 15 minutes. Cell lysis was confirmed by Giemsa stain of cell lysate and examination by light microscopy. Cell lysate preparations were denatured at 65° C. for 5 min and loaded (15-30 μg of protein per lane) onto a 10% polyacrylamide gel. Electrophoresis was performed on a Bio-Rad minigel apparatus. Proteins were transferred to nitrocellulose membranes and blocked for 1 h with Tris-buffered saline containing 5% nonfat dry milk and 0.1% Tween-20. Membranes were then washed and probed with the appropriate antibody diluted in Tris-buffered saline containing 5% bovine serum albumin (for polyclonal antibodies) or 5% nonfat dry milk (for monoclonal antibodies). The antibodies used for detection were 50 μg of CD44s monoclonal antibody (Hybridoma Bank, USA) or 25 μg RHAMM (kindly donated by R. Savani, University of Pennsylvania School of Medicine, USA). The secondary antibodies used were anti-rabbit IgG (New England Bio-labs) and rabbit anti-rat IgG (Bio-Rad), which were conjugated with horseradish peroxidase. Immunoreactive bands were detected by enhanced chemiluminescence, and the sizes of proteins were estimated using prestained molecular weight standards. Immunoreactive bands were quantified by densitometry. analysis using ProXpress™ Imager (Perkin Elmer, Boston, Mass., USA) and the data analysed using Phoretix™ 1D software (Phoretic International, Newcastle, UK).

Highly Invasive Breast Cancer Cells Preferentially Express HAS2

Endogenous levels of mRNA for the various HA synthase isoforms were quantitated in 10 different human breast cancer cell lines using real time PCR and comparative RT-PCR (see Table 3). HAS 1 mRNA was not detected in any of the ten breast cancer cell lines. HAS2 mRNA was detected in all the breast cancer cell lines which demonstrated an invasiveness of >80% where the highly invasive BT-549 and Hs578T cell lines expressed up to 205 times more HAS2 mRNA than the non-invasive MDA-MB 453 cell line. Negligible differences in HAS2 mRNA were observed between exponentially growing and growth arrested cells. All cell lines expressed low levels of HAS3 mRNA, but it was interesting to note that in cells with a low invasive potential (<26%) no HAS3 mRNA was detected in growth arrested cells, while in the highly invasive cell lines the transcription of this gene continued. The expression of HAS3 in all breast cancer cell lines, more particularly in the less invasive cell lines suggests that this HAS isoform is primarily responsible for the synthesis of basal levels of HA production necessary for normal cell function and HAS2 is required for the rapid synthesis of large quantities of HA required for cancer invasion.

The Glycocalyx in Exponentially Growing Breast Cancer Cells is Generated by HAS2

Utilising the HA quantitation and particle exclusion assay it was possible to uniquely demonstrate that when breast cancer cells are in exponential growth phase any cell-associated HA is only detected in cells expressing HAS2 (Table 3). In the exponentially growing, less invasive breast cancer phenotype which preferentially expressed HAS3, none of the synthesised HA was retained as part of the glycocalyx, the retention of the HA into the pericellular matrix only occurred after the cells have reached growth arrest. This finding is contrary to studies in other cell types where it was suggested that HAS3 expression resulted in the retention of a pericellular matrix (Itano et al, 1999a; Liu et al, 1996). During senescence, in general, the quantity of HA liberated into the media by HAS3 expressing cell lines significantly, in some cases total inhibition of HA liberation was observed, followed by the retention of the HA in the cell-associated fraction. During senescence, highly invasive cell lines released 40-60% less HA into the extracellular environment, but retained 2-22 fold more HA in the pericellular matrix. The quantitation of the cell-associated HA was substantiated by the red cell exclusion assay which only demonstrated the presence of a pericellular coat in the exponentially growing MDA-MB 231, BT-549 and Hs578T cell lines.

Figure 8:
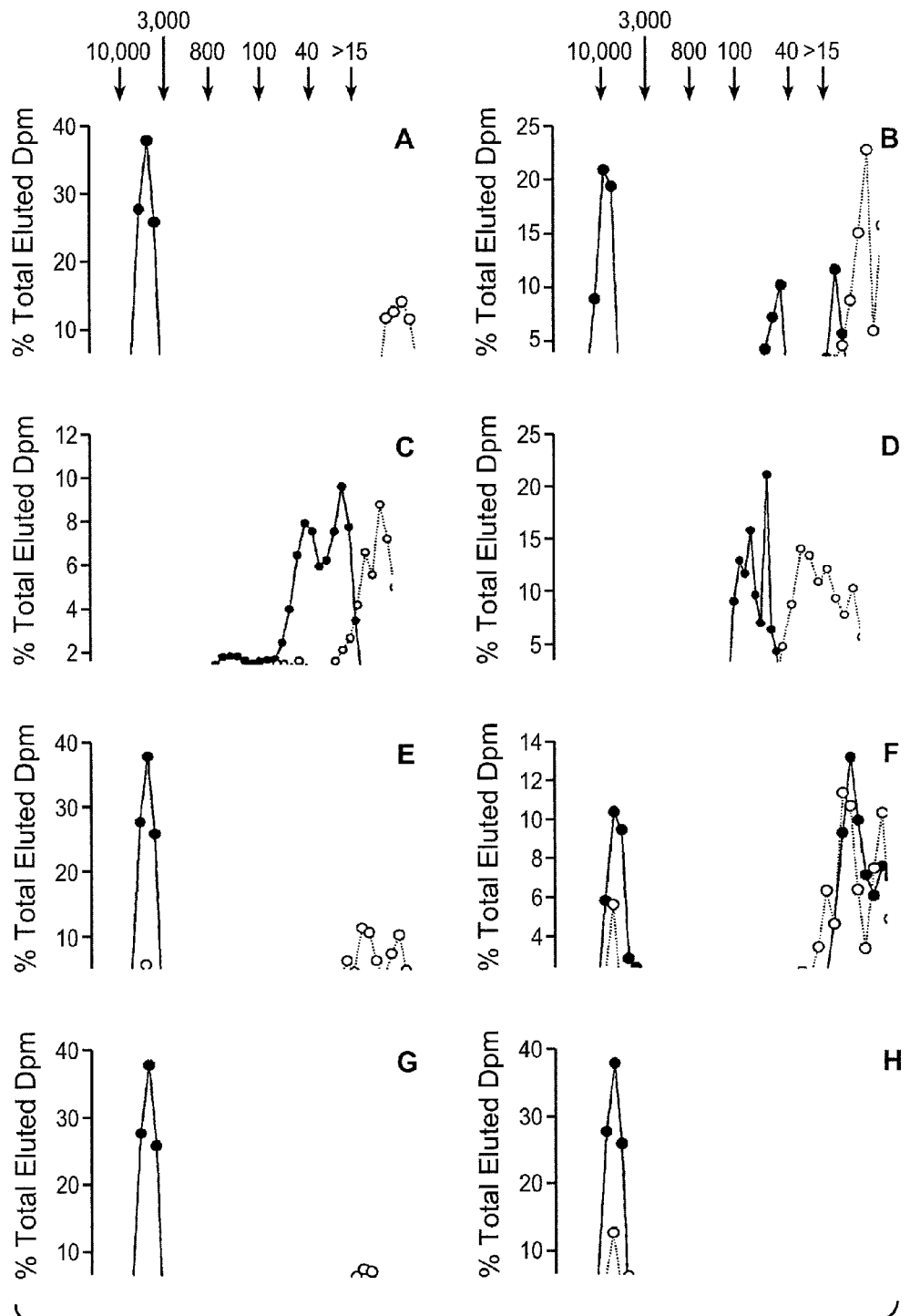
FIG. 8 is a diagrammatic representation demonstrating HAS 2 and HAS3 liberate high molecular weight HA which is rapidly depolymerised. MDA-MB 231 cells were seeded at $7.5 \times 10^5$ cells/75 cm$^2$ culture flask and were grown for 24 h in growth media containing ±400 µg/ml DS and 250 µCi D-[6-$^3$H]glucosamine. At the conclusion of the incubation, the media and cell-associated HA was removed and dialysed ($M_r$ exclusion of 5 kDa). After substantiation that the non-dialysable Dpm was HA (as determined by *Streptomyces hyaluronidase* digestion) it was subjected to size exclusion chromatography in a Sephacryl S-1000 gel eluted in 0.15M NaCl/phosphate buffer, pH 7.25 at 13.6 ml/h. Differences in the $M_r$ of liberated (FIGS. 1A, C, E & G) and cell-associated HA (FIGS. 1B, D, F & G) was determined in the following cell line.

HAS 2 and HAS3 liberate high molecular hyaluronan which is rapidly depolymerised Chromatographic characterisation of the liberated HA (±*Streptomyces* hyaluronidase digestion) from cells which had undergone both exponential proliferation and growth arrest demonstrated that 80-98% of the [$^3$H] glucosamine was incorporated into [$^3$H]HA, with the remaining [$^3$H] dpm identified as a pronase digestible macromolecule of approximately 50 kDa (See Table 4). All graphs represented in FIGS. 8A-H have had any peaks associated with *Streptomyces* hyaluronidase resistant material removed from the profile. The least invasive cell line, MDA-MB 453 which only expressed HAS3 liberated monodisperse HA of 10000 kDa, while the equivalent sample from cells grown without inhibition of the endogenous hyaluronidase (DxS culture) exhibited depolymerisation of 22% of the liberated HA, into a 60 kDa to 6000 kDa with 78% degraded to 30 kDa (FIG. 8A). The most invasive cell lines, BT-549 and Hs578T which both primarily expressed HAS2 and a very low expression of HAS3, both liberated large quantities of 10 000 kDa HA which in the presence of active hyaluronidases, was rapidly degraded into the HA fragments of 10, 20 and 40 kDa (FIGS. 8E & G). The MDA MB-231 which expressed moderate levels of HAS2 and very low levels of HAS3, produced a polydisperse HA which had several peaks with the modal Mr of 600 to 10 000 kDa and smaller fractions at 60 and 200 kDa, while after exposure to endogenous degradation processes these macromolecules were degraded to 20, 40 and 500 kDa (FIG. 8B).

Analysis of the cell-associated HA demonstrated that when the normal HA degradation processes were inhibited by dextran sulphate a very high Mr HA could be detected as well as oligomers of intermediate Mr, ranging from 20 to 200 kDa. When the hyaluronidase and other potential degradative processes were inhibited by dextran sulphate only small fragments of HA ranging from 10 to 70 kDa were found associated with the cell fraction (Table 5).

Increased Expression of Hyal-1 and Hyal-2 Induces Invasiveness in Human Breast Cancer Cell Lines Utilising competitive reverse transcription polymerase chain reaction (RT-PCR), Hyal-1, 2 and 3 was detected in varying quantities in all cell lines, while PH-20 was not detected using these amplification conditions. When comparing the expression of Hyal-1 and Hyal-2 expression in the less invasive cell lines (<30% of a cell population demonstrating migration) the mRNA for both of the enzymes were of approximate equal expression. As cells became more invasive the expression of both the Hyal-1 and Hyal-2 mRNA increased where Hyal-2 was often expressed at levels of 5-7 fold higher than the Hyal-1 mRNA. In the least invasive cell lines the transcription of Hyal-1 and 2 was inhibited during senescence, while in the highly invasive cell lines the level of mRNA expression was maintained or slightly increased during growth arrest.

The cellular Turnover of Hyaluronan Decreases with Increased Cellular Invasion

As seen in Table 4, as the invasive potential of the breast cancer cell increased the turnover rate of liberated HA decreased, indicating that highly invasive cells may require an extracellular environment rich in HA or that the degradative pathways of the cells had reached the maximum functioning capacity. This study has uniquely identified the expression of Hyal-3 in breast cancer where there is an inverse relationship between cell invasiveness and Hyal-3 expression. The identification of Hyal-3 in breast cancer cells was unexpected as this gene has been reported in mammalian testis and bone marrow (Csoka et al, 2001), but as yet has to demonstrate activity in standard hyaluronidase assays (Stern, 2003).

Figure 9:
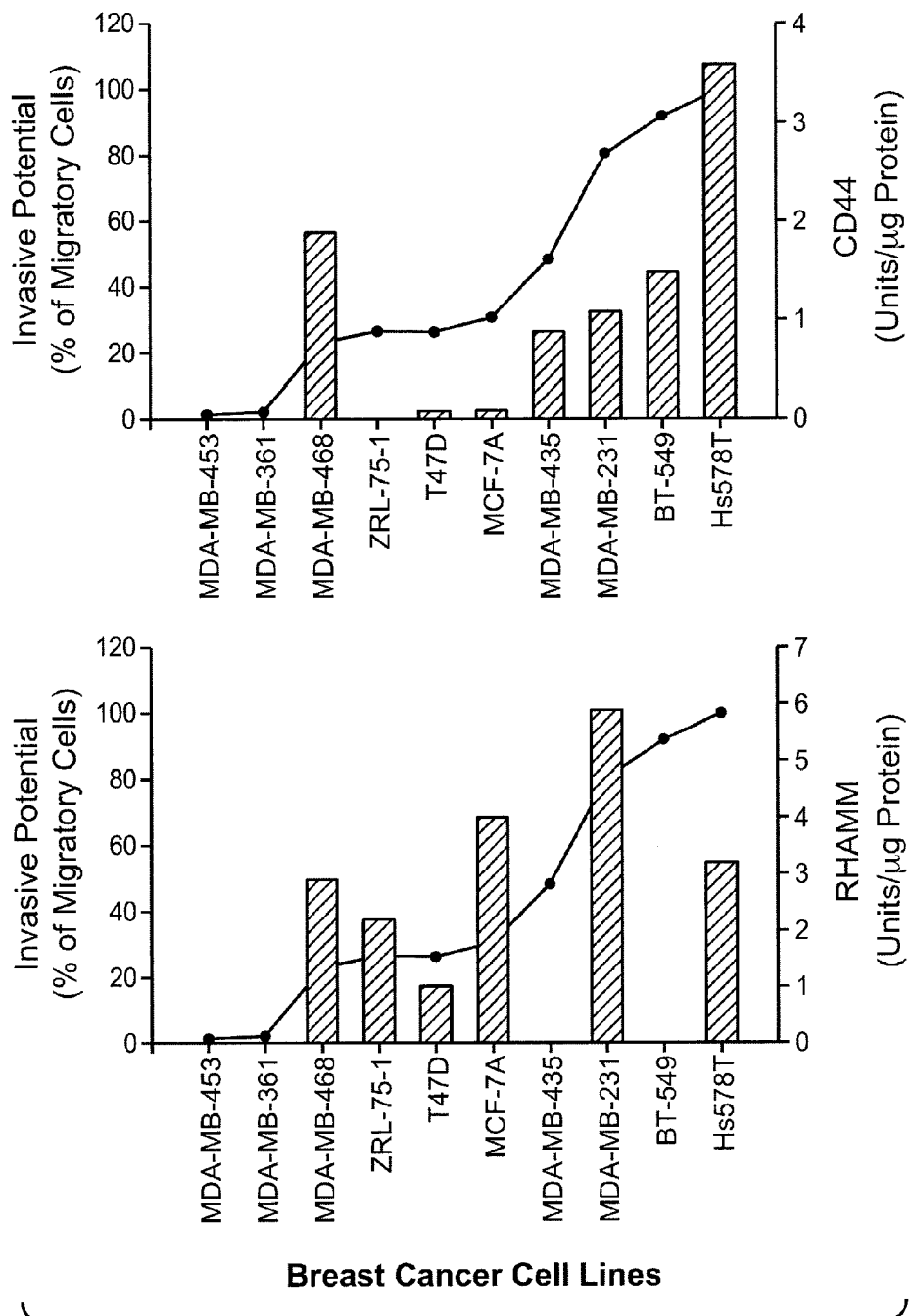
FIG. 9 is a diagrammatic representation demonstrating comparison of the invasive potential of human breast cancer cell lines and HA receptors. The invasive potential of the breast cell lines (*-*) were examined using the Boyden chamber chemoinvasion assay as described in Materials and Methods. The cells that had traversed the matrigel and spread on the lower surface of the filter were expressed as a percentage of the cell count determined for the Hs578T cell line. The data presented represents the mean SD average of triplicate experiments performed on two separate days. Note: percentage variance between triplicate determinations <2%. Quantitation of HA receptors (A) CD44 and (B) RHAMM was determined by immunoblotting where immunoreactive bands were quantified by densitometry analysis using ProXpress™ Imager and the data analysed using Phoretix™ 1 D software.

High Levels of CD44 Epitope Correlates with Increased Cell Invasiveness, Elevated HAS2, Hyal-1 and Hyal-2 Expression Quantitation of the RHAMM receptor did not exhibit a strong correlation with any particular HAS isoform or the prevalent expression of hyaluronidase or cell invasiveness however there did appear to be an inverse relationship between CD44 and RHAMM expression (FIGS. 9A & B). With the exception of the moderately invasive cell line, MDA-MB 468 thee was a proportional relationship between HAS2, Hyal-1 Hyal-2, CD44 and breast cancer cell invasiveness (Tables 3 & 4). When examining the catabolic potential of a breast cancer cell; the higher the CD44 and Hyal-2 expression, the greater the cells' ability to degrade large quantities of HA (Table 4).

TABLE 2

| Gene | Sense Primer | Reverse Primer | Hybridisation Probe |
| --- | --- | --- | --- |
| HAS1 | 5' CCTGCATCAGCGGTCCTCTA 3' (SEQ ID NO: 27) | 5' GCCGGTCA-TCCCCAAAAG 3' (SEQ ID NO: 34) | 5' AACCTCTTGCAGCAGTTTCTTGAGGCC 3' (SEQ ID NO: 41) |
| HAS2 | 5' CAGTCCTGGCTTCGAGCAG 3' (SEQ ID NO: 28) | 5' TTGGGAGAAAAGTCTTTGGCT 3' (SEQ ID NO: 35) | 5' CCATTGAACCAGAGACTTGAAACAGCC C 3'; (SEQ ID NO: 42) |
| HAS3 | 5' TTGCACTGTGGTCGTCAACTT 3' (SEQ ID NO: 29) | 5' GTCGAGGTCAAACGTTGTGAG 3' (SEQ ID NO: 36) | 5' TCAAATCAAAAACAGGCAGGTACAGGTAG TGG 3' (SEQ ID NO: 43) |
| GAPDH | 5' AAGGTGAAGGTCGGAGTCAAC 3' (SEQ ID NO: 30) | 5' GAGTTAAAA-GCAGCCCTGGTG 3' (SEQ ID NO: 37) | 5' TTTGGTCGTATTGGGCGCCTGG 3' (SEQ ID NO: 44) |
| Hyal-1 | 5' GCACAGGGAAGTCACAGATGTATGTGC 3' (SEQ ID NO: 31) | 5' CCACTGGTCACGTTCAGGATGAAG-3' (SEQ ID NO: 38) | |

TABLE 2-continued

| Gene | Sense Primer | Reverse Primer | Hybridisation Probe |
|---|---|---|---|
| Hyal-2 | 5' GATGTGTATCGCC-GGTTATCACGCC 3' (SEQ ID NO: 32) | 5' CGTAGACTGGGAGTGCATGGTTG GC 3'; (SEQ ID NO: 39) | |
| Hyal-3 | 5' GCACTGATGGAGGATACGCTGCG 3' (SEQ ID NO: 33) | 5' GCTGGTGACTGCAGGCCATCGCTGC 3' (SEQ ID NO: 40) | |

TABLE 3

| Breast Cancer Cell Line | Invasive Potential (% of migratory cells) | CD44 Expression (densitometry units/μg protein) | Hyaluronan Synthase Expression* | | | | Hyaluronan Production (fg/cell/24 h) | | | |
|---|---|---|---|---|---|---|---|---|---|---|
| | | | HAS2 | | HAS3 | | Liberated | | Cell-associated | |
| | | | EXP. Phase | PLAT. Phase | EXP. Phase | PLAT. Phase | EXP. Phase | PLAT. Phase | EXP. Phase | PLAT. Phase |
| MDA-MB-453 | 1 | 0 | 0 | 0 | 1 | 0 | 594 | 139 | 0 | 64 |
| MDA-MB-361 | 2 | 0 | 0 | 0 | 1 | 0 | 255 | 46 | 0 | 80 |
| MDA-MB-468 | 23 | 1.9 | 0 | 0 | 3 | 0 | 616 | 0 | 0 | 38 |
| ZRL-75-1 | 26 | 0 | 0 | 0 | 0.5 | 0 | 637 | 627 | 0 | 26 |
| T47D | 26 | 0.1 | 0 | 0 | 2 | 0 | 1523 | 0 | 0 | 71 |
| MCF-7A | 31 | 0.1 | 0 | 0 | 1 | 1 | 1623 | 313 | 0 | 64 |
| MDA-MB-435 | 48 | 0.9 | 0 | 0 | 0.5 | 0.5 | 376 | 92 | 0 | 44 |
| MDA-MB-231 | 80 | 1.1 | 14 | 16 | 1 | 1 | 6450 | 1137 | 250 | 351 |
| BT-549 | 92 | 1.5 | 92 | 91 | 8 | 8 | 13087 | 5278 | 125 | 2793 |
| Hs578T | 100 | 3.6 | 208 | 205 | 0.2 | 0.2 | 12711 | 4567 | 52 | 102 |

*HAS expression as determined by real time RT-PCR where figures are expressed as the fold difference a percentage of the least invasive cell line MDA-MB 453
0 indicates where gene or hyaluronan was not detected

TABLE 4

| Breast Cancer Cell Line | Invasive Potential (% of migratory cells) | CD44 Expression (densitometry units/μg protein) | Hyaluronidase Gene Expression* | | | | | |
|---|---|---|---|---|---|---|---|---|
| | | | Hyal-1 | | Hyal-2 | | Hyal-3 | |
| | | | EXP. Phase | PLAT. Phase | EXP. Phase | PLAT. Phase | EXP. Phase | PLAT. Phase |
| MDA-MB-453 | 1 | 0 | 1 | 0 | 1 | 0 | 1 | 1 |
| MDA-MB-361 | 2 | 0 | 1 | 0 | 1 | 0 | 5 | 2 |
| MDA-MB-488 | 23 | 1.9 | 5 | 0 | 5 | 0 | 10 | 10 |
| ZRL-75-1 | 26 | 0 | 10 | 0 | 11 | 0 | 14 | 0 |
| T47D | 26 | 0.1 | 16 | 0 | 17 | 0 | 5 | 30 |
| MCF-7A | 31 | 0.1 | 5 | 0 | 5 | 0 | 25 | 5 |
| MDA-MB-435 | 48 | 0.9 | 14 | 16 | 103 | 105 | 75 | 76 |
| MDA-MB-231 | 80 | 1.1 | 30 | 30 | 155 | 158 | 35 | 0 |
| BT-549 | 92 | 1.5 | 28 | 30 | 180 | 192 | 5 | 0 |
| Hs578T | 100 | 3.6 | 29 | 35 | 201 | 205 | 0 | 0 |

| Breast Cancer Cell Line | Hyaluronan Turnover (fg/cell/24 h) | | | |
|---|---|---|---|---|
| | Liberated | | Cell-associated | |
| | EXP. Phase | PLAT. Phase | EXP. Phase | PLAT. Phase |
| MDA-MB-453 | 594 (100%) | 139 (100%) | 0 | 6 (9%) |
| MDA-MB-361 | 255 (100%) | 46 (100%) | 0 | 44 (55%) |
| MDA-MB-488 | 616 (100%) | 0 | 0 | 6 (16%) |
| ZRL-75-1 | 594 (93%) | 367 (59%) | 0 | 0.8 (3%) |
| T47D | 1308 (86%) | 0 | 0 | 17 (24%) |
| MCF-7A | 1623 (100%) | 313 (100%) | 0 | 35 (30%) |
| MDA-MB-435 | 376 (100%) | 92 (100%) | 0 | 19 (43%) |

TABLE 4-continued

| | | | | |
|---|---|---|---|---|
| MDA-MB-231 | 2020 (31%) | 880 (77%) | 0 | 46 (13%) |
| BT-549 | 1476 (11%) | 914 (17%) | 61 (49%) | 1405 (50%) |
| Hs578T | 2990 (24%) | 1756 (38%) | 34 (85%) | 41 (40%) |

*Hyal expression as determined by RT-PCR and digitisation of bands where figures fold difference in expression when compared to the least invasive cell line MDA-MB 453
0 indicates where gene or hyaluronan is not detected
( ) Figures in brackets represent the % of HA which is degraded/cell/24 h

TABLE 5

| Breast Cancer Cell Line | Invasive Potential (% of migratory cells) | HAS Gene[a] Expression | | Hyal Gene[b] Expression | | | Characterisation of liberated HA | | | | Characterisation of cell-associated HA | | | |
|---|---|---|---|---|---|---|---|---|---|---|---|---|---|---|
| | | HAS2 | HAS3 | Hyal-1 | Hyal-2 | Hyal-3 | Modal $M_r$ (kDa) | % of HA | $M_r$ of HA degradation products (kDa) | % of HA | Modal Mr (kDa) | % of HA | $M_r$ of HA degradation products (kDa) | % of HA |
| MDA-MB-453 | 1 | 0 | 1 | 1 | 1 | 1 | 10 000 | 100 | 25 | 67 | 60 | 23 | 10 | 22 |
| | | | | | | | | | 70 | 11 | 100 | 24 | 20 | 78 |
| | | | | | | | | | 800 | 3 | 10 000 | 53 | | |
| | | | | | | | | | 3000 | 7 | | | | |
| | | | | | | | | | 6000 | 12 | | | | |
| MDA-MB-231 | 80 | 14 | 1 | 30 | 155 | 35 | 60 | 36 | 20 | 37 | 200 | 39 | 20 | 23 |
| | | | | | | | 200 | 36 | 40 | 41 | 500 | 38 | 40 | 33 |
| | | | | | | | 600 to 10 000 | 28 | 500 | 22 | 660 | 23 | 70 | 44 |
| BT-549 | 92 | 92 | 8 | 28 | 180 | 5 | 10 000 | 100 | 10 | 66 | 20 | 21 | 10 | 9 |
| | | | | | | | | | 20 | 11 | 60 | 41 | 20 | 26 |
| | | | | | | | | | 40 | | 10 000 | 38 | 40 | 46 |
| | | | | | | | | | | | | | 60 | 8 |
| Hs578T | 100 | 208 | 0.2 | 29 | 201 | 0 | 10 000 | 100 | 10 | 9 | 10 000 | 100 | 10 | 27 |
| | | | | | | | | | 20 | 28 | | | 20 | 36 |
| | | | | | | | | | 40 | 41 | | | | |

[a]HAS expression as determined by real time RT-PCR where figures are expressed as the fold difference a percentage of the least invasive cell line MDA-MB 453
[b]Hyal expression as determined by RT-PCR and digitisation of bands where figures fold difference in expression when compared to the least invasive cell line MDA-MB 453

EXAMPLE 22

Antisense-Medicated uppression of Hyaluronan Synthase 2 Inhibits the Tumor Genesis and Progression of Breast Cell Culture.

Aneuploid human breast adenocarcinoma cell line MDA-MB 231 (American Tissue Culture Collection, Rockville, Md., USA) was selected based on the expression of HAS2. Cells were propagated in monolayer culture in Leibovitz L-15 Medium (Sigma, St Louis, Mo., USA), supplemented with supplemented with 10% FCS, 100 units/ml penicillin and 100 mg/ml streptomycin.

Construction of Antisense Expression Vector.

The cDNA open reading frame for human HAS2 was generated by designing gene specific primers from the published sequence of Watanabe and Yamaguchi and consisted of the following primers: sense, 5'-GAGCTGAACAAGATGCAT-TGTGAGAGC-3' (SEQ ID NO: 45) and antisense, 5'-GA-CATGGTGCTTGATGTATGATCTTCCAT-3' (SEQ ID NO: 46). Total RNA harvested from exponentially dividing human dermal fibroblasts was used as the template for RT-PCR, generating a 1.7 kb cDNA fragment of HAS2, which was cloned directly into pGEM®-T vector (Promega, Madison, USA). The cDNA for HAS2 was subsequently subcloned into the pCI-neo expression vector (Promega) and isolated clones containing the insert in the antisense orientation (ASHAS2 construct) were identified by restriction endonuclease mapping and automated sequencing.

Transfection and Validation of MDA-MB 231 Human Breast Cancer Cells with ASHAS2 and Mock Constructs.

The ASHAS2-pCI-Neo construct and mock control (pCI-neo vector without insert) were transfected into human MDA-MB 231 breast cancer cells using Lipofectamine™ plus reagent (Gibco Life Technologies, Melbourne, Victoria, Australia) according to the manufacturer's instructions. For at least one month, prior to commencing studies, transfected cells were selected in the presence of 500 μg/ml G418 antibiotic (Promega). Stable cell lines were established by harvesting and pooling of antibiotic-resistant colonies. Confirmation of the stable incorporation of the antisense HAS2 construct into the genome was performed using PCR on purified genomic DNA. In brief, a gene specific primer for pCI-neo: 5'-GCACAGATGCGTAAGGAG-3' (SEQ ID NO: 47) was used in combination with two specific HAS2 primers of the following sequence: GSP2 sense 5'-GCTGTGTACAT-GACCTCGCGCTTGCCGCC-3' (SEQ ID NO: 48) and GSP4 sense, 5'-GGCGGGAAGTAAACTCGAC-3' (SEQ ID NO: 49). When used in the following combination; pCI-neo/GSP2 and pCI-neo/GSP4, expected size products of 1443 bp and 2223 bp were amplified respectively. The products of PCR were identified by restriction endonuclease mapping and automated sequencing.

Quantification of mRNA for HAS1, 2 and 3.

Real time PCR using gene specific primers and an internal oligonucleotide probe was used to quantitate the relative mRNA levels of HAS1, HAS2, and HAS3 in parental, mock and ASHAS2 transfected cells (Table 2). In brief, total RNA was purified from exponentially growing cells using TRI-reagent (Sigma). The total RNA was used to generate single stranded cDNA by incubating 2 μg RNA with 0.5 μg/μl random primers and superscript reverse trancriptase (Invitrogen, Carlsbad, Calif., USA). For quantitative real time PCR gene specific primers for each HAS isoform and an internal oligonucleotide probe were used. For HAS internal probes the reporter dye 6-carboxylfluorescein (6-FAM™) and quencher 6-carboxytetramethyl rhodamine (TAMRA™) was labelled at the 5' and 3' respectively. For GAPDH internal probes the reporter 6-FAM™ was substituted with VIC™ (Applied Biosystems, Foster City, Calif., USA). The PCR reaction was performed in a final volume of 30 μl and consisted of 1× Taqman reaction mix, 6 μM of HAS forward and reverse primer, 1.5 μM of probe, 1 μM of each GAPDH primer and 500 nM of GAPDH probe. PCR amplification was performed by denaturation for 10 min at 95° C. followed by annealing for 2 min at 50° C. followed by 40 cycles of 15 seconds at 95° C. and 1 min at 60° C. Thermocycling and fluorescence measurement were performed in an ABI Prism 7700® sequence detection system (Applied Biosystems). Relative quantitation was performed by normalizing threshold cycle (Ct) values of each sample gene with Ct values of the GAPDH. ΔCt corresponds to the difference between the Ct of the HAS genes of interest and the Ct of the GAPDH. Data are presented as fold-change difference relative to parental (arbitrarily set to 100) calculated according to the formula describing relative PCR quantitation $2^{-(\Delta CtHAS - \Delta CtGAPDH)}$.

Characterisation of Hyaluronidase Gene Expression.

To determine the hyaluronidase gene expression for HYAL1, 2 and 3, RT-PCR was performed on total RNA extracted from cells in both the exponential and growth arrested phases. The gene specific primer sets were designed from sequences retrieved from GenBank® (refer Table 2). Amplified sequences were visualised by agarose gel electrophoresis containing ethidium bromide and their identity confirmed by automated DNA sequencing. To quantitate the relative abundance of each PCR product, ethidium bromide stained agarose gels containing amplified fragments were subjected to densitometric analysis using ProXpress™ Imager (Perkin Elmer, Boston, Mass., USA) and the data analysed using Phoretix™ 1D software (Phoretic International, Newcastle, UK).

Cell Proliferation Assay.

Exponentially growing, parental, mock and ASHAS2 transfectants were plated into 24-well plates (2.5 cm$^2$/well) at cell densities, ranging from $5\times10^3$ to $9\times10^4$ cells/well. The effect of HAS2 inhibition on cell proliferation was studied for 24, 48, 72, 96, 120 and 144 h. After the defined growth period, cells were detached using 0.25% w/v trypsin and cell number determined using a Coulter counter (Beckman, Coulter, Australia).

Immunohistochemical Identification of Hyaluronan Synthase, Hyaluronidases and CD44

The comparative effect of HAS2 inhibition on the expression of HA synthase, hyaluronidase and HA receptors was performed on parental, mock and ASHAS2 transfected MDA-MB 231 cells. Eight-well chamber slides were plated at a density of $2\times10^4$ cells/well and cells were attached for 24 h. Cells were fixed in Histochoice (Sigma) for 15 min then washed 3×5 min in PBS. Heterophile proteins were blocked by incubation with 10% FCS for 10 min, followed by a PBS rinse. The antisera or antibodies were against CD44H (DAKO, Copenhagen, Denmark) HYAL1, HYAL2, (kindly donated by R. Stern, University of San Francisco, USA), HAS2 (kindly donated by P. Heldin, Ludwig Institute for Cancer Research, Uppsala, Sweden) were diluted in PBS containing 1% human serum/1% FCS where detection antibodies were applied for 60 min at 25° C. Endogenous peroxidase activity was blocked by immersion in 0.3% $H_2O_2$ in methanol for 20 min. Following an additional PBS wash, swine anti rabbit or rat anti mouse peroxidase-conjugated secondary antiserum (DAKO) was applied for 60 min at RT, followed by 3×5 min washes in PBS. Epitope was visualised with Sigma Fast DAB (3,3'diaminobenzidine, Sigma) after application for 5-10 min at RT. Slides were washed in tap water for 10 min, counterstained with haematoxylin, dehydrated and mounted.

Cell Cycle Analysis by Now Cytometry.

The transfected and control cells were seeded at $2\times10^5$ cells/25 cm$^2$ and grown with 2 mM thymidine until 50% confluent. After reaching 50% confluence, cells were grown in thymidine-free culture medium. Cells were harvested, by trypsinisation at 0, 4, 8, 12, 16, 20, 24, 28, 32, and 36 h followed by fixation in 95% ethanol for 2 h at 4° C. Cells were pre-treated with RNAase (100 μg/ml) (Sigma) and 50 μg/ml propidium iodide (Sigma) for 30 min at 37° C. before determining the stage of cell cycle stage using a FACS-Calibur™ analytical instrument (Becton Dickinson, San Jose, Calif., USA).

Cell migration assay.

Invasion assays were performed using modified Boyden chambers with polycarbonate Nucleopore membranes (Corning, Corning, N.Y., USA). Pre-coated filters (6.5 mm in diameter, 12 μm pore-size, Matrigel® 100 μg/cm$^2$) were rehydrated with 100 μl of Leibovitz L-15 media supplemented with 0.1% w/v BSA (Sigma). Exponentially growing cells were harvested with trypsin/EDTA (Sigma). Before addition to the top chamber of the Boyden apparatus, $3\times10^5$ cells/1 ml chamber were washed twice with serum-free growth medium containing 0.1% w/v BSA. Normal growth media containing 10% v/v FCS was used as the chemo attractant. After incubation for 6 h at 37° C., non-invaded cells on the upper surface of the filter were wiped with a cotton swab, and migrated cells on the lower surface of the filter were fixed and stained with Diff-Quick® kit. Invasiveness was determined by counting cells in five microscopic fields per well, and the extent of invasion was expressed as an average number of cells per microscopic field. Each experiment was performed in triplicate on two separate days where data is represented as % of migrating cells compared to the parental cell line.

Particle Exclusion Assay and Cell Morphology.

The HA-dependent pericellular matrix was visualised around breast cancer cells from control and transfected cultures by the exclusion of fixed human erythrocytes as previously described by Clarris and Fraser. Morphological differences as well as the particle exclusion assay in the control and transfected MDA-MB 231 cells were photographed on a Nikon Optiflot inverted phase contrast microscope (Nikon) 24 and 60 h after plating.

Quantitation of Liberated HA.

Triplicate cultures of parental, mock transfected and ASHAS2 human breast cancer MDA-MB 231 cells were seeded at $2.5\times10^5$ cells/25 cm$^2$ and incubated for 24, 48, 72, 96, 120 and 144 h. At the conclusion of the incubation period, cells were harvested by trypsinisation and counted using a Coulter counter. Media was used for quantitation of liberated HA. The liberated HA was quantitated using an enzyme-linked HA binding protein assay (HABP) (Corgenix Inc, Westminster, Colo., USA). The assay was performed according to the manufacturer's instructions. In brief, duplicate 100 μl of samples and the HA standards (0, 50, 100, 200, 500 and 800 ng/ml) were aliquoted into a 96 well plate coated with HABP, and incubated at room temperature (RT) for 60 min.

Samples were washed four times with PBS. One hundred μl of HABP conjugated to horse-radish peroxidase was added and incubated at RT for 30 min. After additional PBS washes, the reaction was visualised with 100 μl of 3,3',5,5'-tetramethylbenzidine (TMB) after a 30 min, RT incubation. The reaction was stopped with 100 μl of 0.36N sulphuric acid and read at 450 nm (650 nm reference) in a BioRad 350 microplate reader. Growth media which had not been exposed to cells was used to determine the endogenous HA levels. Endogenous HA levels were subtracted from all HA estimation results.

Characterisation of Hyaluronan Molecular Weight Using Size Exclusion Chromatography.

Cells were seeded at $7.5 \times 10^5$ cells/75 cm$^2$ culture flask and were grown for 24 h in growth media containing 250 μCi D-[6-$^3$H]glucosamine hydrochloride (Perkin Elmer). At the conclusion of the 24 h incubation period, the media was removed and exhaustively dialysed ($M_r$ exclusion of 6 kDa) against 10 mM Tris-HC/0.15M sodium chloride/0.02% sodium azide pH 7.4 at 4° C. The dialysate and dialysis fluid were chromatographically analysed for the identification of [$^3$H]HA and its degradation products. [$^3$H]HA of >5 kD was subjected to size exclusion chromatography in a Sephacryl S-1000 gel eluted in 0.15M NaCl/phosphate pH 7.25 which contained 19 mM NaH$_2$PO$_4$, 38 mM Na$_2$HPO$_4$ and 94 mM NaCl at 13.6 ml/h. The dialysis fluid (molecules <5 kDa) was subjected to size exclusion chromatography in a Superose 12 gel eluted in the above-mentioned buffer at an elution rate of 20 ml/h. Molecular weight estimations were calculated using calibration data for HA in Sephacryl S-1000 and Superose 12, where data was generated from varying MW of HA ranging from 800 Da to 10,000 kDa (CPN, Czech Republic and Pharmacia). To ensure that the D[6-$^3$H]glucosamine hydrochloride was used as a sole precursor for HA production, the non-dialysable (molecules >5 kDa) Dpm was subjected to digestion by 10 TRU of *Streptomyces* hyaluronidase (Calbiochem, Germany) at pH 6, 37° C. for 24 h. Digested material was subjected to chromatography in both Sephacryl S-1000 and Superose 12 where profiles were compared to equivalent undigested samples.

Generation of Mammary Fat Subcutaneous Tumours.

Animal studies were conducted with full ethical approval from the relevant institutional ethics committee, and in accordance with the Australian National Health and Medical Research Councils guidelines for the care and use of laboratory animals. Five-week-old CBA nude mice (Walter and Eliza Hall, Melbourne, Victoria, Australia) were randomly divided into three groups (n=11/group) for the generation of parental, mock and ASHAS2 tumours. Cells were harvested in the logarithmic growth phase by scraping, resuspended to a final density of $2 \times 10^6$ cells in L-15 medium supplemented with 0.1% glucose ±5 mg/ml Matrigei followed by immediate injected into the mammary fat. Tumour growth was recorded twice weekly by measuring three perpendicular diameters (d1, d2, d3). Tumour volume was then calculated using the formula: ($\frac{1}{6}$)π(d1d2d3). On day 84 after initiation of the tumours mice were humanely killed. The liver, kidneys, brain and lungs removed at autopsy and stored at −20° C. until Alu PCR analysis was performed. For pathological assessment half of the primary tumour was fixed in 4% formaldehyde and embedded in paraffin, 5 μm sections were examined after hematoxylin and eosin staining.

Intracardiac Inoculation of Breast Cancer Cells.

Before intracardiac tumour inoculation mice were anaesthetised with an intraperitoneal mixture of ketamine (50 mg/kg) and xylazine (5 mg/kg). The MDA-MB 231 cells were prepared as previously described and resuspended to $1 \times 10^5$ cells/0.1 ml. The cell suspension was drawn into a 1ml syringe fitted with a 25-gauge needle and 0.1 ml injected into the left ventrical. Mice were laid on a heated pad for recovery before returning to the cages. Periodically, radiographic analysis for bone osteolysis was performed. For this, mice were anaesthetised (as previously described) and X-rayed in a prone position against the X-Omat film (Eastsman Kodak Co., Rochester, N.Y., USA) and exposed with X-rays of 35 kV for 30sec using a Cabinet X-ray system-Faxitron Series, Hewlett-Packard Co. (Model MX20 with a 20 μm focal source; Faxitron x-ray Corp., Illinois, USA). Animal health and survival rate was observed until their euthanasia due to one of the following medical reasons; severe weights lose, hyperventilation, paralysis, or bone fracture. Collected organs: liver, kidneys, brain and lungs were removed and stored at −20° C. until Alu PCR analysis was performed. To determine the median survival time a survival curve was plotted using Prism stats program (Kaplan-Meier Survival) with the days elapsed following intracardiac inoculations. P value was calculated for the comparison of the survival curves.

Alu PCR Quantification of Metastasis.

Quantitative Alu PCR was used to detect metastasis of MDA-MB 231 from the primary tumour to secondary organs. In brief, DNA was extracted by grinding samples under liquid nitrogen and resuspending in a DNA lysis buffer (100 mM NaCl, 20 mM Tris-HCl pH 8.0, 20 mM EDTA pH 8.0, 0.4% (v/v) SDS). DNA was purified using phenol—CH loroform methodology followed by ethanol precipitation and reconstitution in TE buffer. The purified DNA was adjusted to a final concentration of 10 ng/μl in TE buffer pH7.2, aliquoted and stored at −20° C. until analysis. To remove exogenous human DNA contamination the reaction mix, prior to addition of primers, was treated with 17 U/ml nuclease S7 (Roche Diagnostics, Germany) in the presence of 1 mM CaCl$_2$ at 37° C. for 24 h prior to PCR. Nuclease S7 was then inactivated at 90° C. for 30 min following the addition of 4 mM EGTA. Quantitative Alu PCR was then performed on purified genomic DNA samples (long) in a GeneAmp 5700 Sequence Detection System (Applied Biosystems). Each sample was tested in duplicate in a final reaction volume of 25 μl consisting of 0.625 U Taq DNA polymerase (Roche; Mannheim, Germany), 10 mM Tris-HCl pH 8.3, 1.5 mM MgCl$_2$, 50 mM KCl, 200 μM dNTPs, 8% DMSO, 1 μg/ml 6-carboxy-X-rhodamines. (Molecular Probes; Eugene, Oreg. USA), 1 in 40000 dilution of SYBR Green I (Molecular Probes) and 100 nM of each Alu primer (Alu sense 5'-GTGAAACCCCGTCTCTAC-TAAAAATACAAA-3' (SEQ ID NO:50); Alu antisense 5'-GCGATCTCGGCTCACTGCAA-3' (SEQ ID NO:51). Following initial denaturation incubation at 95° C. for 2 min, amplification occurred over 40 cycles, which consisted of denaturation at 95° C. for 5 seconds, annealing at 65° C. for 60 seconds, and extension at 75° C. for 15 seconds during which the intensity of fluorescence was measured. A dissociation curve was then generated from 60° C. to 95° C. On each 96-well reaction plate, a standard curve was prepared by serially diluting human DNA into mouse DNA that permitted the quantification of the tissue burden of human tumour cells in the mouse organs removed at autopsy.

Conformation of Antisense HAS2 Stable Transfection in MDA-MB 231 Cells

Incorporation of the antisense HAS2-pCl-neo construct into the genome of MDA-MB 231 was confirmed by PCR analysis of highly purified genomic DNA extracted from transfected cells. When used in the following combination; pCl-neo/GSP2 and pCl-neo/GSP4 expected size products of 1443 bp and 2223 bp were reproducibly amplified from stable clones harbouring the antisense HAS2 construct. Genomic DNA isolated from parental and mock transfected tested negative.

Figure 10:
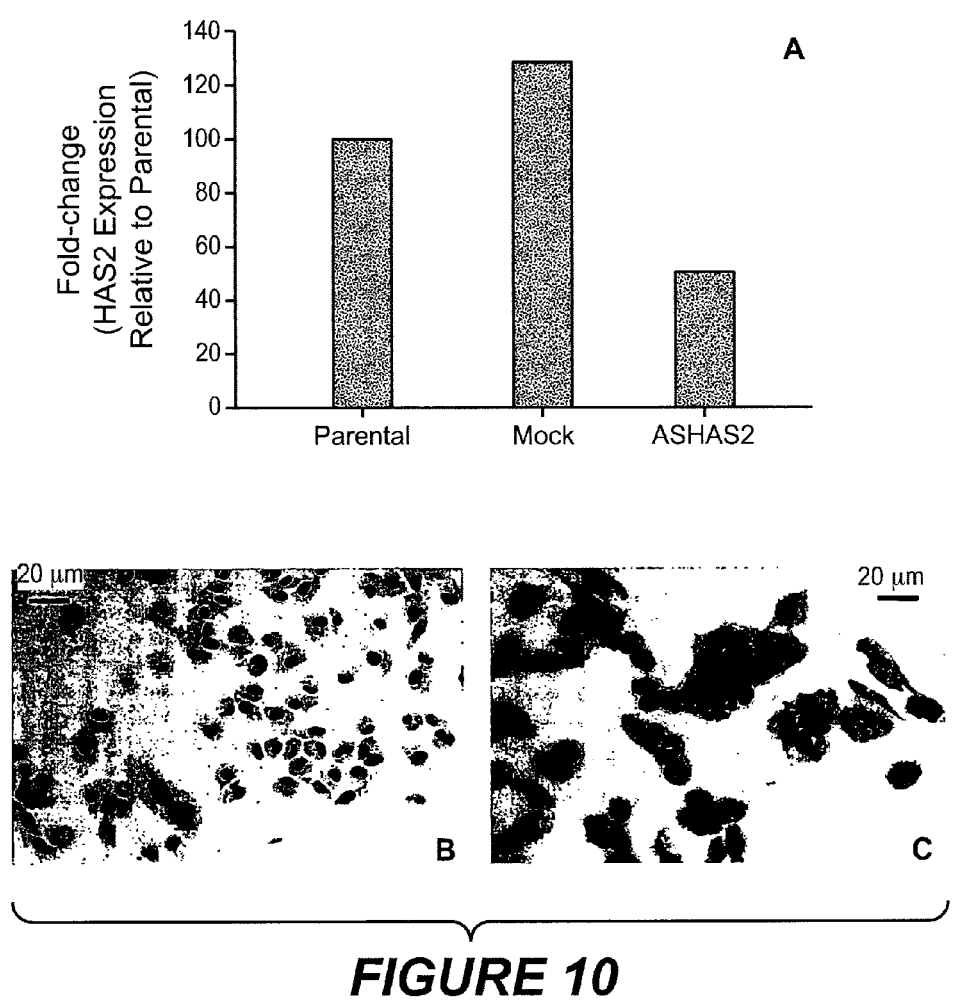
FIG. 10 are graphical and photographical representations of mRNA expression of the hyaluronan synthase family and immunodetection of HAS2 in parental MDA-MB 231 and antisense transfectants, respecfully. A: Total RNA was extracted from exponentially dividing cultures of parental MDA-MB 231, mock transfectants and stable clones expressing ASHAS2 mRNA. The level of mRNA for HAS2 was quantitated by real time RT-PCR. B: Immunodetection of HAS2 protein on stable clones expressing antisense mRNA to HAS2 parental MDA-MB 231 and, C: on the parental MDA-MB 231 cell line. (Scale bar 20 µm).

Transfection of MDA-MB 231 Breast Cancer Cells with Antisense HAS2 Reduces HAS mRNA and Totally Inhibits the Expression of the HAS2 Protein Endogenous levels of mRNA for HAS2 in parental cells were quantitated using real time RT-PCR and compared with the values obtained from mock and antisense HAS2 transfectants. Concomitant to these experiments, HAS1 and HAS3 mRNA levels were also quantitated using real time PCR with HYAL1, 2 and 3 expression characterised by standard RT-PCR methodology. To allow comparison of real time HAS expression between transfected and parental cells the level of each mRNA quantitated was normalised with respect to their internal GAPDH controls. When comparing the endogenous level of HAS2 mRNA expression in parental cells and transfectants, there were no observed differences between the parental and mock-transfected cell lines. In contrast, mRNA expression in ASHAS2 stable transfected cells was decreased by 50% when compared with parental and mock transfectants respectively ($p=0.008$) (FIG. 10A). Moderate HAS3 expression was also detected and was comparable in parental, mock and antisense transfected cells, where HAS1 could not be detected in any of the treatment groups (data not shown). Immunohistochemical detection of HAS2 with isoform-specific monoclonal antibody demonstrated that stable transfection with ASHAS2 resulted in the effective blocking of translation of the HAS2 protein (FIG. 10B). Whereas both parental and mock transfected cells exhibited a high degree of HAS2 expression as indicated by positive epitope staining (FIG. 10C).

Inhibition of HAS2 Alters Hyaluronidase Expression

Figure 11:
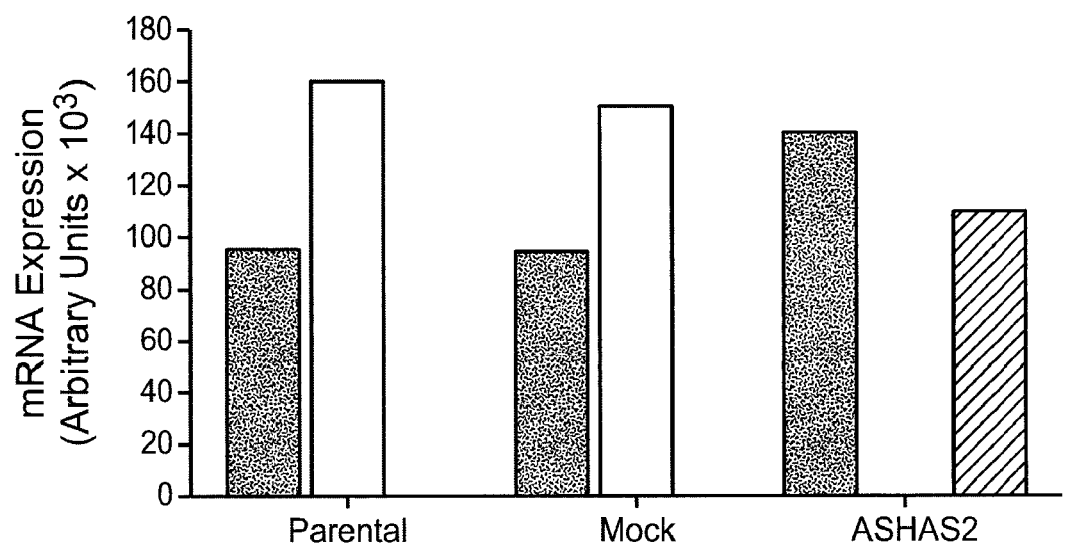
FIG. 11 is a graphical representation comparing hyaluronidase gene expression by parental, mock and HAS2 antisense transfected MDA-MB 231. Total RNA extracted from parental, mock and ASHAS2 transfected MDA-MB 231 was analysed by RT-PCR to detect the presence of the hyaluronidase genes, HYAL-1, 2 and 3. PCR products were resolved by agarose gel electrophoresis containing ethidium bromide. Band volume in stained gels was then subjected to densitometric analysis to allow comparison of levels for each HYAL gene expression between parental, mock and ASHAS2 transfected cells. Closed bar: HYAL1; open bar: HYAL2; diagonal hatched bar: HYAL3. Note: percentage variance between triplicate determinations <2%.

Antisense inhibition of HAS2 significantly altered the expression of HYAL1, 2 and 3 (FIG. 11). HYAL3 could not be detected in either parental or mock transfectants, but the inhibition of HAS2 resulted in the expression of HYAL3 (FIG. 11). Inhibition of HAS2 expression, however, resulted in the down regulation of gene expression for HYAL2 mRNA to the point where it was not detectable even after 35 cycles of PCR. This observation is reinforced by the lack of immunoreactivity of ASHAS2 MDA-MB 231 stable transfectants with the HYAL2 antibody where staining localised to the plasma membrane and also appeared as cytoplasmic vesicles. HYAL1 expression in antisense transfectants was moderately up regulated when compared with both parental and mock controls. These observations were consistent from total RNA extracted from either sub-confluent or confluent cultures.

CD44 was Down-Regulated by the Inhibition of HAS2

Figure 12:
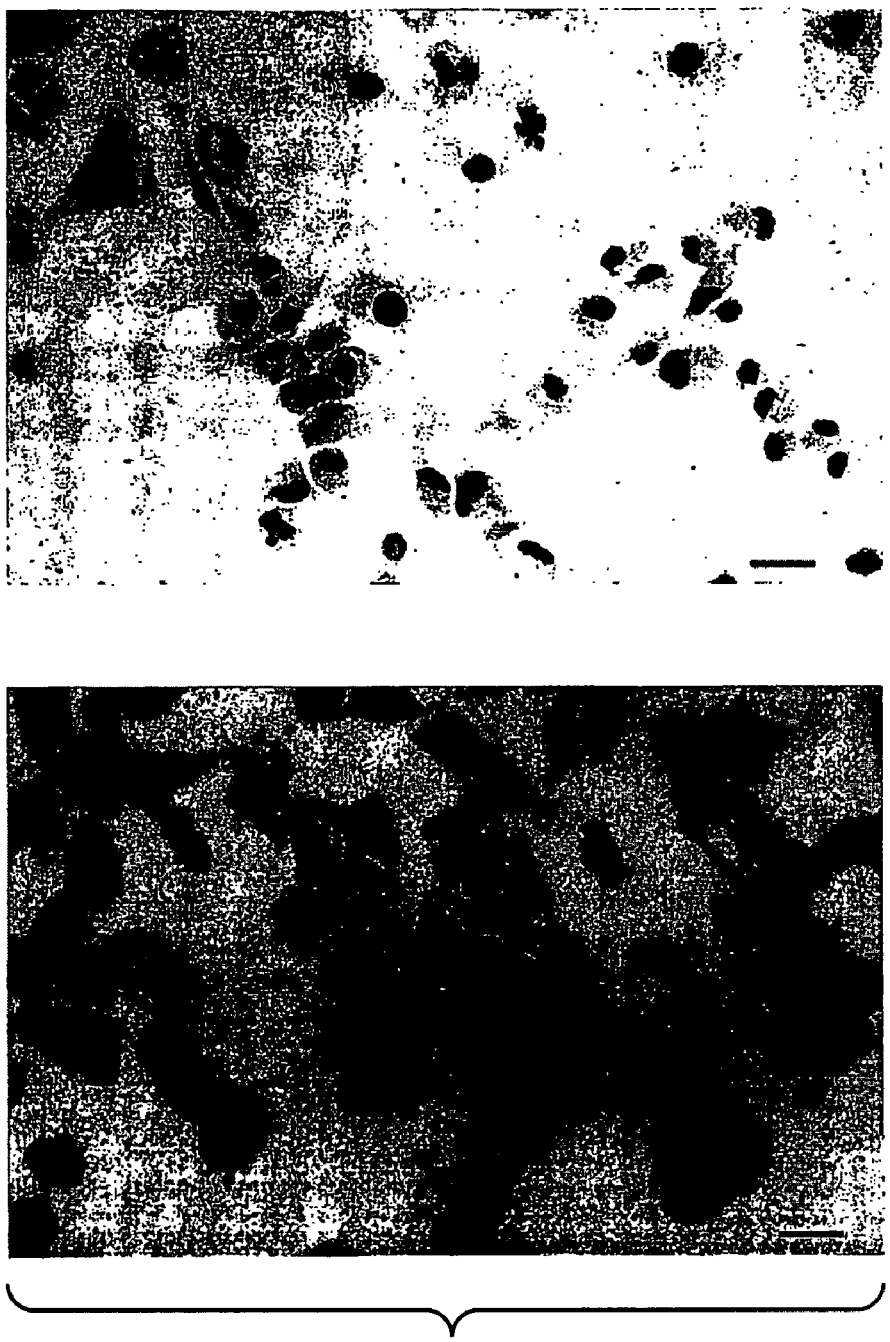
FIG. 12 is a photographical representation showing Immunohistochemical reactivity of parental MDA-MB 231 and antisense transfectants to CD44. Sub-confluent stable transfectants of MDA-MB 231 expressing antisense mRNA to HAS2 (A), and (B) parental MDA-MB 231 were reacted with an anti-human CD44. (Scale bar 20 µm).

The expression of the HA receptor, CD44 was down regulated in the ASHAS2 cells (FIG. 12A) when compared with parental and mock transfectants (FIG. 12B). The staining for CD44 in both controls was most evident in the plasma membrane with areas of intense focal membrane staining.

Antisense Inhibition of HAS2 Alters Hyaluronan Metabolism

Figure 13:
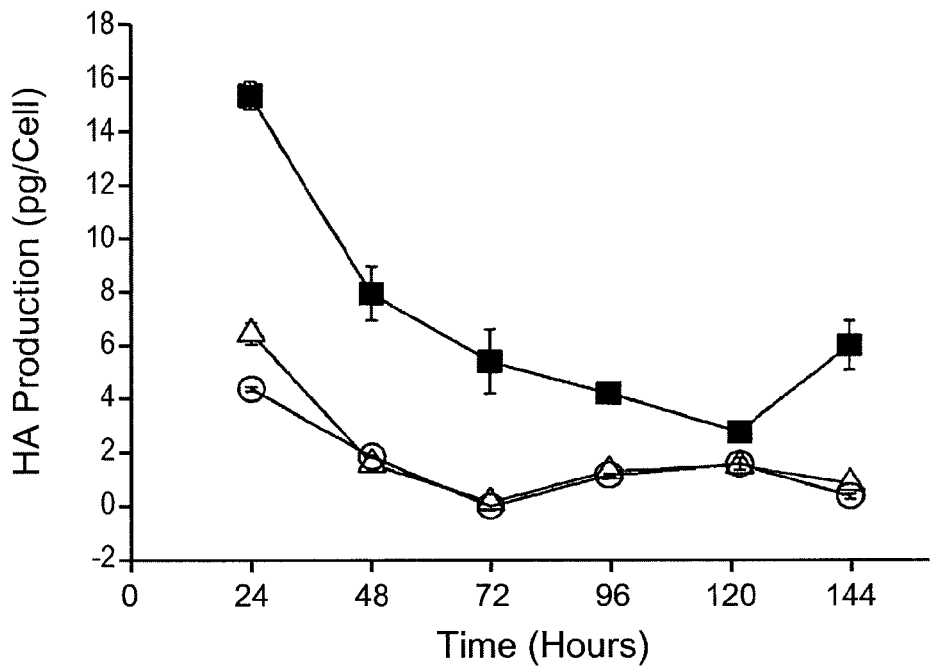
FIG. 13 is a graphical representation of the quantification and comparison of hyaluronan synthesis in parental, mock and ASHAS2 transfected MDA-MB 231. Cells were seeded at $2.5 \times 10^5$/cells in 25 cm$^2$ culture flasks and incubated at 37° C. for 24, 48, 72, 96, 120 and 144 h. At each time point cells were trypsinised and quantitated using an automated coulter counter. HA concentration in the harvested culture medium was determined using a hyaluronic acid binding protein (HABP) assay. HA synthesis by parental and mock transfected MDA-MB 231 was expressed as HA synthesised (pg/cell). Data represent the average of triplicate determinations at each time point ±SD. Δ-Δ: parental MDA-MB 231; ○-○: mock transfectants; ■-■: ASHAS2 transfectants.

Due to the altered HAS and HYAL expression in ASHAS2 MDA-MB 231 transfectants the amount of liberated HA was quantitated. ASHAS2 MDA-MB 231 transfectants liberated significantly greater quantities of HA when compared with either the parental cell line or mock transfectants (FIG. 13). Over the duration of the experiment, ASHAS2 cultures synthesised an average of 6.94 pg HA/cell/day with one noticeable exception at 24 h after plating, where synthesis was increased to approximately 15.4 pg/cell/day, in contrast to parental and mock transfectants that synthesised approximately 2 and 1.6 pgHA/cell/day, respectively.

Antisense Inhibition of HAS2 did not Affect Cell-Associated Hyaluronan

The exclusion of fixed erythrocytes was used to indirectly visualise the HA pericellular matrix. When compared with parental and mock transfectants, the inhibition of HAS2 did not result in any gross difference in the thickness of the HA pericellular matrix and subsequent cell-associated HA.

Figure 14:
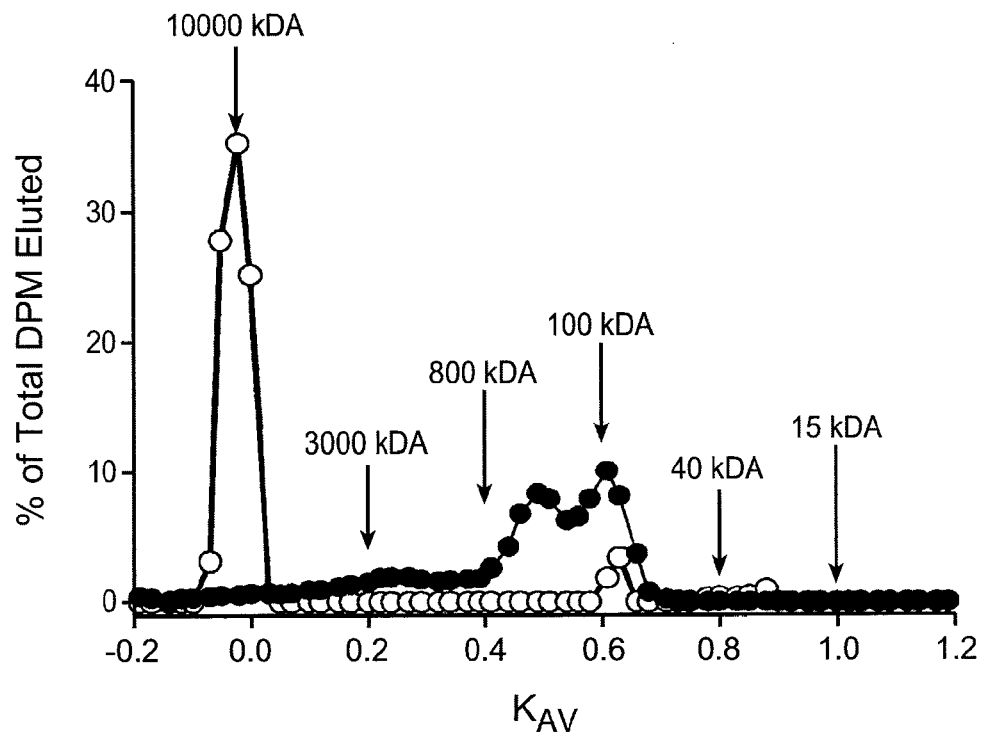
FIG. 14 is a graphical representation of the characterisation of the molecular weight of HA synthesised by parental and MDA-MB 231 stable transfectants harbouring ASHAS2. Cells were seeded at $7.5 \times 10^5$ cells in 75 cm$^2$ culture flasks and grown for 24h in complete medium supplemented with 250 µCi of D-[6-$^3$H]-glucosamine hydrochloride. To determine the MW of $^3$H-HA in the medium, samples were subjected to size exclusion chromatography on a Sephacryl S-1000 SF eluted in 0.15M NaCl/phosphate pH 7.25 at 13.6 ml/h. This figure demonstrates the differences in molecular weight synthesized by parental MDA-MB 231 and their transfected counterparts harbouring antisense mRNA to HAS2. Eluted fractions were proven to be HA as determined by *Streptomyces hyaluronidase* digestion. (●-●:parental cell line; ○-○: ASHAS2 MDA-MB 231 stable transfectants)

Modulation of HAS2 Expression Alters the Molecular Weight of Hyaluronan Produced by MDA-MB 231 Breast Cancer Cells Media removed from the ASHAS2 MDA-MB 231 transfectants was highly viscous when compared to control cell lines. Digestion of the media with *Streptomyces* hyaluronidase demonstrated that >98% the [$^3$H] glucosamine had been incorporated into [$^3$H] HA, with the remaining 2% of [$^3$H] dpm was associated with Pronase digestible macromolecules of ~50 kDa. All figures represent data where this reactivity been removed. The MW of HA synthesised by parental, mock and antisense transfected cells was determined by Sephacryl S-1000 size exclusion chromatography. The parental cell line synthesised three distinct MW of HA which were estimated to be 100, 400 and 3000 kDa potentially reflecting the synthetic products of the prevalently expressed HAS isoforms, HAS2 and 3 respectively (FIG. 14). In contrast, antisense HAS2 transfectants synthesised HA corresponding to a MW of >10,000 kDa where a minor fraction (5.2%) corresponding to a molecular weight 100 kDa was also detected.

Figure 15:
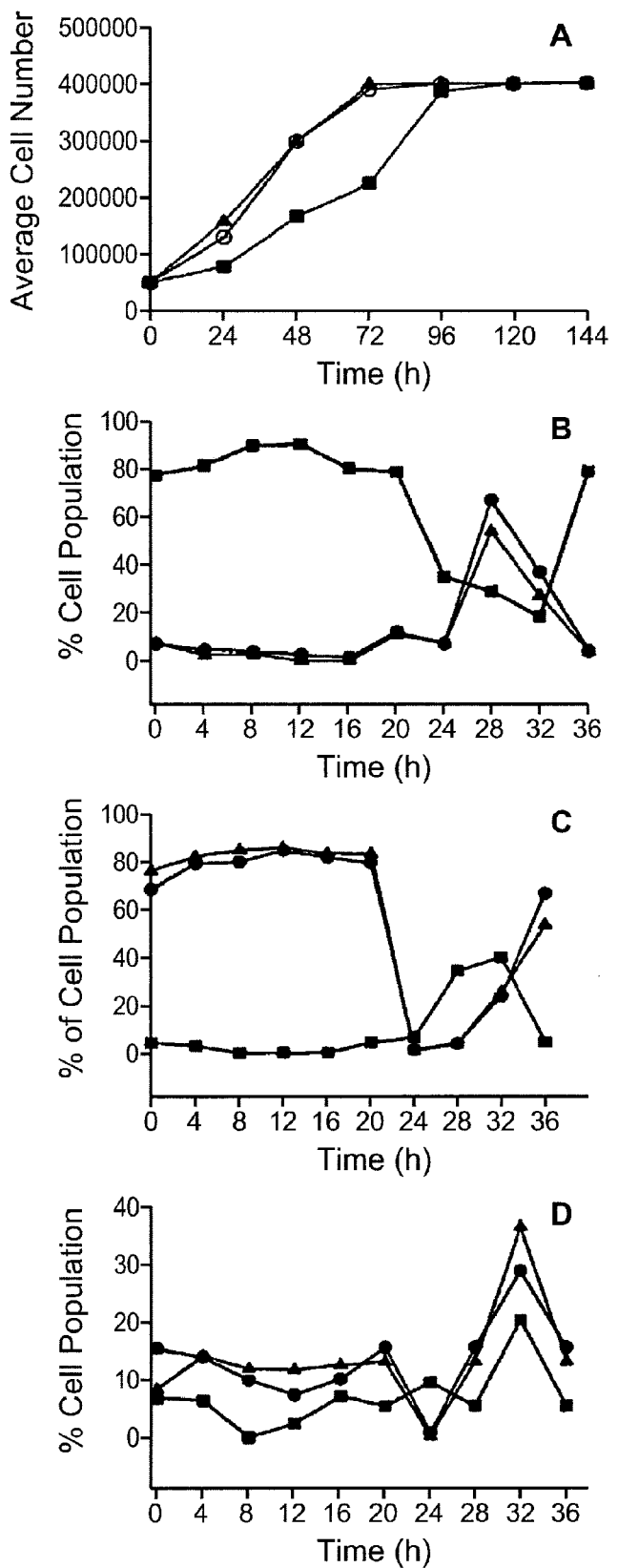
FIG. 15 is a graphical representation showing the effect of antisense inhibition of HAS2 on cell proliferation and cell cycle in parental, mock and ASHAS2 transfected MDA-MB 231. A: Parental, mock and ASHAS2 transfectants were harvested at approximately 80% confluency and seeded in to 24-well plates at a cell density of $5 \times 10^3$ cells/well (2.5 cm$^2$). The rate of cell growth was then followed for 24, 48, 72, and 96 h after plating. All cell counts were determined using an automated Coulter counter. Data represents the average of triplicate determinations at each time point ±SD. ■: ASHAS2 stable transfectants; ▲: parental cell line; 0: mock transfectants. Note: percentage variance between triplicate determinations <2%. B: The transfected and control cells were seeded at $2\times10^5$ cells/25 cm$^2$ flask in the presence of 2 mM thymidine and grown until 50% confluent. Cells were harvested and the proportion of cells in a particular cell cycle stage was then determined in a FACS-Calibur™ analytical instrument. B: population of cells in $G_0/G1$; C: in S phase, and D: in $G_2/M$ phase. Note: the delay in 24 hours of entry into S phase in the ASHAS2 MDA-MB 231 transfectants. ■: ASHAS2 stable transfectants; ▲: parental cell line; ●: mock transfectants.

HAS2 Inhibition Decreases Breast Cancer Cell Proliferation and Arrests the Cell Cycle in $G_0/G_1$ Comparison of the effect of antisense inhibition of HAS2 on cell proliferation and the progression of cell cycle during periods of active cell growth demonstrated that in both parental and mock-transfected cells, a doubling of cell number occurred every 24 h where plateau growth phase was reached at 72 h (FIG. 15A). In ASHAS2 stable transfectants the lack of a functional HAS2 altered cell proliferation by exhibiting a lag period of approximately 24 h, reaching growth arrest by 96 to 120 h (FIG. 15A). Concomitant to these observations flow cytometric analysis was also performed on parental, mock and ASHAS2 transfectants to determine relative DNA content at defined time points after plating at sub-confluent densities. The percentage of the ASHAS2 transfected cells in the cell cycle phases $G_0/G_1$, S and $G_2/M$ 20 h after plating were 79%, 4% and 5% as seen FIGS. 15B, C and D respectively. In contrast the corresponding figures in the parental cell line for the cell cycle phases, $G_0/G_1$, S and $G_2/M$ were approximately 10%, 84% and 13% respectively (FIGS. 15B, C and D). Mock transfectants were comparable to the parental cell line. In contrast, antisense inhibition of HAS2 caused a transient delay (approximately 24 h) of entry into S phase (FIG. 15C). These results are consistent with the observation in the 24 h lag period in growth rate observed in the proliferation assay.

Suppression of HAS2 Reduces the Migration of Human Breast Cancer

Figure 16:
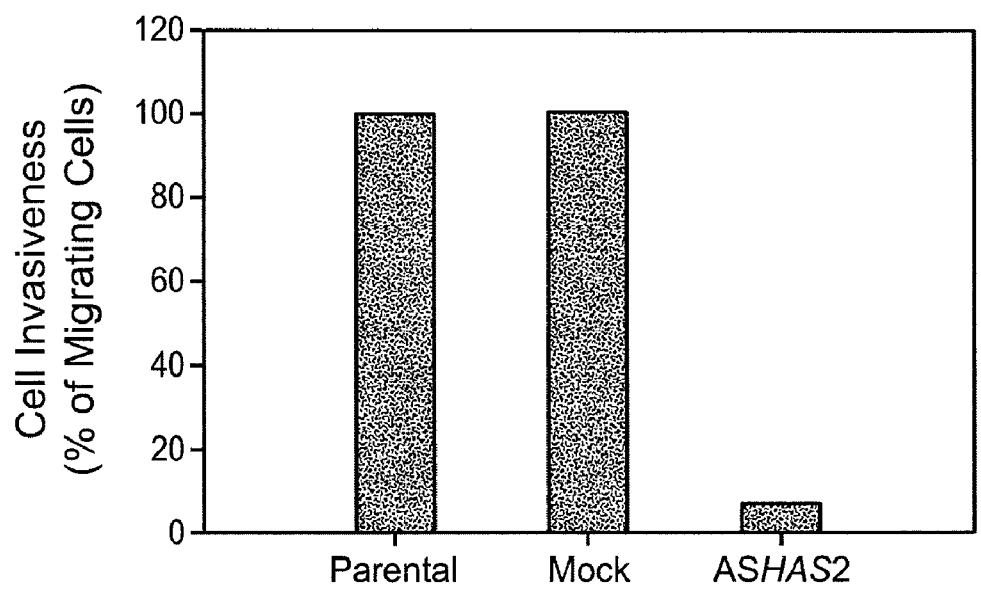
FIG. 16 is graphical representation showing inhibition of in vitro invasiveness of MDA-MB 231 expressing antisense mRNA to HAS2. The invasive potential of parental MDA-MB 231, mock (vector only) and antisense HAS2 transfected cells were examined using the Boyden chamber chemoinvasion assay. The cells that had traversed the matrigel and spread on the lower surface of the filter were expressed as a percentage of the cell count determined for the parental MDA-MB 231 cell line. The data presented represent the average of triplicate experiments performed on two separate days±SD. Note: percentage variance between triplicate determinations <2%.

Migration of the breast cancer cells was ameliorated by the inhibition of HAS2 as indicated by the inability of the ASHAS2 transfectants to migrate across a Matrigel membrane (FIG. 16). Comparison of cellular migratory rates demonstrated that both the parental and mock transfectants displayed typical invasive phenotypes with 100% of the cell populations permeating the Matrigel, in contrast, only 7% of the HAS2 stable transfectants maintained the ability to invade the Matrigel membrane.

Figure 17:
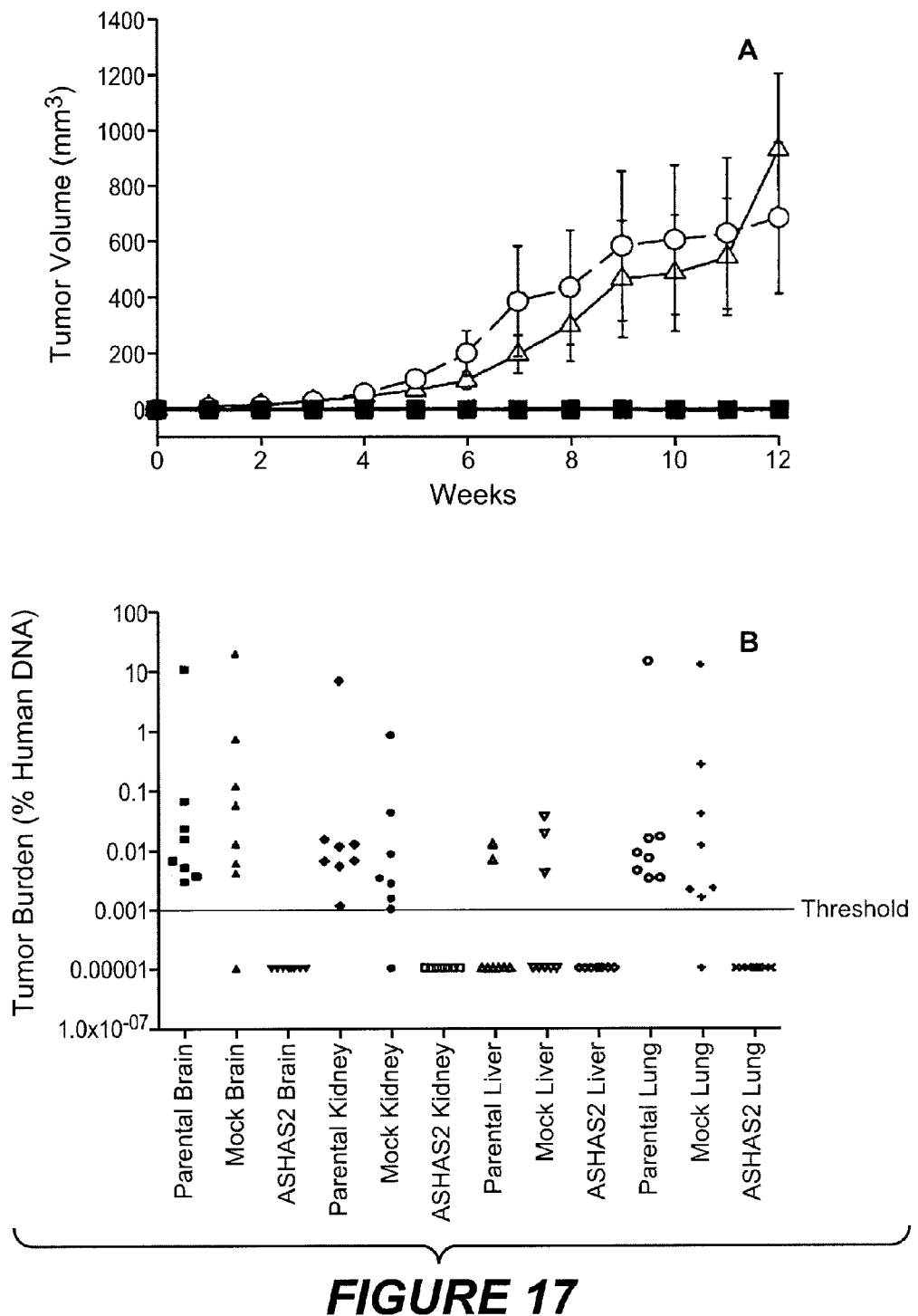
FIG. 17 is a graphical representation showing the effect of HAS2 antisense inhibition on the tumorgenicity and metastasis in MDA-MB 231. A: Parental, mock and ASHAS2 transfectants were inoculated into the mammary fat pad of nude mice. Primary tumor growth was followed over a 12-week period with tumour progression recorded twice weekly. The results graphed represent the average tumor volume (mm$^3$)±SEM, where n =9-13. B: Alu PCR was utilised to determine the extent of soft organ metastasis from brain, kidney, liver and lung. Results are expressed as the percentage of human tumour DNA in mouse soft organs, n =8 per group.

HAS2 Inhibition Totally Inhibits the Initiation and Progression of Primary Breast Cancer in vivo Mice intradermally inoculated with parental or mock-transfected MDA-MB 231 readily established primary tumours that were comparable in growth over the duration of the 12-week experiment (FIG. 17A). In contrast, however, mice inoculated with ASHAS2 transfectants did not establish primary tumours (FIG. 17A). To ensure that the lack of tumour growth was not a result of a poor cell viability of the cell inoculum, in one set of experiments, Matrigel was also included in the inoculation medium. Again, no primary tumour could be detected over the duration of the 12-week experiment. When quantitating the spread of the primary cancer, the highly sensitive Alu PCR assay demonstrated that metastasis in animals inoculated with parental and mock-transfected was most prevalent in brain and lung, but was also detected in kidneys and liver transfectants. Mice injected with MDA-MB 231 ASHAS2 did not exhibit metastasis to any organs (FIG. 17B).

Figure 18:
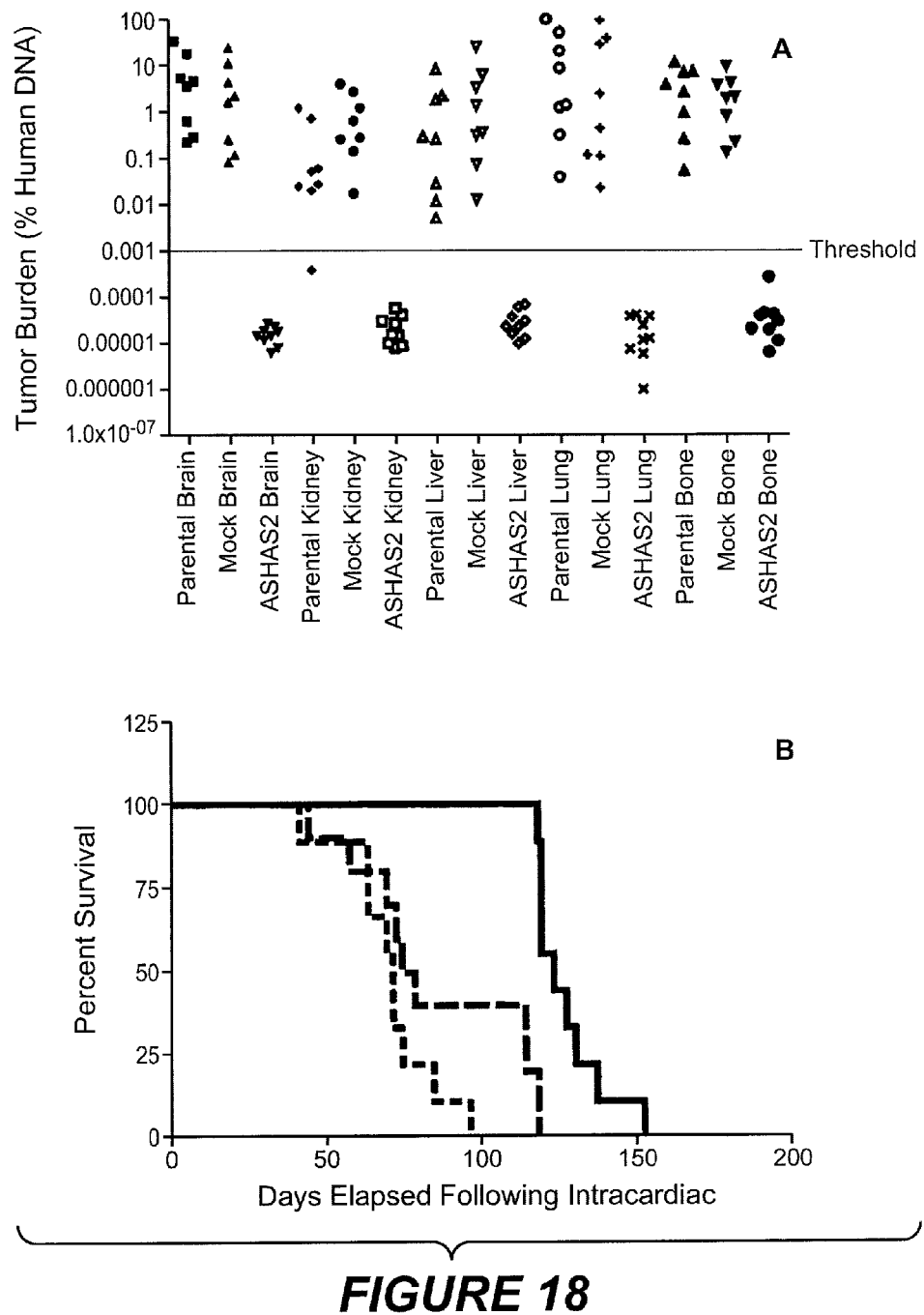
FIG. 18 is a graphical representation showing the effect of HAS2 antisense inhibition on the metastasis and in animal survival. A: Alu PCR was utilised to determine the extent of soft organ metastasis after intracardiac inoculation of nude mice from brain, kidney, liver, lung and bone. Results are expressed as the percentage of human tumour DNA in mouse soft organs, n=9 per group. No metastasis to these organs could be detected where animals had been inoculated with MDA-MB 231 ASHAS2 transfected cells. B: Survival rate of the parental, mock and ASHAS2 transfectants mice were plotted using Prism stats program (Kaplan-Meier Survival) with the days elapsed following intracardiac inoculations. There were no different in the animal survival rate (P=0.0840) between the parental and mock transfected mice. Survival curve for ASHAS2 was significantly different (P<0.0001) from the both control groups. MDA-MB 231 ASHAS2 transfectants (solid); parental cell line (short dash); mock transfectants (long dash).

Modulation of HAS2 Inhibited the Formation of Secondary Tumours and Increased Animal Survival When quantitating the metastasis of the breast cancer after intracardiac inoculation, animals inoculated with parental and mock-transfected demonstrated prevalent spread of the cancer to the brain, liver, kidneys, lung and bone while mice injected with MDA-MB 231 ASHAS2 did not exhibit metastasis to any organs (FIG. 18A). Bone lesions were observed in several mice from the control groups while ASHAS2 inoculated mice did not present with any bone lesions. Mice inoculated with parental or mock-transfected MDA-MB 231 cells demonstrated a significantly shorter survival period, 72 days and 77 days when compared to the ASHAS2 animals which had a mean survival time of 124 days (p=0.0001) (FIG. 18B).

EXAMPLE 23

Production of HAS Antiserum

On the basis of the predicted amino acid sequence for hHAS1, three short antigenic peptides were designed and synthesised by solid phase amino acid synthesis and purified by reverse-phase high-pressure chromatography. The peptides were determined to be 99.9% pure as shown by mass spectrometry. The production, purification, conjugation to diphtheria toxoid (DT), and purity testing of the peptides were performed by Chiron Mimitopes (Melbourne, Australia). The sequence of each immunising peptide is shown in Table 7.

TABLE 7

Characteristics of the immunising peptides used to raise polyclonal antibodies to HA synthase.

| Immunising peptide | Amino acid sequence | Hypothesised species cross reactivity | |
|---|---|---|---|
| | | mouse | human |
| HAS418 | AARGPLDAATCRALLYPRARV (SEQ ID NO: 24) 49→58 'Cys' 94→103 | -ve | +ve |

TABLE 7-continued

Characteristics of the immunising peptides used to raise polyclonal antibodies to HA synthase.

| Immunising peptide | Amino acid sequence | Hypothesised species cross reactivity | |
|---|---|---|---|
| | | mouse | human |
| HAS419 | GGLVRSVAHEA (SEQ ID NO: 25) 480→490 | -ve | +ve |
| HAS421 | GAYREVEAEDPGRLAVE (SEQ ID NO: 26) 146→162 | +ve | +ve |

HAS immunising peptides 418 and 419 were selected on areas of heterogeneity between species indicating that they would be human-specific, while HAS421 was homologous to both mouse and human.

Border Leicester Merino cross-bred sheep were injected intramuscularly at two sites with the peptides (0.2-0.5 mg) dissolved in complete Freund's adjuvant and again two weeks later in incomplete Freud's adjuvant. At day 35, the sheep were bled, and the serum separated by centrifugation, and stored at -20° C. All serum collected was tested with an enzyme-linked immunosorbent assay for antibodies specific for the peptide and carrier protein. The immunising peptide was coupled to thiopropyl-Sepharose 6B gel (Amersham Pharmacia Biotech, Uppsala, Sweden) by cyanogen bromide activation and the specific antibodies were extracted from the polyclonal sheep HAS antiserum by affinity chromatography. In brief 5 mL of serum was mixed with 3 mL of PBS and mixed with affinity/ligand resin for 1 hour at room temperature, followed by three washes of 5 mL PBS. The antibodies were eluted in 0.1 M glycine pH2.8 and were immediately neutralised to pH7.2 by the addition of 0.1 M NaOH.

HAS polyclonal antibodies were then concentrated in an Amicon cell concentrator fitted with a YM30 Diaflo filter. The protein concentration of each affinity purified antibody was determined by the BCA assay (Pierce, U.S.A). The sterility of the antibodies used in immunohistochemistry or immunoblotting was assured by the addition of 0.1% w/v sodium azide, before storage at -20° C. in aliquots. Antibodies intended for addition to cell cultures was stored at -20° C. without azide.

Those skilled in the art will appreciate that the invention described herein is susceptible to variations and modifications other than those specifically described. It is to be understood that the invention includes all such variations and modifications. The invention also includes al steps, features, compositions and compounds referred to or indicated in this specification individually or collectively, and any and all combinations of any two or more steps or features.

BIBLIOGRAPHY

Altschul et al., *J. Mol. Biol.*: 215,430-410, 1990
Antibodies: A Laboratory Manual, Harlow and Lane (eds.), Cold Spring Harbor Laboratory Press, Cold Spring Harbor, N.Y., (1988)
Banerji et al., *J. Cell Biol.*: 144, 789-801, 1999
Bird, *Science* 242: 423, 1988
Bourguignon et al., *Biol. Chem.*: 272, 27913-27918, 1997
Brazma and Vilo, *FEBS Lett.*: 480, 17-24, 2000
Camenisch et al., *J. Clin. Invest.*: 106, 349-360, 2000
Caulli et al., *J. Cell Biochem. Suppl.*: 31, 286-296, 1998
Celis et al., *FEBS Lett*: 480, 2-16, 2000

Clackson et al., *Nature* 352:624-628, 1991
Clarris et al., On the pericellular zone of some mammalian cells in vitro. *Exp Cell Res* 49:181-193, 1968
Csoka et al., The six hyaluronidase-like genes in the human and mouse genomes. *Matrix Biol* 20: 499-508, 2001
Culty et al., *J. Cell Physiol.:* 160, 275-286, 1994
Elbashir et al., *Nature:* 411, 494-498, 2001
Elbashire et al., *Genes Dev.:* 15, 188-120, 2001
Entwistle et al., *J. Cell. Biochem.:* 61, 569-577, 1996
Erickson et al., *Science* 249: 527-533, 1990
Fire et al, *Nature:* 391, 806-811, 1998
Fries et al., *Virchows. Archiv.:* 424: 7-12, 1994
Fuchs et al., *Anal. Biochem.:* 286, 91-98, 2000
Going and Gusterson, *Eur. J. Cancer.:* 35, 1895-1904, 1999
Gunthert et al., *Cell.:* 65, pp. 13-24, 1991
Guo and Kempheus, *Cell:* 81,611-620, 1995
Hodgson (*Bio/Technology* 9: 19-21, 1991)
Huston et al., *Proc. Natl. Acad. Sci. USA* 85: 5879, 1988
Itano et al., *Biochem. Biophys. Res. Comm.:* 222, 816-821, 1996
Itano et al., Three isoforms of mammalian hyaluronan synthases have distinct enzymatic properties. *J Biol Chem* 274: 25085-25092, 1999
Itano et al., *Cancer Res.:* 59, 2499-2504, 1999
Itano et al., *Proc. Natl. Acad. Sci.:* 99, 3609-3614, 2002
Johnson et al., "Peptide Turn Mimetics" in *Biotechnology and Pharmacy*
Jones et al., *Nature* 321:522-525, 1986
Jungblut et al., *Electrophoresis:* 20, 2100-2110, 1999
Jurecic and Belmont, *Curr. Opin. Microbiol.:* 3, 316-321, 2000
Kabat et al. in Sequences of Proteins of Immunological Interest, 5th Ed., US Dept. of Health and Human Services, PHS, NIH, NIH Publication No. 91-3242, 1991
Kennet et al. (eds.), Monoclonal Antibodies, Hybridomas: A New Dimension in Biological Analyses, Kennet et al. (eds.), Plenum Press, New York (1980); and Antibodies: A Laboratory Manual, Harlow and Lane (eds.), Cold Spring Harbor Laboratory Press, Cold Spring Harbor, N.Y., (1988).
Knudson and Knudson, *FASEB.* 7: pp. 1233-1241, 1993
Knudson and Knudson, The hyaluronan receptor, CD44, 1999
Knudson et al., The role and regulation of tumor-associated hyaluronan. In: The Biology of Hyaluronan. (Editors: Evered, D. & Whelan, J) Ciba foundation symposium 143. 1 Wiley and Sons, Chichester: pp. 150-169, 1989
Kohler et al., *Nature* 256:495 (1975)
Kojima et al., *Cancer Res.:* 35, 542-547, 1975
Kortt et al., *Protein Engineering* 10: 423, 1997
Kosaki et al., *Cancer Res.:* 59, 1141-1145, 1999
Larrick et al., *Bio/Technology* 7-934, 1989
Larson et al., *Cytometry:* 41, 203-208, 2000
Larsson et al., *J. Biotechnol.:* 80, 143-157, 2000
Laurent and Fraser, *Hyal. FASEB J.:* 6, 2397-2404, 1992
Laurent and Killander, *J. Chromatogr.:* 14, pp. 317-330, 1964
Liu et al., *Proc. Natl. Acad. Sci. USA* 84: 3439, 1987
Liu et al., *Cancer Res.:* 61, 5207-5214, 2001
Madden et al., *Drug Disc. Today:* 5, 415-423, 2000
Marks et al., *J. Mol. Biol.* 222:581-597, 1991
Mathew and Dorfman, *Physiol. Rev.:* 35, 381-402, 1955
McKee, et al., *J. Biol. Chem.:* 272, 8013-8018, 1997
Montgomery et al., *Proc. Natl. Acad. Sci, USA:* 95,15502-15507, 1998
Morrison et al., *Proc. Natl. Acad. Sci. USA* 81:6851-6855, 1984
Munder et al. (*Appl. Microbiol. Biotechnol.* 52(3): 311-320, 1999
Ng and Schwartz, *J. Biol. Chem.:* 264, 11776-11783, 1989
Oksala et al., *J. Histochem. Cytochem.:* 43, 125-135, 1995
Pauli and Knudson, *Human Path.:* 19, 628-639, 1988
Pezzuto et al., Eds., Chapman and Hall, New York, 1993
Philipson and Schwartz, *J. Biol. Chem.:* 259, pp. 5017-5023, 1984
Philipson et al., *Biochem.:* 24, 7899-7906, 1985
Prashar and Weissman, *Meth-Enzymol.:* 303, 258-272, 1999
Prelim, P and Mausolf, *Biochem. J:* 235, 887-889; 1986
Prelim, P, *Biochem. J.:* 220, pp. 597-600, 1984
Prelim P, Release of hyaluronate from eukaryotic cells. *Biochem J* 267: 185-189, 1990
Presta, *Curr. Op. Struct. Biol.* 2:593-596, 1992
Reichmann et al., *Nature* 332:323-329, 1988
Rilla et al., *J. cell Sci.:* 115, 3633-3643, 2002
Shyjan et al., *J. Biol. Chem.:* 271, pp. 23395-23399, 1996
Simpson et al., *American J. Path.:* 161, pp. 849-857, 2002
Spicer and McDonald, *J. Biol. Chem.:* 273, 1923-1932, 1998
Spicer and Nguyen, *Biochem. Soc. Trans.:* 27, 109-115, 1999
Spicer et al., *Genomics.:* 41, 493-497, 1997
Spicer et al., *J. Biol. Chem.:* 272, 8957-8961, 1997
Stern R, Devising a pathway for hyaluronan catabolism: are we there yet? *Glycobiology* 13:105R-115R, 2003
Sutcliffe et al., *Proc. Natl. Acad. Sci. USA.:* 97, 1976-1981, 2000
Sy et al., *J. Exp. Med.:* 174, pp. 859-866, 1991
Tabara et al., *Sci.:* 282, 430-431, 1998
Tester et al., *Clin. & Exp. Metast.:* 0, 1-7, 2002
Thompson et al., *J. Cell Physiol.:* 150, 534-544, 1992
Tijsterman et al., *Science:* 295, 694-697, 2002
Timmons and Fire, *Nature:* 395, 854, 1998
Timmons et al., *Gene:* 263, 103-112, 2001
Tool, B., Glycosaminoglcans in morphogenesis. In: Cell Biology of the extracellular matrix. (Editor. Hay, E. D.) Plenum Press, New York: pp. 259-294, 1981
Toole, B. P., *Current Opin. in Cell Biol.:* 2, 839-844, 1990
Toole, B. P., *J. Inter. Med.:* 242, 35-40, 1997
Turley and Torrance, *Exp. Cell. Res.:* 161, 17-28, 1985
Tuschl et al., *Genes Dev.:* 13, 3191-3197, 1999
U.S. Pat. No. 4,816,567
U.S. Pat. No. 4,946,778
Udabage et al., Inhibition of hyaluronan degradation by dextran sulphate facilitates characterisation of hyaluronan synthesis: an in vitro and in vivo study *Glycoconjugate J* (in Press), 2004
Victor et al., *J. Cancer:* 82, 77-83, 1999
Ward et al., *Nature* 334: 544, 1989
Watanabe and Yamaguchi, *J. Biol. Chem.:* 271, 22945-22948, 1996
Weissmann and Meyer, *J. Am. Chem. Soc.:* 76, pp. 1753, 1954
Wells, *Methods Enzymol.* 202: 2699-2705, 1991
Winter and Harris, *TIPS* 14: 139, 1993
Young et al., *Nat. Biotechnol.* 16(10): 946-950, 1998
Xing etal., *Oral Diseases:* 4, 241-247, 1998
Zhang and Madden, *Genome Res.:* 7,649-656, 1997
Zhang et al., *Cancer Res.:* 55, 428-433, 1995

What is claimed as new and desired to be protected by Letters Patent of the United States is:

1. An isolated antibody which reduces the level of hyaluronan synthase (HAS) activity wherein said antibody specifically binds targeted antigen of SEQ ID NO:26 within HAS 1.

2. The isolated antibody of claim 1, wherein the antibody is selected from a monoclonal antibody, polyclonal antibody, and antigen-binding fragment and a humanized antibody.

3. The isolated antibody of claim 2, wherein the antibody is a monoclonal antibody or an antigen-binding fragment thereof.

4. The isolated antibody of claim 1, wherein the HAS activity is selected from the group consisting of HAS1, HAS2 and HAS3 activity.

5. The isolated antibody of claim 4, wherein the antibody is selected from a monoclonal antibody, polyclonal antibody, and antigen-binding fragment and a humanized antibody.

6. The isolated antibody of claim 5, wherein the antibody is a monoclonal antibody or an antigen-binding fragment thereof.

7. A pharmaceutical composition comprising an antibody of claim 1 and one or more pharmaceutically acceptable carriers and/or diluents.

* * * * *

SEQUENCE LISTING

<160> NUMBER OF SEQ ID NOS: 51

<210> SEQ ID NO 1
<211> LENGTH: 27
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Sense primer for human HAS2

<400> SEQUENCE: 1
gagctgaaca agatgcattg tgagagc                                27

<210> SEQ ID NO 2
<211> LENGTH: 29
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Antisense primer for human HAS2

<400> SEQUENCE: 2
gacatggtgc ttgatgtatg atcttccat                              29

<210> SEQ ID NO 3
<211> LENGTH: 18
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Primer for PCINeo

<400> SEQUENCE: 3
gcacagatgc gtaaggag                                          18

<210> SEQ ID NO 4
<211> LENGTH: 29
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Sense Primer for GSP2

<400> SEQUENCE: 4
gctgtgtaca tgacctcgcg cttgccgcc                              29

<210> SEQ ID NO 5
<211> LENGTH: 19
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Sense primer for GSP4

<400> SEQUENCE: 5
ggcgggaagt aaactcgac                                         19

<210> SEQ ID NO 6
<211> LENGTH: 20
<212> TYPE: DNA
<213> ORGANISM: Artificial Sequence
<220> FEATURE:

-continued

<223> OTHER INFORMATION: Synthetic Construct
<220> FEATURE:
<223> OTHER INFORMATION: Sense primer for HAS1

<400> SEQUENCE: 6
cctgcatcag cggtcctcta                                          20

<210> SEQ ID NO 7
<211> LENGTH: 18
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Antisense primer for HAS1

<400> SEQUENCE: 7
gccggtcatc cccaaaag                                            18

<210> SEQ ID NO 8
<211> LENGTH: 27
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Sense primer for HAS2

<400> SEQUENCE: 8
aacctcttgc agcagtttct tgaggcc                                  27

<210> SEQ ID NO 9
<211> LENGTH: 19
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Sense primer for HAS2

<400> SEQUENCE: 9
cagtcctggc ttcgagcag                                           19

<210> SEQ ID NO 10
<211> LENGTH: 21
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Antisense primer for HAS2

<400> SEQUENCE: 10
ttgggagaaa agtctttggc t                                        21

<210> SEQ ID NO 11
<211> LENGTH: 28
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Sense primer for HAS2

<400> SEQUENCE: 11
ccattgaacc agagacttga aacagccc                                 28

<210> SEQ ID NO 12

```
<211> LENGTH: 21
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Sense primer for HAS3

<400> SEQUENCE: 12
ttgcactgtg gtcgtcaact t                                          21

<210> SEQ ID NO 13
<211> LENGTH: 21
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Antisense primer for HAS3

<400> SEQUENCE: 13
gtcgaggtca aacgttgtga g                                          21

<210> SEQ ID NO 14
<211> LENGTH: 32
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Sense primer for HAS3

<400> SEQUENCE: 14
tcaaatcaaa aacaggcagg tacaggtagt gg                              32

<210> SEQ ID NO 15
<211> LENGTH: 21
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Sense primer for GAPDH

<400> SEQUENCE: 15
aaggtgaagg tcggagtcaa c                                          21

<210> SEQ ID NO 16
<211> LENGTH: 21
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Antisense primer for GAPDH

<400> SEQUENCE: 16
gagttaaaag cagccctggt g                                          21

<210> SEQ ID NO 17
<211> LENGTH: 22
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Sense primer for GAPDH

<400> SEQUENCE: 17
```
tttggtcgta ttgggcgcct gg                                              22

<210> SEQ ID NO 18
<211> LENGTH: 27
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Sense primer for HYAL1

<400> SEQUENCE: 18
gcacagggaa gtcacagatg tatgtgc                                         27

<210> SEQ ID NO 19
<211> LENGTH: 24
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Antisense primer for HYAL1

<400> SEQUENCE: 19
ccactggtca cgttcaggat gaag                                            24

<210> SEQ ID NO 20
<211> LENGTH: 25
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Sense primer for HYAL2

<400> SEQUENCE: 20
gatgtgtatc gccggttatc acgcc                                           25

<210> SEQ ID NO 21
<211> LENGTH: 25
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Antisense primer for HYAL2

<400> SEQUENCE: 21
cgtagactgg gagtgcatgg ttggc                                           25

<210> SEQ ID NO 22
<211> LENGTH: 23
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Sense primer for HYAL3

<400> SEQUENCE: 22
gcactgatgg aggatacgct gcg                                             23

<210> SEQ ID NO 23
<211> LENGTH: 25
<212> TYPE: DNA
<213> ORGANISM: Artificial Sequence
<220> FEATURE:
<223> OTHER INFORMATION: Synthetic Construct
<220> FEATURE:

-continued

<223> OTHER INFORMATION: Antisense primer for HYAL3

<400> SEQUENCE: 23
gctggtgact gcaggccatc gctgc          25

<210> SEQ ID NO 24
<211> LENGTH: 21
<212> TYPE: PRT
<213> ORGANISM: Homo sapiens

<400> SEQUENCE: 24

Ala Ala Arg Gly Pro Leu Asp Ala Ala Thr Cys Arg Ala Leu Leu Tyr
1               5                   10                  15

Pro Arg Ala Arg Val
            20

<210> SEQ ID NO 25
<211> LENGTH: 11
<212> TYPE: PRT
<213> ORGANISM: Homo sapiens

<400> SEQUENCE: 25

Gly Gly Leu Val Arg Ser Val Ala His Glu Ala
1               5                   10

<210> SEQ ID NO 26
<211> LENGTH: 17
<212> TYPE: PRT
<213> ORGANISM: Homo sapiens

<400> SEQUENCE: 26

Gly Ala Tyr Arg Glu Val Glu Ala Glu Asp Pro Gly Arg Leu Ala
1               5                   10                  15

Val Glu

<210> SEQ ID NO 27
<211> LENGTH: 20
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Sense primer for HAS1

<400> SEQUENCE: 27
cctgcatcag cggtcctcta          20

<210> SEQ ID NO 28
<211> LENGTH: 19
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Sense primer for HAS2

<400> SEQUENCE: 28
cagtcctggc ttcgagcag          19

<210> SEQ ID NO 29
<211> LENGTH: 21
<212> TYPE: DNA
<213> ORGANISM: Artificial Sequence
<220> FEATURE:
<223> OTHER INFORMATION: Synthetic Construct
<220> FEATURE:

<223> OTHER INFORMATION: Sense primer for HAS3

<400> SEQUENCE: 29
ttgcactgtg gtcgtcaact t         21

<210> SEQ ID NO 30
<211> LENGTH: 21
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Sense primer GAPDH

<400> SEQUENCE: 30
aaggtgaagg tcggagtcaa c         21

<210> SEQ ID NO 31
<211> LENGTH: 27
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Sense primer for HYAL1

<400> SEQUENCE: 31
gcacagggaa gtcacagatg tatgtgc         27

<210> SEQ ID NO 32
<211> LENGTH: 25
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Sense primer for HYAL2

<400> SEQUENCE: 32
gatgtgtatc gccggttatc acgcc         25

<210> SEQ ID NO 33
<211> LENGTH: 23
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Sense primer for HYAL3

<400> SEQUENCE: 33
gcactgatgg aggatacgct gcg         23

<210> SEQ ID NO 34
<211> LENGTH: 18
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Antisense primer for HAS1

<400> SEQUENCE: 34
gccggtcatc cccaaaag         18

<210> SEQ ID NO 35
<211> LENGTH: 21
<212> TYPE: DNA

```
<213> ORGANISM: Artificial Sequence
<220> FEATURE:
<223> OTHER INFORMATION: Synthetic Construct
<220> FEATURE:
<223> OTHER INFORMATION: Antisense primer for HAS2

<400> SEQUENCE: 35
ttgggagaaa agtctttggc t                                          21

<210> SEQ ID NO 36
<211> LENGTH: 21
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Antisense primer for HAS3

<400> SEQUENCE: 36
gtcgaggtca aacgttgtga g                                          21

<210> SEQ ID NO 37
<211> LENGTH: 21
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Antisense primer for GAPDH

<400> SEQUENCE: 37
gagttaaaag cagccctggt g                                          21

<210> SEQ ID NO 38
<211> LENGTH: 24
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Antisense primer for HYAL1

<400> SEQUENCE: 38
ccactggtca cgttcaggat gaag                                       24

<210> SEQ ID NO 39
<211> LENGTH: 25
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Antisense primer for HYAL2

<400> SEQUENCE: 39
cgtagactgg gagtgcatgg ttggc                                      25

<210> SEQ ID NO 40
<211> LENGTH: 25
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Antisense primer for HYAL3

<400> SEQUENCE: 40
gctggtgact gcaggccatc gctgc                                      25
```

```
<210> SEQ ID NO 41
<211> LENGTH: 27
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Hybridisation probe for HAS1

<400> SEQUENCE: 41
aacctcttgc agcagtttct tgaggcc                                          27

<210> SEQ ID NO 42
<211> LENGTH: 28
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Hybridisation probe for HAS2

<400> SEQUENCE: 42
ccattgaacc agagacttga aacagccc                                         28

<210> SEQ ID NO 43
<211> LENGTH: 32
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Hybridisation probe for HAS3

<400> SEQUENCE: 43
tcaaatcaaa aacaggcagg tacaggtagt gg                                    32

<210> SEQ ID NO 44
<211> LENGTH: 22
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Hybridisation probe for GAPDH

<400> SEQUENCE: 44
tttggtcgta ttgggcgcct gg                                               22

<210> SEQ ID NO 45
<211> LENGTH: 27
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Sense primer for HAS2

<400> SEQUENCE: 45
gagctgaaca agatgcattg tgagagc                                          27

<210> SEQ ID NO 46
<211> LENGTH: 29
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Antisense primer for HAS2
```

```
<400> SEQUENCE: 46
gacatggtgc ttgatgtatg atcttccat                                    29

<210> SEQ ID NO 47
<211> LENGTH: 18
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Primer for pCL-neo

<400> SEQUENCE: 47
gcacagatgc gtaaggag                                                18

<210> SEQ ID NO 48
<211> LENGTH: 29
<212> TYPE: DNA
<213> ORGANISM: Artificial Sequence
<220> FEATURE:
<223> OTHER INFORMATION: Synthetic Construct
<220> FEATURE:
<223> OTHER INFORMATION: GSP2 sense primer

<400> SEQUENCE: 48
gctgtgtaca tgacctcgcg cttgccgcc                                    29

<210> SEQ ID NO 49
<211> LENGTH: 19
<212> TYPE: DNA
<213> ORGANISM: Artificial Sequence
<220> FEATURE:
<223> OTHER INFORMATION: Synthetic Construct
<220> FEATURE:
<223> OTHER INFORMATION: GSP4 sense primer

<400> SEQUENCE: 49
ggcgggaagt aaactcgac                                               19

<210> SEQ ID NO 50
<211> LENGTH: 30
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Alu sense primer

<400> SEQUENCE: 50
gtgaaacccc gtctctacta aaaatacaaa                                   30

<210> SEQ ID NO 51
<211> LENGTH: 20
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Alu antisense primer

<400> SEQUENCE: 51
gcgatctcgg ctcactgcaa                                              20
```